United States Patent
Lee et al.

(10) Patent No.: US 11,844,271 B2
(45) Date of Patent: Dec. 12, 2023

(54) ORGANIC COMPOUND, COMPOSITION, ORGANIC OPTOELECTRONIC DEVICE, AND DISPLAY APPARATUS

(71) Applicants: SAMSUNG SDI CO., LTD., Yongin-si (KR); SAMSUNG ELECTRONICS CO., LTD., Suwon-si (KR)

(72) Inventors: Hanill Lee, Suwon-si (KR); Byungku Kim, Suwon-si (KR); Youngsung Park, Suwon-si (KR); Chang Ju Shin, Suwon-si (KR); Dongkyu Ryu, Suwon-si (KR); Seungjae Lee, Suwon-si (KR); Kipo Jang, Suwon-si (KR); Sung-Hyun Jung, Suwon-si (KR)

(73) Assignees: SAMSUNG SDI CO., LTD., Yongin-si (KR); SAMSUNG ELECTRONICS CO., LTD., Suwon-si (KR)

( * ) Notice: Subject to any disclaimer, the term of this patent is extended or adjusted under 35 U.S.C. 154(b) by 296 days.

(21) Appl. No.: 16/954,722

(22) PCT Filed: Dec. 18, 2018

(86) PCT No.: PCT/KR2018/016133
§ 371 (c)(1),
(2) Date: Jun. 17, 2020

(87) PCT Pub. No.: WO2019/132374
PCT Pub. Date: Jul. 4, 2019

(65) Prior Publication Data
US 2020/0388765 A1 Dec. 10, 2020

(30) Foreign Application Priority Data
Dec. 27, 2017 (KR) .................. 10-2017-0181463

(51) Int. Cl.
*C07D 409/14* (2006.01)
*H10K 85/60* (2023.01)
(Continued)

(52) U.S. Cl.
CPC ......... *H10K 85/654* (2023.02); *C07D 209/86* (2013.01); *C07D 405/14* (2013.01);
(Continued)

(58) Field of Classification Search
CPC ............................ C07D 409/14; C07D 405/14
(Continued)

(56) References Cited

U.S. PATENT DOCUMENTS 8,541,112 B2 9/2013 Otsu et al.
2015/0207082 A1 7/2015 Dyatkin et al.

FOREIGN PATENT DOCUMENTS

CN 105899501 A 8/2014
CN 108191842 A 6/2018
(Continued)

OTHER PUBLICATIONS

International Search Report dated Apr. 2, 2019 for PCT/KR2018/016133.
Chinese Office action and Search Report dated Feb. 28, 2023.

*Primary Examiner* — Jeffrey H Murray
(74) *Attorney, Agent, or Firm* — Lee IP Law, P.C.

(57) ABSTRACT

The present invention relates to an organic compound represented by Chemical Formula 1, a composition, an organic optoelectronic device, and a display device.

16 Claims, 1 Drawing Sheet

(51) Int. Cl.
*C07D 209/86* (2006.01)
*C07D 405/14* (2006.01)
*C07D 487/04* (2006.01)
*C09K 11/02* (2006.01)
*H10K 50/11* (2023.01)
*H10K 101/10* (2023.01)

(52) U.S. Cl.
CPC ......... *C07D 409/14* (2013.01); *C07D 487/04* (2013.01); *C09K 11/025* (2013.01); *H10K 85/6574* (2023.02); *H10K 85/6576* (2023.02); *H10K 50/11* (2023.02); *H10K 2101/10* (2023.02)

(58) Field of Classification Search
USPC .......................... 544/180, 333; 548/418, 440
See application file for complete search history.

(56) References Cited

FOREIGN PATENT DOCUMENTS

| | | | | |
|---|---|---|---|---|
| CN | 109071513 A | | 12/2018 | |
| JP | 5181676 B2 | | 1/2013 | |
| JP | 2017-107992 A | | 6/2017 | |
| KR | 10-2015-0083385 A | | 7/2015 | |
| KR | 10-2015-0088176 A | | 7/2015 | |
| KR | 10-2015-0117173 A | | 10/2015 | |
| KR | 10-2017-0039209 A | | 4/2017 | |
| KR | 10-1730779 B1 | | 4/2017 | |
| KR | 10-2017-0086277 A | | 7/2017 | |
| KR | 10-2017-0102000 A | | 9/2017 | |
| KR | 10-2017-0120413 A | | 10/2017 | |
| KR | 10-1788094 B1 | | 10/2017 | |
| KR | 10-2018-0051355 A | | 5/2018 | |
| KR | 10-2018-0068869 A | | 6/2018 | |
| KR | 2018068869 | * | 6/2018 | ............. C09K 11/06 |
| KR | 10-2018-0099436 A | | 9/2018 | |
| KR | WO2018084423 | * | 11/2018 | ........... C07D 405/14 |
| KR | 10-2019-0030963 A | | 3/2019 | |
| KR | WO2019054833 | * | 3/2019 | ........... C07D 405/04 |
| WO | WO 2015-105251 A1 | | 7/2015 | |
| WO | WO 2016-129672 A1 | | 8/2016 | |
| WO | WO 2018-084423 A2 | | 5/2018 | |

* cited by examiner

[FIG. 1]
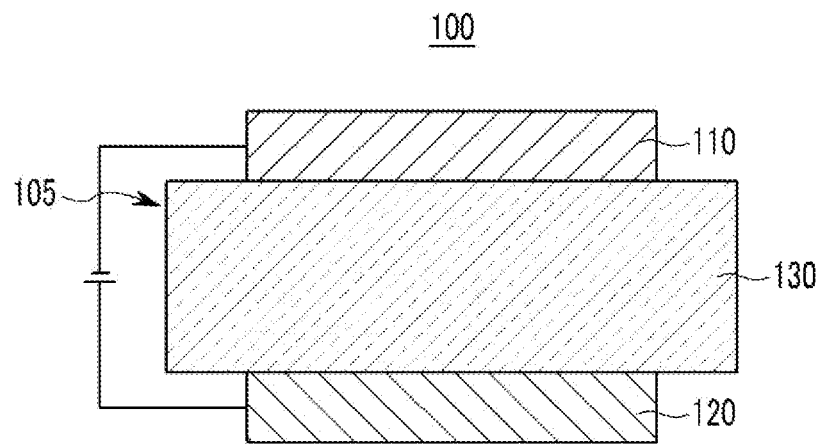
[FIG. 2]
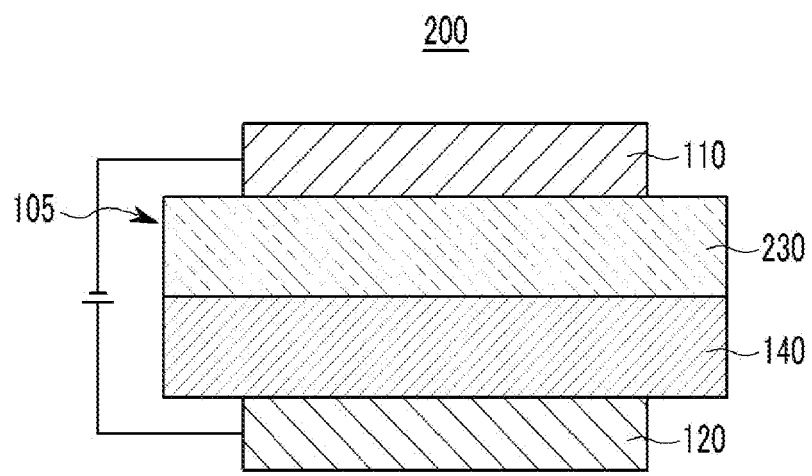

ORGANIC COMPOUND, COMPOSITION, ORGANIC OPTOELECTRONIC DEVICE, AND DISPLAY APPARATUS

CROSS REFERENCE TO RELATED APPLICATIONS

This is the U.S. national phase application based on PCT Application No. PCT/KR2018/016133, filed Dec. 18, 2018, which is based on Korean Patent Application No. 10-2017-0181463, filed Dec. 27, 2017, the entire contents of all of which are hereby incorporated by reference.

TECHNICAL FIELD

An organic compound, a composition, an organic optoelectronic device, and a display device are disclosed.

BACKGROUND ART

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light and performance of the organic light emitting diode may be affected by organic materials disposed between electrodes.

DISCLOSURE

Technical Problem

An embodiment provides an organic compound capable of realizing an organic optoelectronic device having high efficiency and a long life-span.

Another embodiment provides a composition capable of realizing an organic optoelectronic device having high efficiency and a long life-span.

Another embodiment provides an organic optoelectronic device including the organic compound or composition.

Another embodiment provides a display device including the organic optoelectronic device.

Technical Solution

According to an embodiment, an organic compound represented by Chemical Formula 1 is provided.

[Chemical Formula 1]

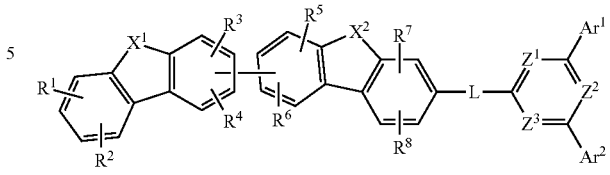

In Chemical Formula 1,
$Z^1$ to $Z^3$ are independently N or $CR^a$,
at least two of $Z^1$ to $Z^3$ are N,
$Ar^1$ and $Ar^2$ are independently hydrogen, deuterium, a substituted or unsubstituted C1 to C30 alkyl group, a substituted or unsubstituted C6 to C30 aryl group, a substituted or unsubstituted pyridinyl group, a substituted or unsubstituted pyrimidinyl group, a substituted or unsubstituted triazinyl group, a halogen, a cyano group, or a combination thereof,
L is a single bond or a substituted or unsubstituted C6 to C20 arylene group,
$X^1$ and $X^2$ are independently O or S, and
$R^1$ to $R^8$ and $R^a$ are independently hydrogen, deuterium, a substituted or unsubstituted C1 to C30 alkyl group, a substituted or unsubstituted C6 to C30 aryl group, a substituted or unsubstituted C3 to C30 heterocyclic group, a substituted or unsubstituted silyl group, a substituted or unsubstituted amine group, a halogen, a cyano group, or a combination thereof.

According to another embodiment, a composition includes the organic compound (first organic compound) and a second organic compound including a carbazole moiety represented by Chemical Formula 2.

[Chemical Formula 2]

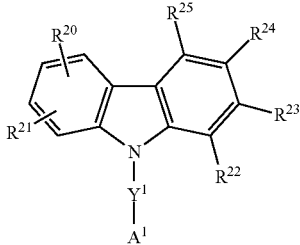

In Chemical Formula 2,
$Y^1$ is a single bond, a substituted or unsubstituted C6 to C30 arylene group, or a divalent substituted or unsubstituted C2 to C30 heterocyclic group,
$A^1$ is a substituted or unsubstituted C6 to C30 aryl group, or a substituted or unsubstituted C2 to C30 heterocyclic group,
$R^{20}$ to $R^{25}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, and
$R^{22}$ to $R^{25}$ are independently present or adjacent groups of $R^{22}$ to $R^{25}$ are linked to each other to form a ring.

According to another embodiment, an organic optoelectronic device includes an anode and a cathode facing each other, and an organic layer disposed between the anode and the cathode, wherein the organic layer includes the organic compound or the composition.

According to another embodiment, a display device including the organic optoelectronic device is provided.

Advantageous Effects

An organic optoelectronic device having high efficiency and a long life-span may be realized.

DESCRIPTION OF DRAWINGS

FIGS. 1 and 2 are cross-sectional views showing organic light emitting diodes according to embodiments.

BEST MODE

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in a specific example of the present invention, the "substituted" refers to replacement of at least one hydrogen of a substituent or a compound by deuterium, a C1 to C20 alkyl group, a C6 to C30 aryl group, or a C2 to C30 heteroaryl group. In addition, in a specific example of the present invention, the "substituted" refers to replacement of at least one hydrogen of a substituent or a compound by deuterium, a C1 to C5 alkyl group, a C6 to C18 aryl group, a pyridinyl group, a quinolinyl group, an isoquinolinyl group, a dibenzofuranyl group, a dibenzothiophenyl group, or a carbazolyl group. In addition, in a specific example of the present invention, the "substituted" refers to replacement of at least one hydrogen of a substituent or a compound by deuterium, a C1 to C5 alkyl group, a C6 to C18 aryl group, a dibenzofuranyl group, or a dibenzothiophenyl group. In addition, in a specific example of the present invention, the "substituted" refers to replacement of at least one hydrogen of a substituent or a compound by deuterium, a methyl group, an ethyl group, a propyl group, a butyl group, a phenyl group, a biphenyl group, a terphenyl group, a naphthyl group, a triphenyl group, a dibenzofuranyl group, or a dibenzothiophenyl group.

In the present specification, when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may include a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but is not limited thereto.

In the present specification, hole properties refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, an organic compound according to an embodiment is described.

The organic compound according to an embodiment is represented by Chemical Formula 1.

[Chemical Formula 1]

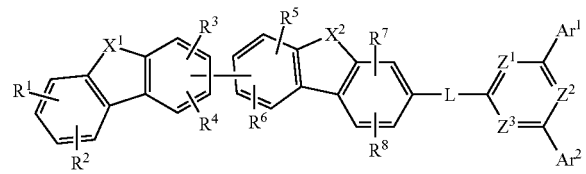

In Chemical Formula 1, $Z^1$ to $Z^3$ are independently N or $CR^a$, at least two of $Z^1$ to $Z^3$ are N, $Ar^1$ and $Ar^2$ are independently hydrogen, deuterium, a substituted or unsubstituted C1 to C30 alkyl group, a substituted or unsubstituted C6 to C30 aryl group, a substituted or unsubstituted pyridinyl group, a substituted or unsubstituted pyrimidinyl group, a substituted or unsubstituted triazinyl group, a halogen, a cyano group, or a combination thereof, L is a single bond or a substituted or unsubstituted C6 to C20 arylene group, $X^1$ and $X^2$ are independently O or S, and $R^1$ to $R^8$ and W are independently hydrogen, deuterium, a substituted or unsubstituted C1 to C30 alkyl group, a substituted or unsubstituted C6 to C30 aryl group, a substituted or unsubstituted C3 to C30 heterocyclic group, a substituted or unsubstituted silyl group, a substituted or unsubstituted amine group, a halogen, a cyano group, or a combination thereof.

The organic compound may have a structure that easily receives electrons when an electric field is applied, by including a pyrimidine or triazine ring, and accordingly, a driving voltage of the organic optoelectronic device including the organic compound may be lowered.

In addition, the organic compound may have a relatively high glass transition temperature by including two heteroatom-containing fused rings that are directly bonded, thereby reducing crystallinity of the organic compound during process or operation and preventing degradation to promote thermal stability of the organic compound and to improve life-span of the device including the organic compound is applied. For example, the organic compound may have a glass transition temperature of about 50° C. to 300° C.

In addition, in the organic compound, the pyrimidine or triazine ring is directly or indirectly bound at position 3 of the heteroatom-containing fused ring, and charge mobility and stability may be high, and accordingly, efficiency and life-span of the device including the organic compound may be improved, for example, compared with the case of binding at position 1, 2 or 4 of the heteroatom-containing fused ring.

Therefore, the device including the organic compound may realize a device having a low driving voltage, a high efficiency, and a long life-span.

For example, two of $Z^1$ to $Z^3$ may be nitrogen (N) and the other one may be $CR^a$.

For example, $Z^1$ and $Z^2$ may be nitrogen and $Z^3$ may be $CR^a$.

For example, $Z^2$ and $Z^3$ may be nitrogen and $Z^1$ may be $CR^a$.

For example, $Z^1$ and $Z^3$ may be nitrogen and $Z^2$ may be $CR^a$.

For example, $Z^1$ to $Z^3$ may be nitrogen (N).

For example, $Ar^1$ and $Ar^2$ may independently be hydrogen, deuterium, a substituted or unsubstituted C6 to C30 aryl group, a substituted or unsubstituted pyridinyl group, a substituted or unsubstituted pyrimidinyl group, a substituted or unsubstituted triazinyl group, or a combination thereof.

For example, $Ar^1$ and $Ar^2$ may independently be a substituted or unsubstituted phenyl group, a substituted or unsubstituted biphenyl group, a substituted or unsubstituted terphenyl group, a substituted or unsubstituted naphthyl group, a substituted or unsubstituted triphenylenyl group, a substituted or unsubstituted pyridinyl group, a substituted or unsubstituted pyrimidinyl group, or a substituted or unsubstituted triazinyl group. Herein, "substituted" may, for example, refer to replacement of at least one hydrogen by deuterium, a C1 to C20 alkyl group, a C6 to C20 aryl group, a pyridinyl group, a pyrimidinyl group, a triazinyl group, a halogen, a cyano group, or a combination thereof, but is not limited thereto.

For example, L may be a single bond, a substituted or unsubstituted phenylene group, a substituted or unsubstituted biphenylene group, or a substituted or unsubstituted terphenylene group.

For example, L may be a single bond, a substituted or unsubstituted m-phenylene group, a substituted or unsubstituted p-phenylene group, a substituted or unsubstituted o-phenylene group, a substituted or unsubstituted m-biphenylene group, a substituted or unsubstituted p-biphenylene group, a substituted or unsubstituted o-biphenylene group, a substituted or unsubstituted m-terphenylene group, a substituted or unsubstituted p-terphenylene group, or a substituted or unsubstituted o-terphenylene group. Herein, "substituted" may for example refer to replacement of at least one hydrogen by deuterium, a C1 to C20 alkyl group, a C6 to C20 aryl group, a halogen, a cyano group, or a combination thereof, but is not limited thereto.

For example, L may be a single bond, a phenylene group, a biphenylene group, a terphenylene group, a cyano-substituted phenylene group, a cyano-substituted biphenylene group, or a cyano-substituted terphenylene group.

For example, $X^1$ and $X^2$ may be the same or different.

For example, $X^1$ and $X^2$ may be the same and $X^1$ and $X^2$ may be each O.

For example, $X^1$ and $X^2$ may be the same and $X^1$ and $X^2$ may be each S.

For example, $X^1$ and $X^2$ may be different and $X^1$ may be S and $X^2$ may be O or $X^1$ may be O and $X^2$ may be S.

The organic compound may be represented by, for example, one of Chemical Formulae 1A to 1D depending on a linking position of the fused ring.

[Chemical Formula 1A]

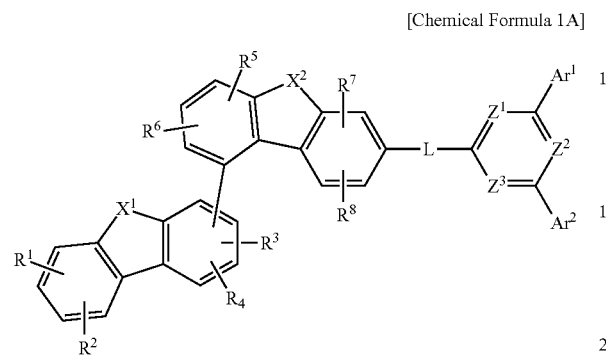

[Chemical Formula 1B]

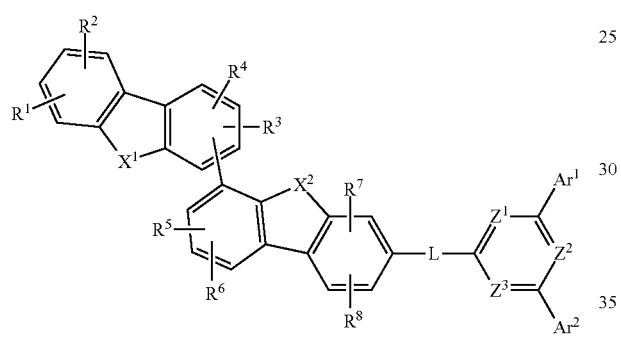

[Chemical Formula 1C]

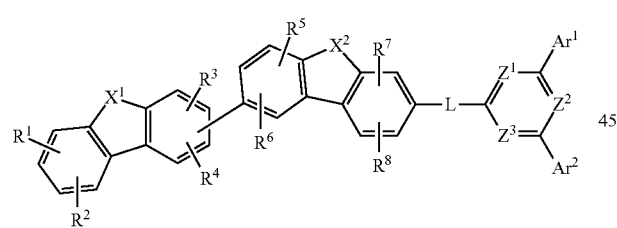

[Chemical Formula 1D]

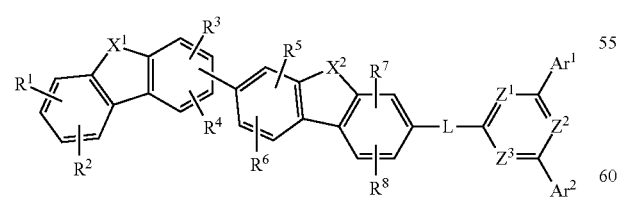

In Chemical Formulae 1A to 1D, $Z^1$ to $Z^3$, $Ar^1$, $Ar^2$, L, $X^1$, $X^2$, and $R^1$ to $R^8$ are the same as described above.

For example, Chemical Formula 1A may be represented by, for example, one of Chemical Formulae 1Aa to 1Ad, depending on a linking position between two fused rings.

[Chemical Formula 1Aa]

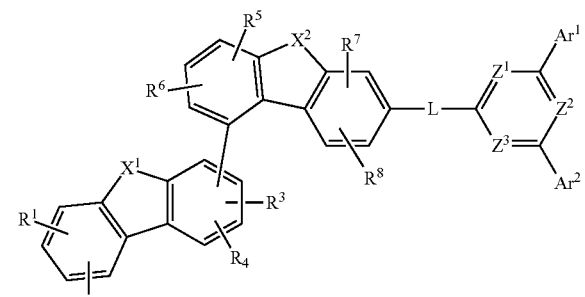

[Chemical Formula 1Ab]

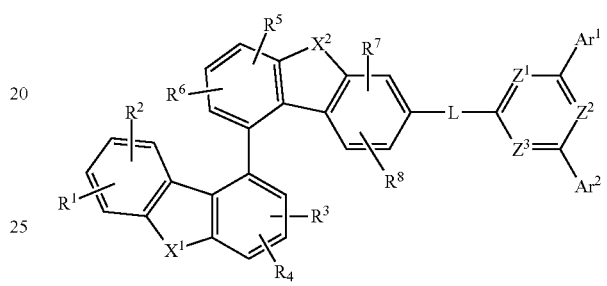

[Chemical Formula 1Ac]

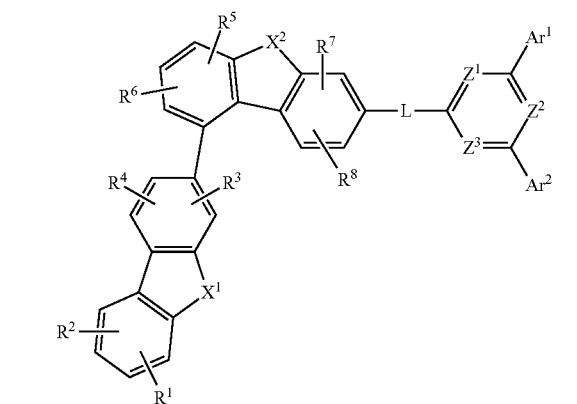

[Chemical Formula 1Ad]

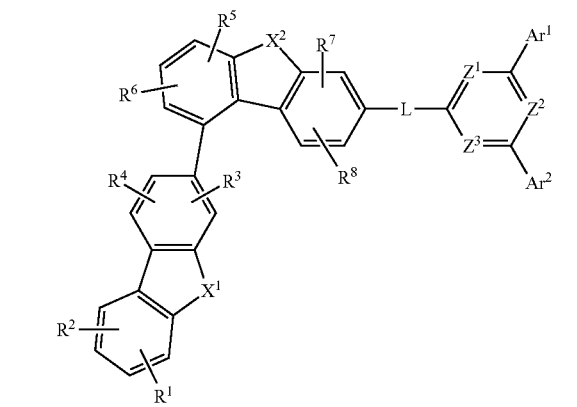

In Chemical Formulae 1Aa to 1Ad, $Z^1$ to $Z^3$, $Ar^1$, $Ar^2$, L, $X^1$, $X^2$, and $R^1$ to $R^8$ are the same as described above.

For example, Chemical Formula 1A may be represented by Chemical Formula 1Aa or 1Ab.

For example, Chemical Formula 1B may be represented by, for example, one of Chemical Formulae 1Ba to 1Bd, depending on a linking position between two fused rings.

[Chemical Formula 1Ba]

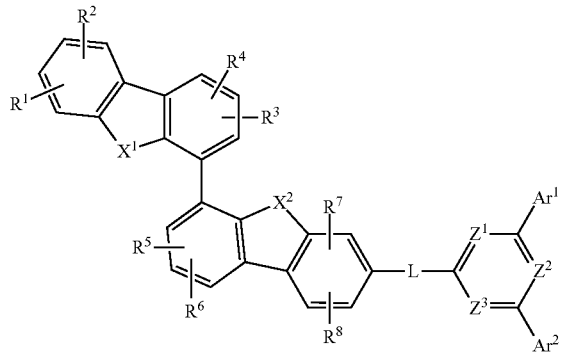

[Chemical Formula 1Bb]

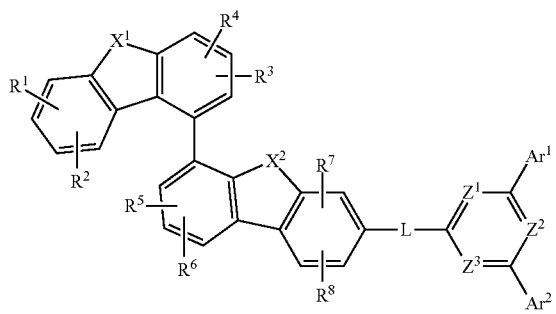

[Chemical Formula 1Bc]

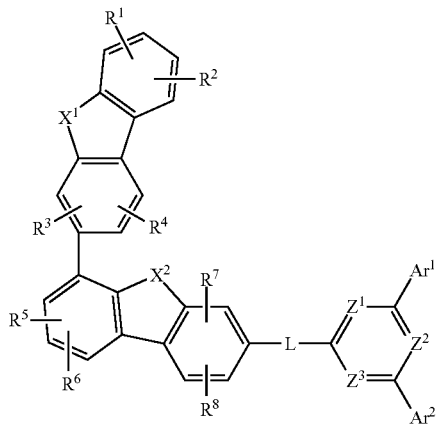

[Chemical Formula 1Bd]

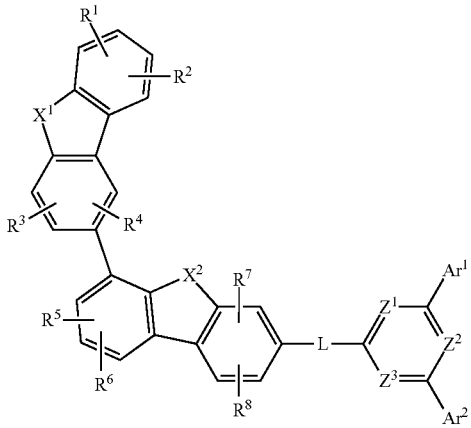

In Chemical Formulae 1Ba to 1Bd, $Z^1$ to $Z^3$, $Ar^1$, $Ar^2$, L, $X^1$, $X^2$, and $R^1$ to $R^8$ are the same as described above.

For example, Chemical Formula 1B may be represented by Chemical Formula 1Ba or 1Bb.

For example, Chemical Formula 1C may be represented by, for example, one of Chemical Formulae 1Ca to 1Cd, depending on a linking position between two fused rings.

[Chemical Formula 1Ca]

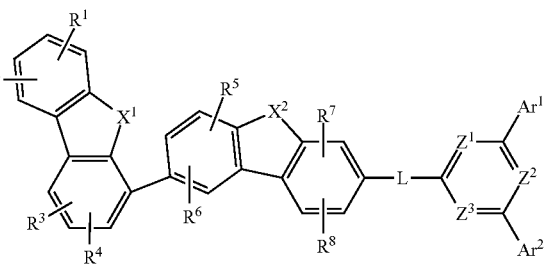

[Chemical Formula 1Cb]

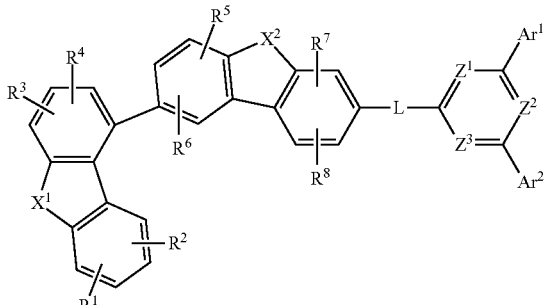

[Chemical Formula 1Cc]

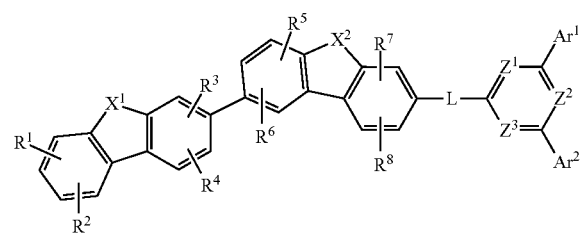

[Chemical Formula 1Cd]

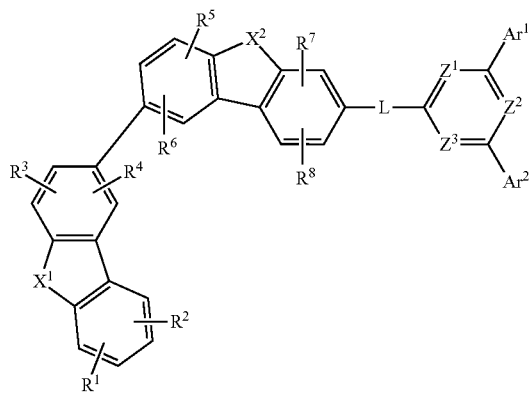

In Chemical Formulae 1Ca to 1Cd, $Z^1$ to $Z^3$, $Ar^1$, $Ar^2$, L, $X^1$, $X^2$, and $R^1$ to $R^8$ are the same as described above.

For example, Chemical Formula 1D may be represented by, for example, one of Chemical Formulae 1 Da to 1Dd depending on a linking position between two fused rings.

[Chemical Formula 1Da]

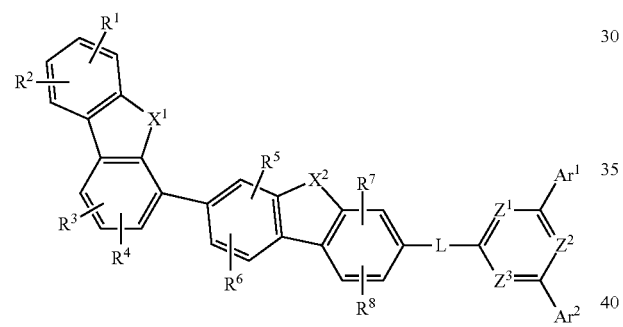

[Chemical Formula 1Db]

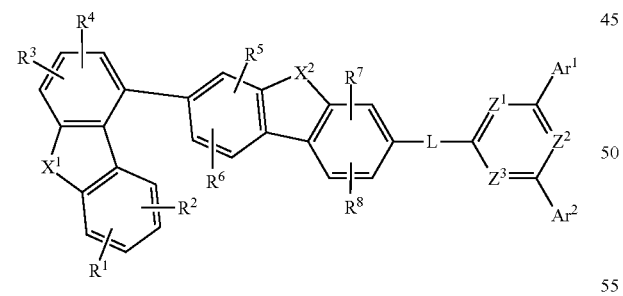

[Chemical Formula 1Dc]

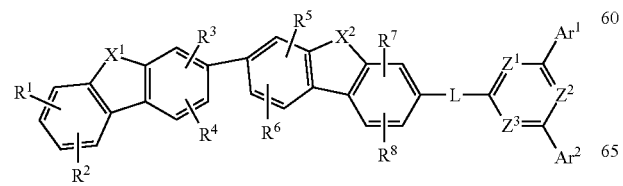

[Chemical Formula 1Dd]

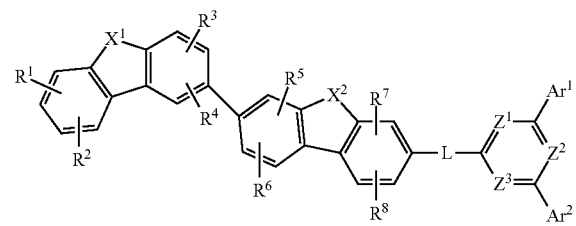

In Chemical Formulae 1 Da to 1Dd, $Z^1$ to $Z^3$, $Ar^1$, $Ar^2$, L, $X^1$, $X^2$, and $R^1$ to $R^8$ are the same as described above.

The organic compound may be, for example, one selected from compounds listed in Group 1, but is not limited thereto.

[Group 1]

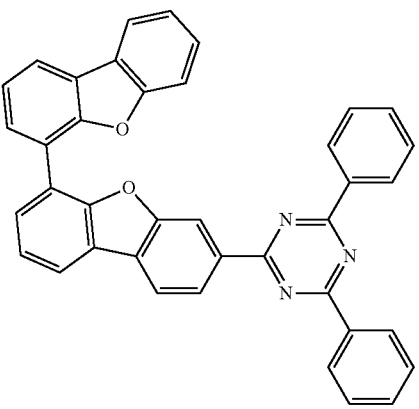

1

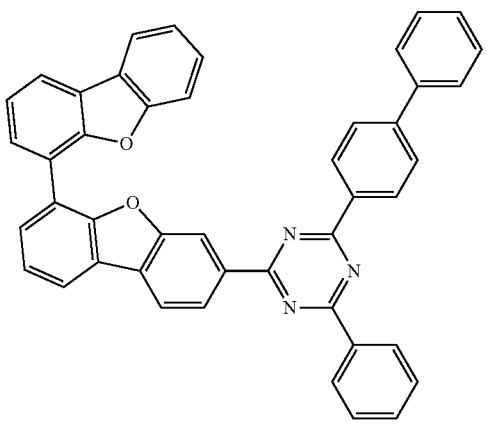

2

3
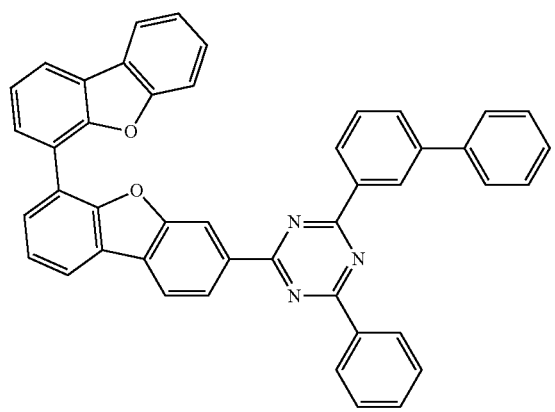
4
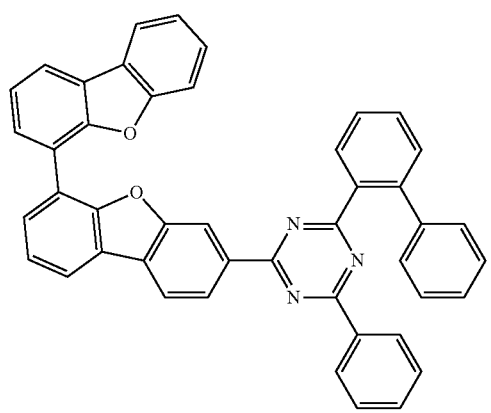
5
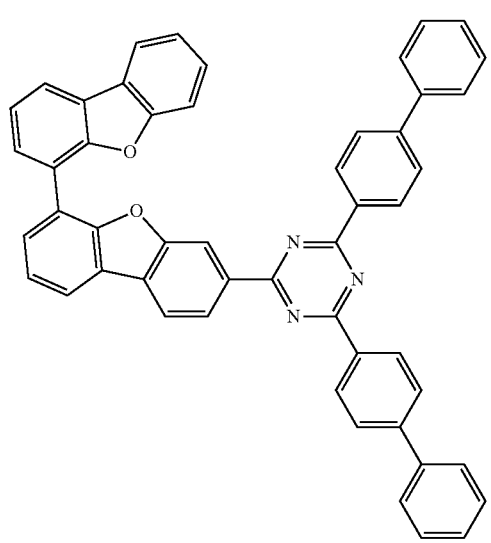
6
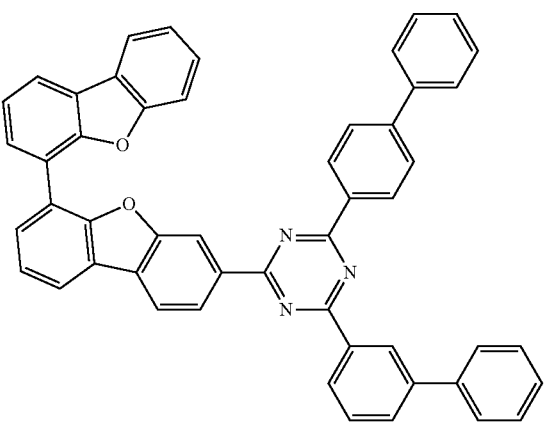
7
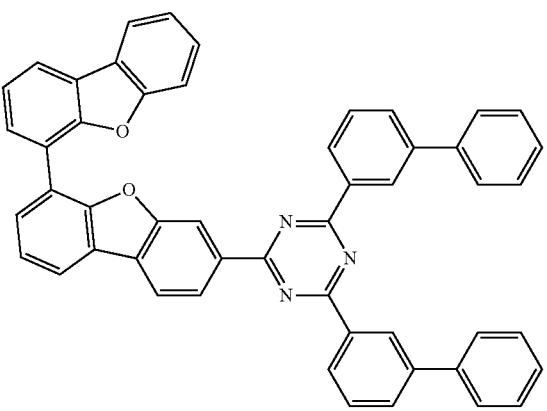
8
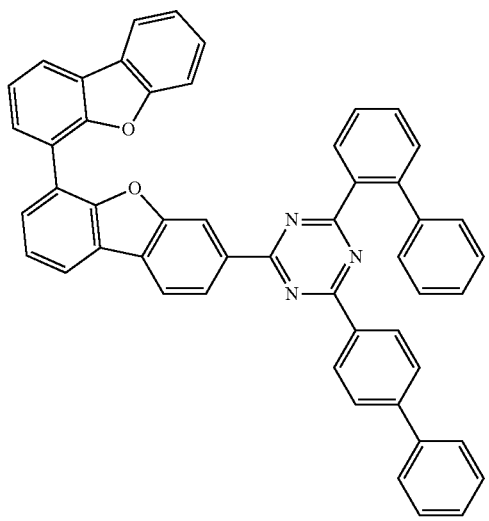

9
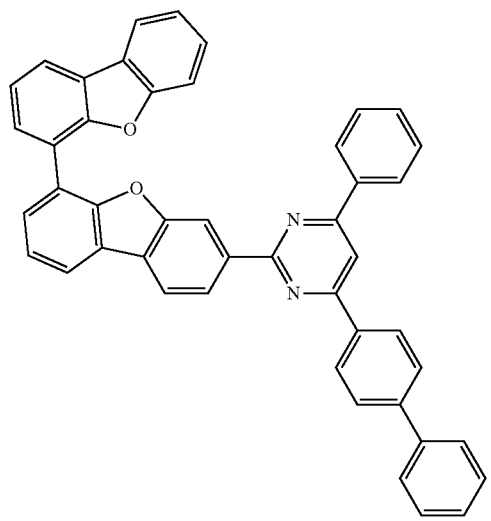
10
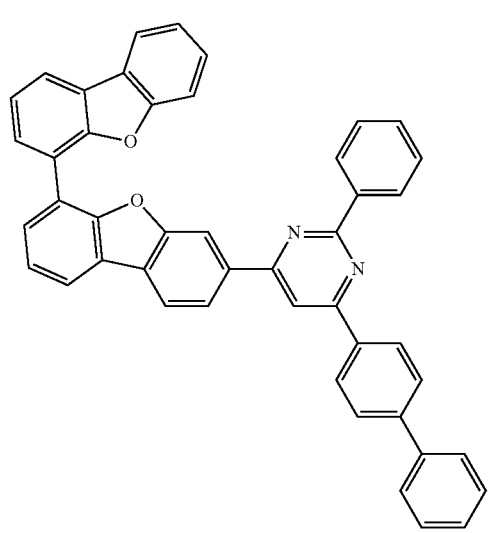
11
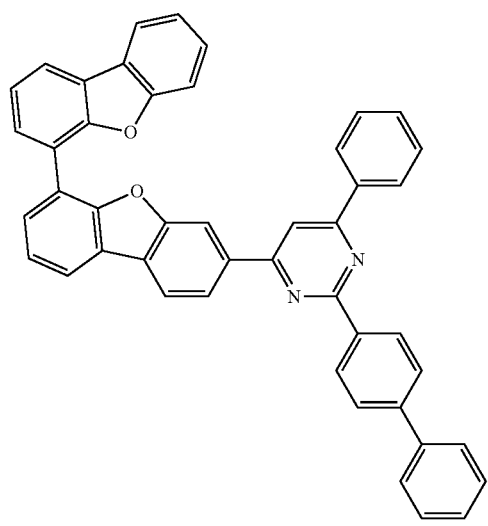
12
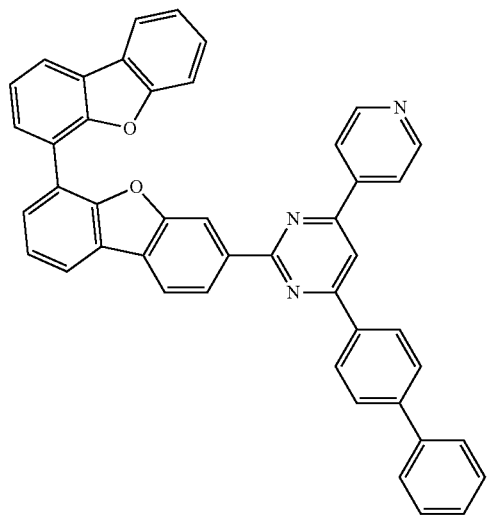
13
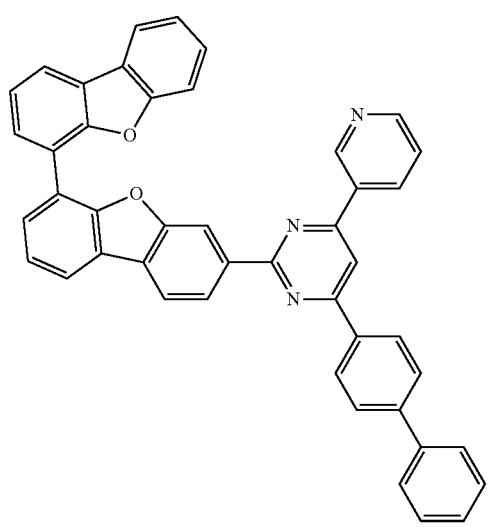
14
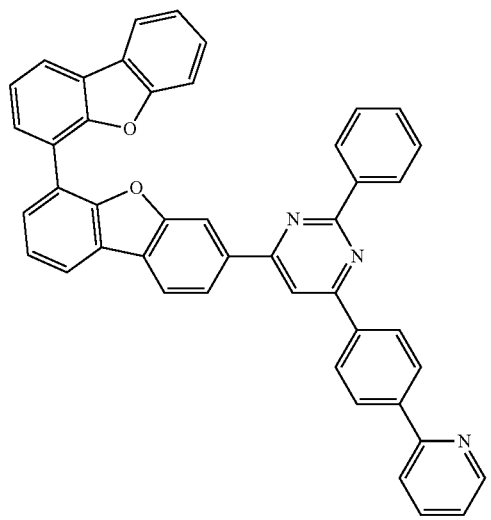

15
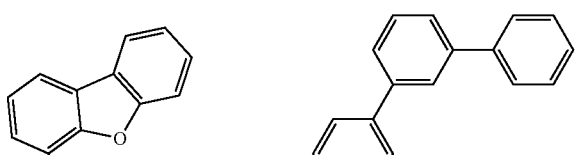
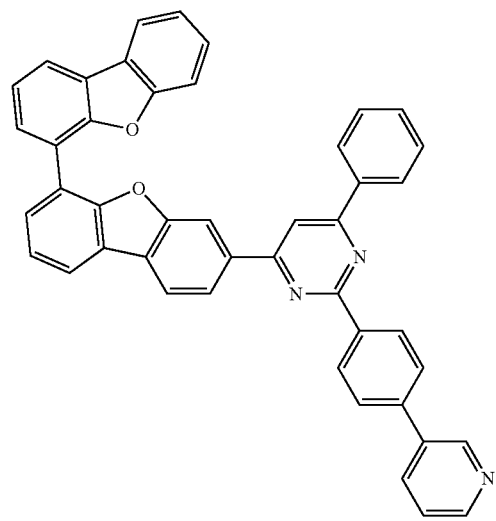
16
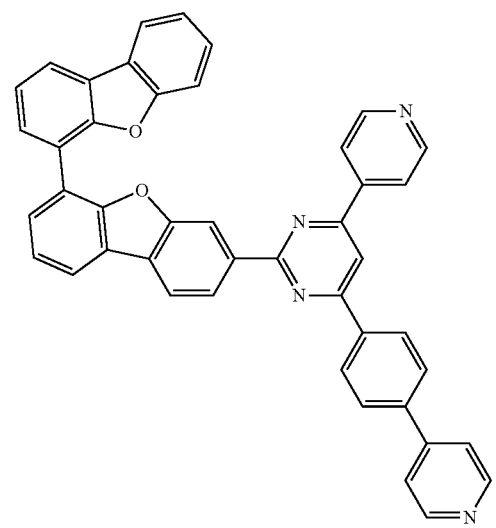
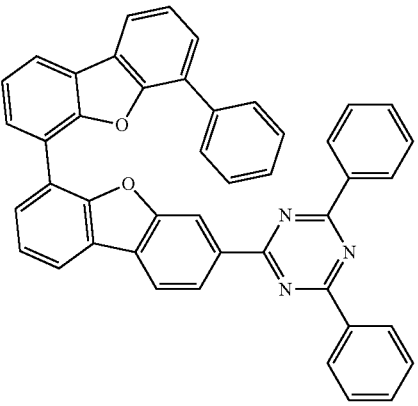
17
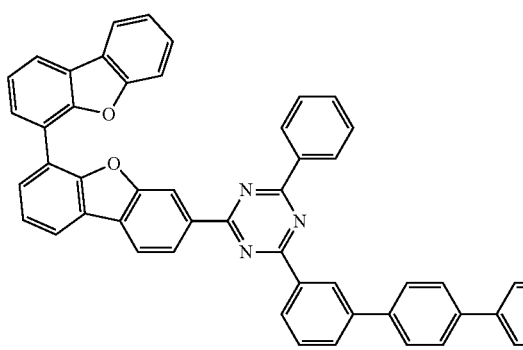
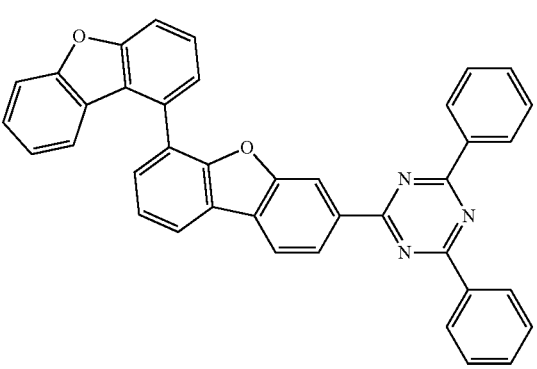

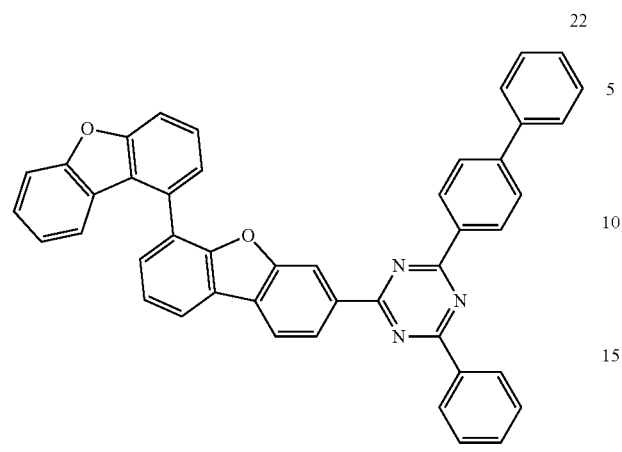
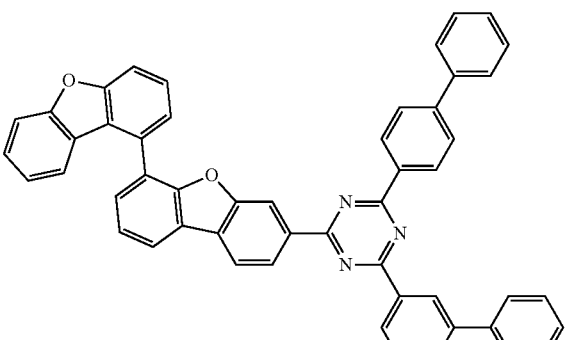
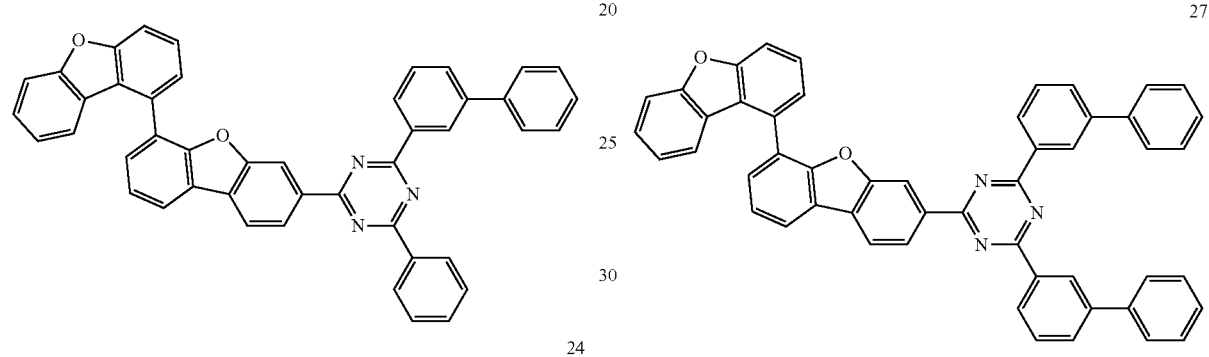
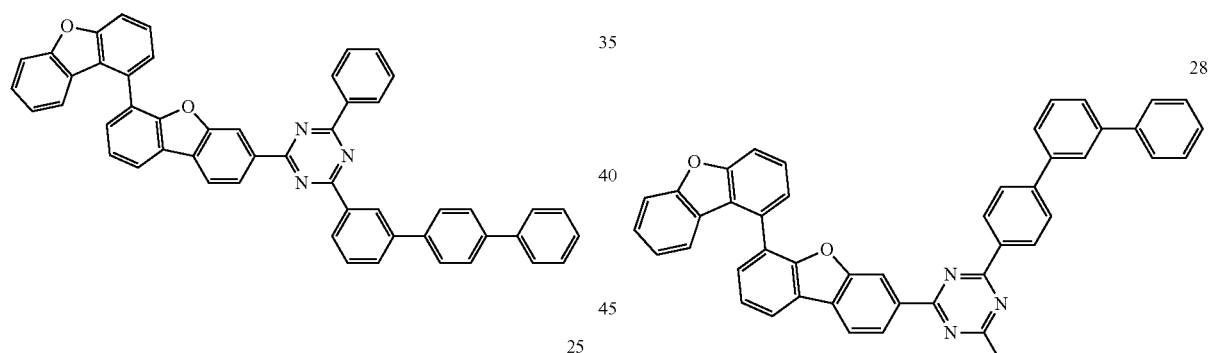
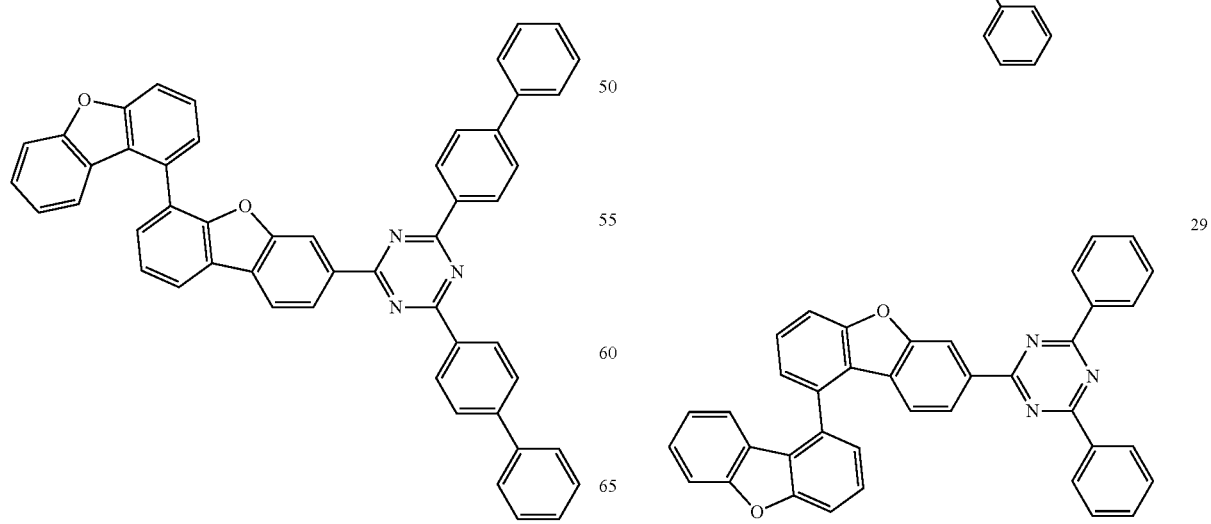

30
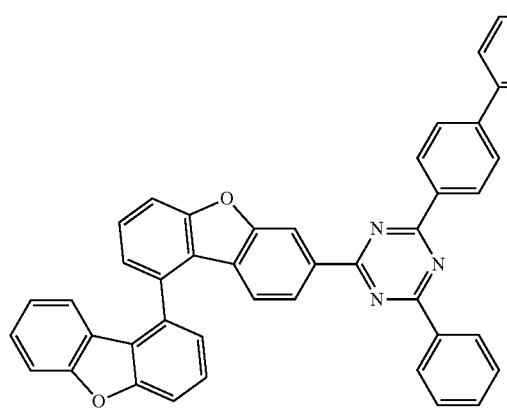
31
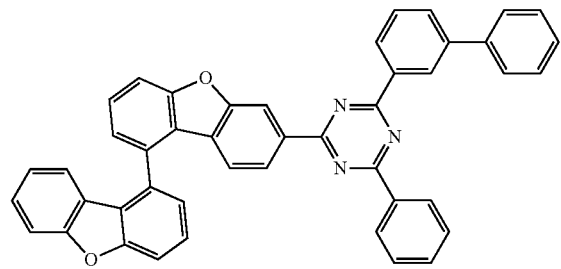
32
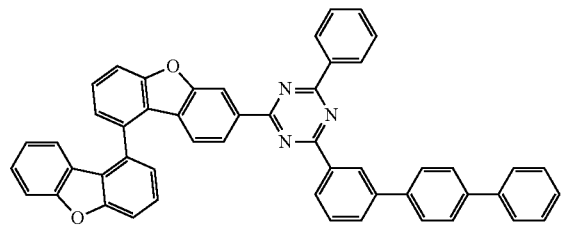
33
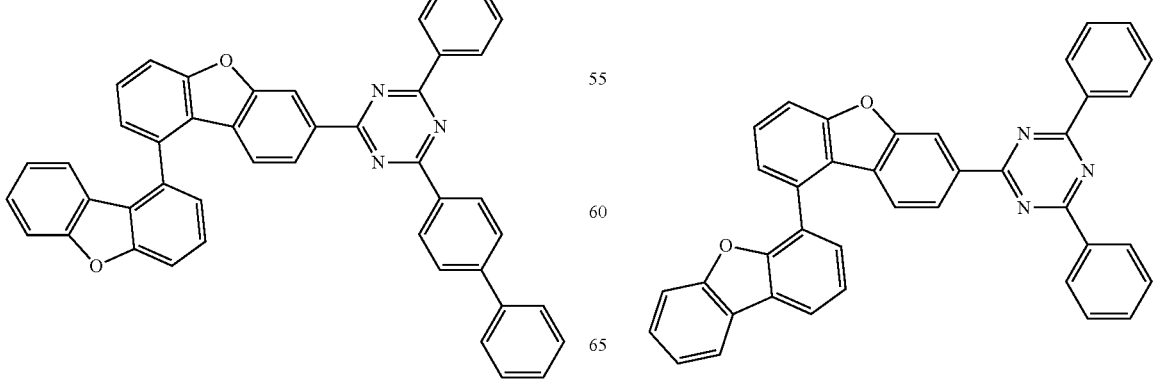
34
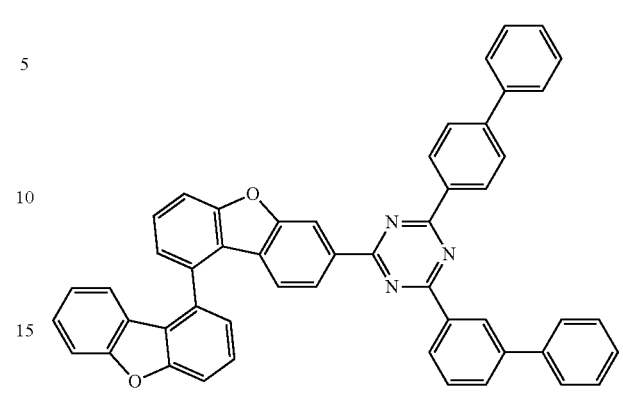
35
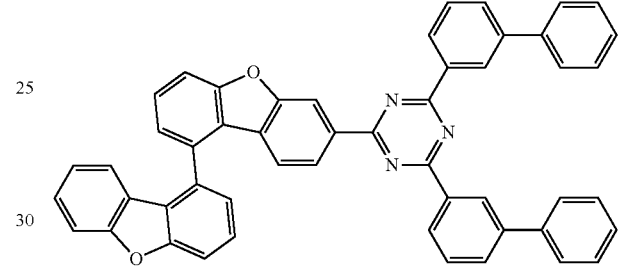
36
37
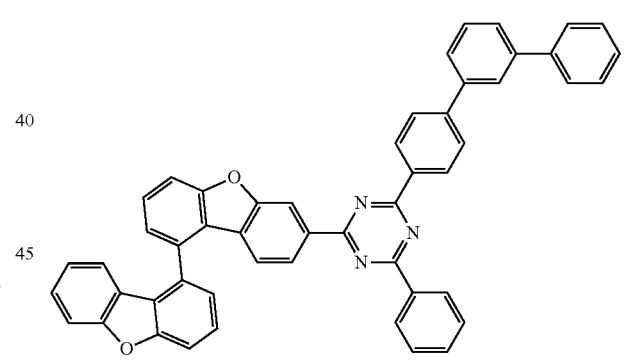

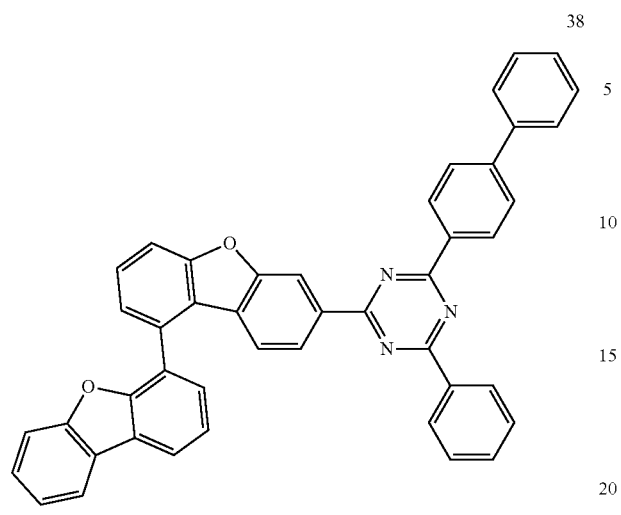
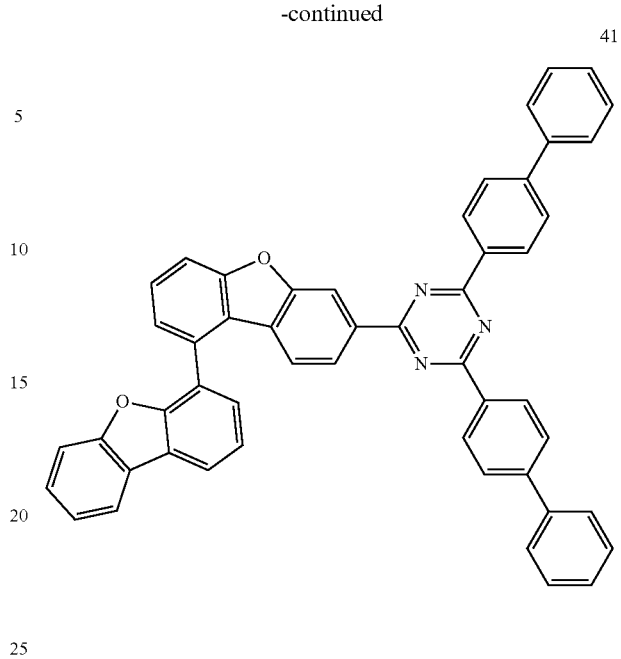
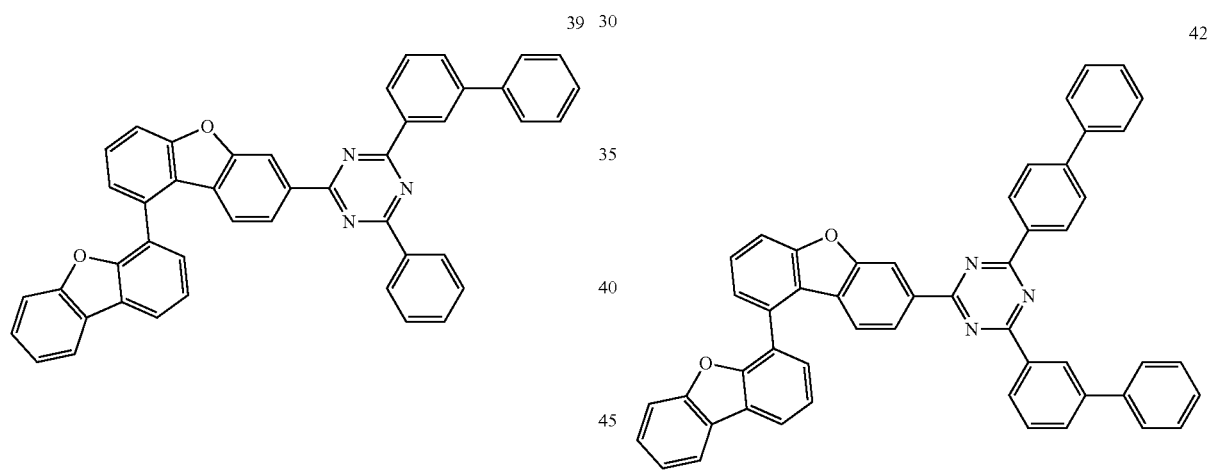
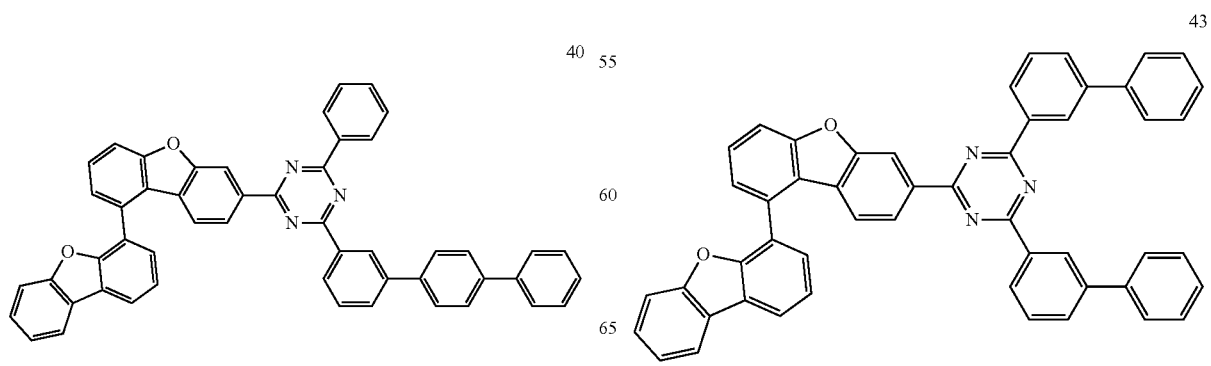

-continued
44
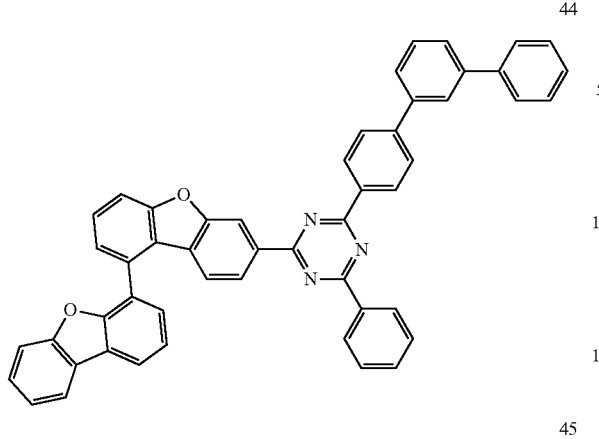
45
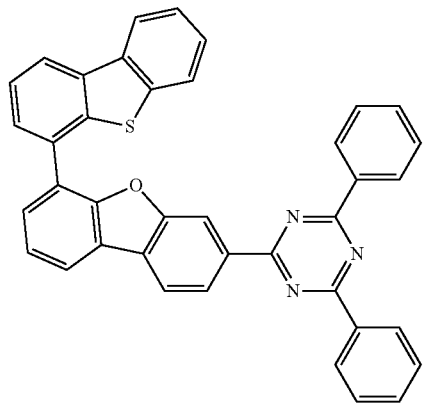
46
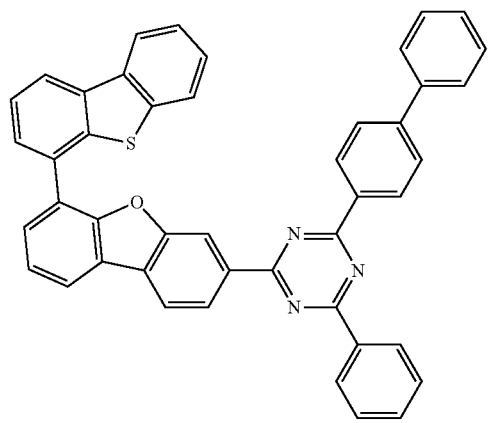
47
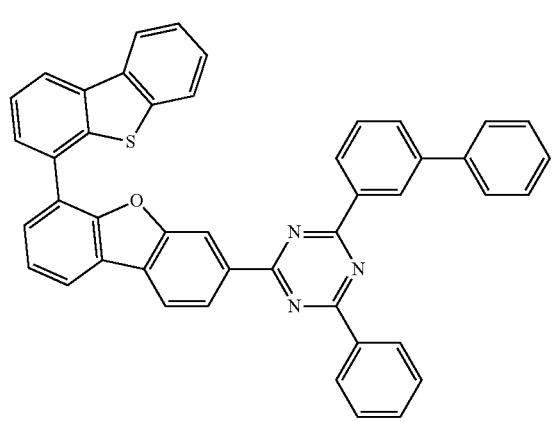
-continued
48
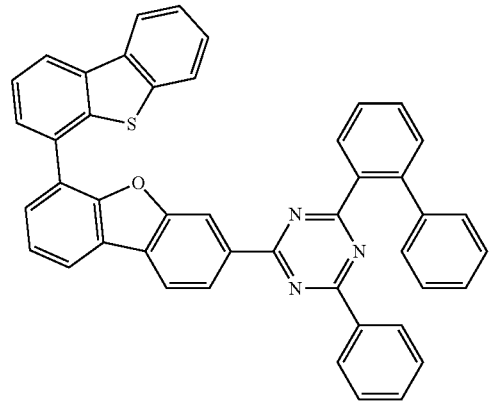
49
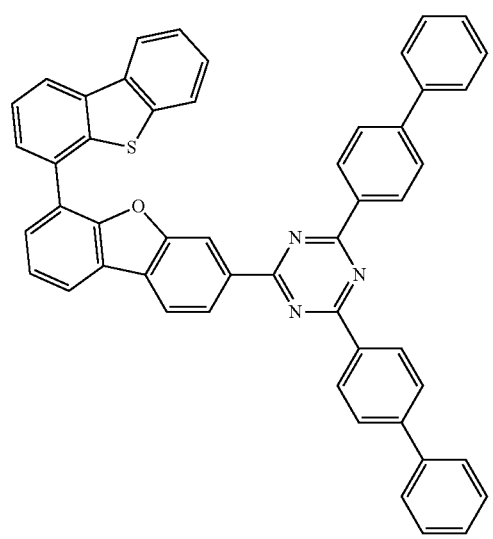
50
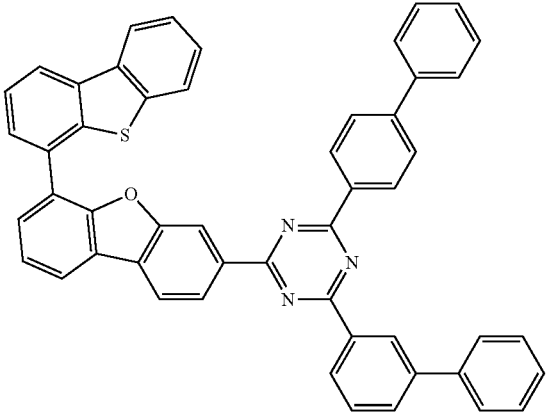

51
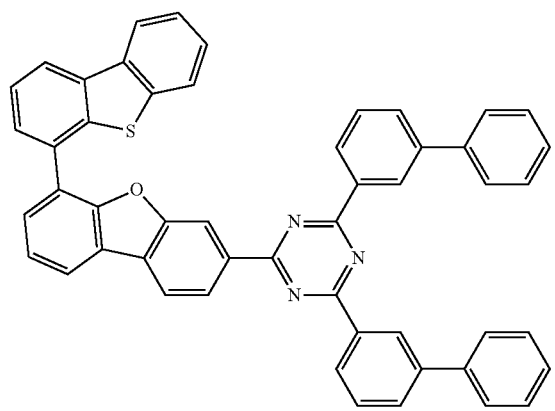
52
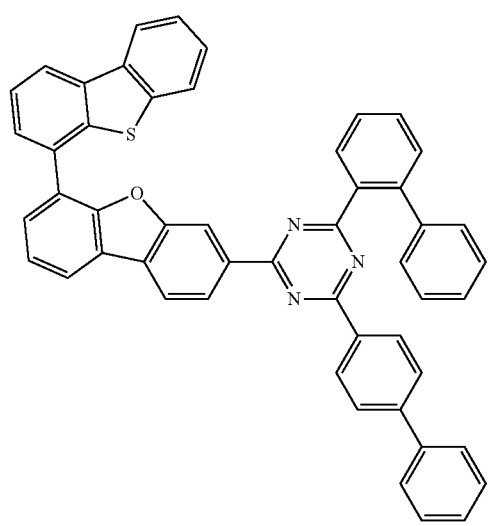
53
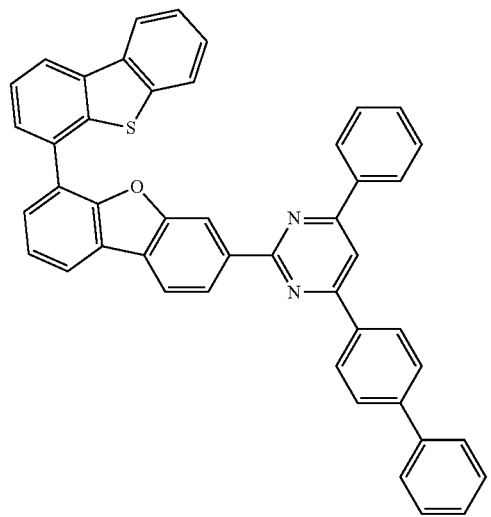
54
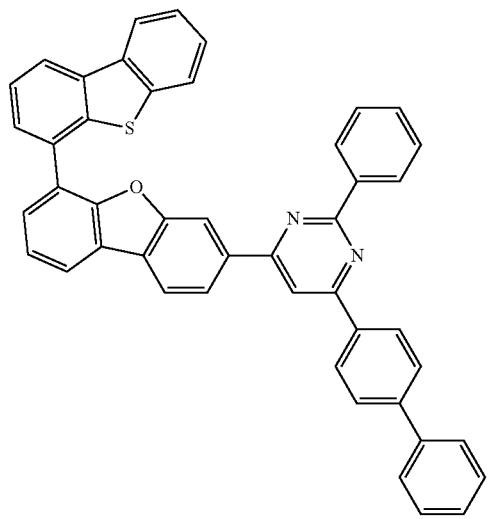
55
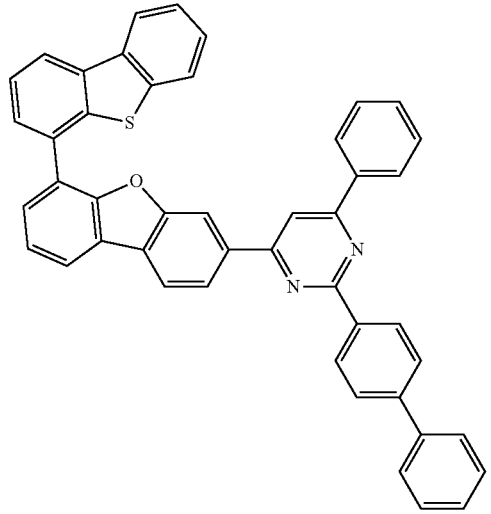
56
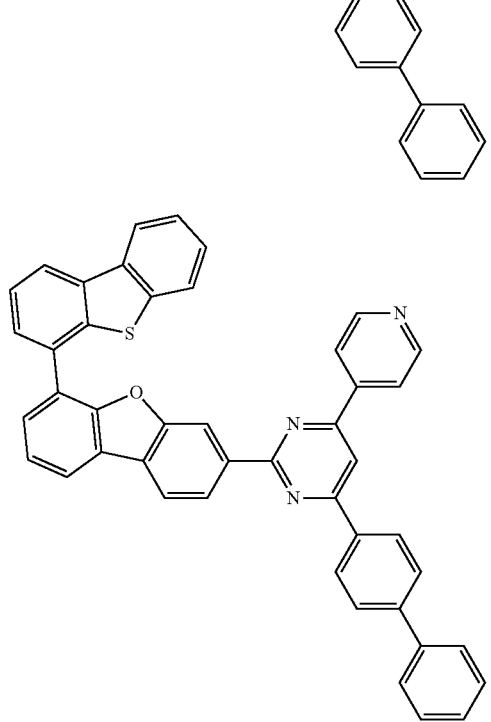

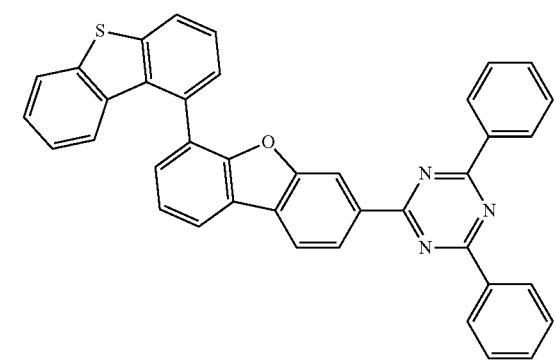
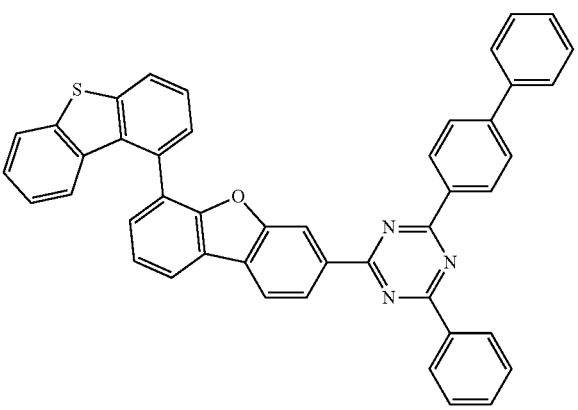
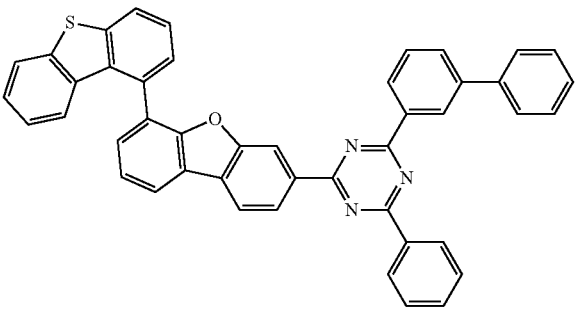
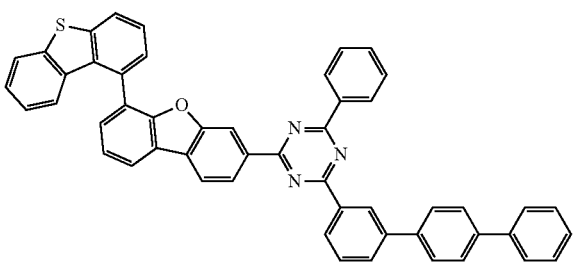
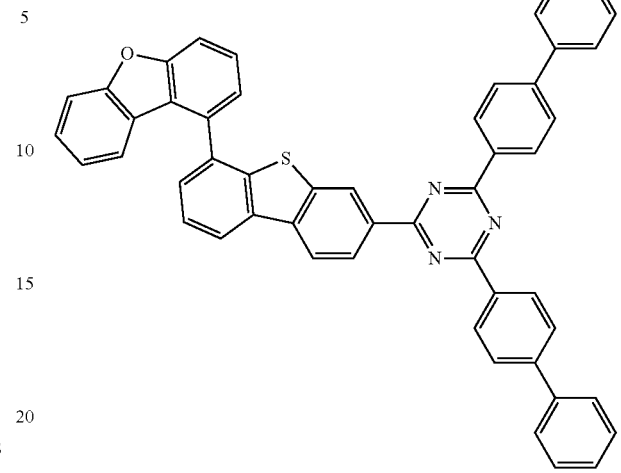

65
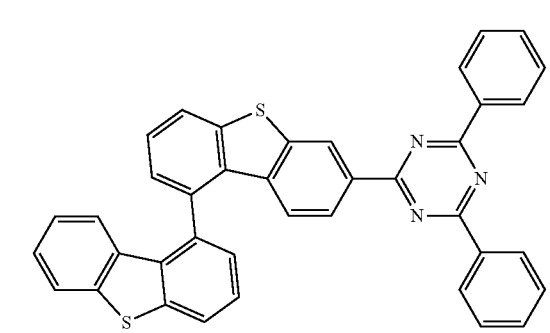
66
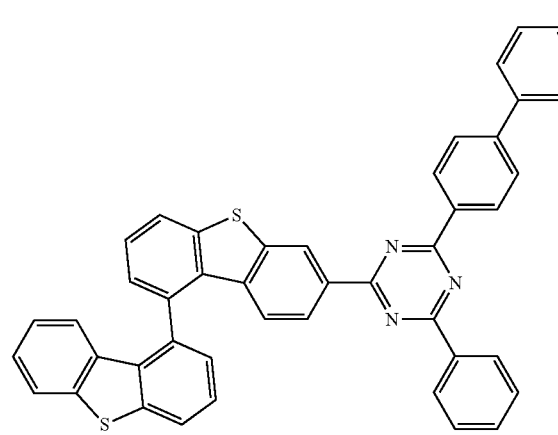
67
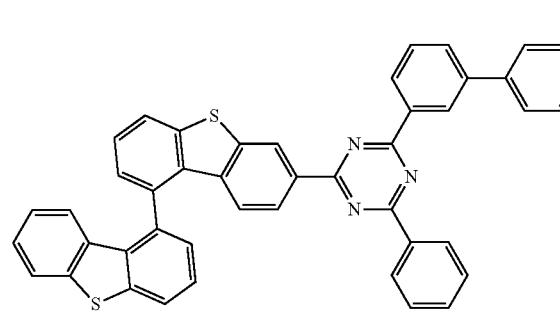
68
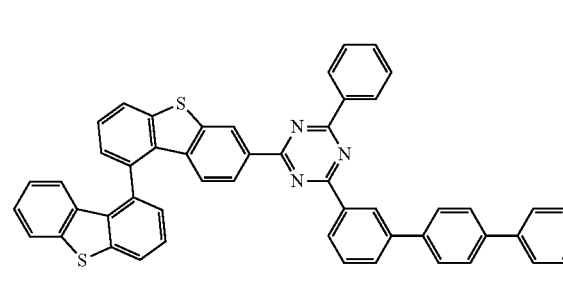
69
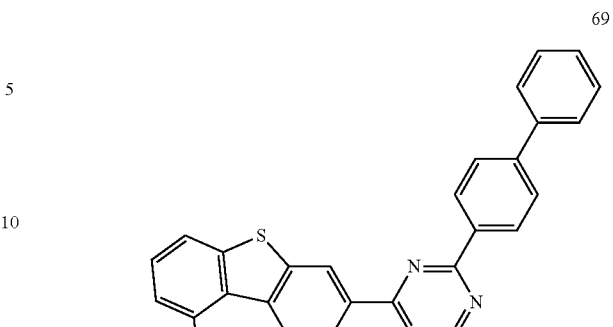
70
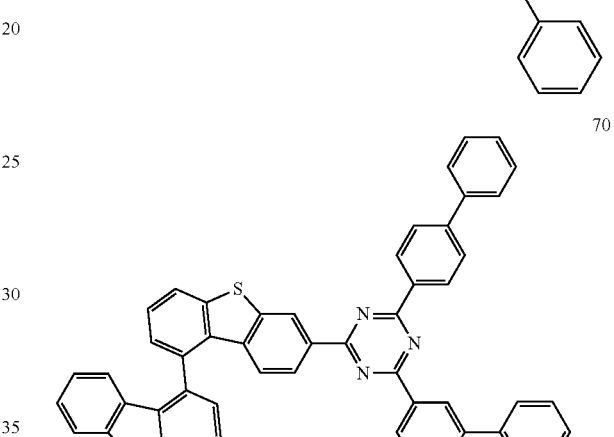
71
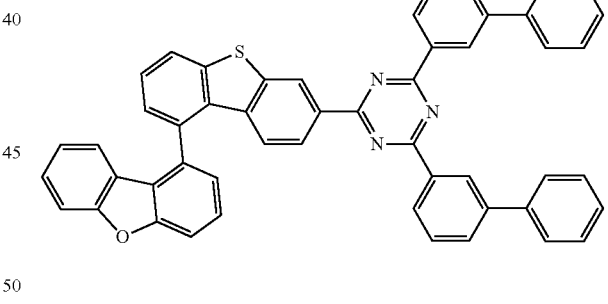
72
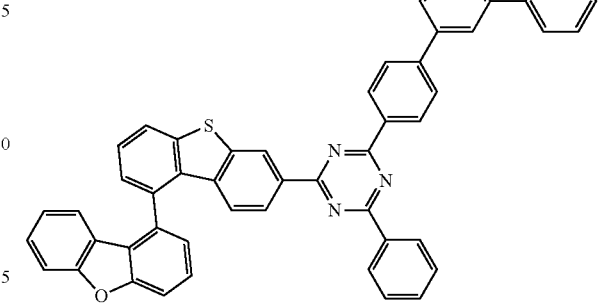

73
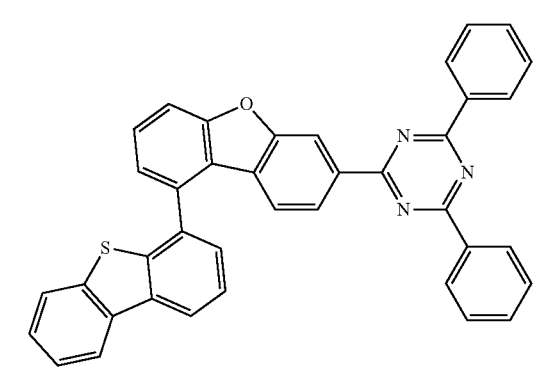
74
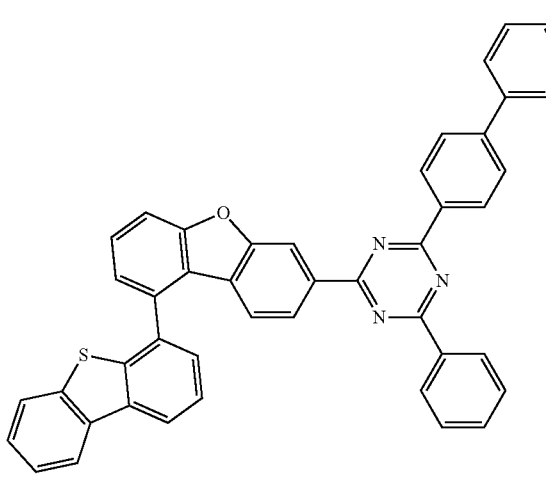
75
77
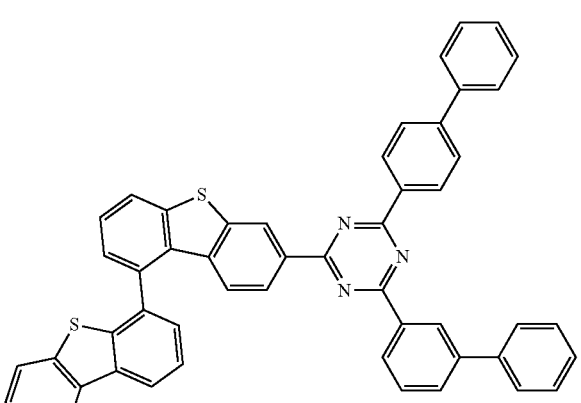
78
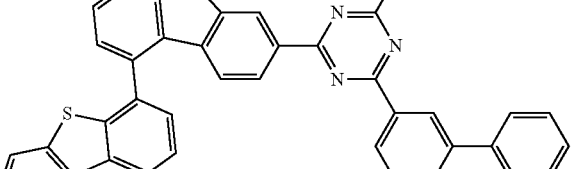
76
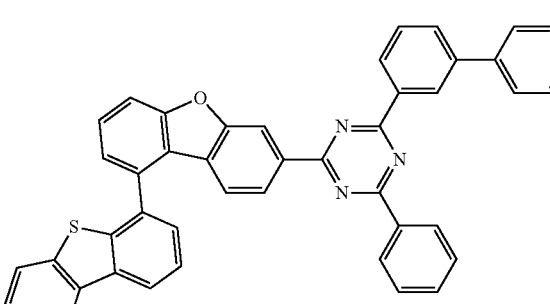
79
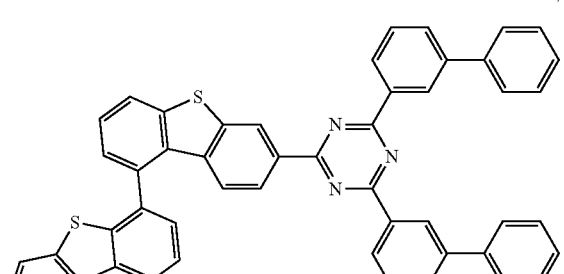

80
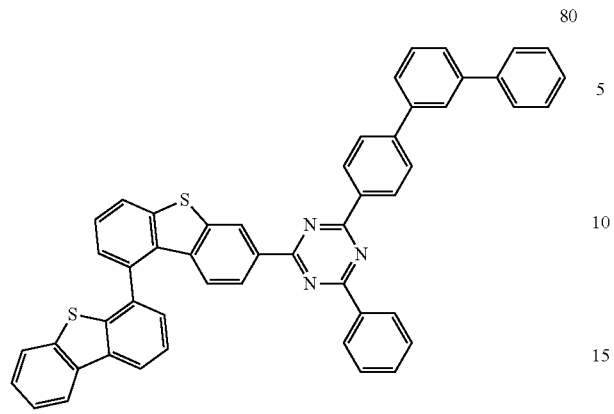
81
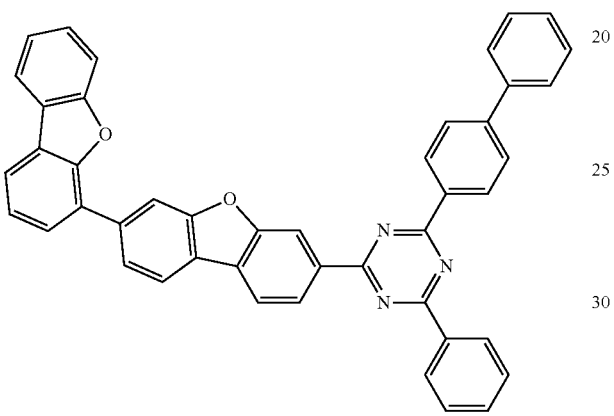
82
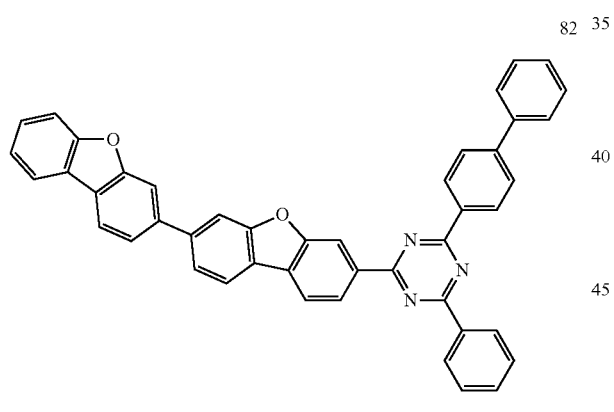
83
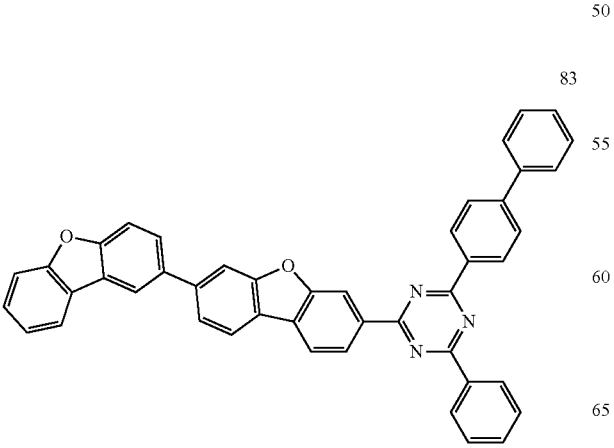
84
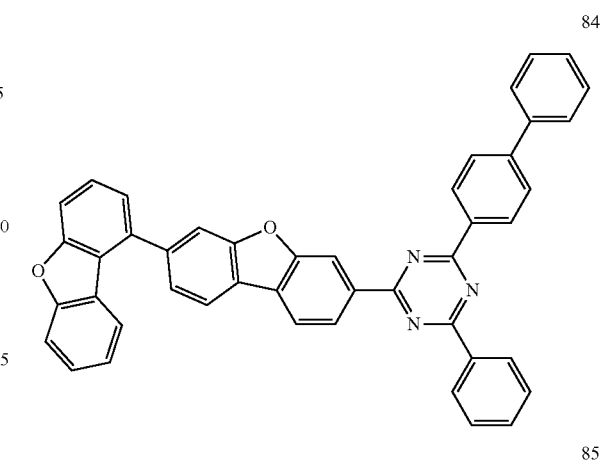
85
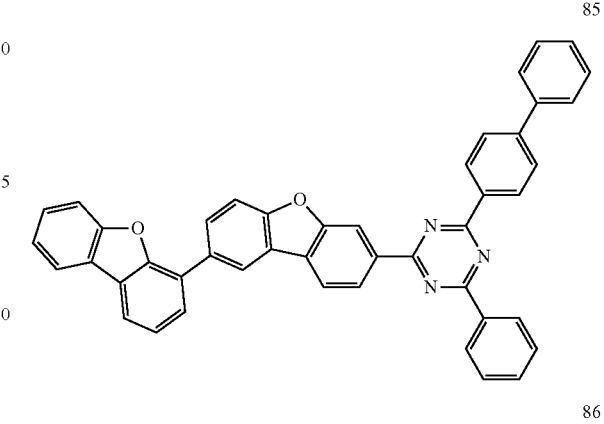
86
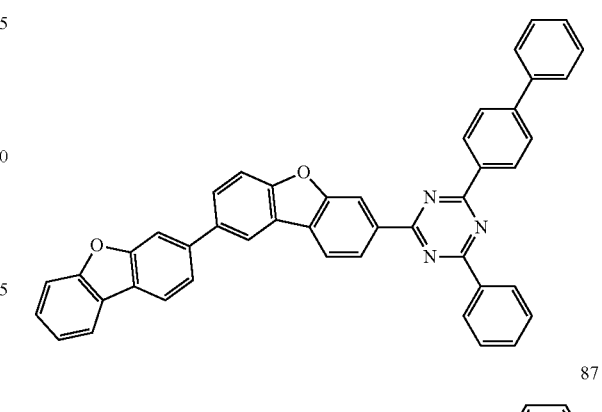
87
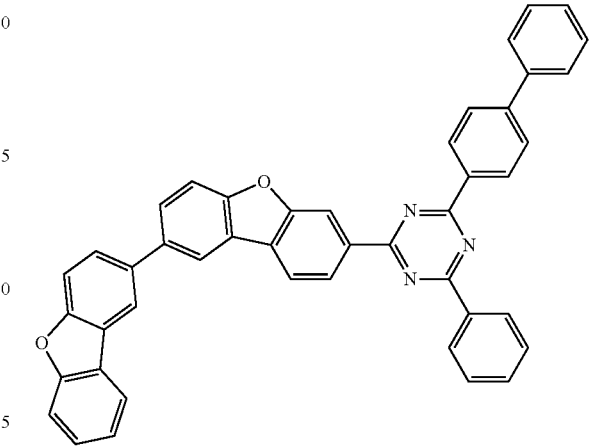

88
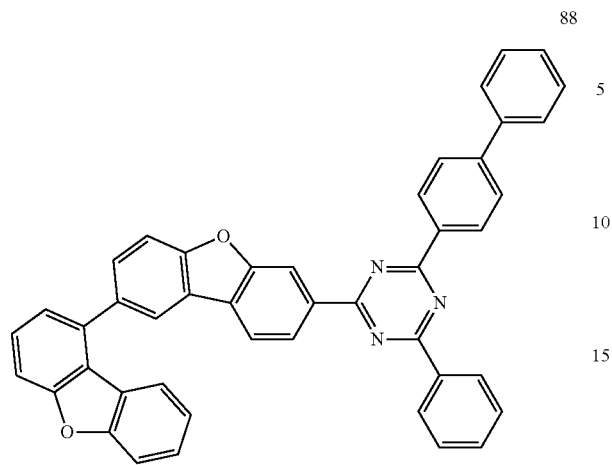
89
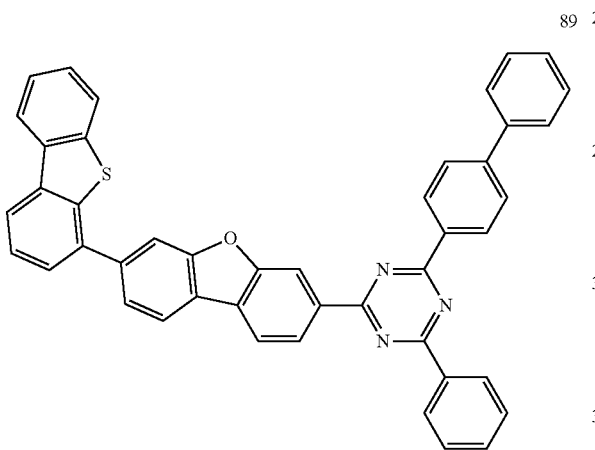
90
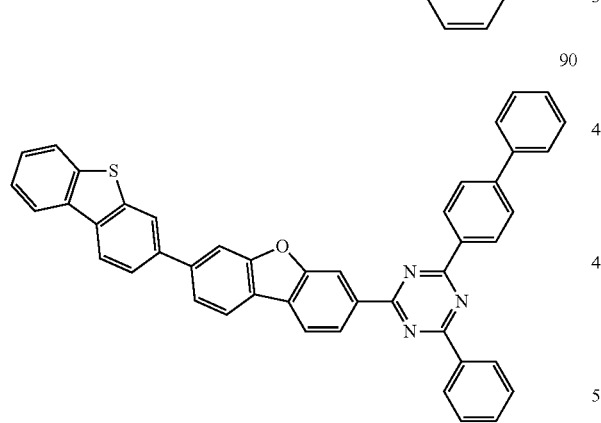
91
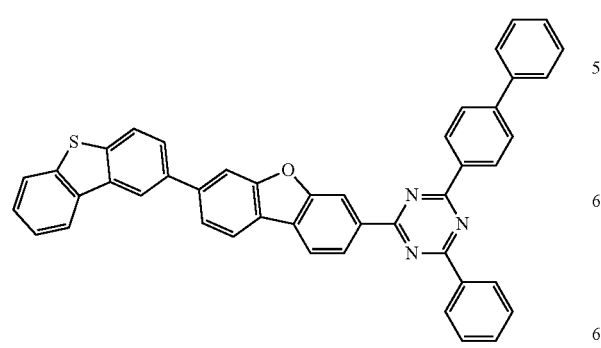
92
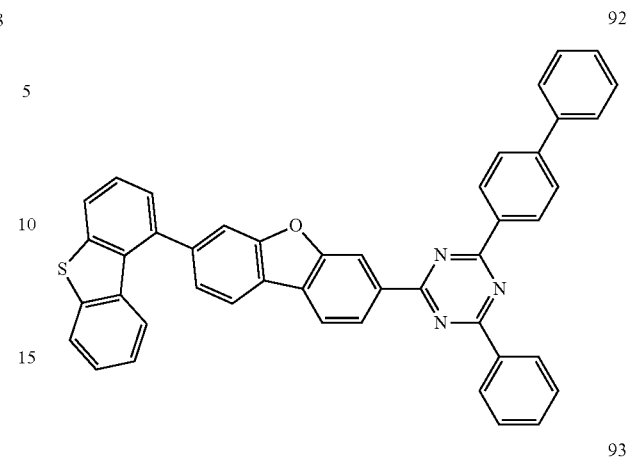
93
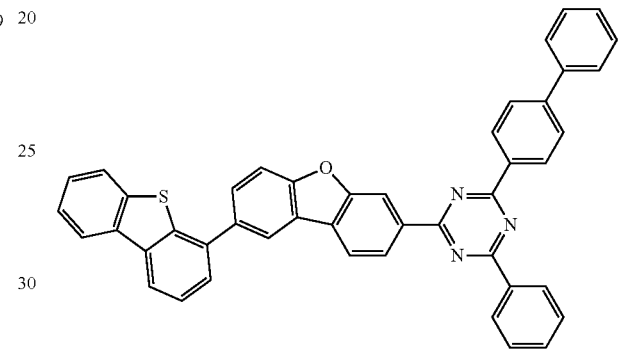
94
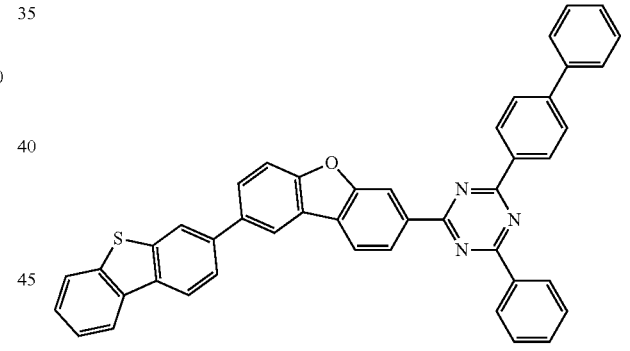
95
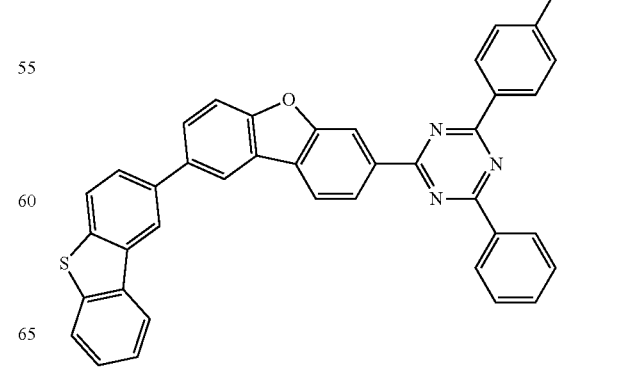

96
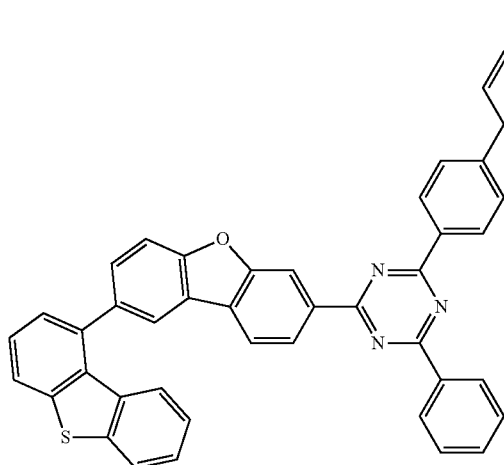
100
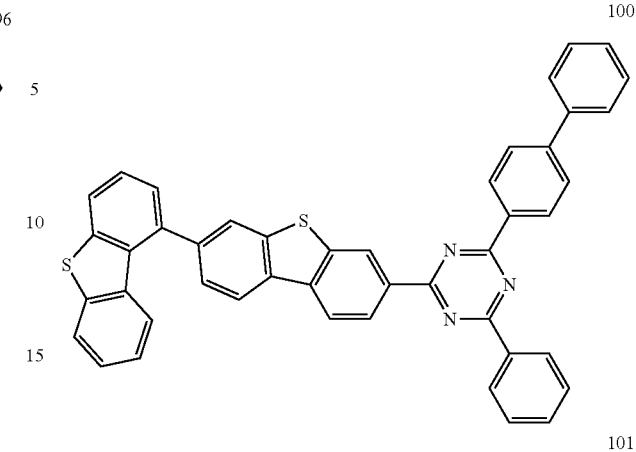
97
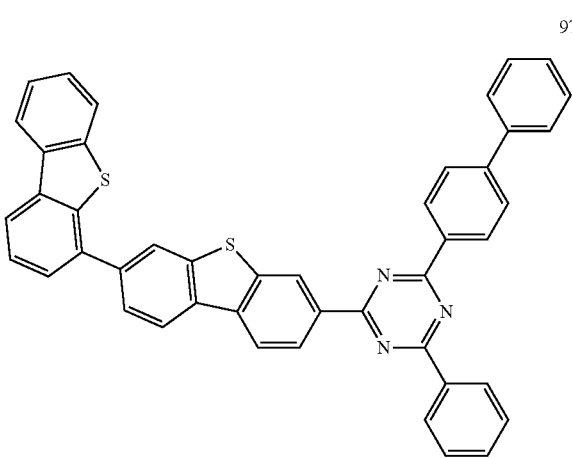
101
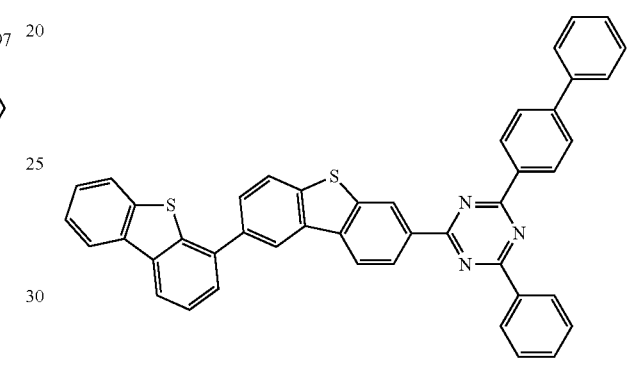
98
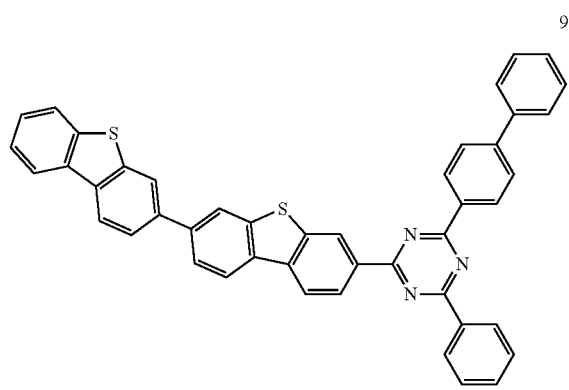
102
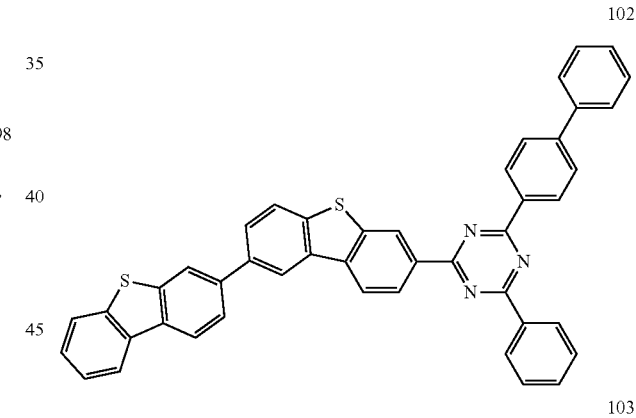
99
103
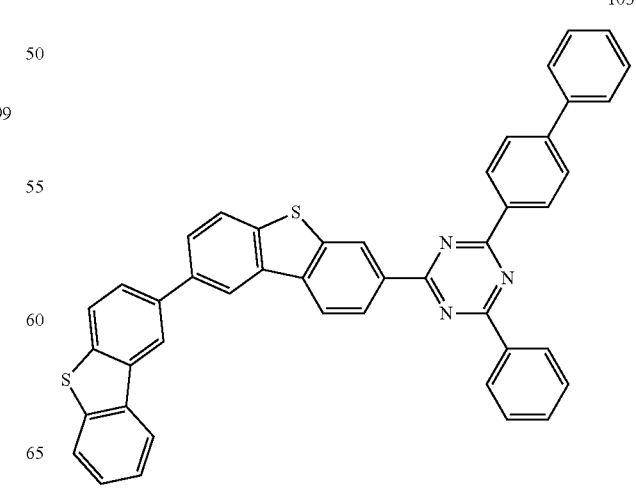

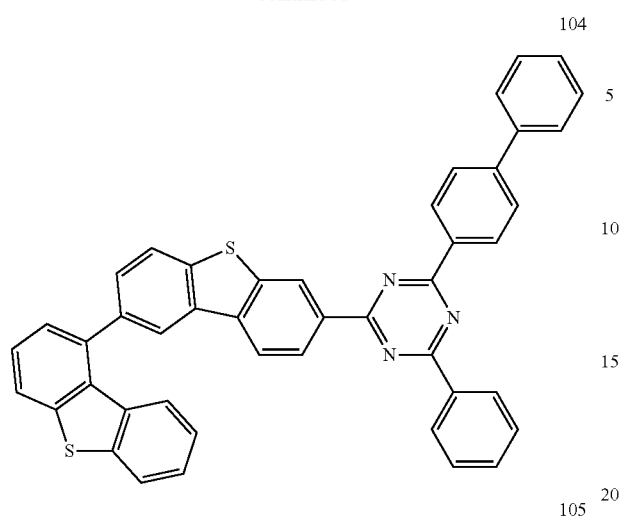
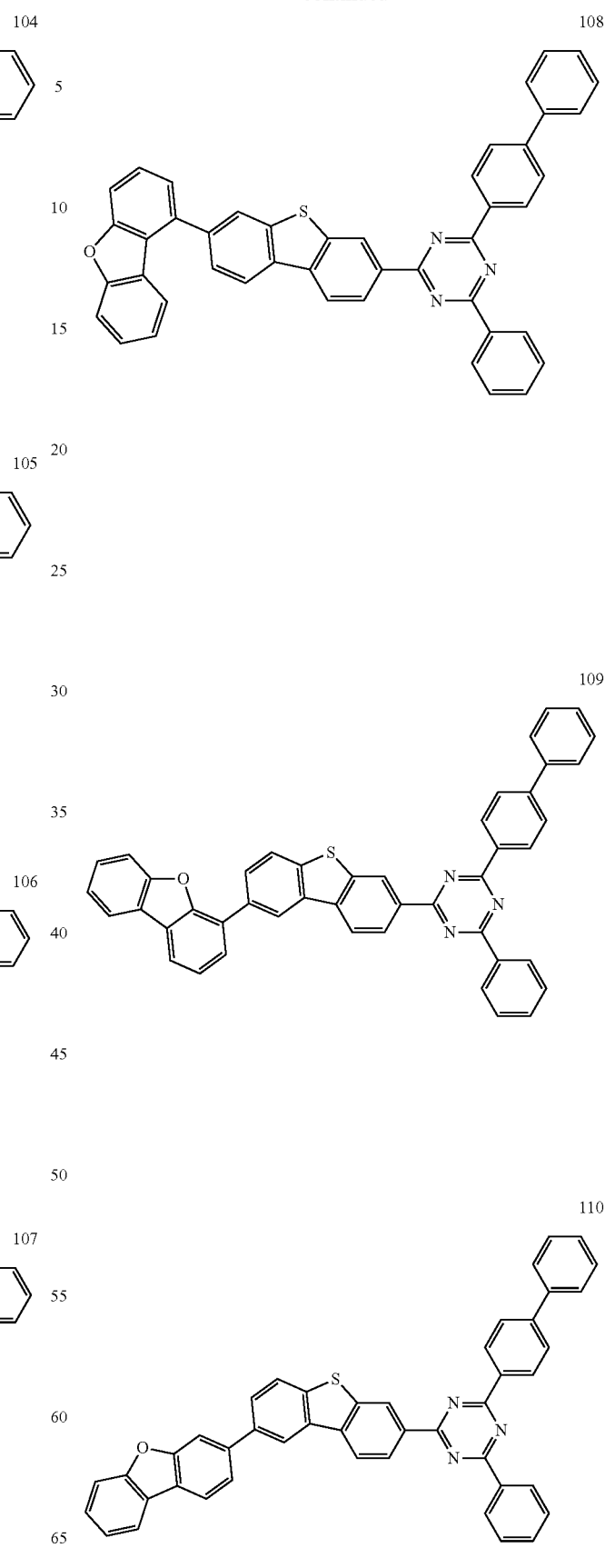

111
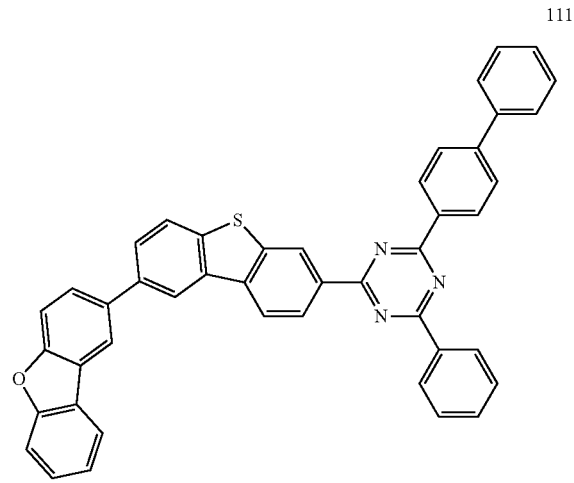
112
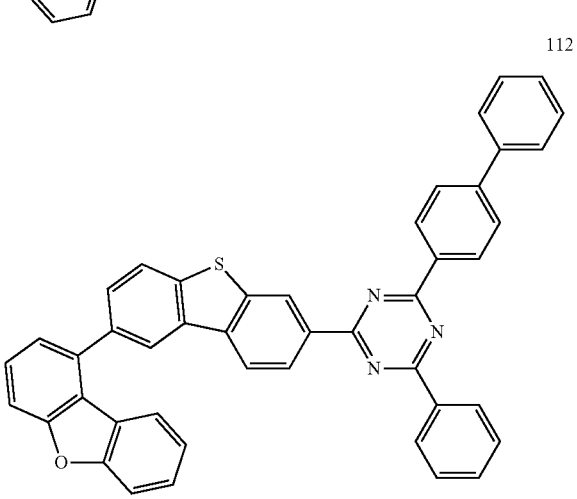
113
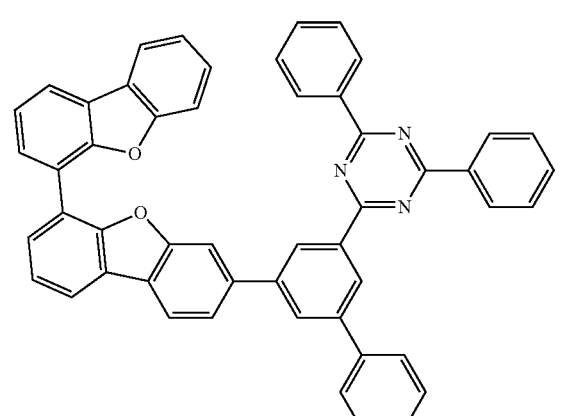
114
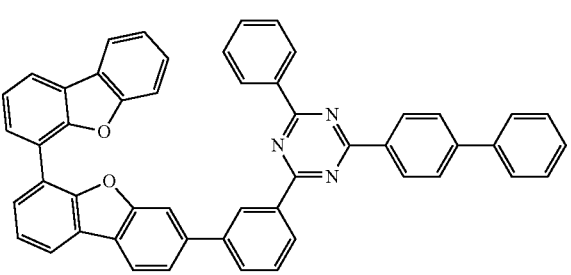
115
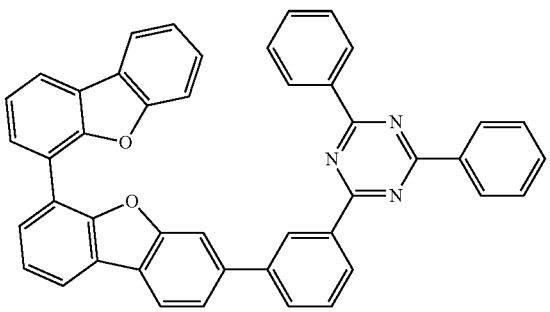
116
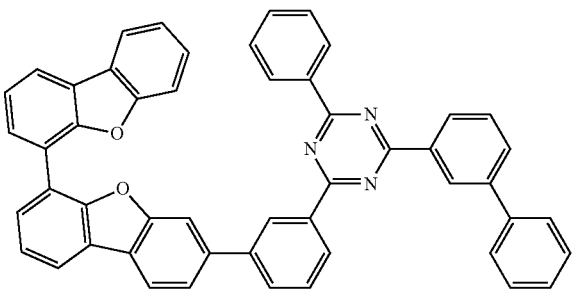
117
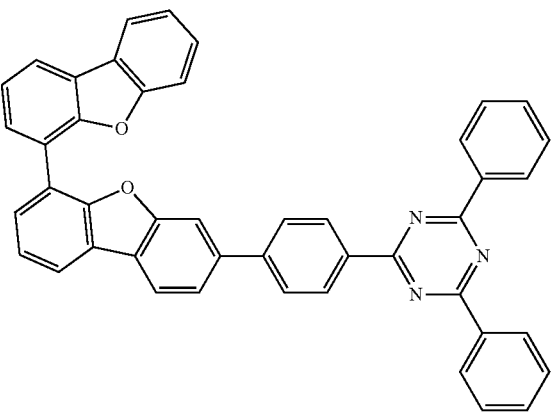
118
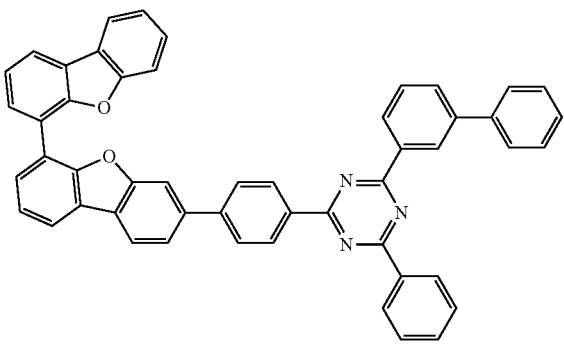

-continued
119
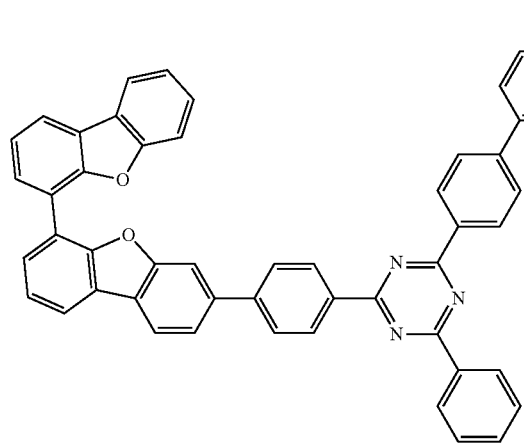
123
124
125
126
127
120
121
122
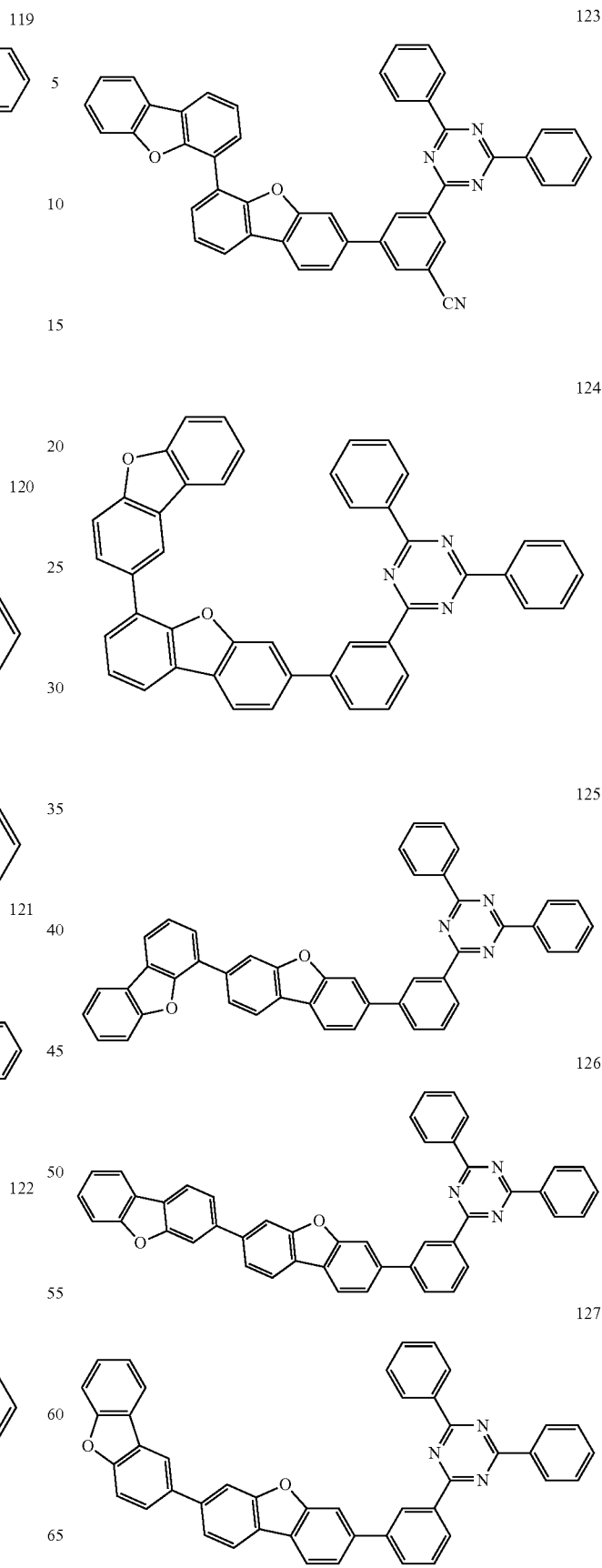

128
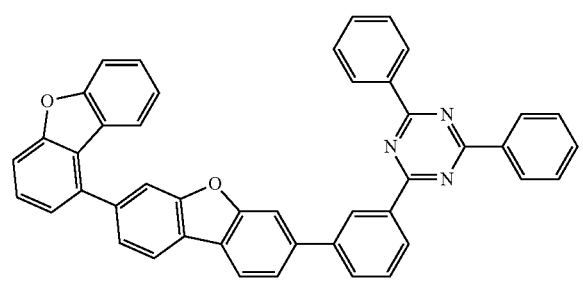
129
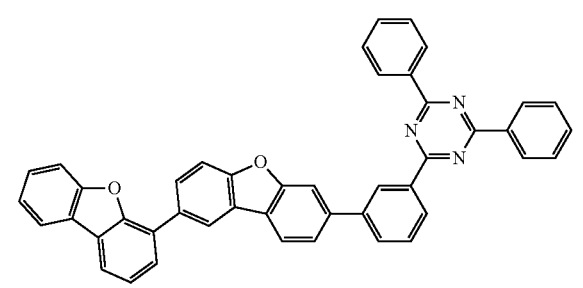
130
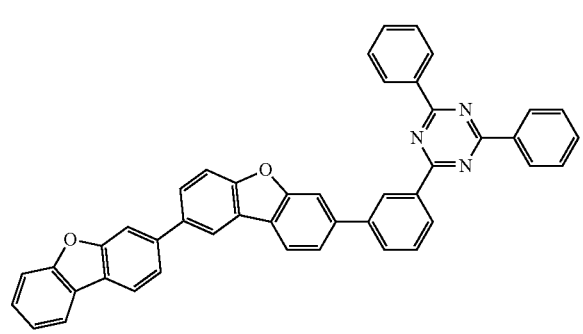
131
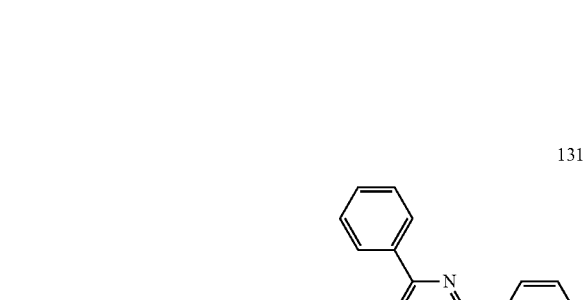
132
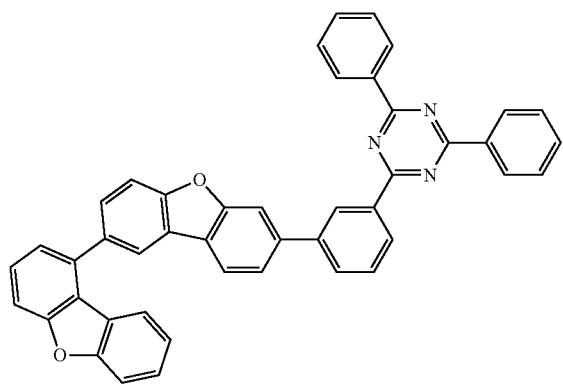
133
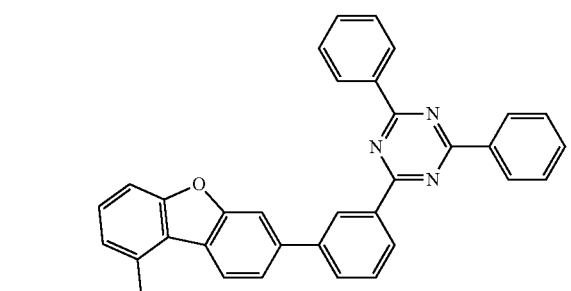
134
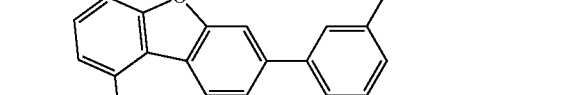

135
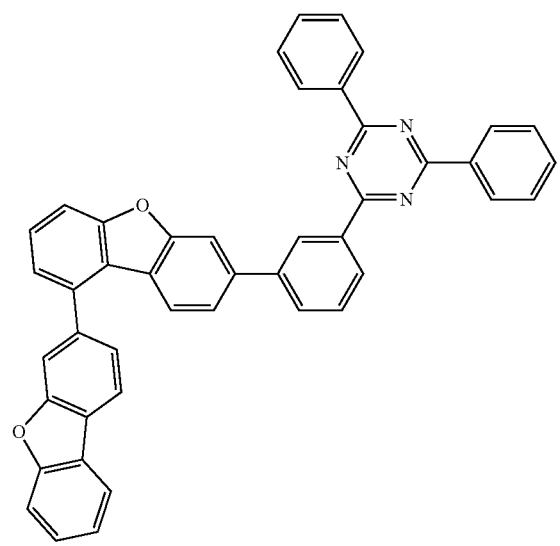
136
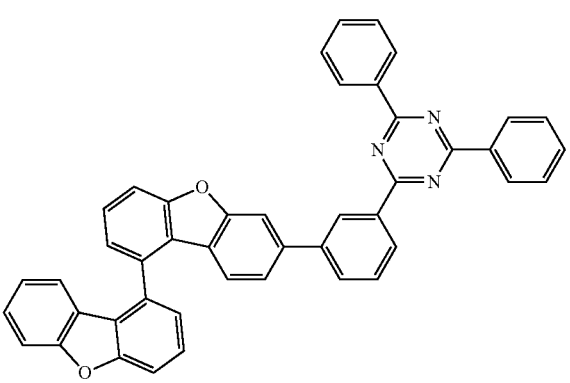
137
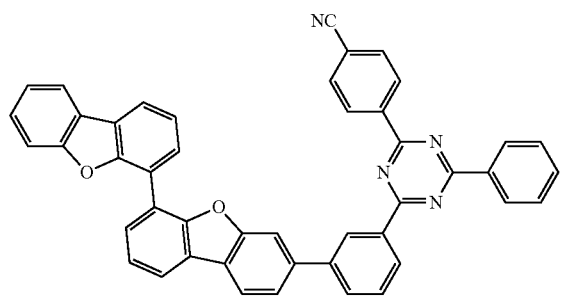
138
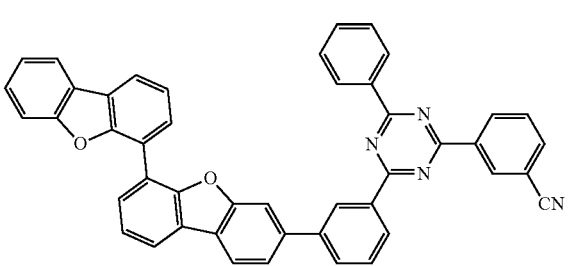
139
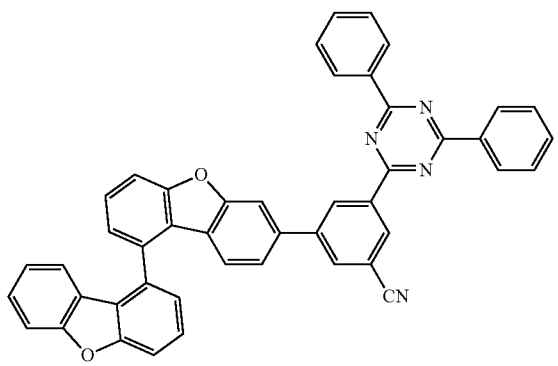
140
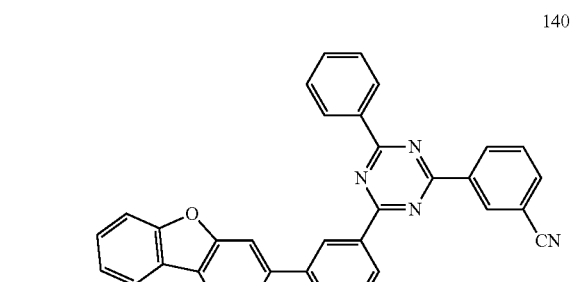
141
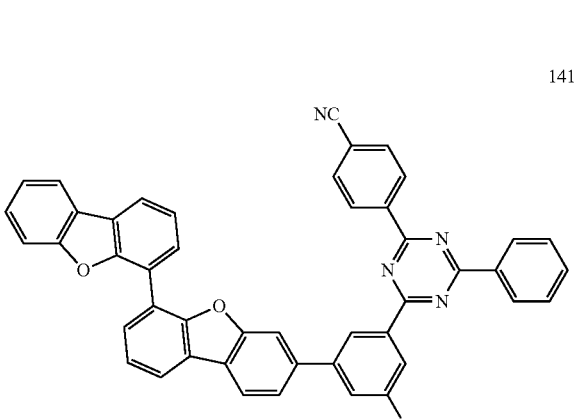
142
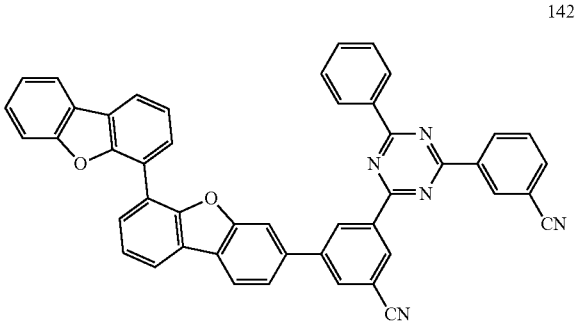

143
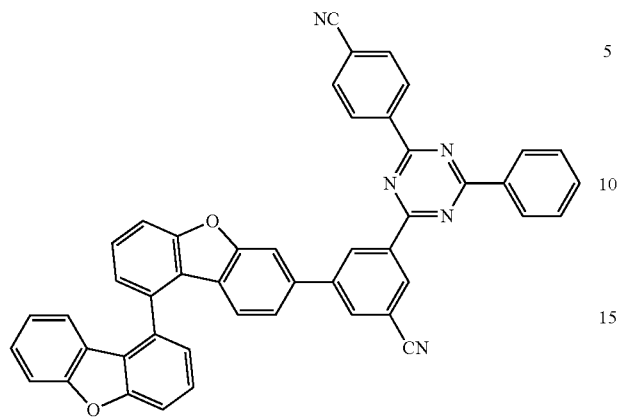
144
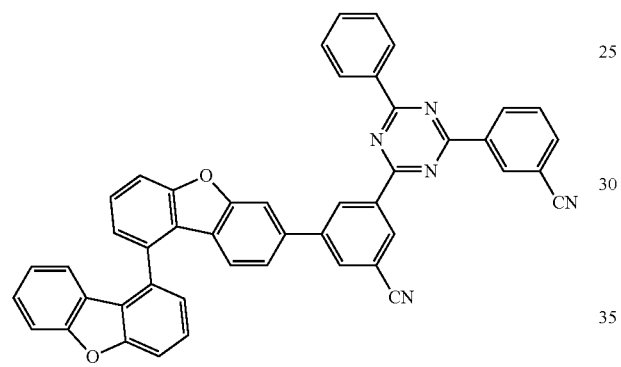
145
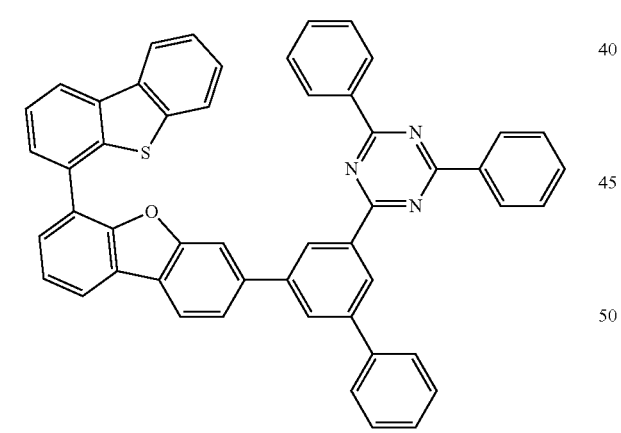
146
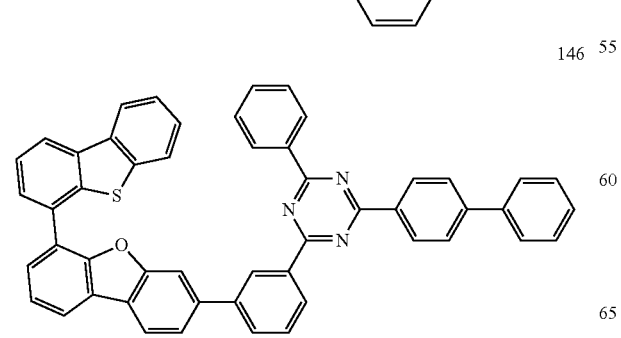
147
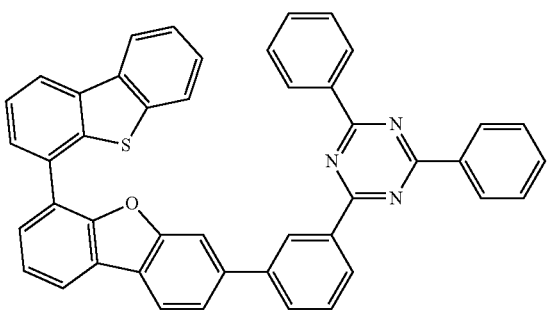
148
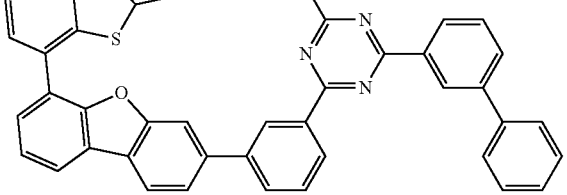
149
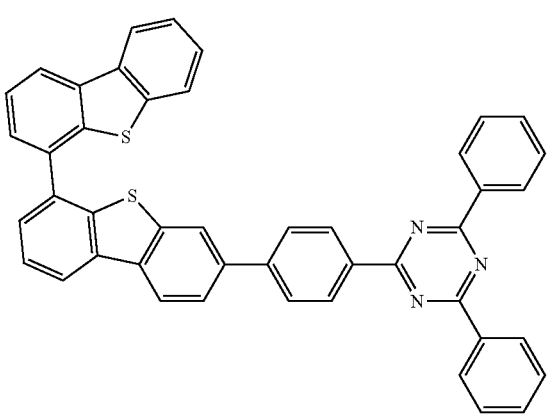
150
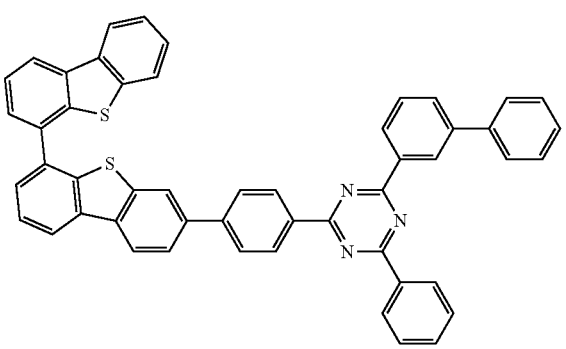

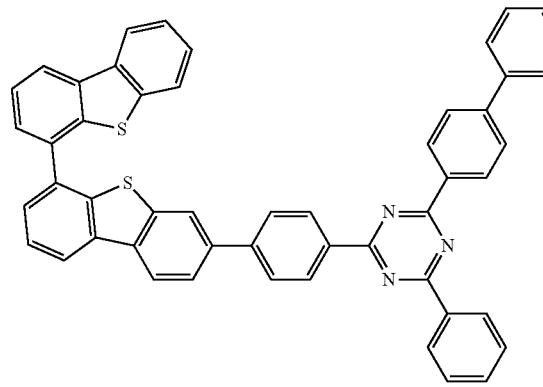
151
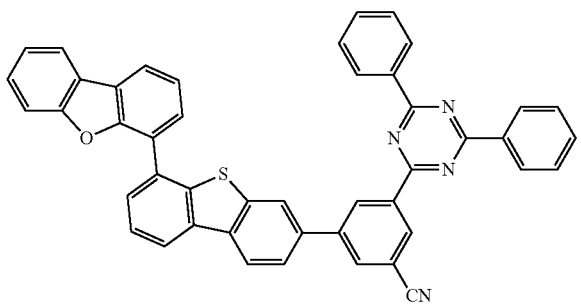
155
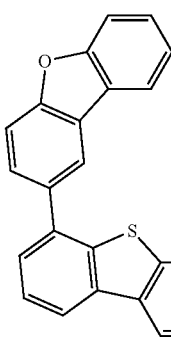
152
156
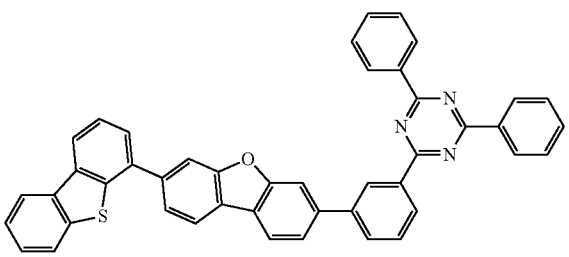
153
157
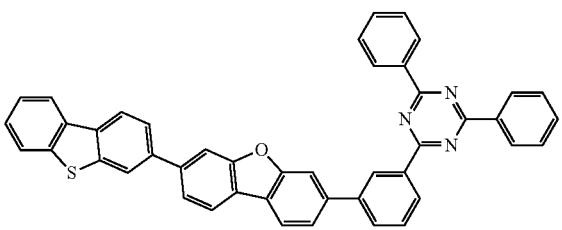
154
158
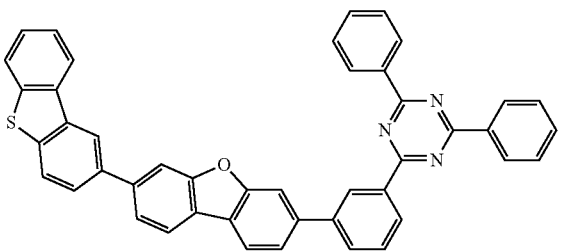
159

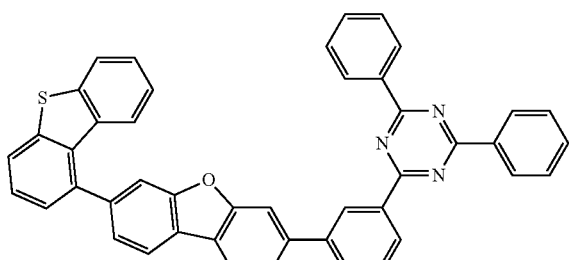
160
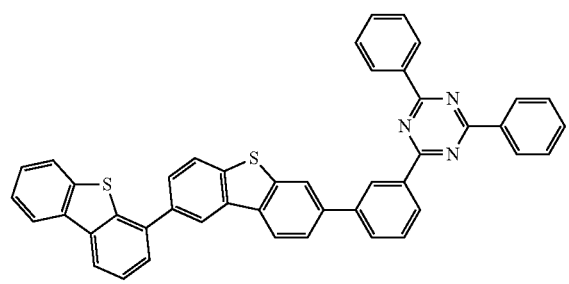
161
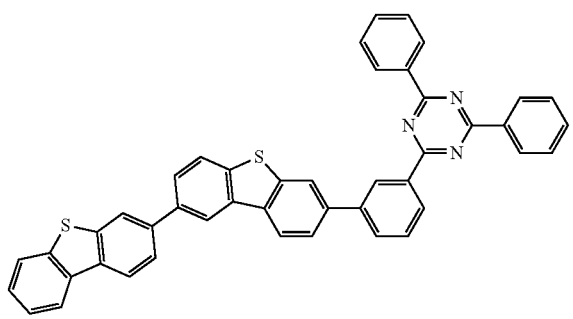
162
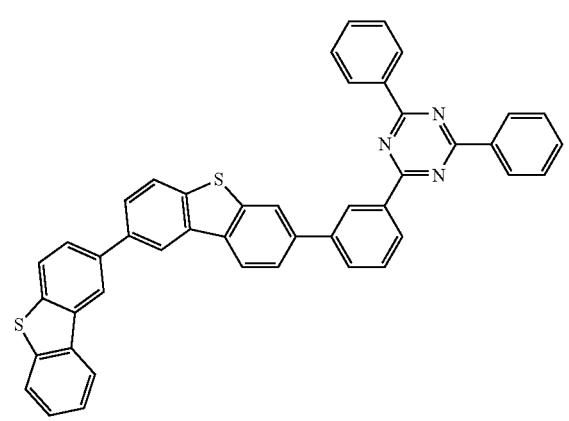
163
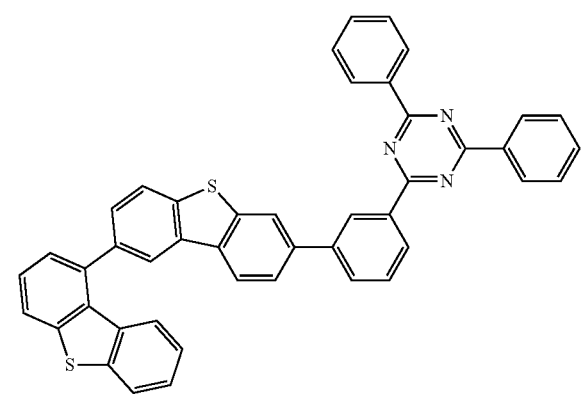
164
165
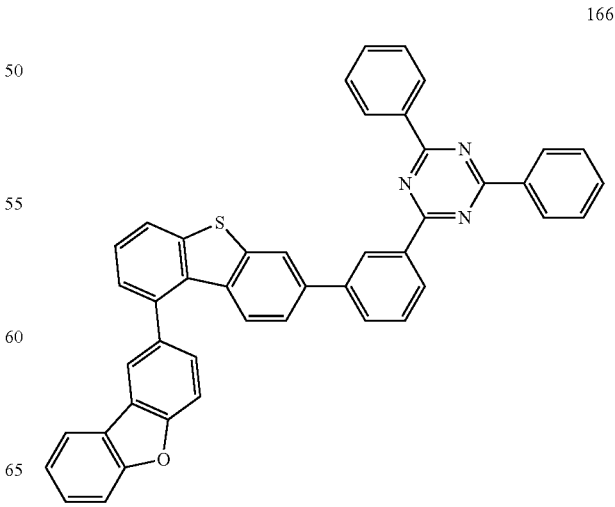
166

167
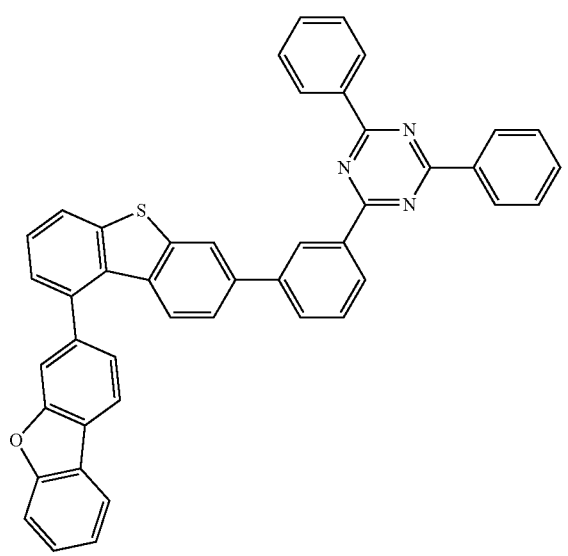
168
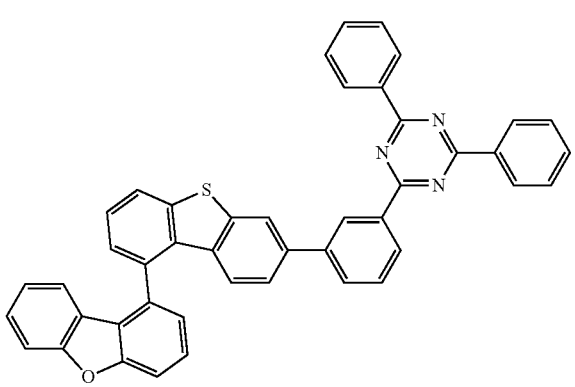
169
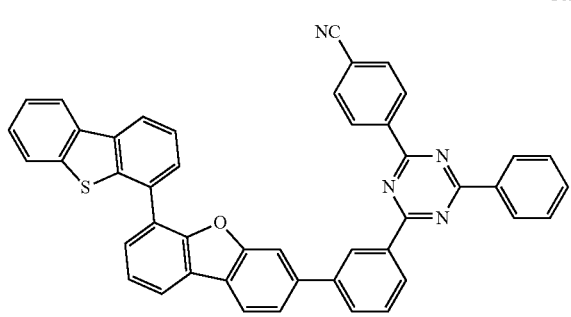
170
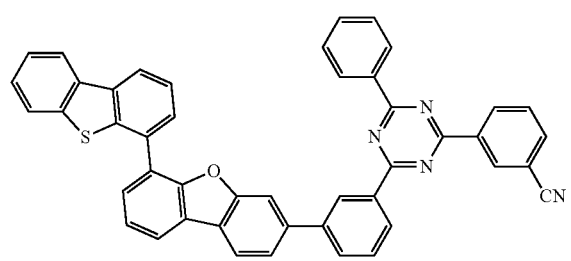
171
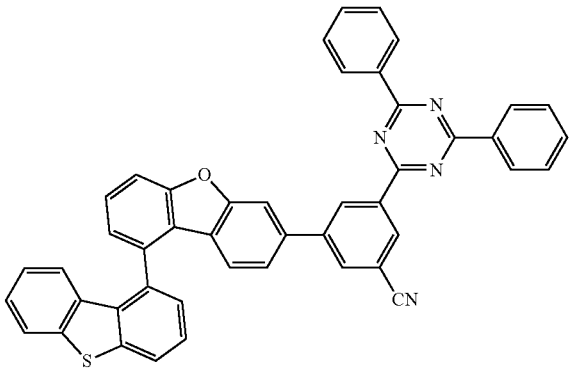
172
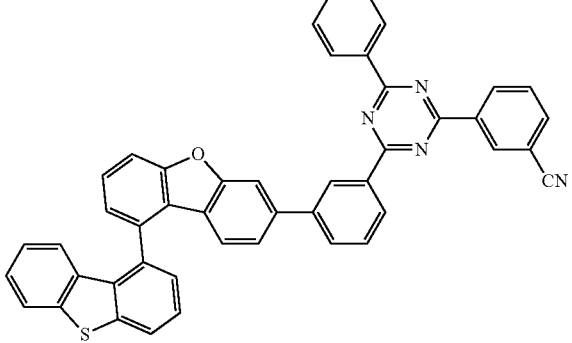
173
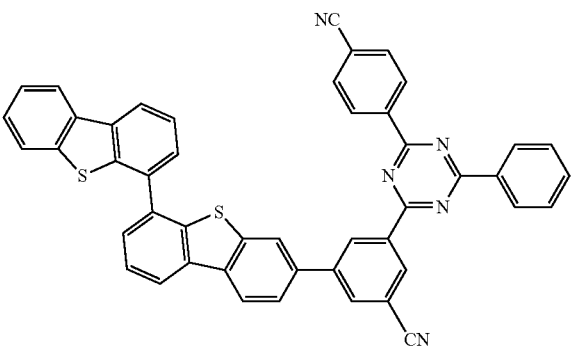
174
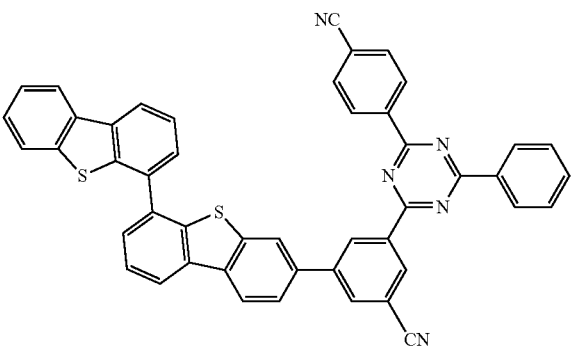

175
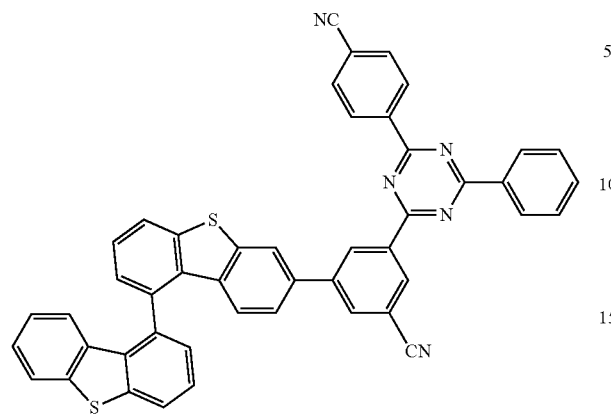
176
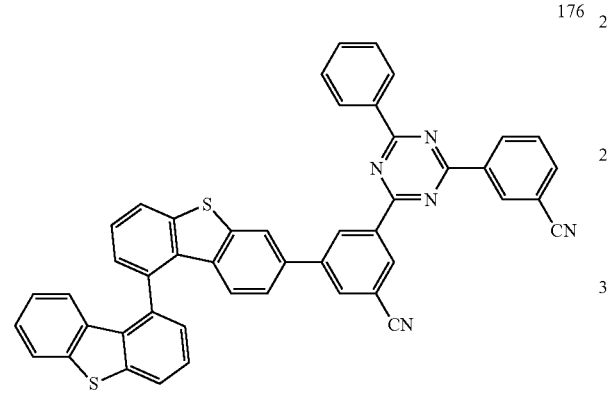
177
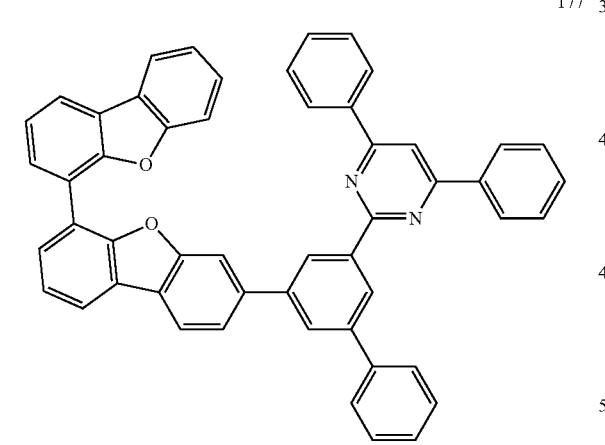
178
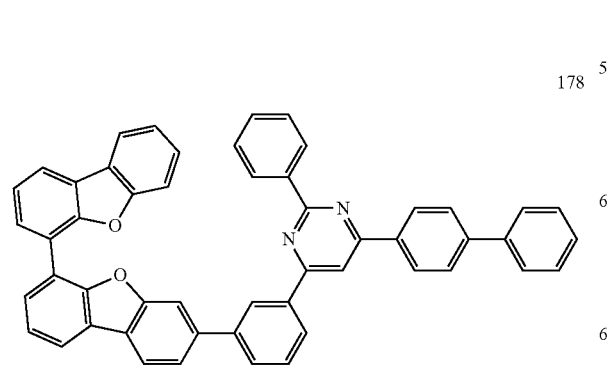
179
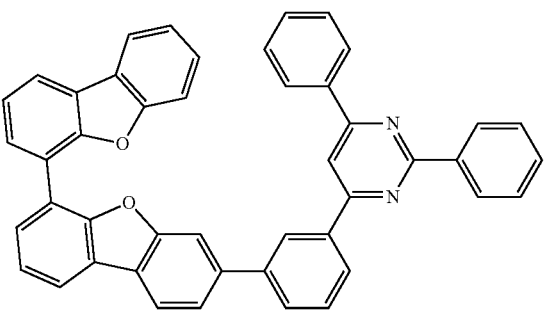
180
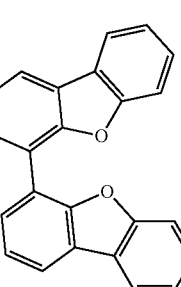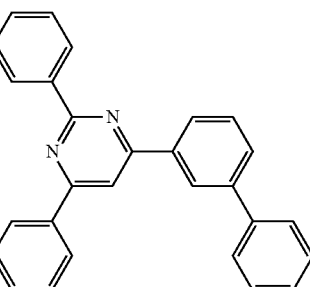
181
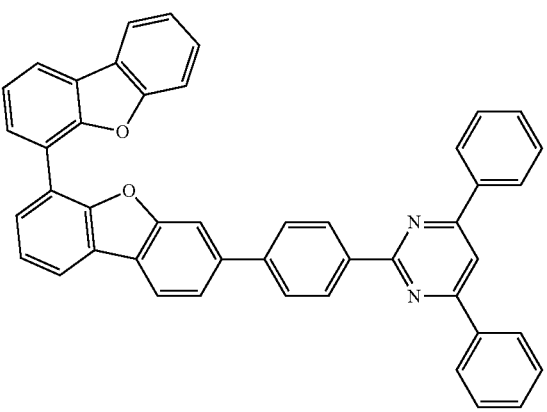
182
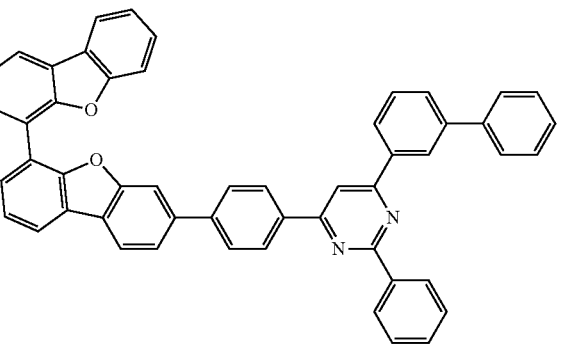

183
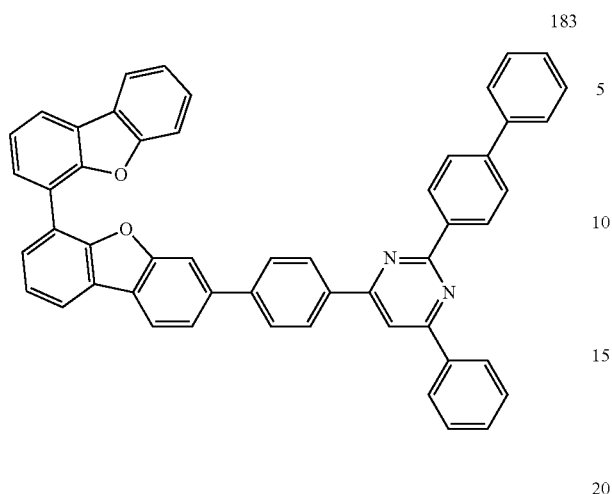
184
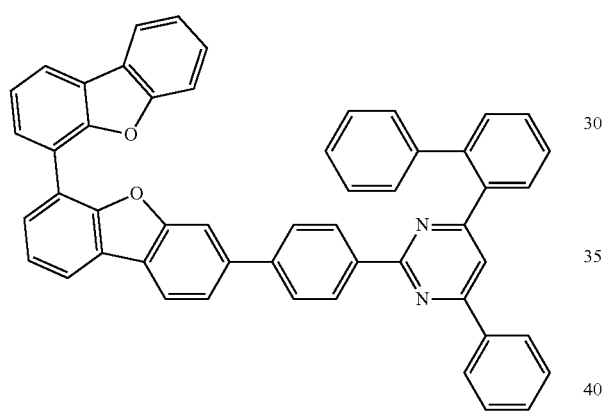
185
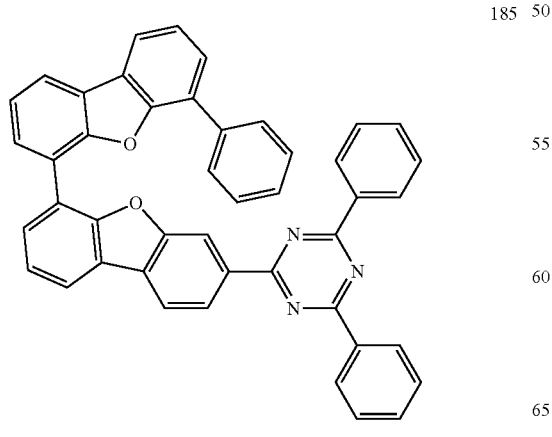
186
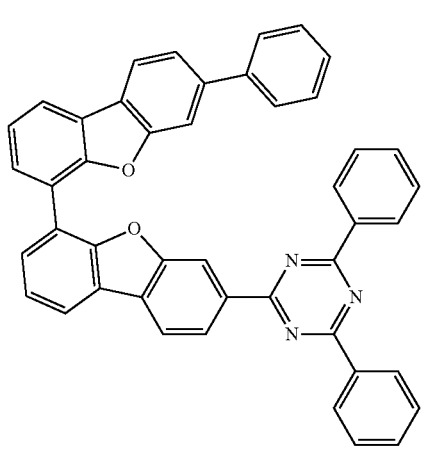
187
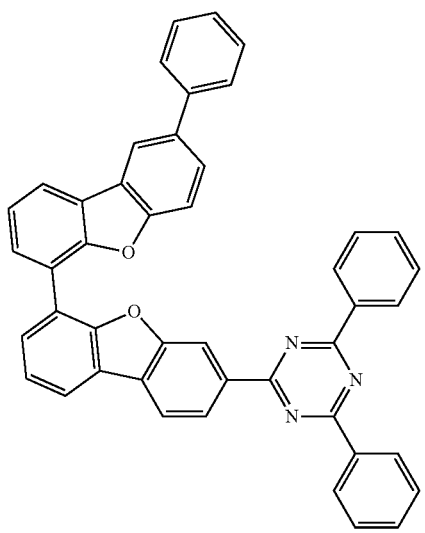
188
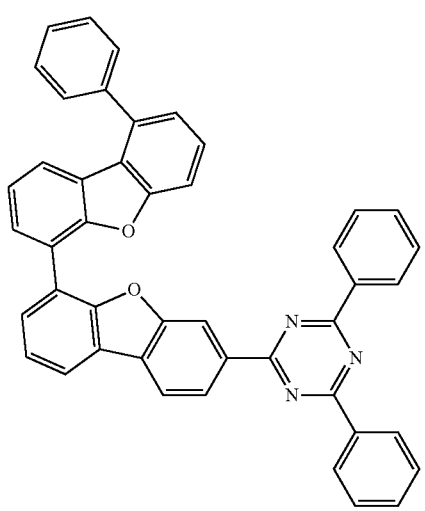

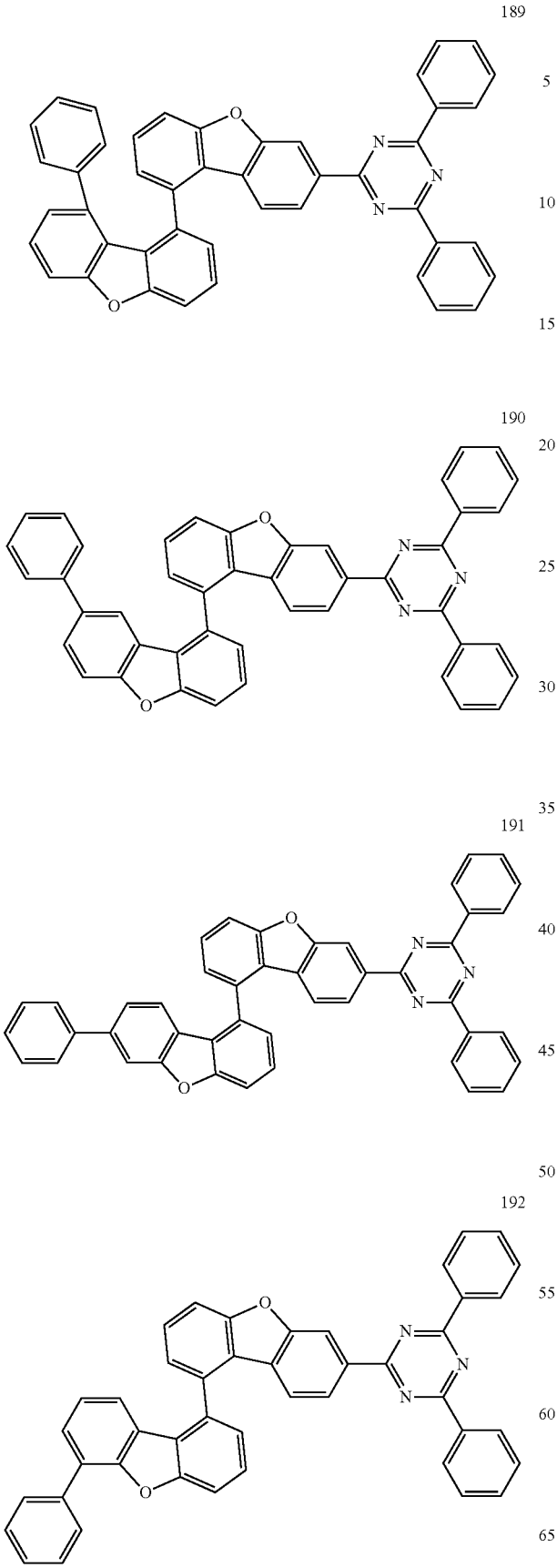
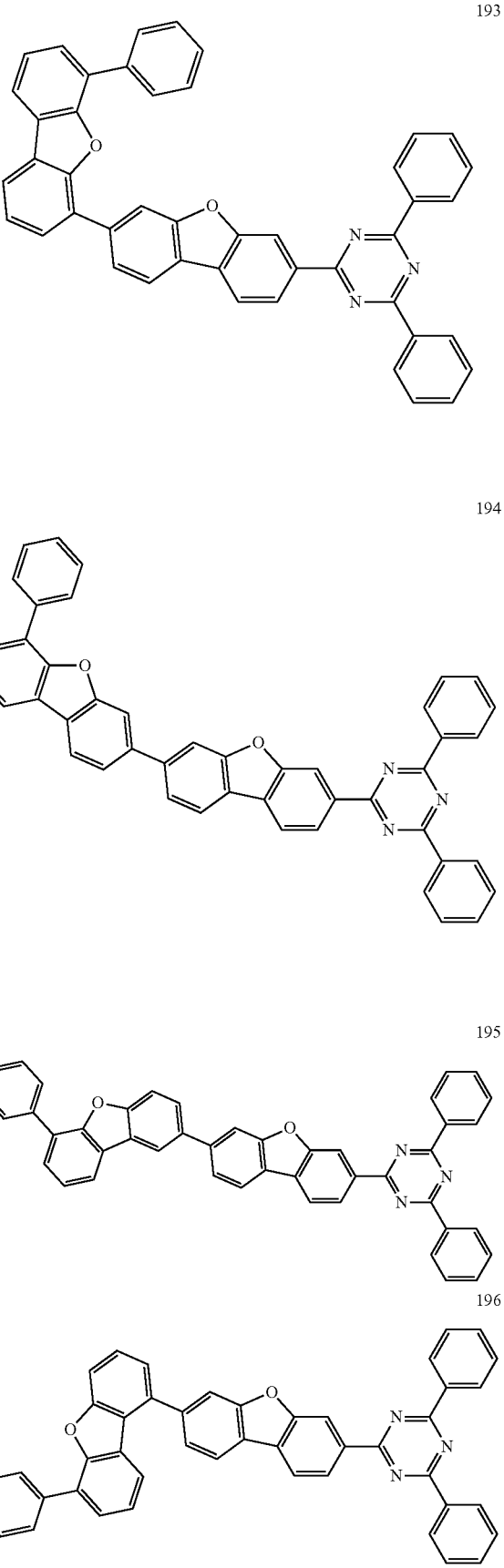

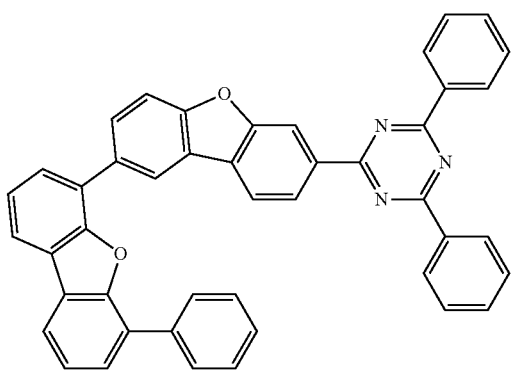

197

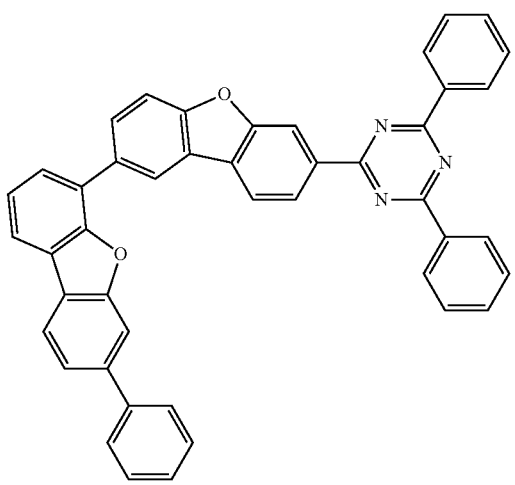

198

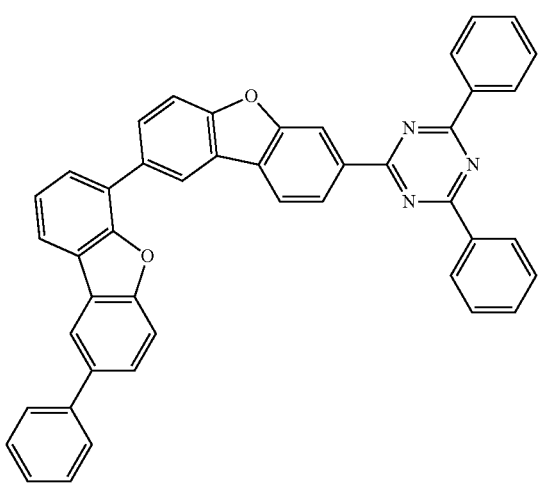

199

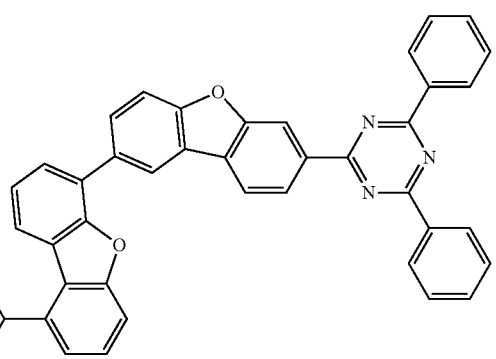

200

The aforementioned organic compound may be applied to an organic optoelectronic device alone or in combination with another organic compound. When the aforementioned organic compound is used with another organic compound, they may be applied in a form of a composition.

Hereinafter, a composition according to an embodiment is described.

The composition according to an embodiment may include the aforementioned organic compound (hereinafter referred to as "first organic compound") and an organic compound having hole characteristics (hereinafter referred to as "second organic compound").

The second organic compound may include, for example, a carbazole moiety and may be, for example, a substituted or unsubstituted carbazole compound, a substituted or unsubstituted biscarbazole compound, or a substituted or unsubstituted indolocarbazole compound, but is not limited thereto.

For example, the second organic compound may include, for example, a carbazole moiety represented by Chemical Formula 2.

[Chemical Formula 2]

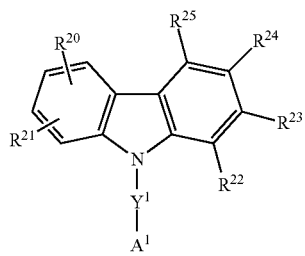

In Chemical Formula 2, $Y^1$ is a single bond, a substituted or unsubstituted C6 to C30 arylene group, or a divalent substituted or unsubstituted C2 to C30 heterocyclic group, $A^1$ is a substituted or unsubstituted C6 to C30 aryl group, or a substituted or unsubstituted C2 to C30 heterocyclic group, $R^{20}$ to $R^{25}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, and $R^{22}$ to $R^{25}$ are independently present or adjacent groups of $R^{22}$ to $R^{25}$ are linked to each other to form a ring.

For example, in the definition of Chemical Formula 2, "substituted" may refer to replacement of at least one hydrogen by deuterium, a C1 to C10 alkyl group, a C6 to C12 aryl group, or a C2 to C10 heteroaryl group, and for example replacement of at least one hydrogen by deuterium, a phenyl group, an ortho-biphenyl group, a meta-biphenyl group, a para-biphenyl group, a terphenyl group, a naphthyl group, a dibenzofuranyl group, or a dibenzothiophenyl group.

For example, the second organic compound may be a compound represented by Chemical Formula 2A.

[Chemical Formula 2A]

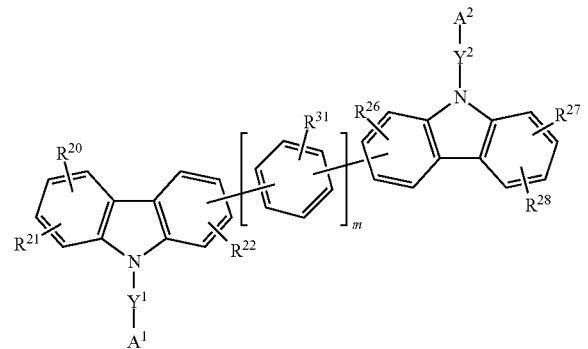

In Chemical Formula 2A, $Y^1$ and $Y^2$ may independently be a single bond, a substituted or unsubstituted C6 to C30 arylene group, a divalent substituted or unsubstituted C2 to C30 heterocyclic group, or a combination thereof, $A^1$ and $A^2$ may independently be a substituted or unsubstituted C6 to C30 aryl group, a substituted or unsubstituted C2 to C30 heterocyclic group, or a combination thereof, $R^{20}$ to $R^{22}$, $R^{26}$ to $R^{28}$, and $R^{31}$ may independently be hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, m may be an integer of 0 to 2.

For example, $Y^1$ and $Y^2$ of Chemical Formula 2A may independently be a single bond, a substituted or unsubstituted phenylene group, or a substituted or unsubstituted biphenylene group, and for example a single bond, a meta-phenylene group, a para-phenylene group, a meta-biphenylene group, or a para-biphenylene group.

For example, $A^1$ and $A^2$ of Chemical Formula 2A may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, or a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof. For example, $A^1$ and $A^2$ of Chemical Formula 2A may independently be a substituted or unsubstituted phenyl group, a substituted or unsubstituted biphenyl group, a substituted or unsubstituted dibenzothiophenyl group, a substituted or unsubstituted dibenzofuranyl group, or a substituted or unsubstituted carbazolyl group.

For example, $R^{20}$ to $R^{22}$ and $R^{26}$ to $R^{28}$ of Chemical Formula 2A may independently be hydrogen, a substituted or unsubstituted C6 to C30 aryl group, or a substituted or unsubstituted C2 to C30 heterocyclic group, and for example may be all hydrogen.

For example, m of Chemical Formula 2A may be 0 or 1, for example, m may be 0.

For example, in Chemical Formula 2A, two carbazole groups may be 2,3-bonded, 3,3-bonded, or 2,2-bonded, for example, 3,3-bonded.

For example, the compound represented by Chemical Formula 2A may be represented by Chemical Formula 2A-1.

[Chemical Formula 2A-1]

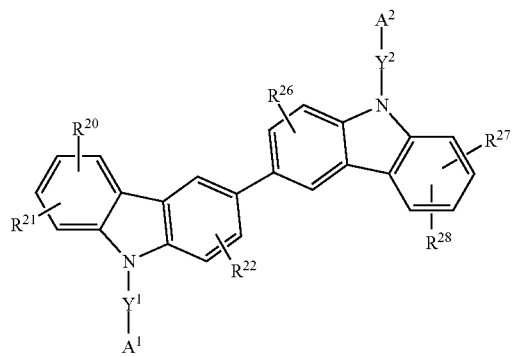

In Chemical Formula 2A-1, $Y^1$, $Y^2$, $A^1$, $A^2$, $R^{20}$ to $R^{22}$, and $R^{26}$ to $R^{28}$ are the same as described above.

For example, the compound represented by Chemical Formula 2A may be a compound that combines one of the carbazole cores listed in Group 2 and the substituents (*—$Y^1$-$A^1$ and *—$Y^2$-$A^2$) listed in Group 3, but is not limited thereto.

[Group 2]

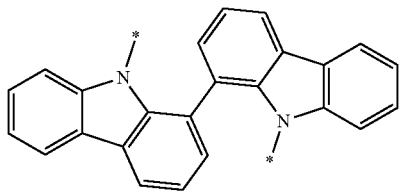

C-1

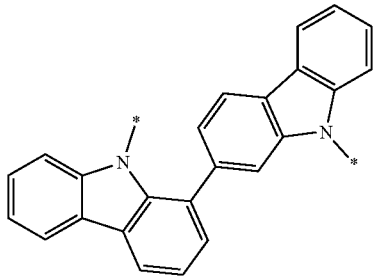

C-2

C-3
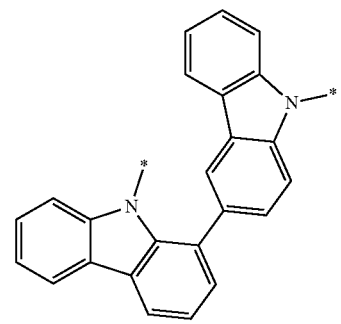
C-4
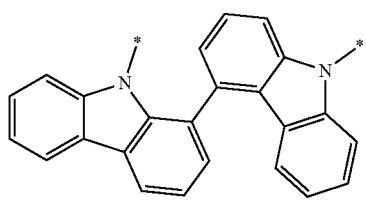
C-5
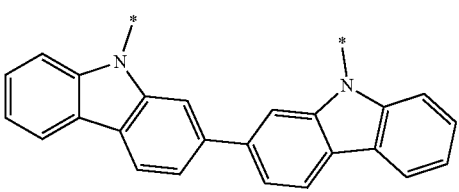
C-6
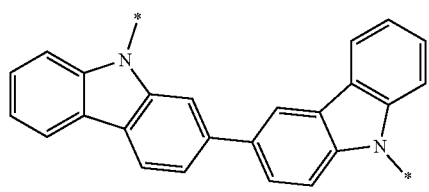
C-7
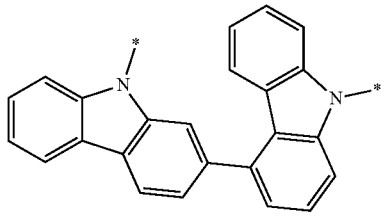
C-8
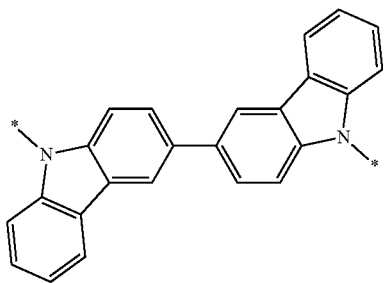
C-9
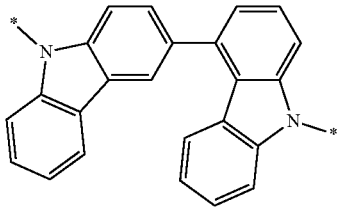
C-10
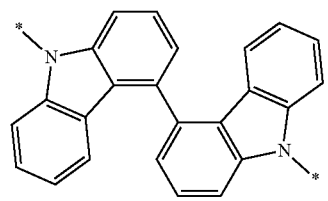
C-11
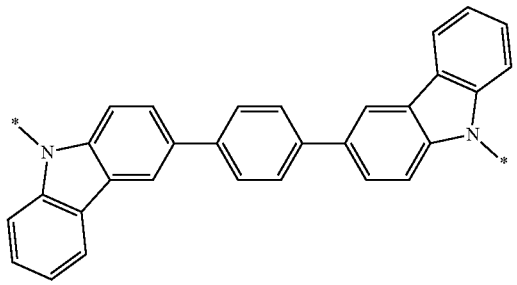
C-12
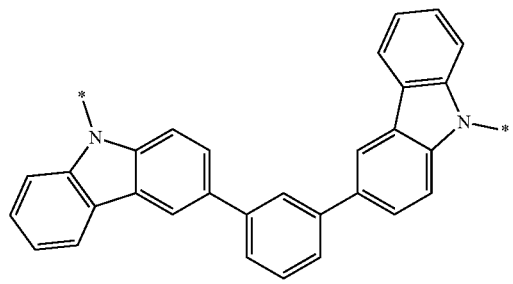
C-13
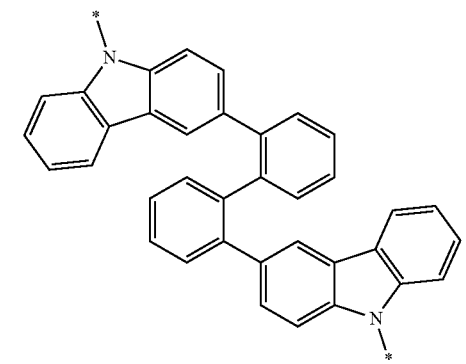

C-14
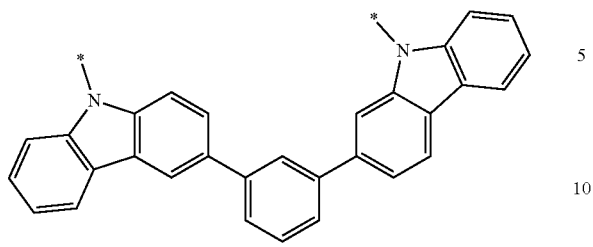
C-15
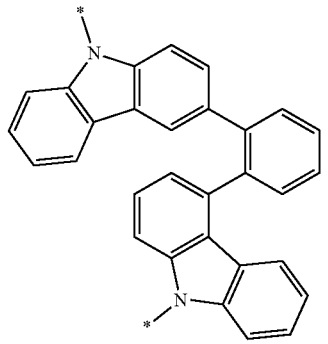
C-16
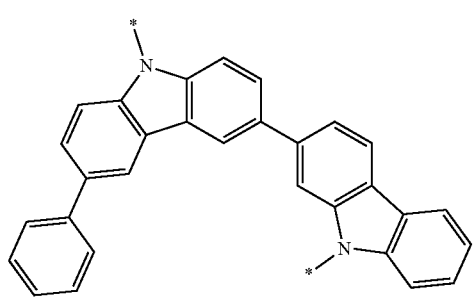
C-17
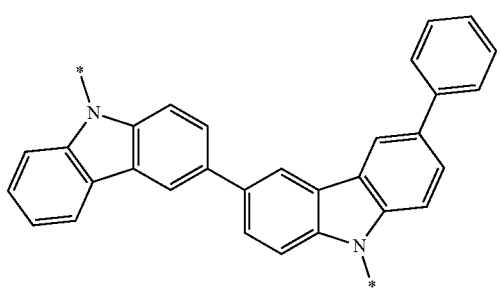
C-18
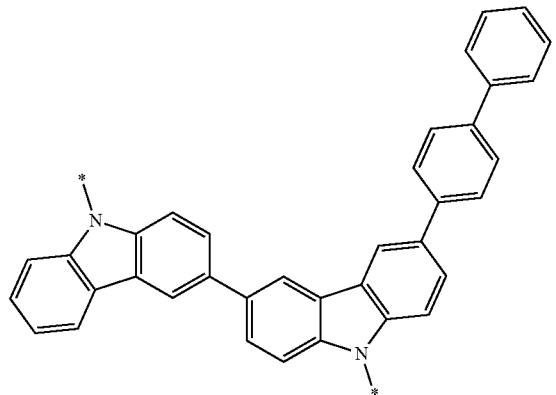
[Group 3]
B-1
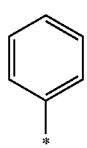
B-2
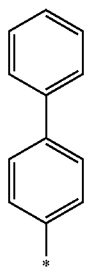
B-3
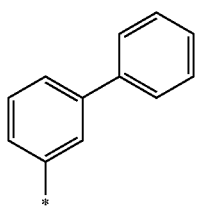
B-4
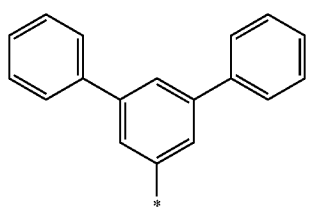
B-5
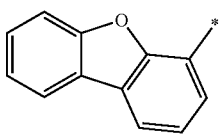
B-6
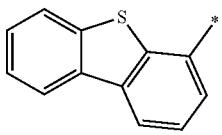
B-7
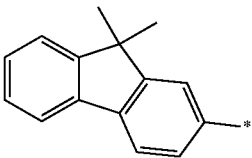
B-8
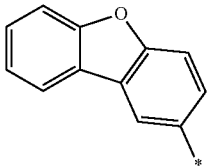

B-9 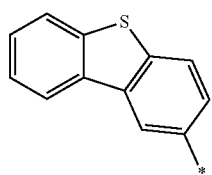
B-10 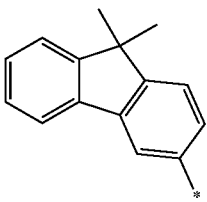
B-11 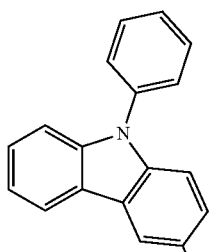
B-12 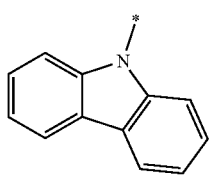
B-13 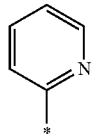
B-14 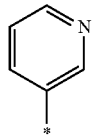
B-15 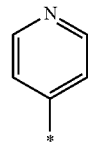
B-16 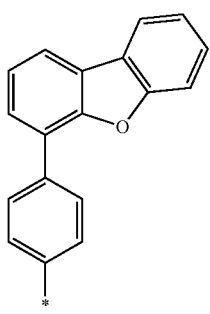
B-17 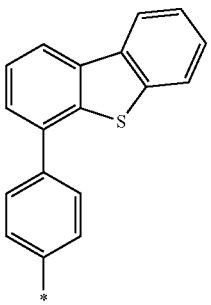
B-18 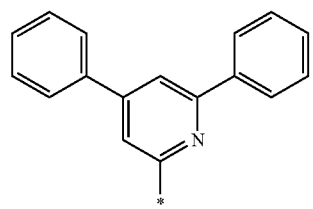
B-19 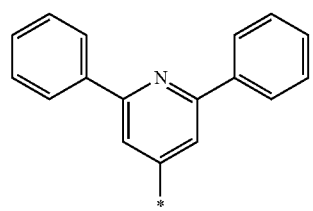
B-20 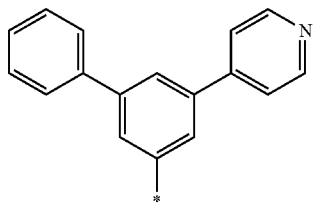
B-21 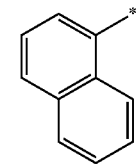
B-22 
B-23

B-24 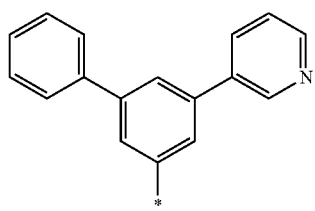
B-27 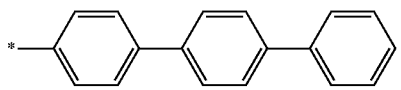
B-25 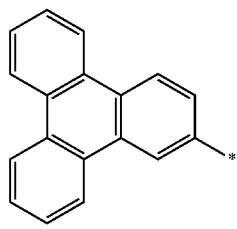
B-28 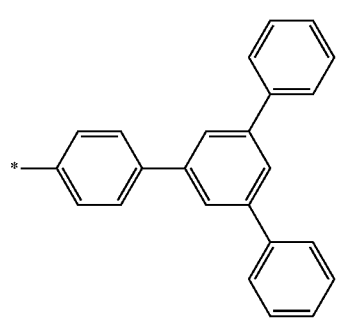
B-26 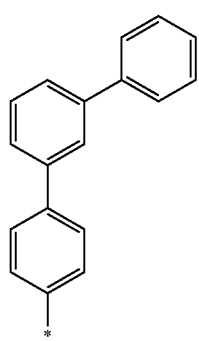
In Groups 2 and 3, * is a linking point.
For example, the compound represented by Chemical Formula 2A may be, for example, one of the compounds listed in Group 4, but is not limited thereto.
[Group 4]
[E-1] 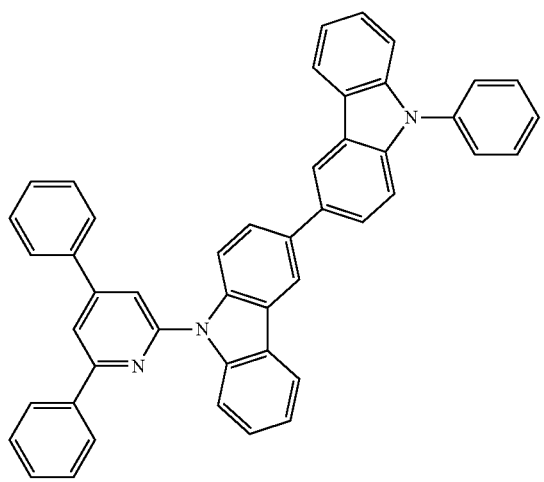
[E-2] 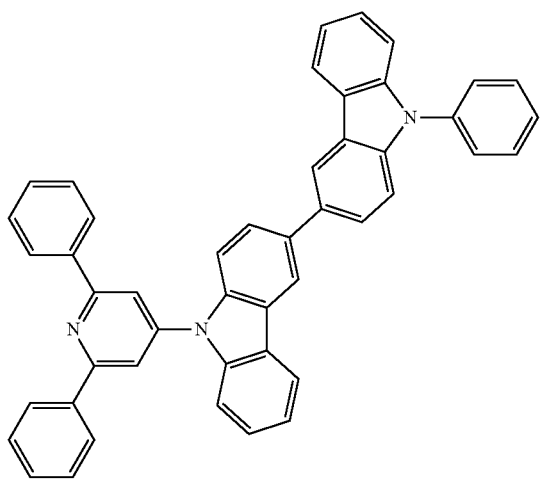

-continued
[E-3]
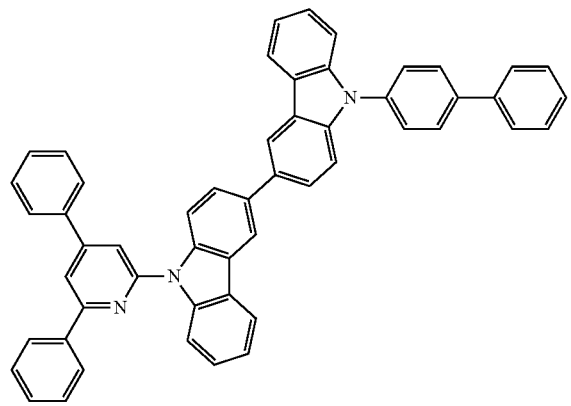
[E-4]
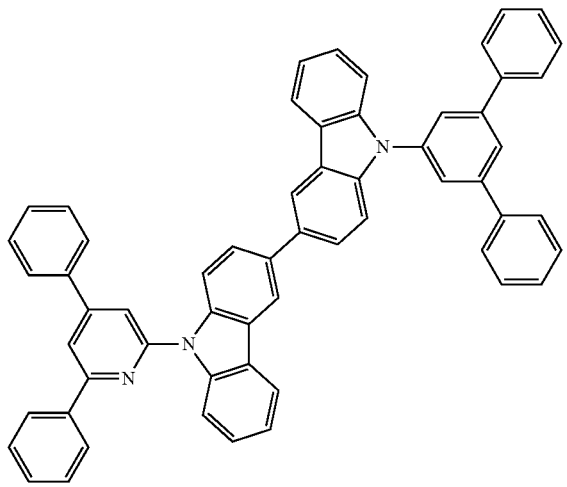
[E-5]
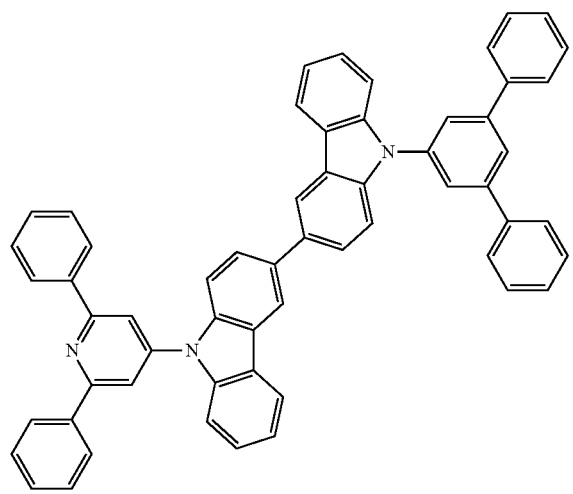
[E-6]
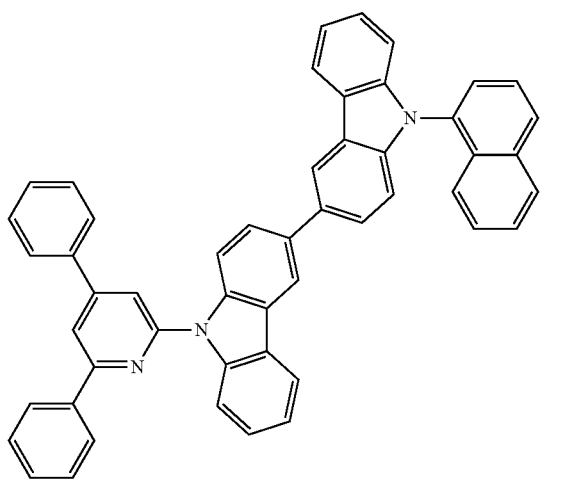
[E-7]
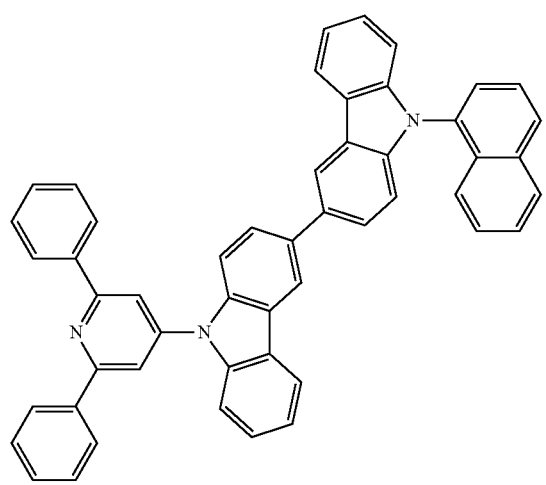
[E-8]
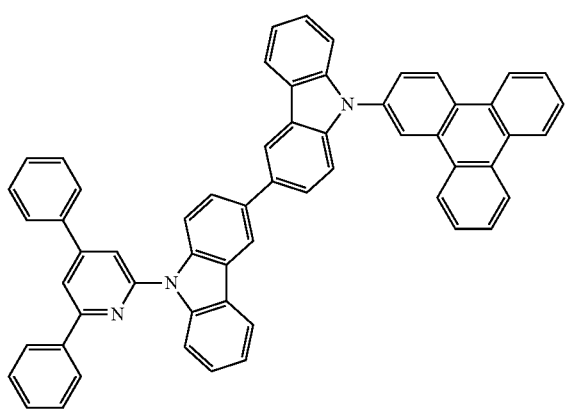

-continued
[E-9]
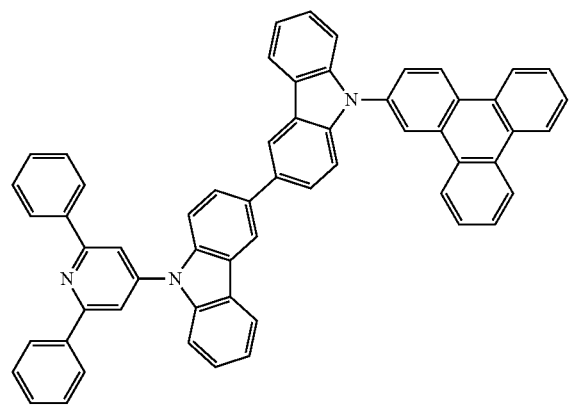
[E-10]
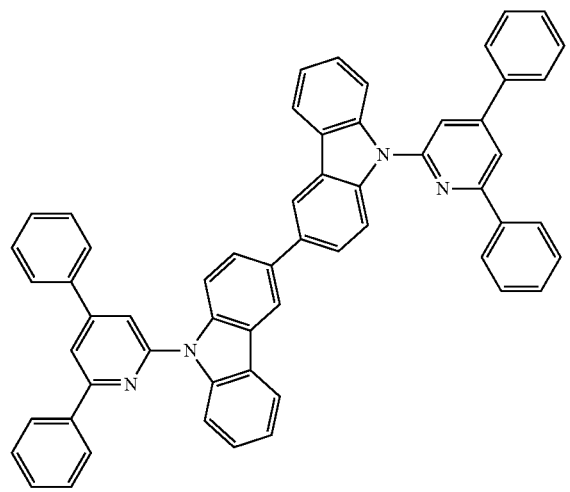
[E-11]
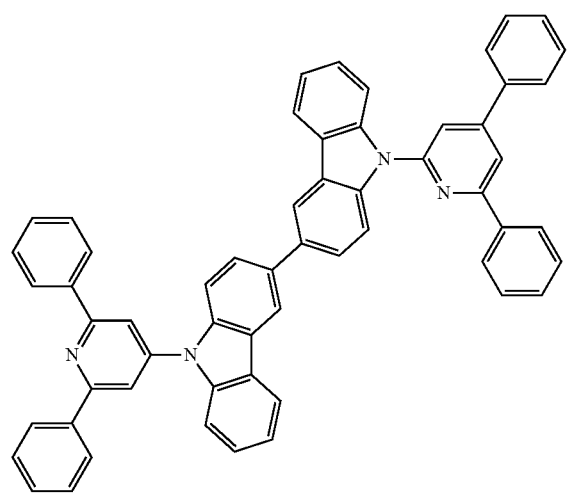
[E-12]
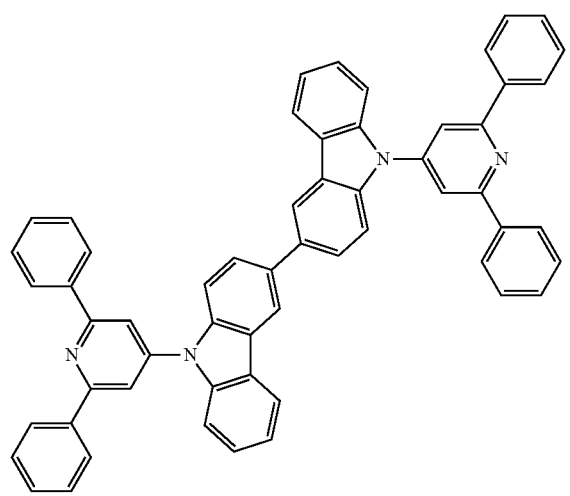
[E-13]
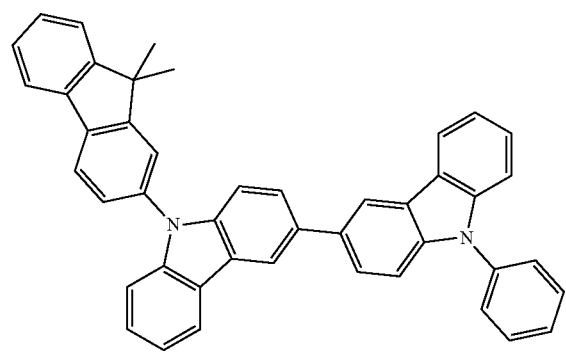
[E-14]
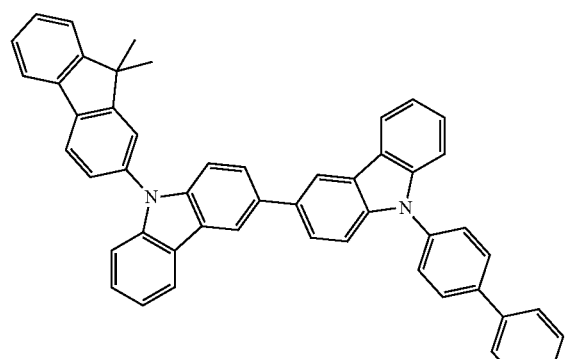

-continued
[E-15]
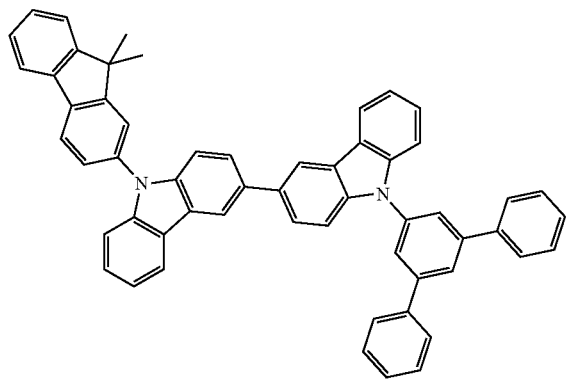
[E-16]
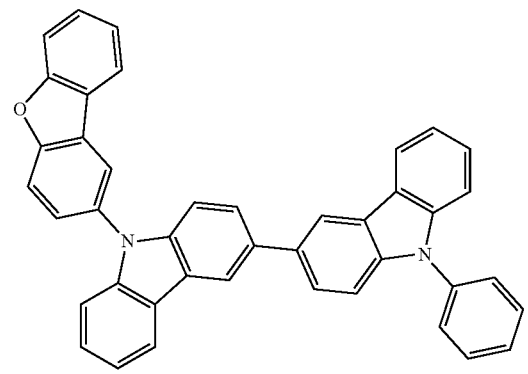
[E-17]
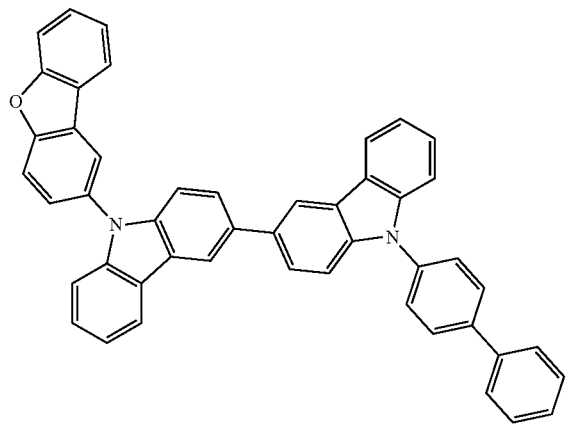
[E-18]
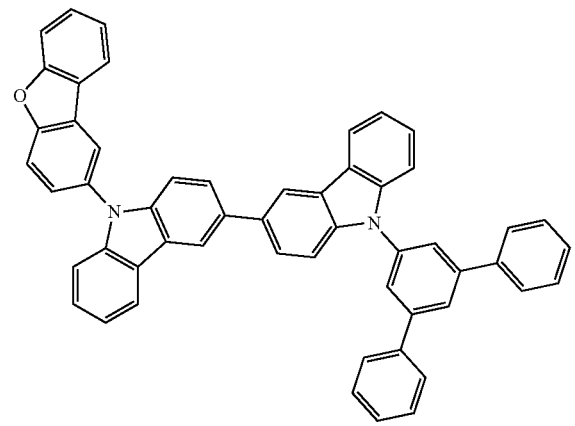
[E-19]
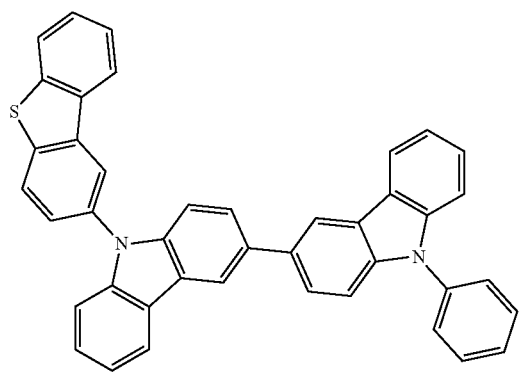
[E-20]
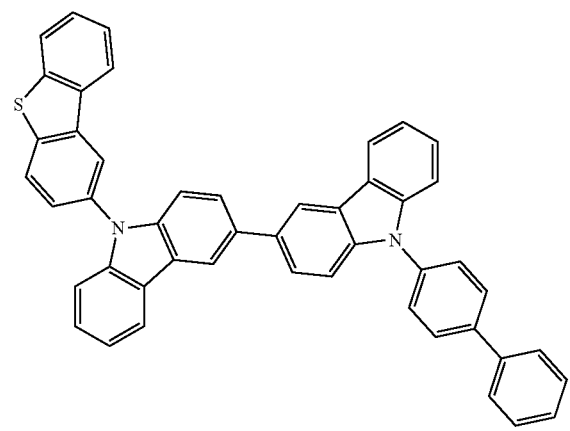

-continued
[E-21]
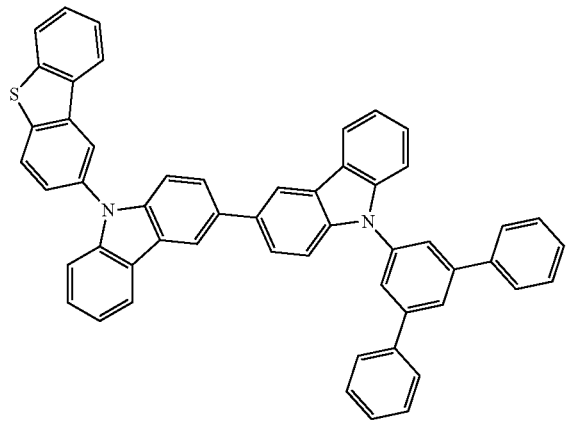
[E-22]
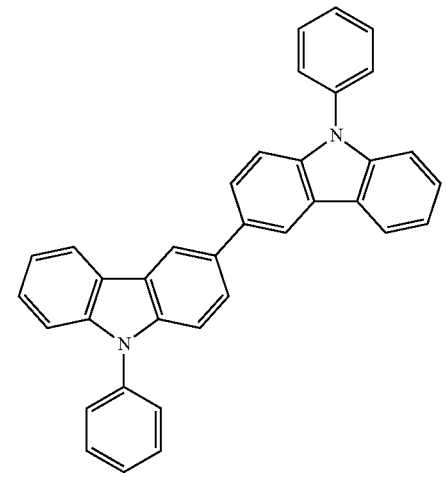
[E-23]
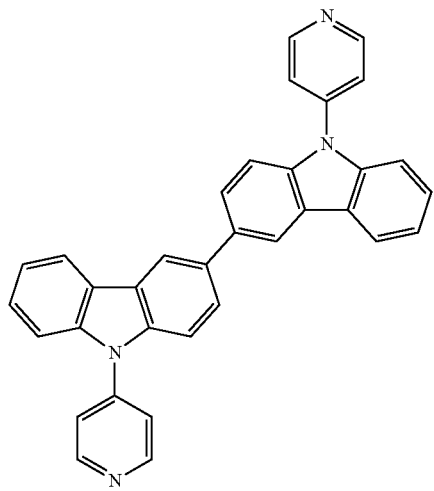
[E-24]
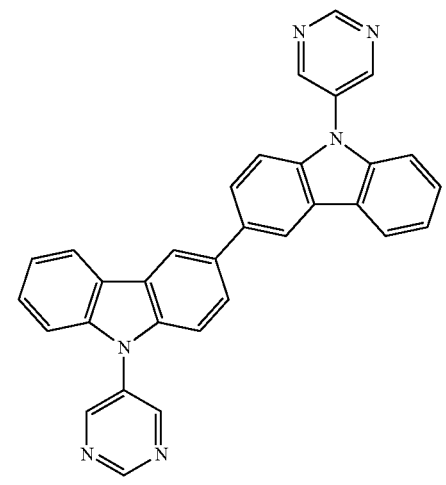
[E-25]
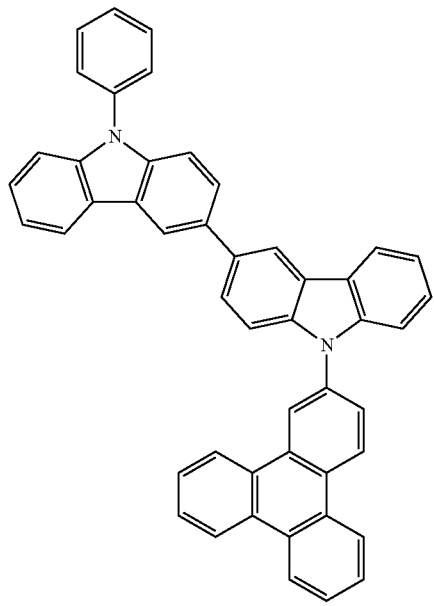
[E-26]
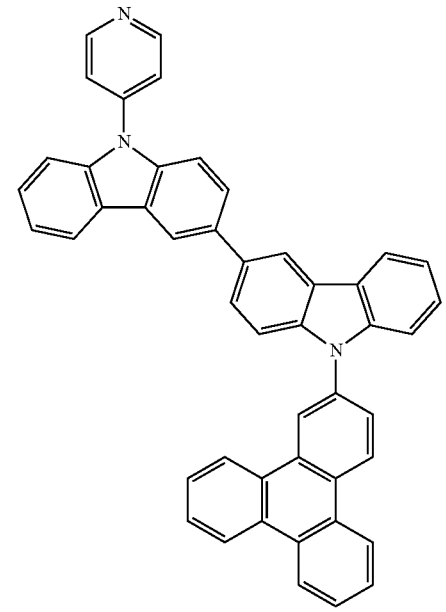

-continued
[E-27]
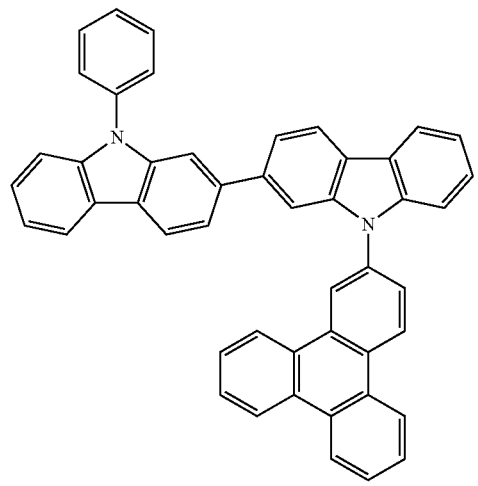
[E-28]
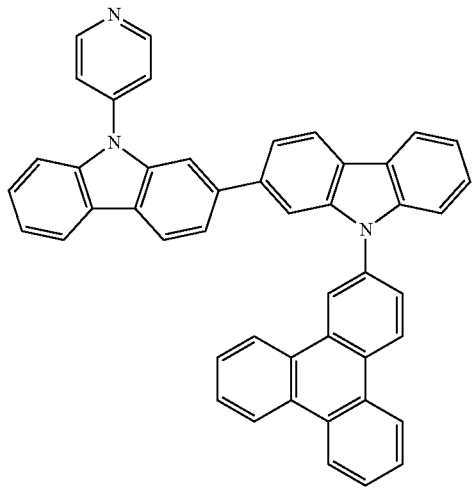
[E-29]
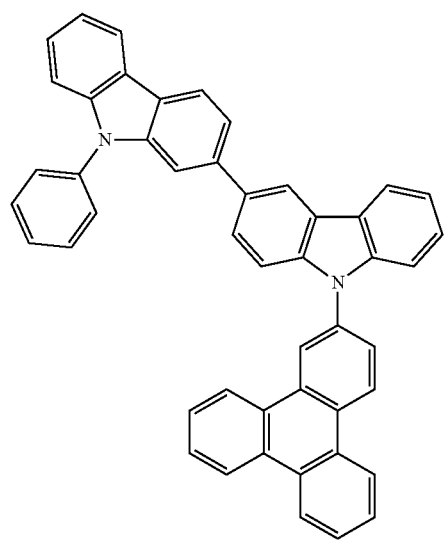
[E-30]
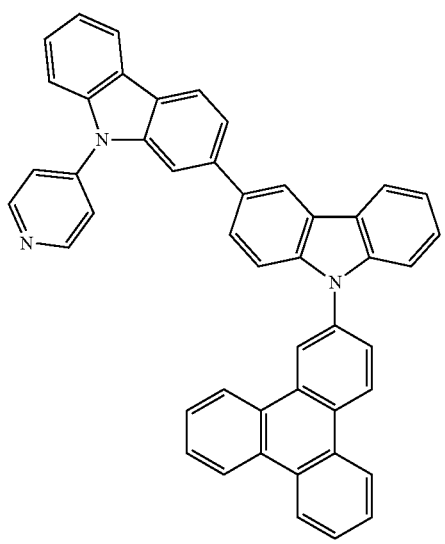
[E-31]
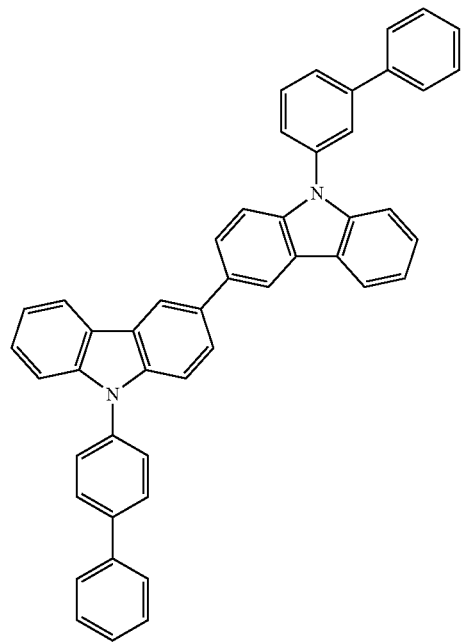
[E-32]
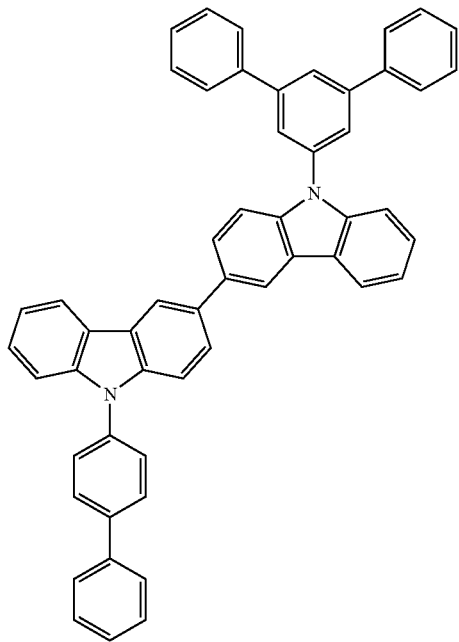

-continued
[E-33]
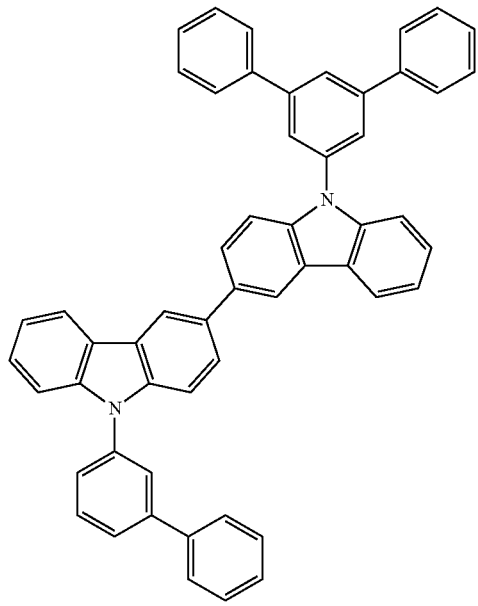
[E-34]
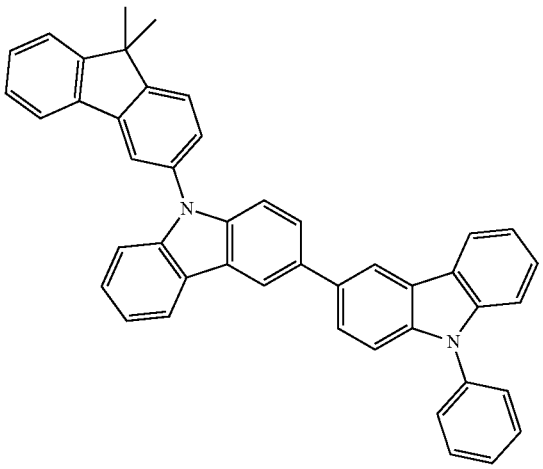
[E-35]
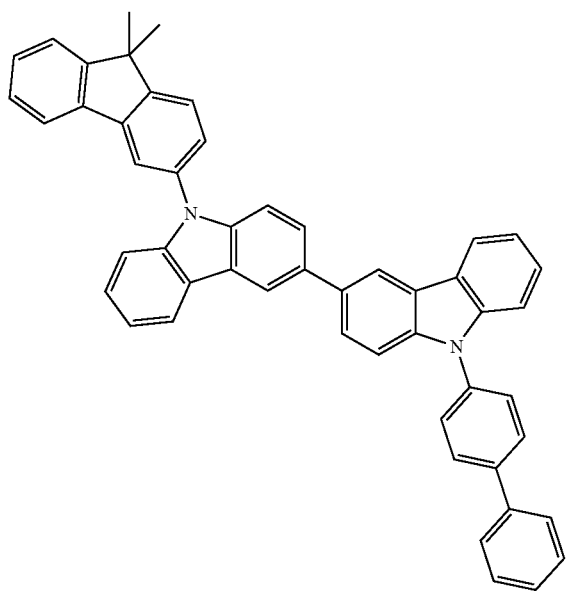
[E-36]
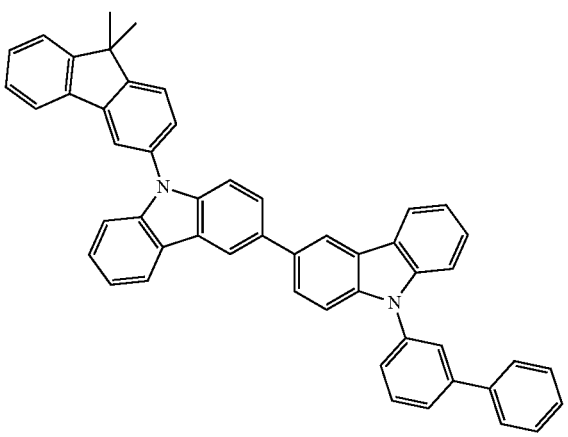

[E-37]
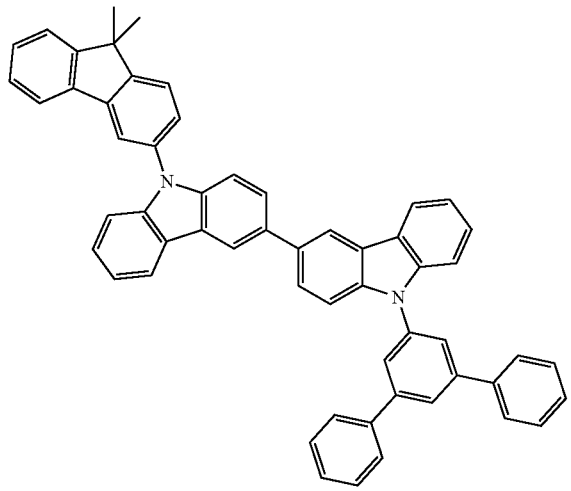
[E-38]
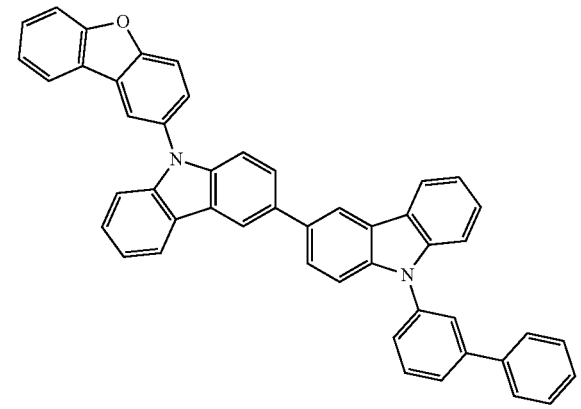
[E-39]
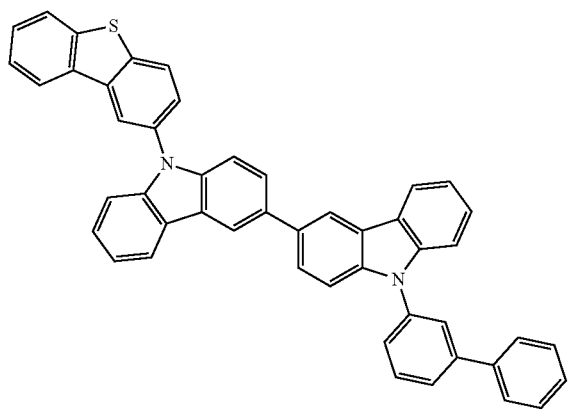
[E-40]
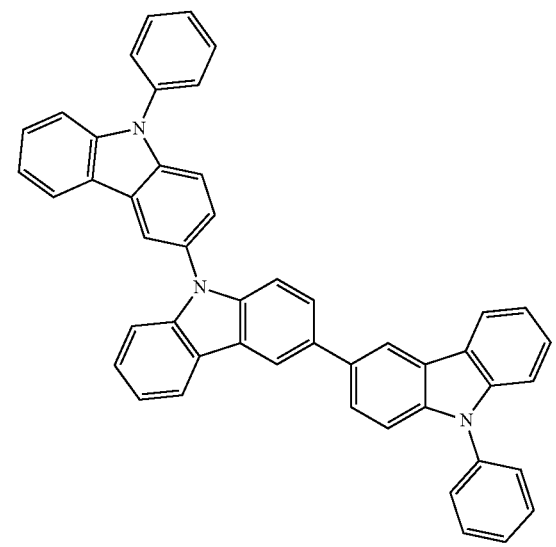
[E-41]
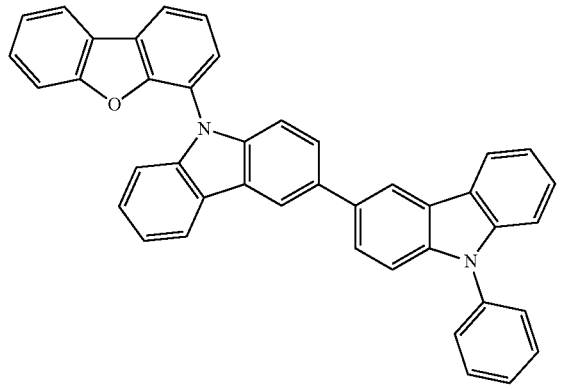
[E-42]
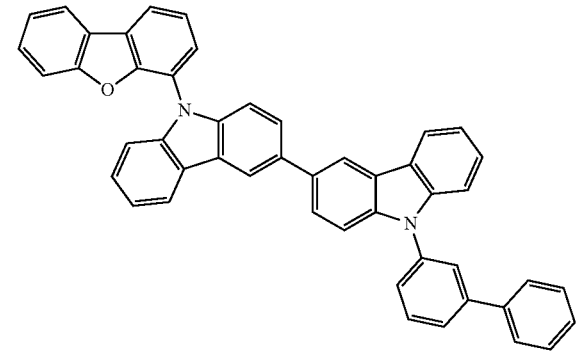

-continued
[E-43]
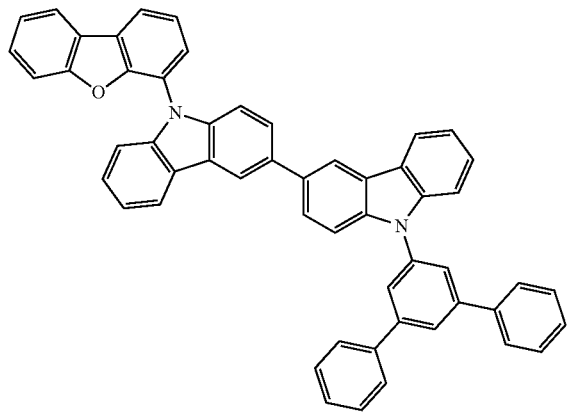
[E-44]
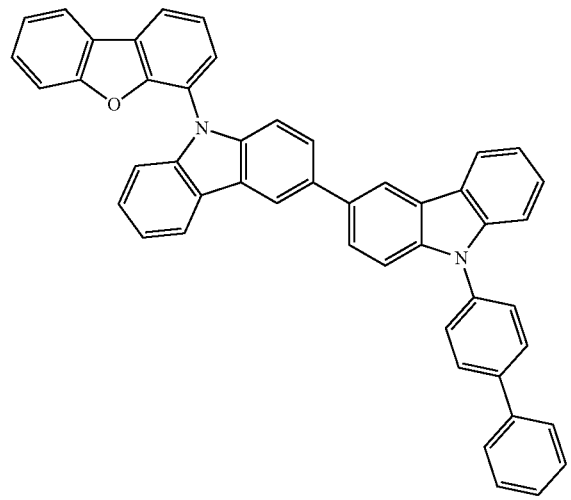
[E-45]
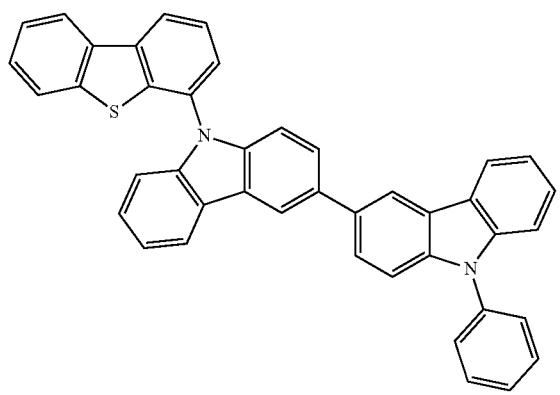
[E-46]
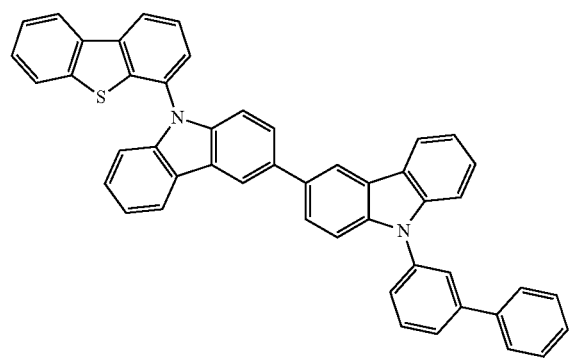
[E-47]
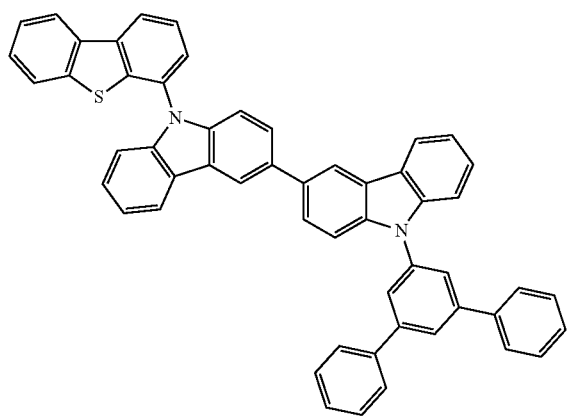
[E-48]
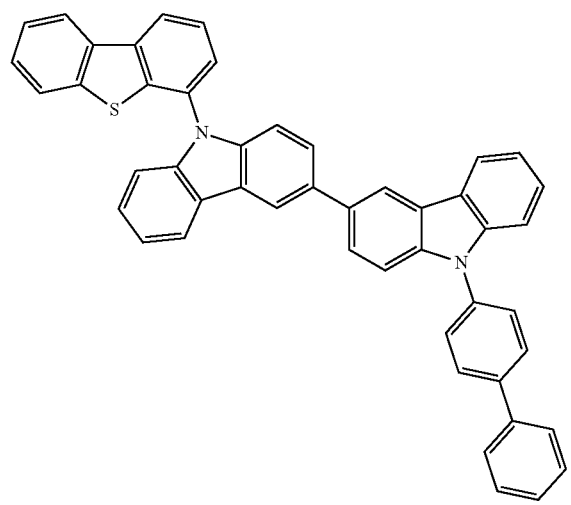

[E-49]
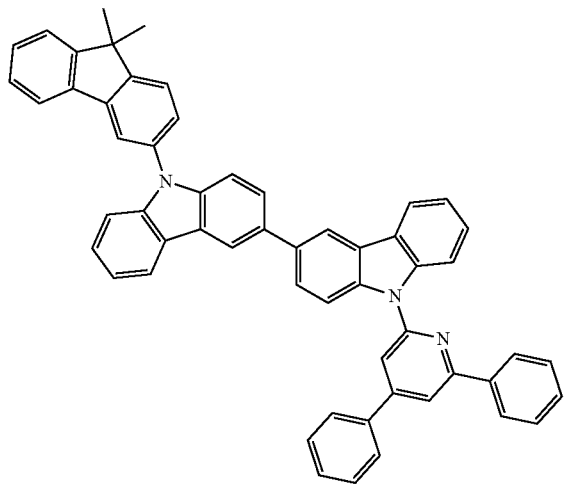
[E-50]
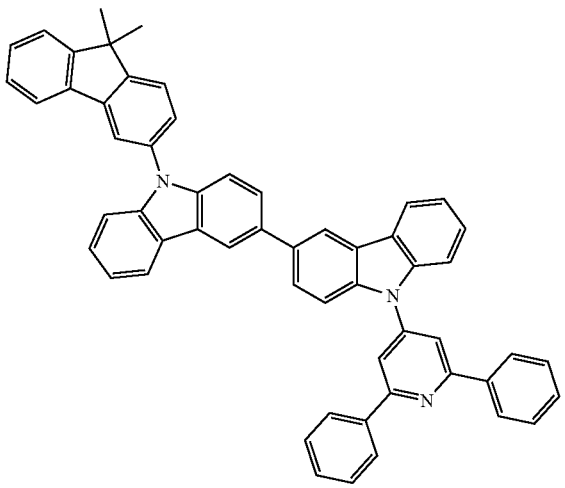
[E-51]
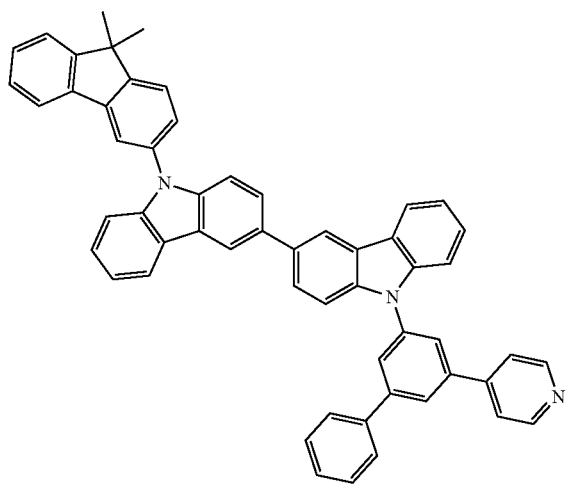
[E-52]
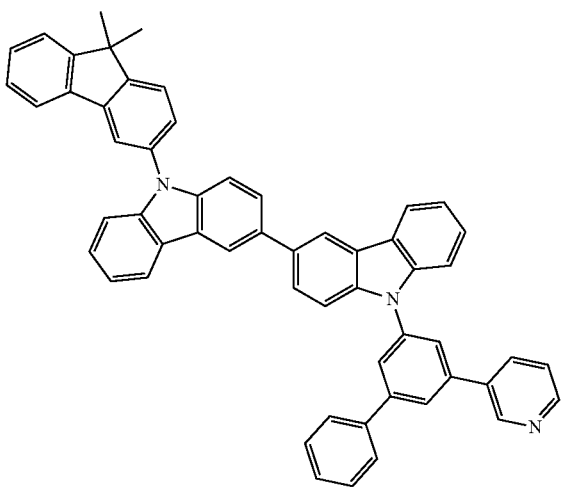
[E-53]
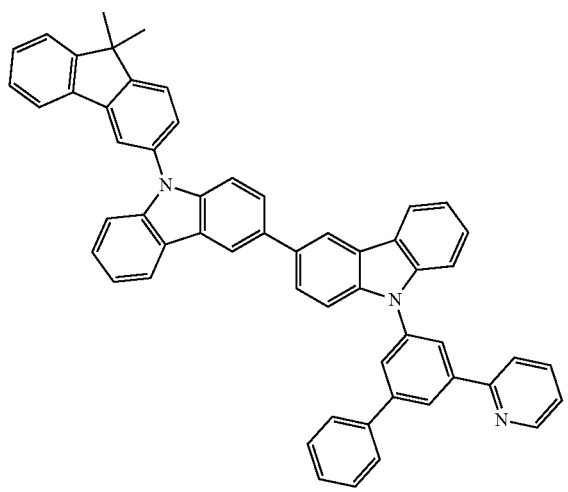
[E-54]
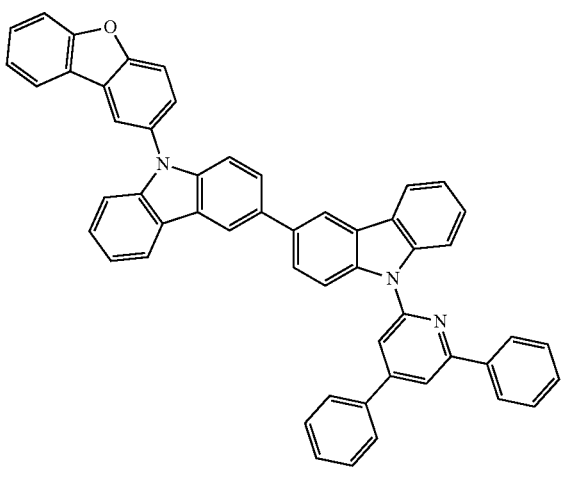

[E-55]
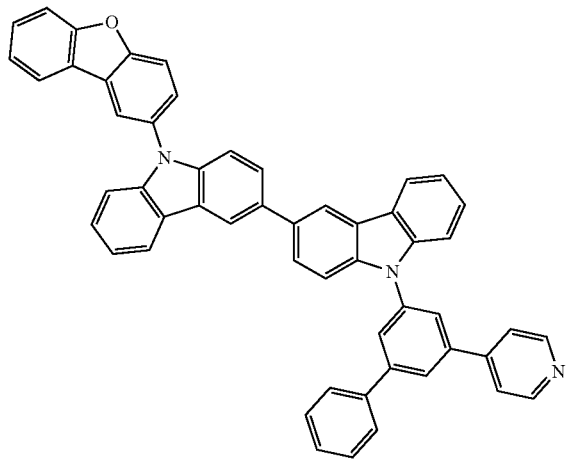
[E-56]
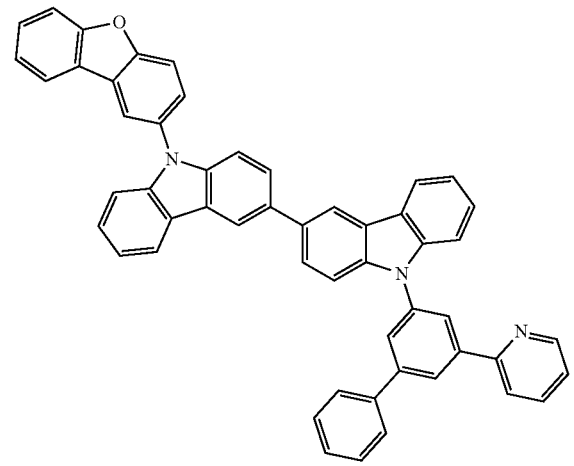
[E-57]
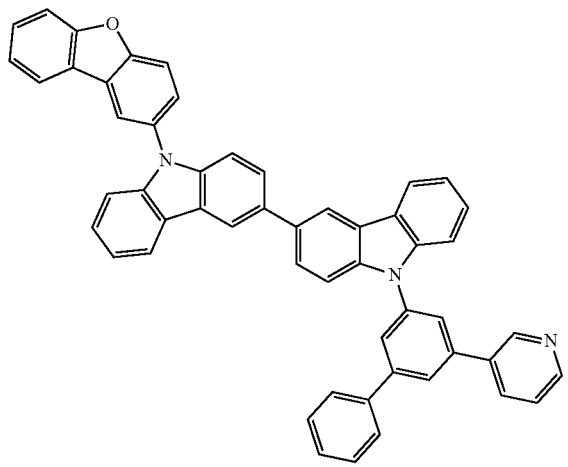
[E-58]
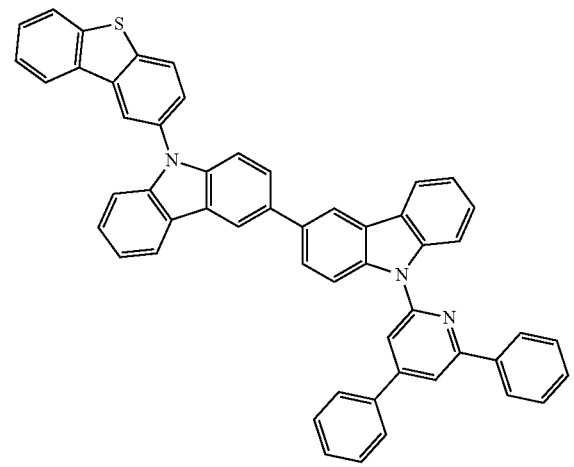
[E-59]
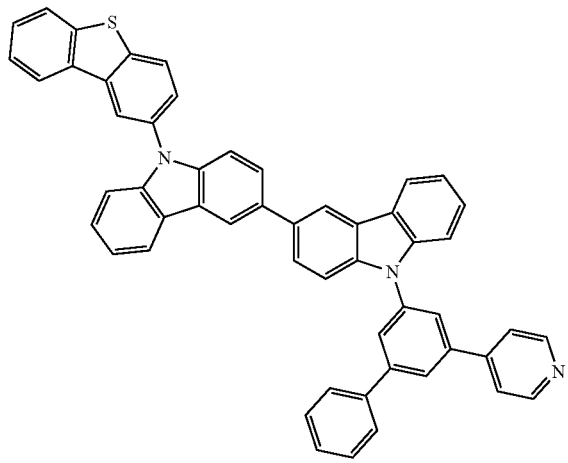
[E-60]
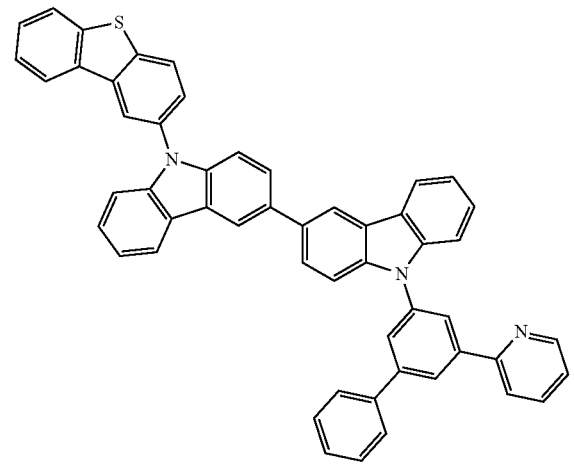

-continued
[E-61]
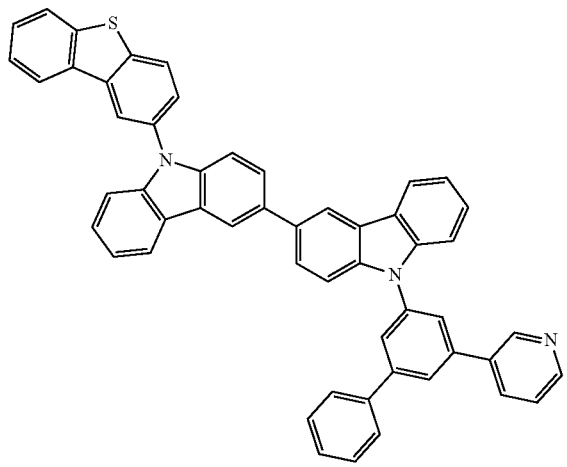
[E-62]
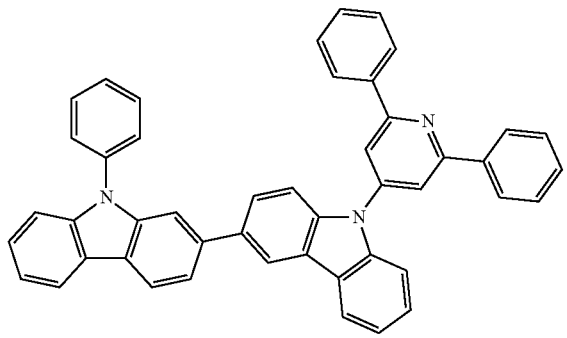
[E-63]
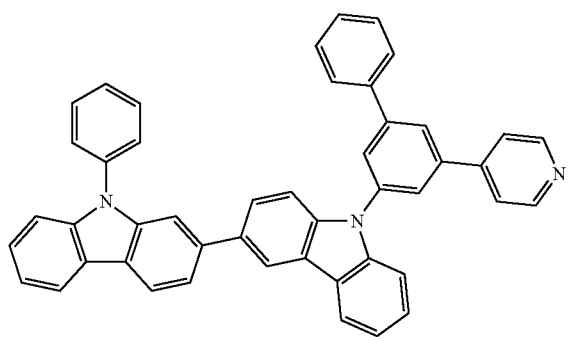
[E-64]
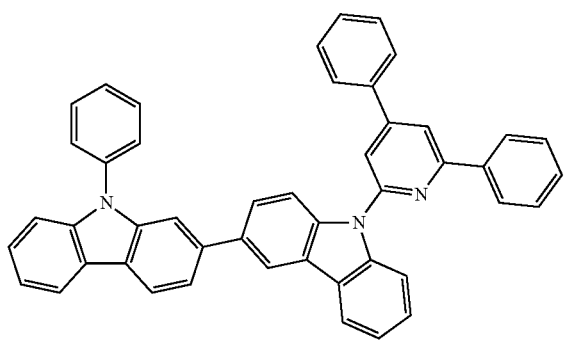
[E-65]
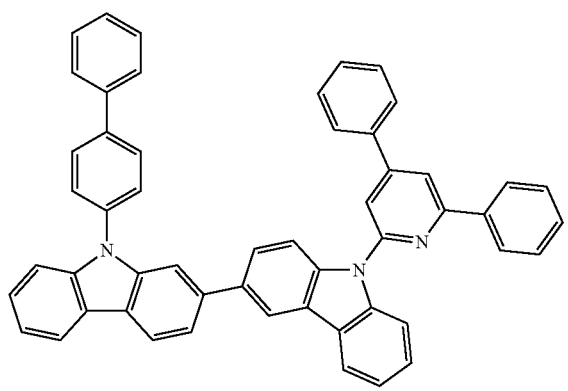
[E-66]
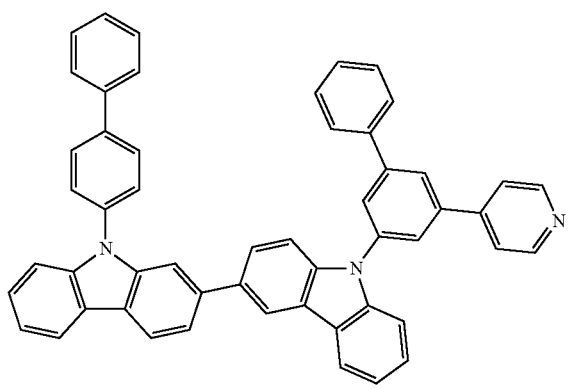
[E-67]
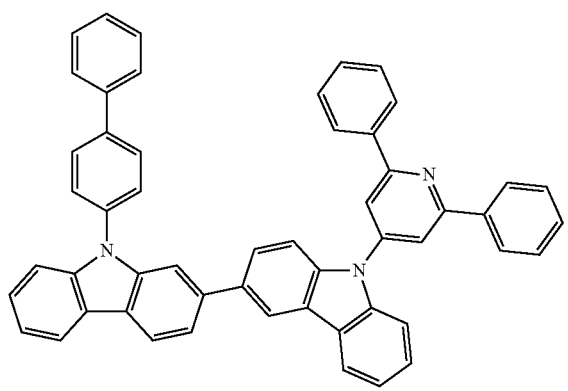
[E-68]
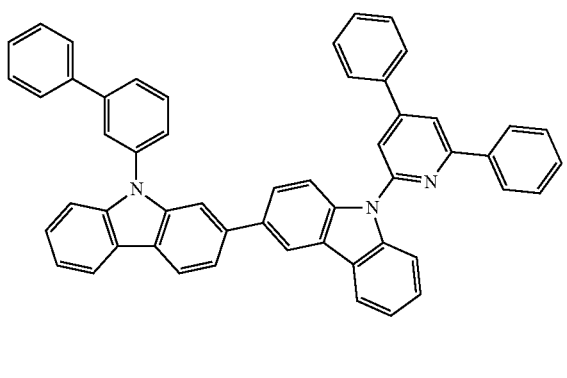

-continued
[E-69]
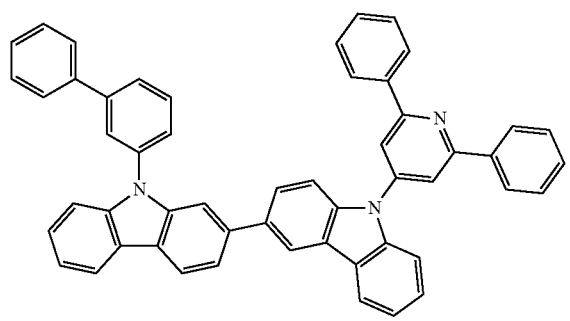
[E-70]
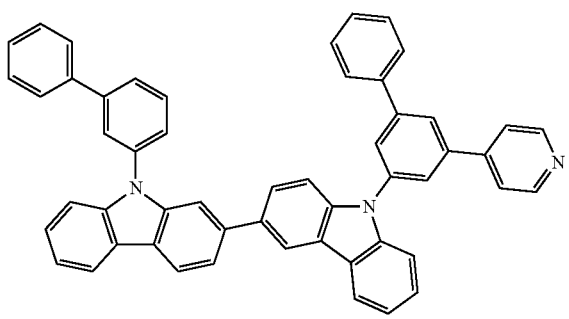
[E-71]
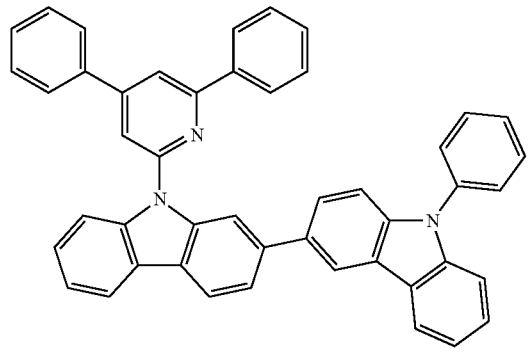
[E-72]
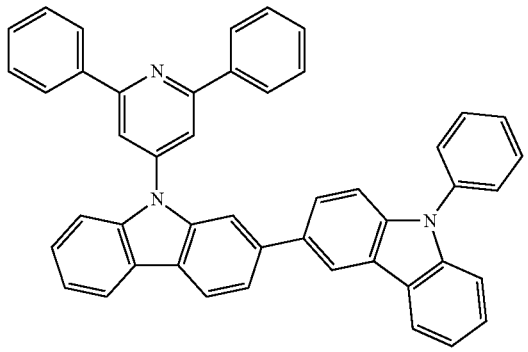
[E-73]
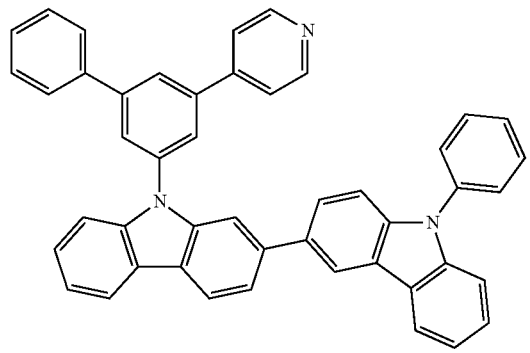
[E-74]
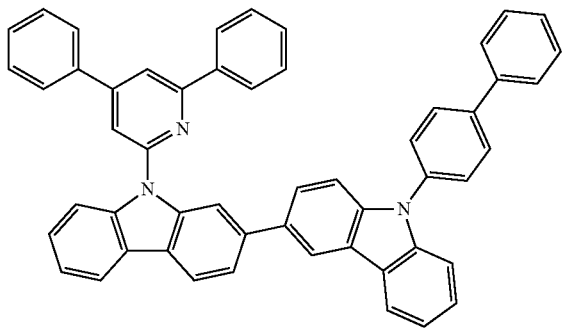
[E-75]
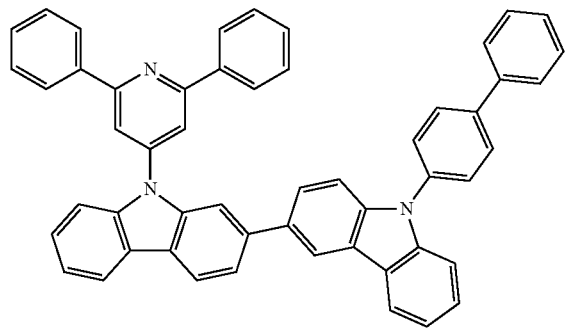
[E-76]
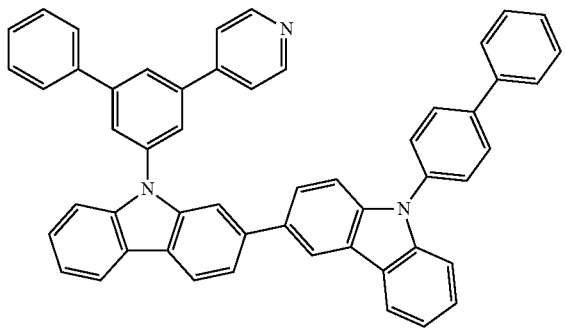

-continued
[E-77]
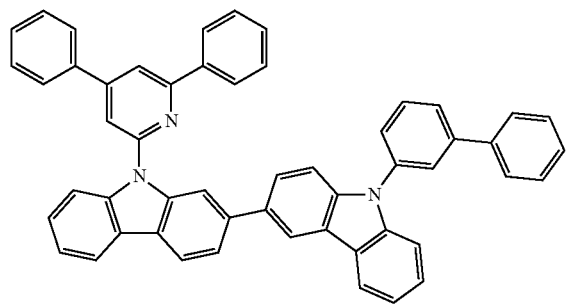
[E-78]
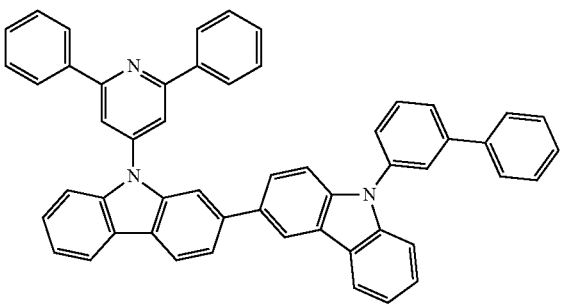
[E-79]
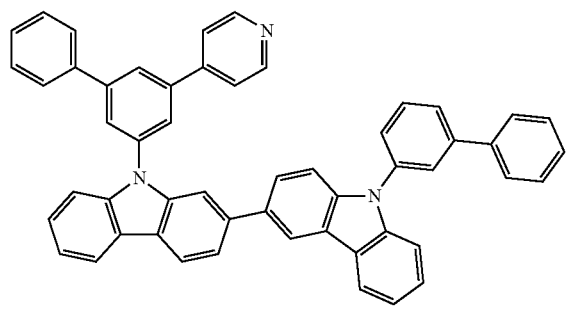
[E-80]
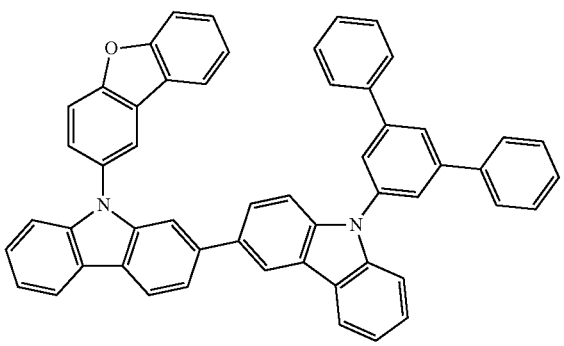
[E-81]
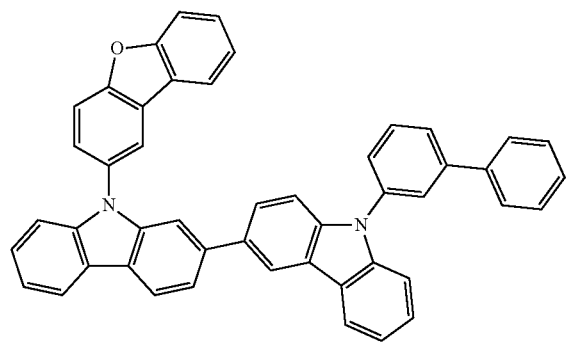
[E-82]
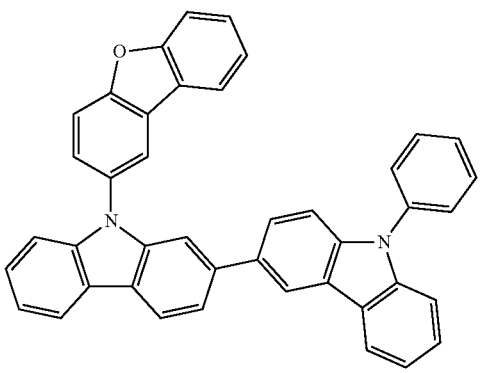
[E-83]
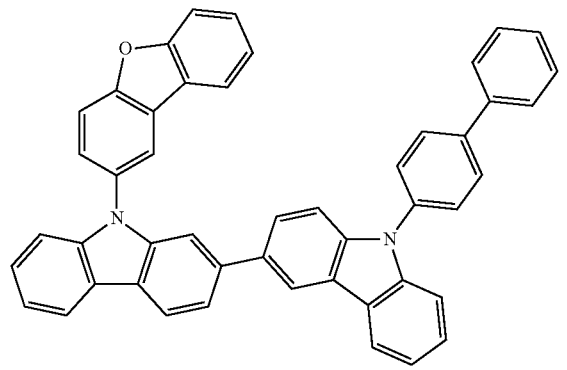
[E-84]
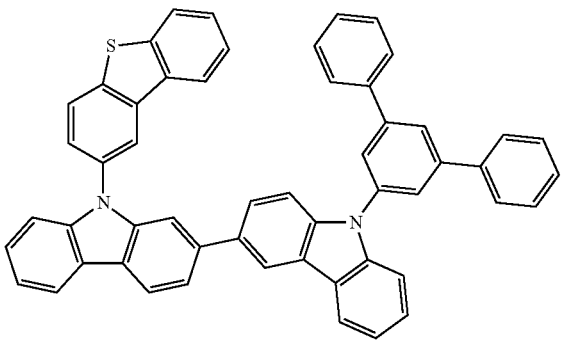

-continued
[E-85]
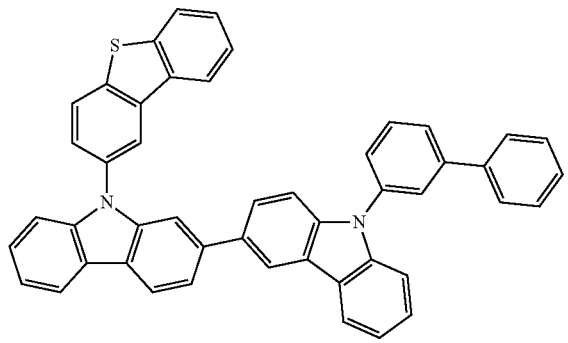
[E-86]
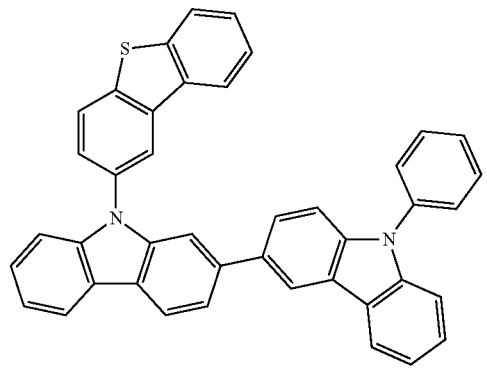
[E-87]
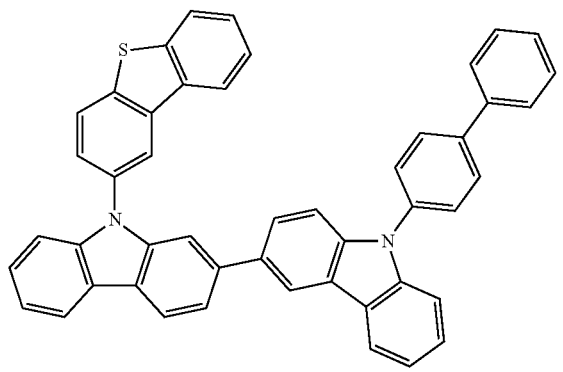
[E-88]
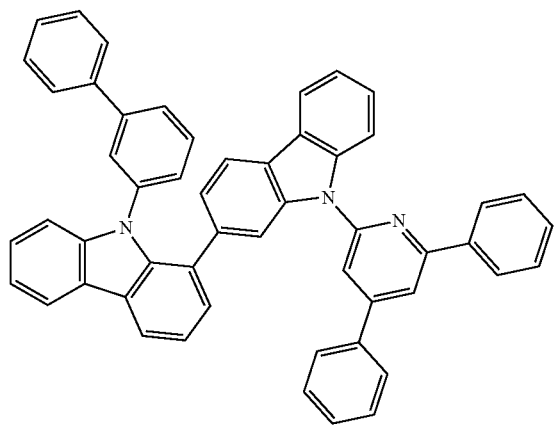
[E-89]
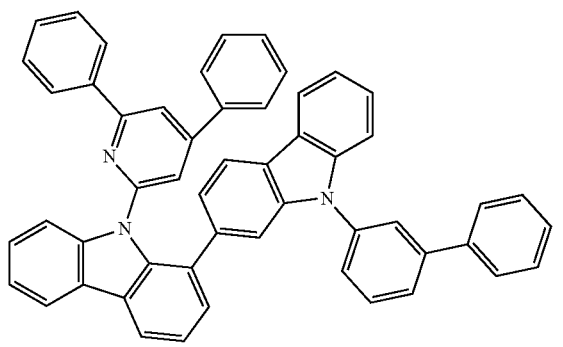
[E-90]
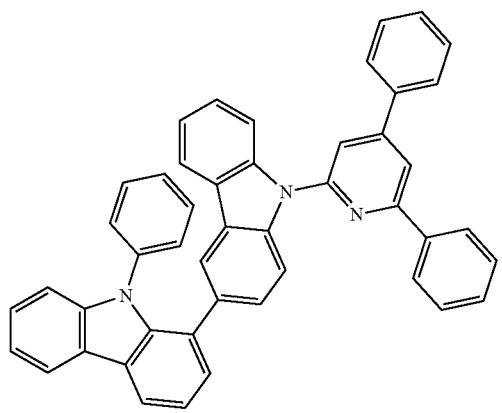
[E-91]
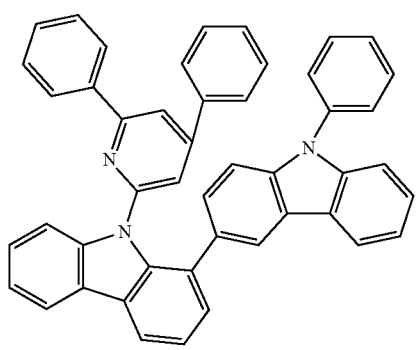
[E-92]
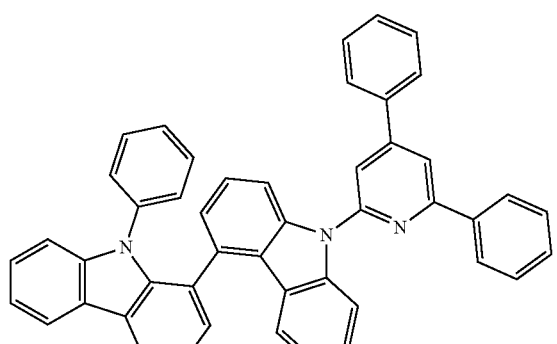

-continued
[E-93]
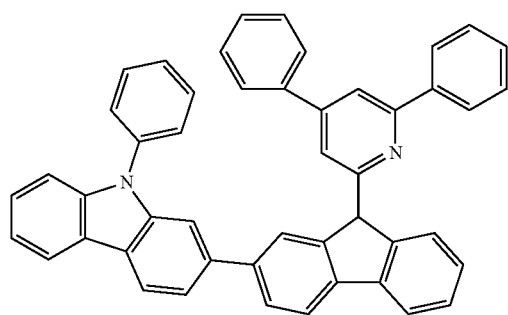
[E-94]
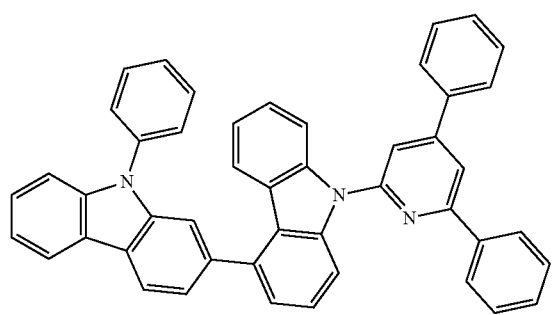
[E-95]
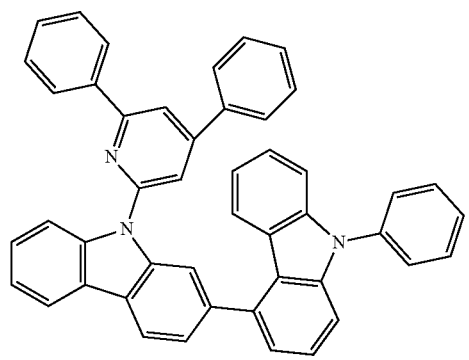
[E-96]
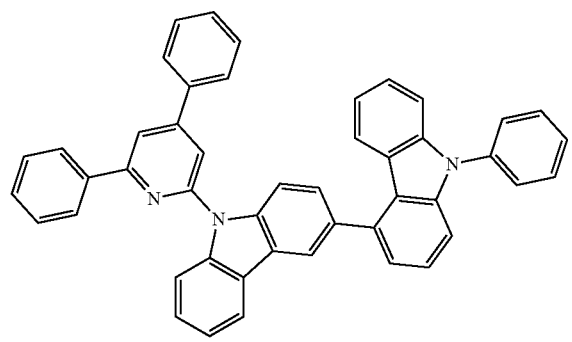
[E-97]
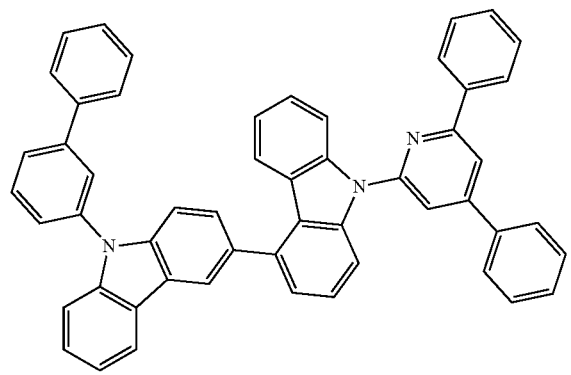
[E-98]
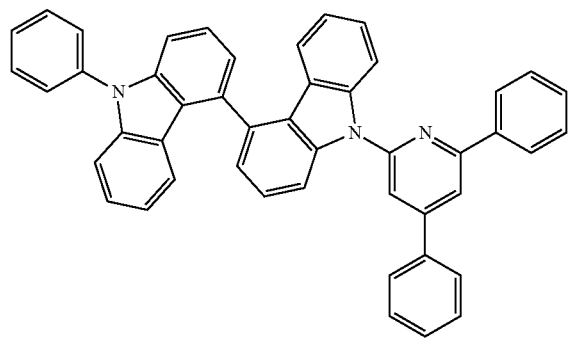

-continued
[E-99]
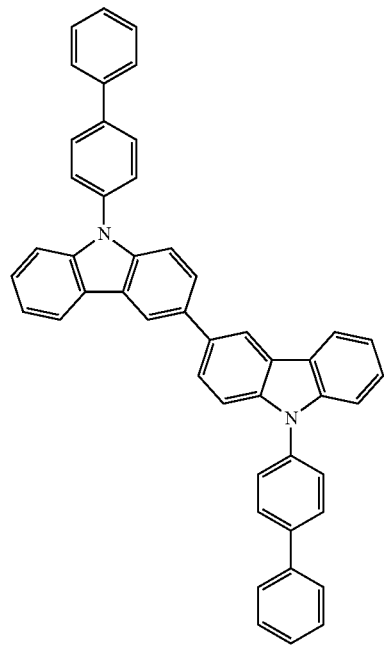
[E-100]
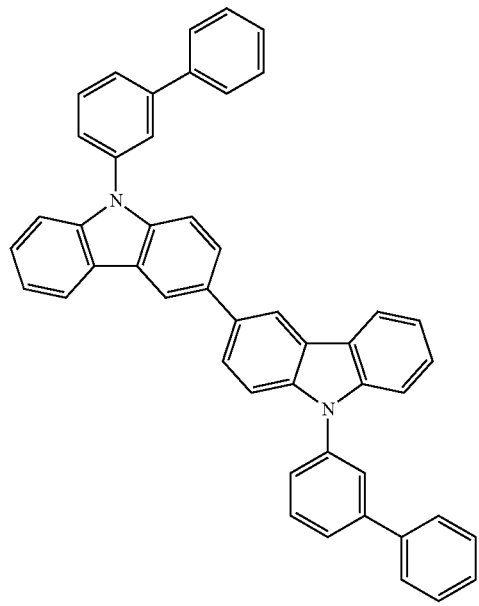
[E-101]
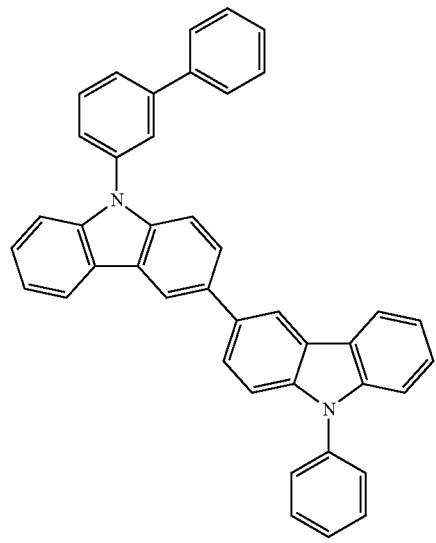
[E-102]
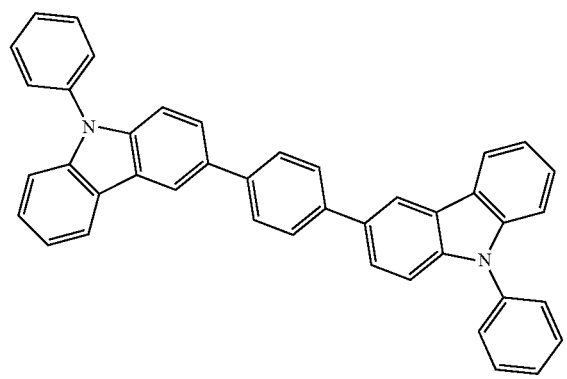

-continued
[E-103]
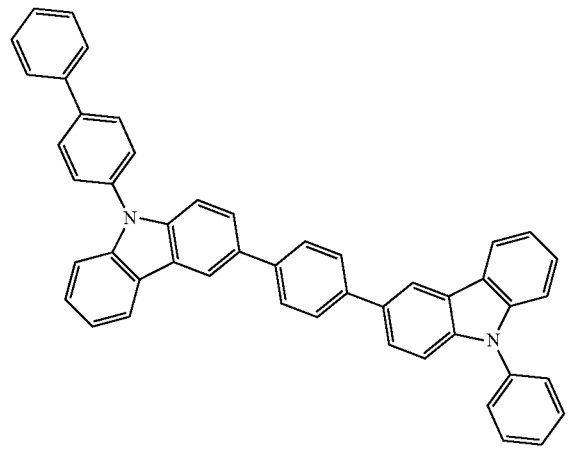
[E-104]
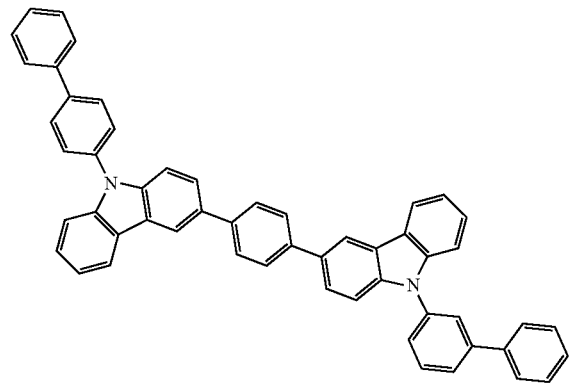
[E-105]
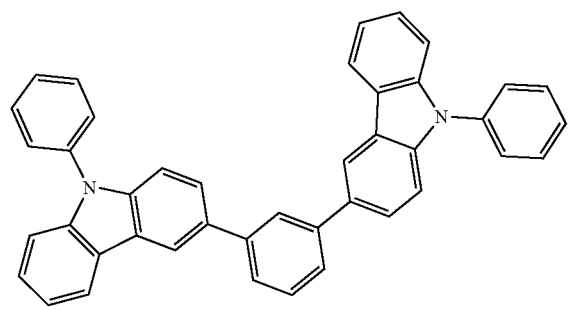
[E-106]
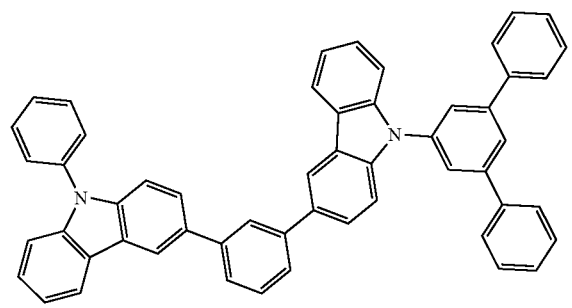
[E-107]
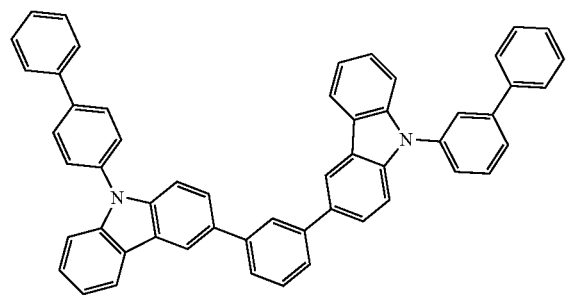
[E-108]
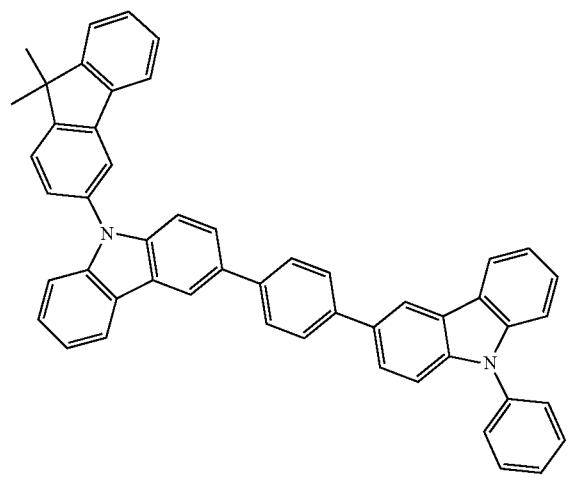

-continued
[E-109]
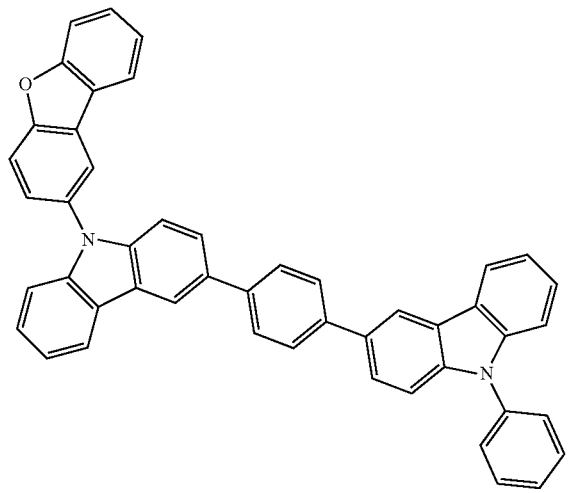
[E-110]
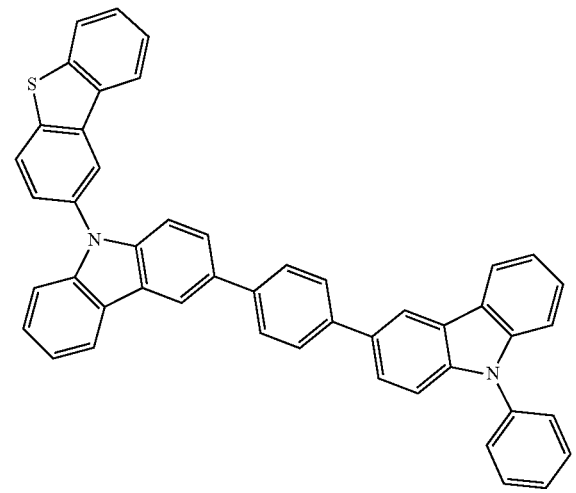
[E-111]
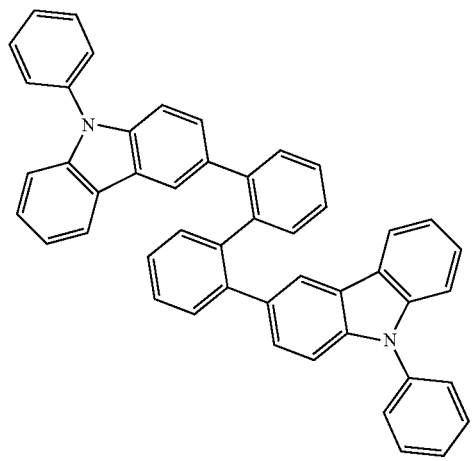
[E-112]
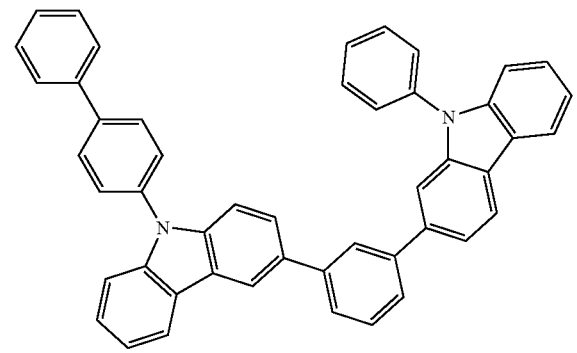
[E-113]
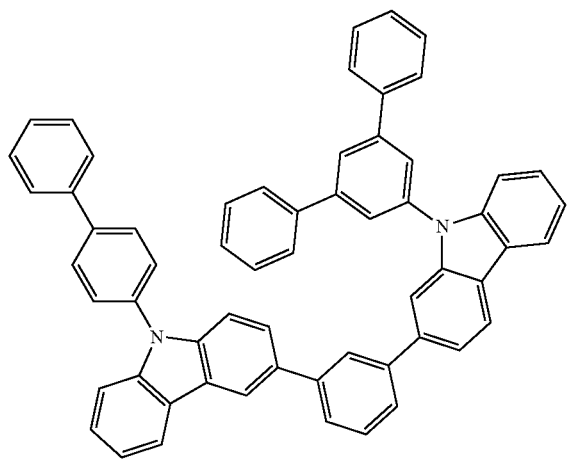
[E-114]
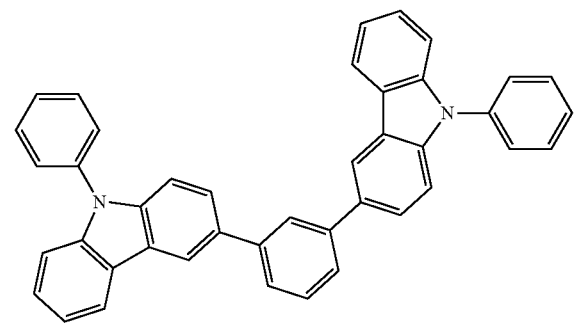

-continued
[E-115]
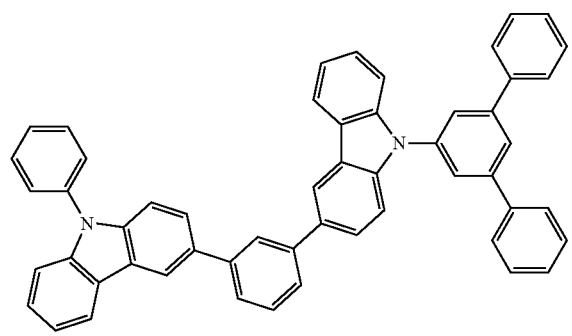
[E-116]
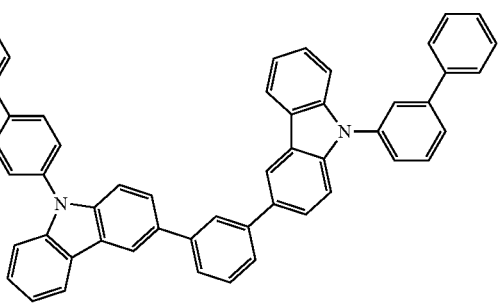
[E-117]
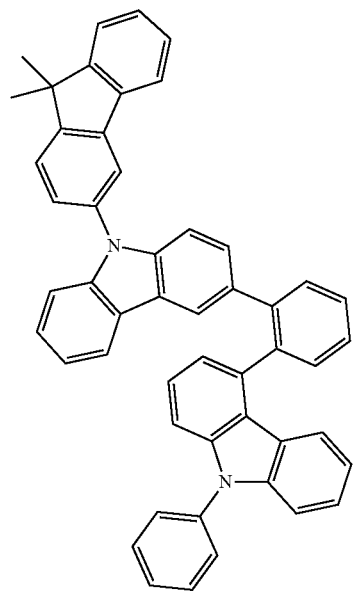
[E-118]
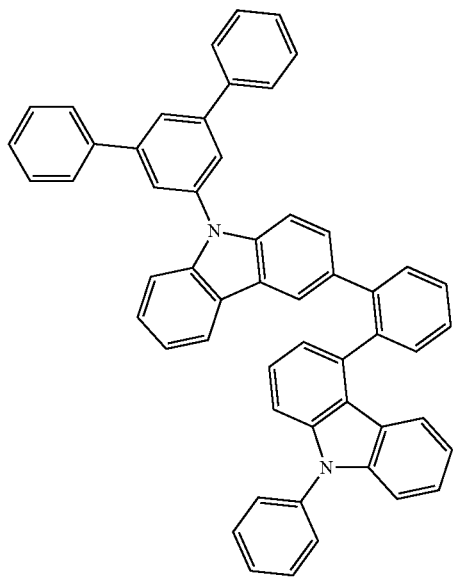
[E-119]
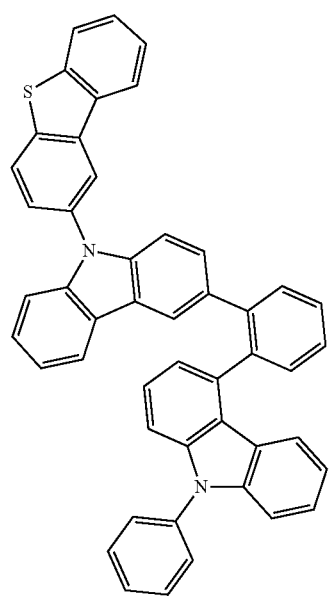
[E-120]
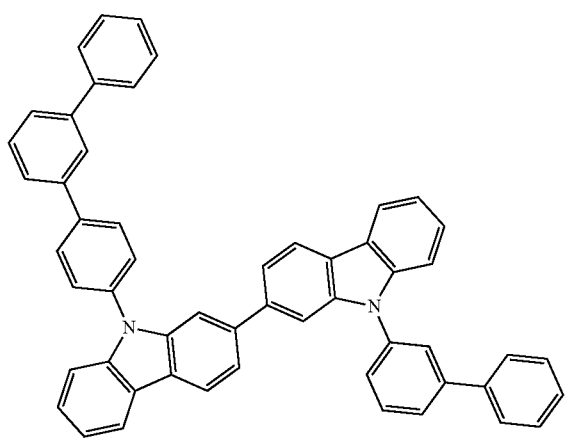

[E-121]
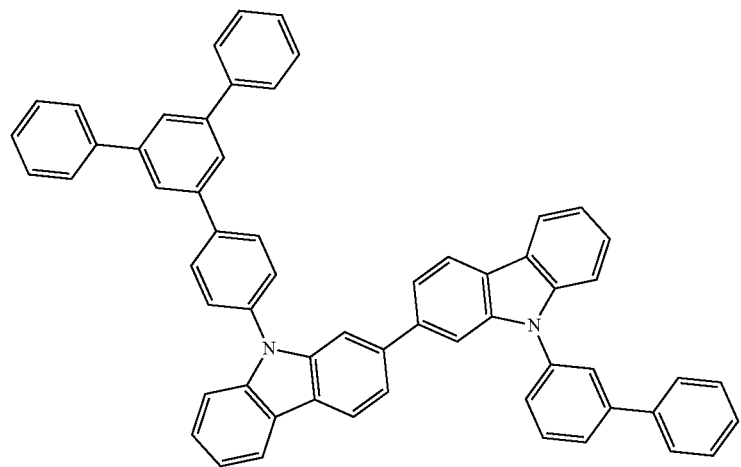
[E-122]
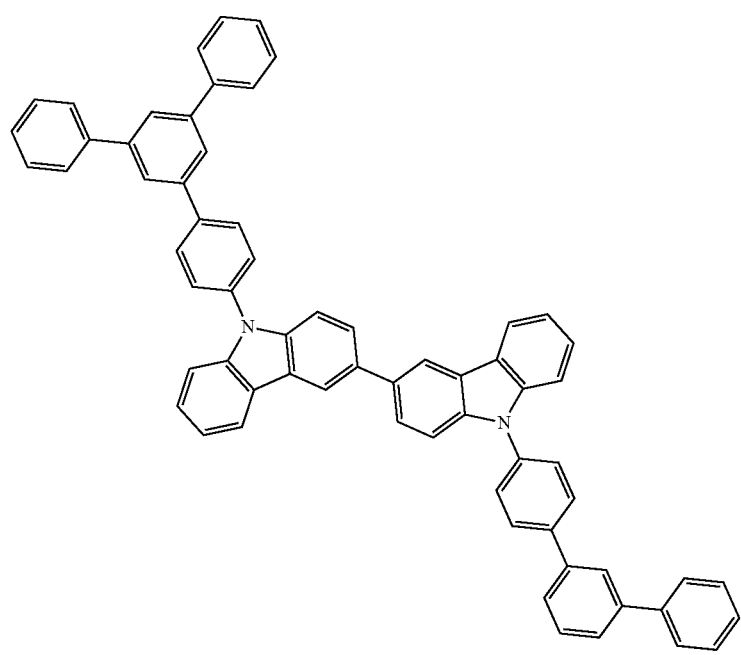

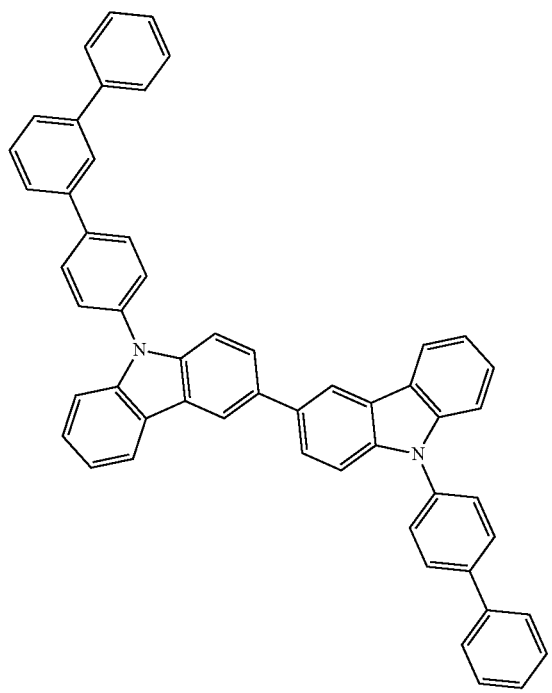
[E-123]
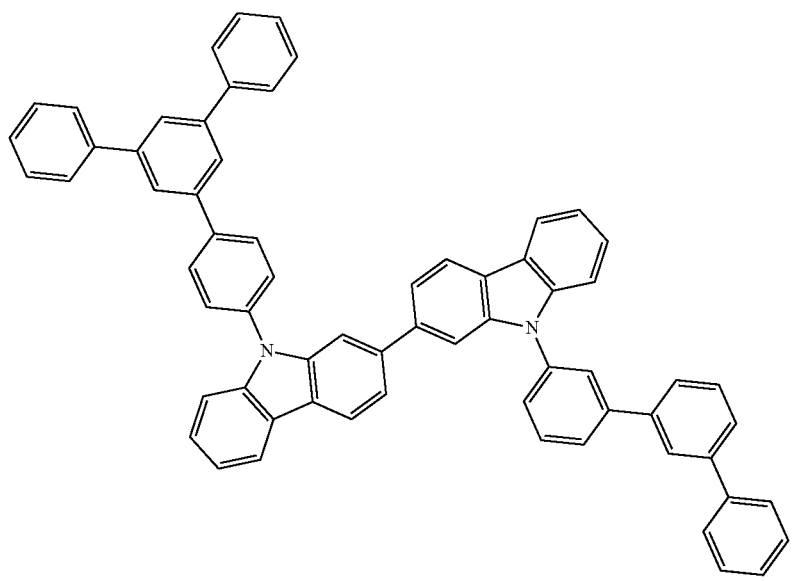
[E-124]

[E-125]
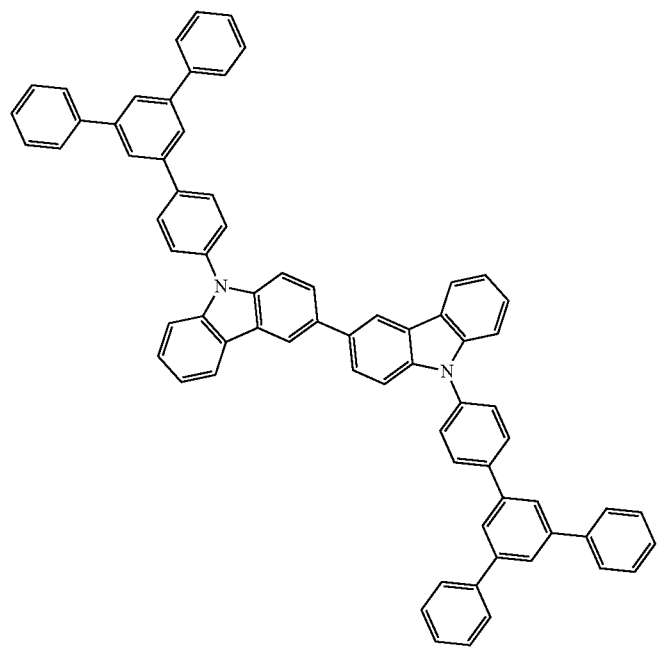
[E-126]
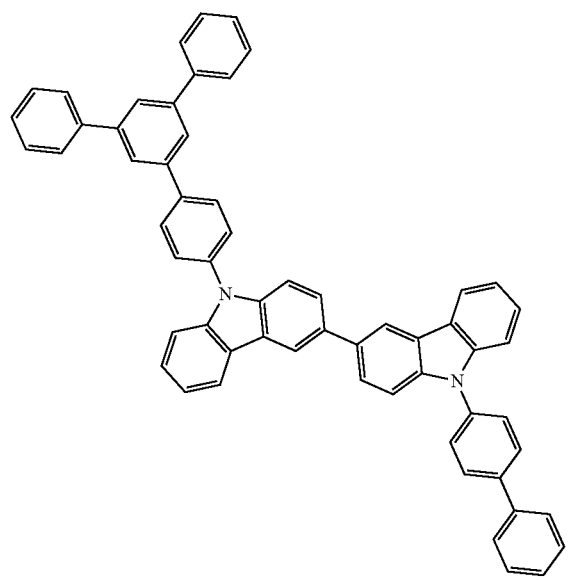
[E-127]
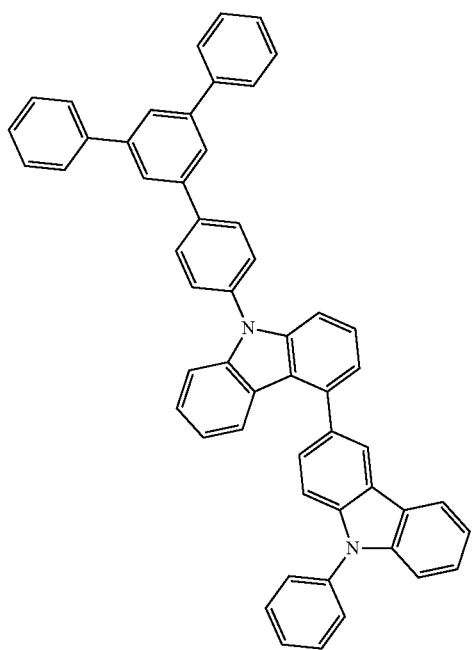

-continued
[E-128]
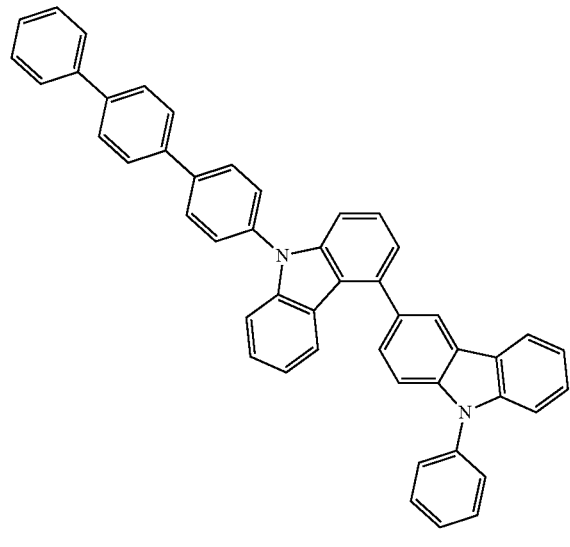
[E-129]
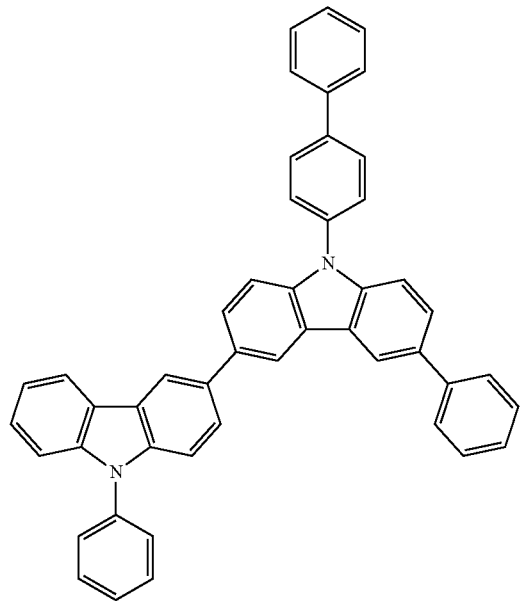
[E-130]
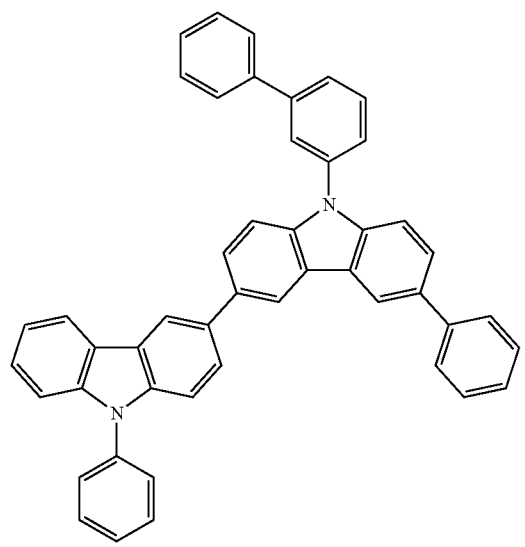
[E-131]
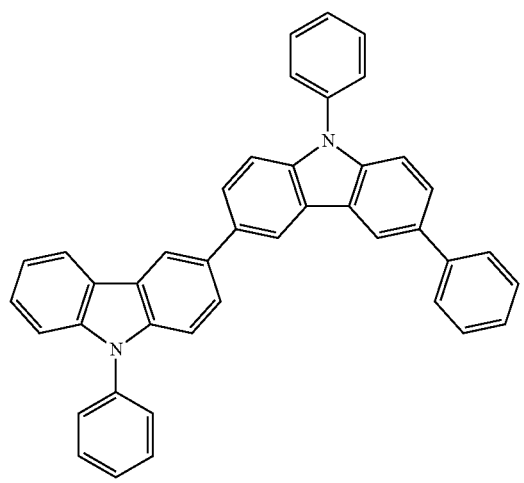

-continued
[E-132]
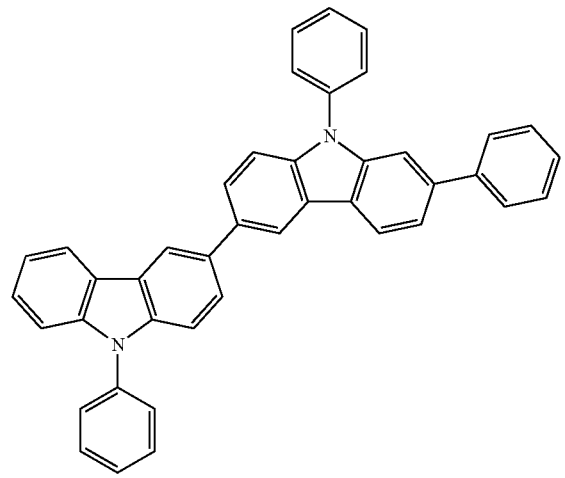
[E-133]
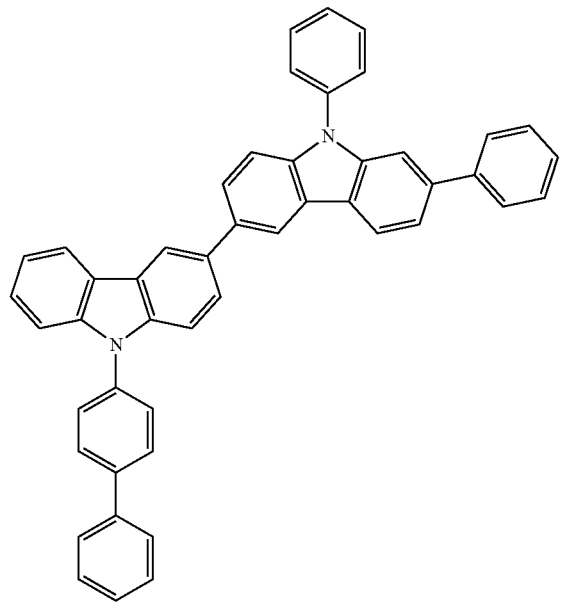
[E-134]
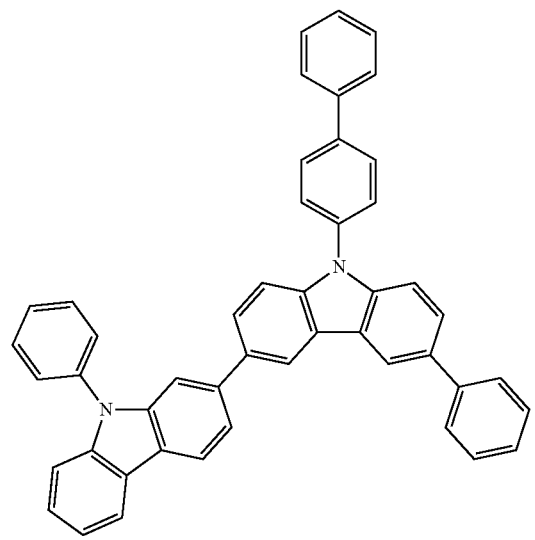
[E-135]
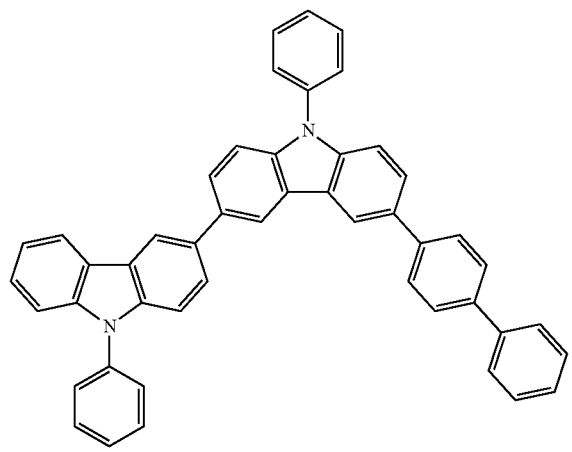

-continued
[E-136]
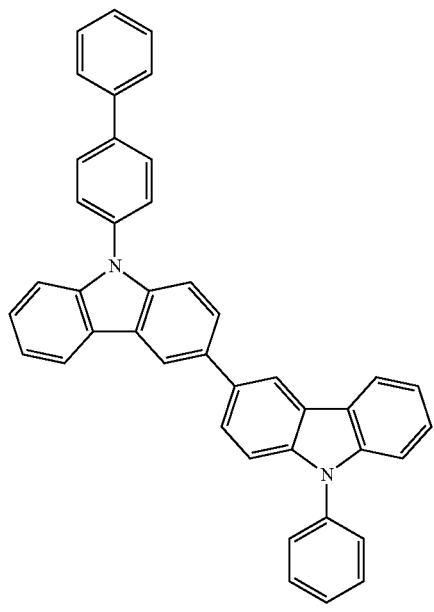
[E-137]
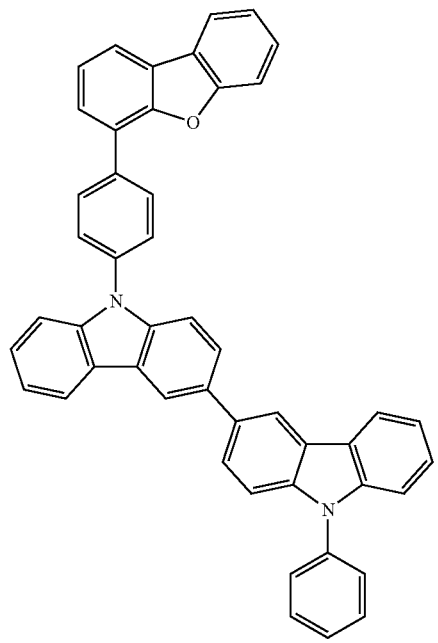
[E-138]
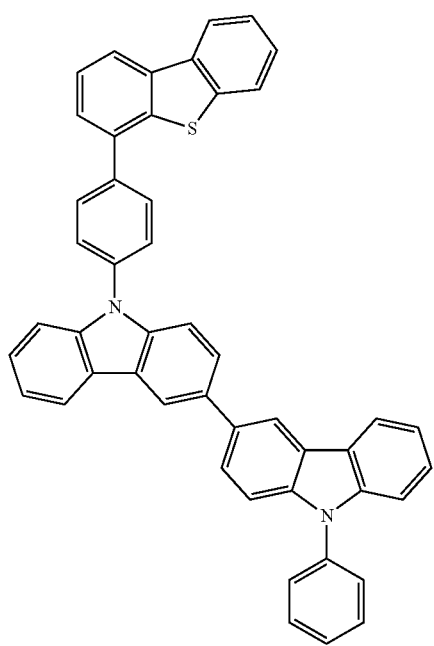

For example, the second organic compound may be an indolocarbazole compound represented by a combination of Chemical Formulae 2B-1 and 2B-2.

[Chemical Formula 2B-1]

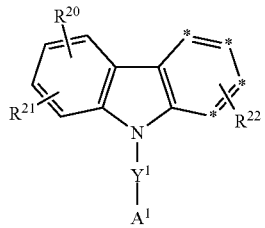

[Chemical Formula 2B-2]

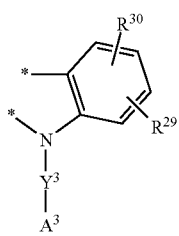

$Y^1$ and $Y^3$ may independently be a single bond, a substituted or unsubstituted C6 to C30 arylene group, a divalent substituted or unsubstituted C2 to C30 heterocyclic group, or a combination thereof, $A^1$ and $A^3$ may independently be a substituted or unsubstituted C6 to C30 aryl group, a substituted or unsubstituted C2 to C30 heterocyclic group, or a combination thereof, $R^{20}$ to $R^{22}$, $R^{29}$, and $R^{30}$ may independently be hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, two adjacent *'s in Chemical Formula 2B-1 may be combined with two *'s in Chemical Formula 2B-2, and the other two *'s of Chemical Formula 2B-1 may be each $CR^c$ and $CR^d$, wherein $R^c$ and $R^d$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof.

For example, $Y^1$ and $Y^3$ of Chemical Formula 2B-1 and 2B-2 may independently be a single bond, a substituted or unsubstituted phenylene group or a substituted or unsubstituted biphenylene group.

For example, $A^1$ and $A^3$ of Chemical Formula 2B-1 and 2B-2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

For example, the indolocarbazole compound represented by a combination of Chemical Formulae 2B-1 and 2B-2 may be represented by one of Chemical Formulae 2B-a to 2B-e.

[Chemical Formula 2B-a]

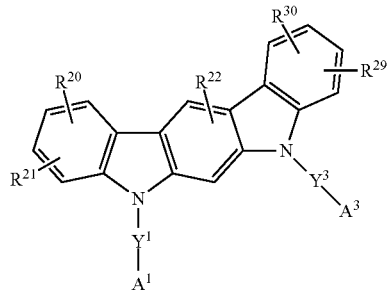

[Chemical Formula 2B-b]

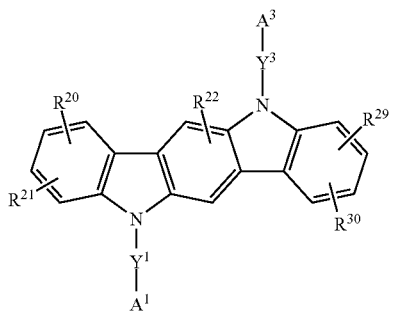

[Chemical Formula 2B-c]

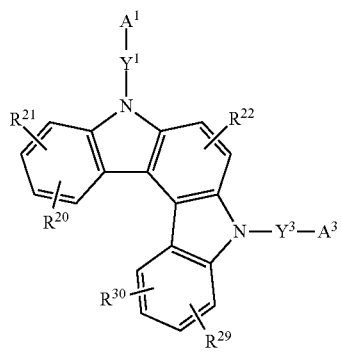

[Chemical Formula 2B-d]

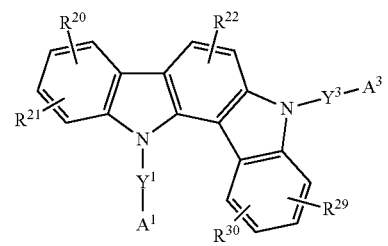

[Chemical Formula 2B-e]

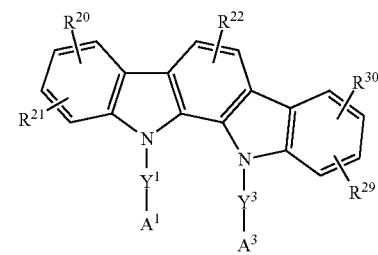

In Chemical Formulae 2B-a to 2B-e, $Y^1$, $Y^3$, $A^1$, $A^3$, $R^{20}$ to $R^{22}$, $R^{29}$, and $R^{30}$ are the same as described above.

For example, the compound represented by the combination of Chemical Formulae 2B-1 and 2B-2 may be, for example, one of the compounds listed in Group 5, but is not limited thereto.
[Group 5]
[F-1]
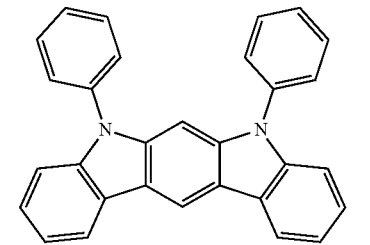
[F-2]
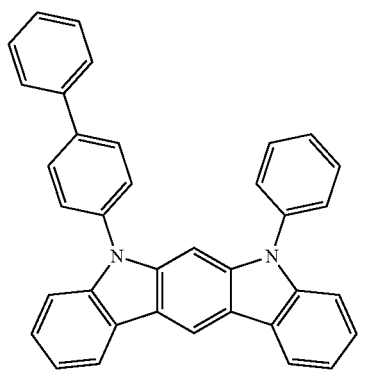
[F-3]
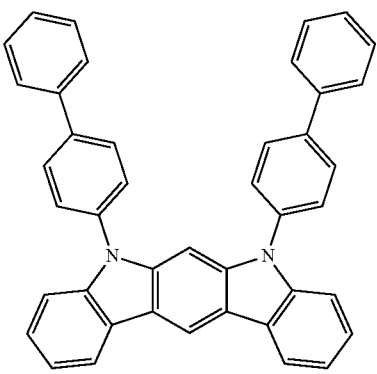
[F-4]
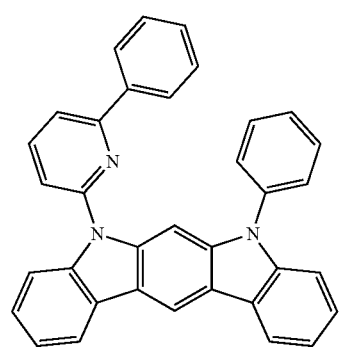
[F-5]
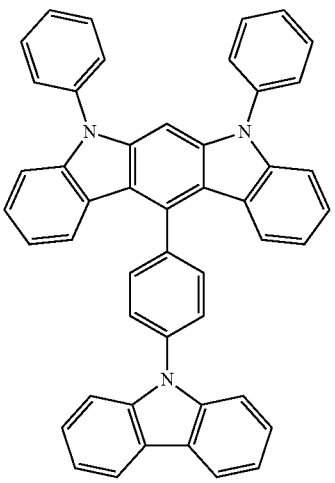
[F-6]
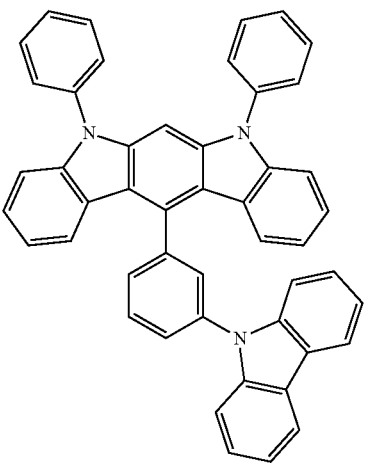
[F-7]
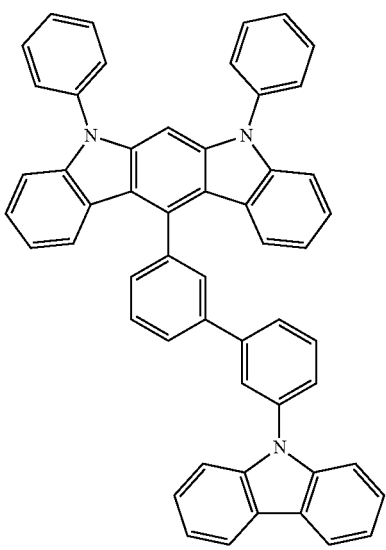

[F-8]
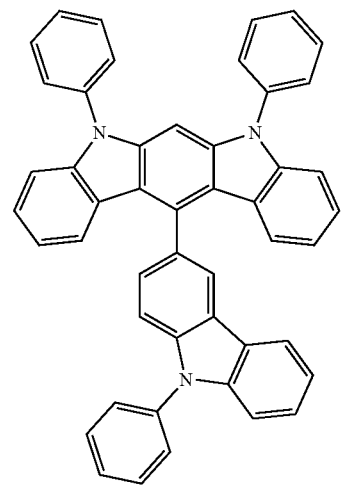
[F-9]
[F-10]
[F-11]
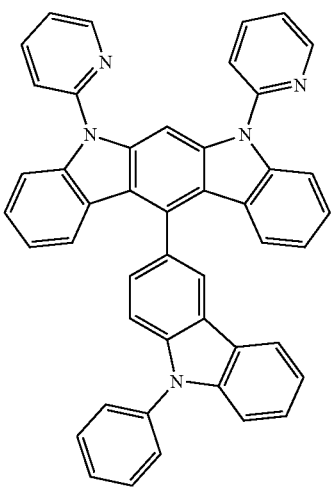
[F-12]
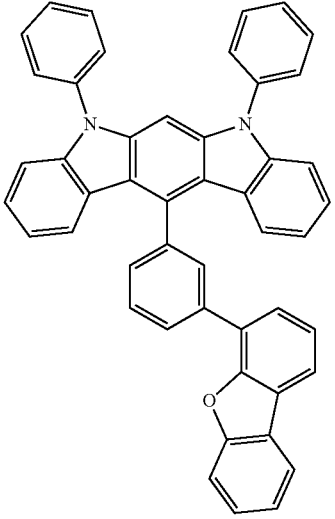
[F-13]
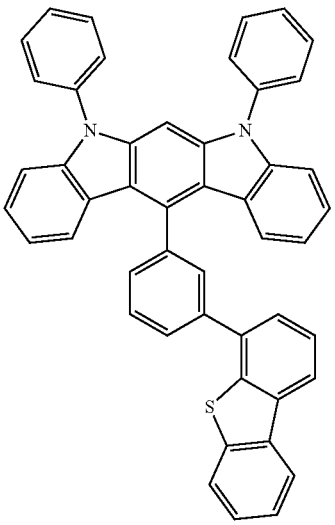

[F-14]
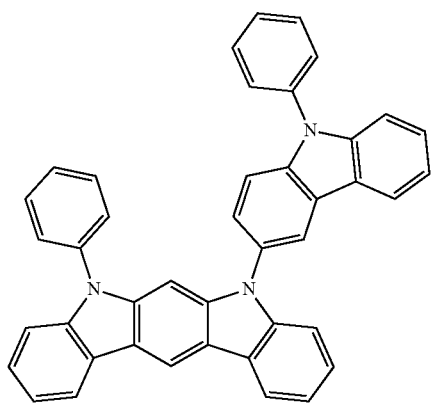
[F-15]
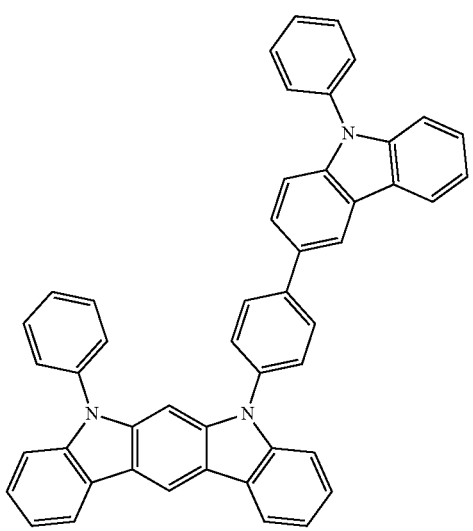
[F-16]
[F-17]
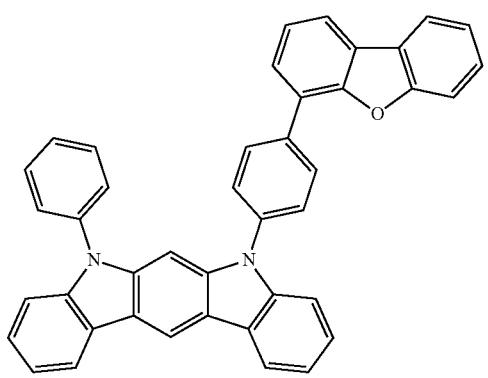
[F-18]
[F-19]
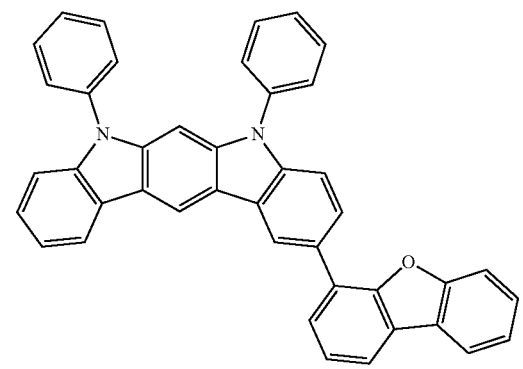

[F-20]
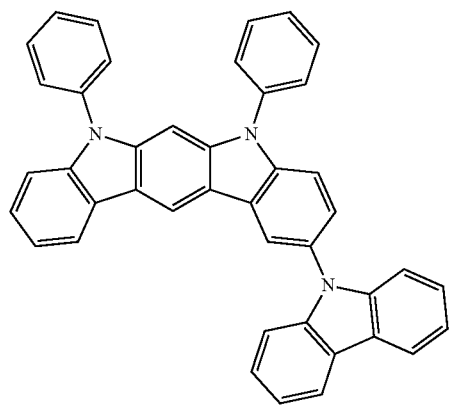
[F-21]
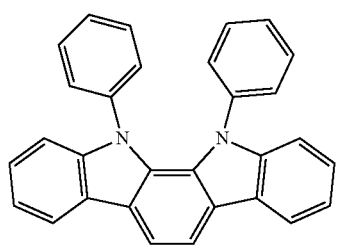
[F-22]
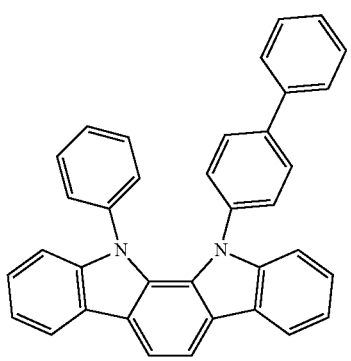
[F-23]
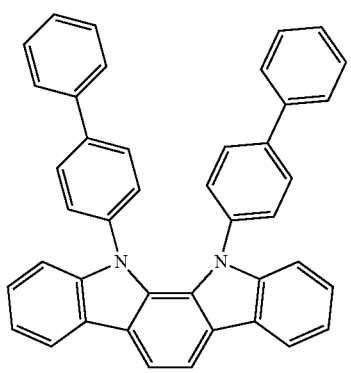
[F-24]
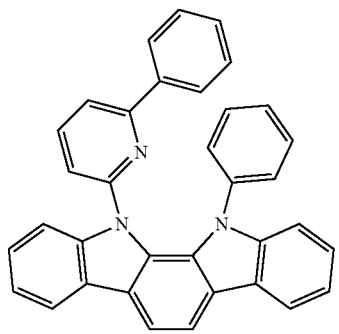
[F-25]
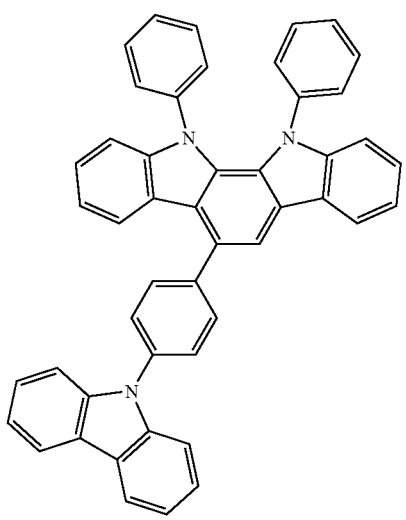
[F-26]
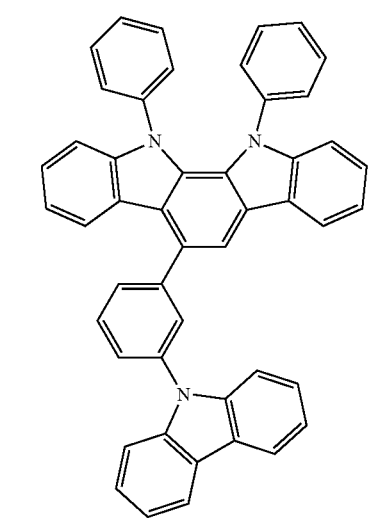

[F-27]
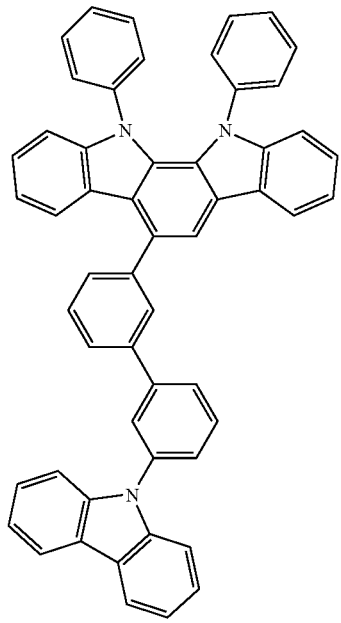
[F-28]
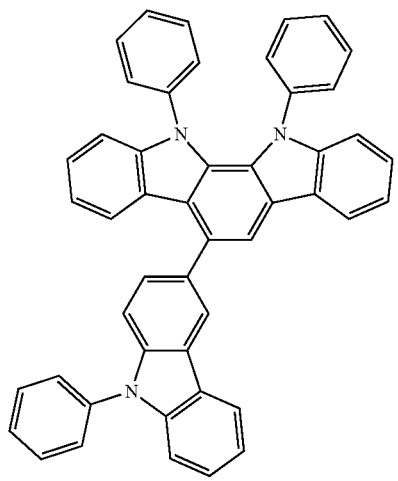
[F-29]
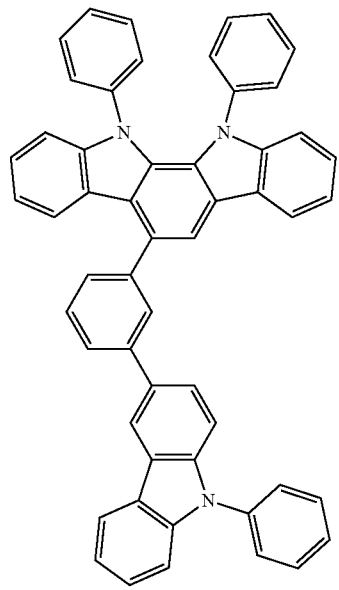
[F-30]
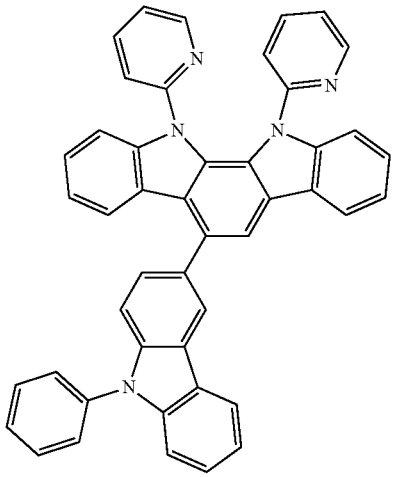
[F-31]

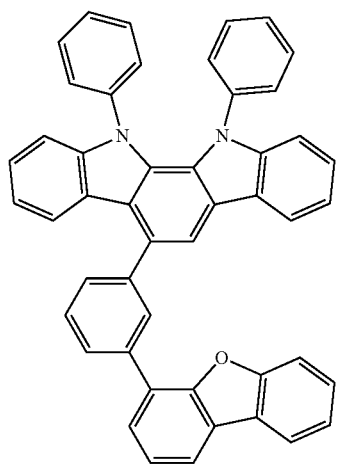
[F-32]
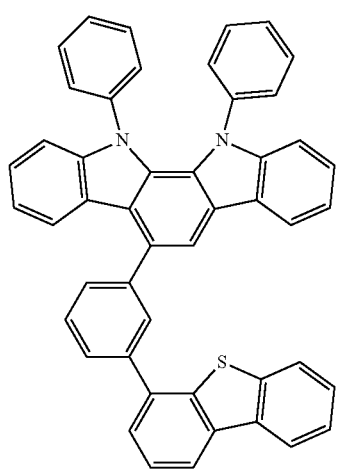
[F-33]
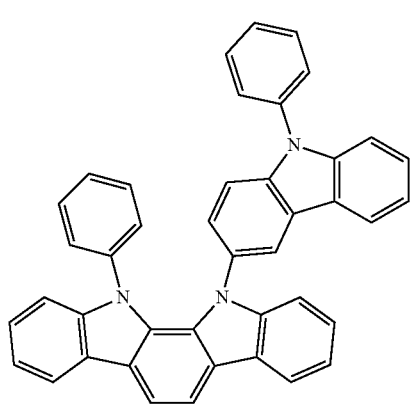
[F-34]
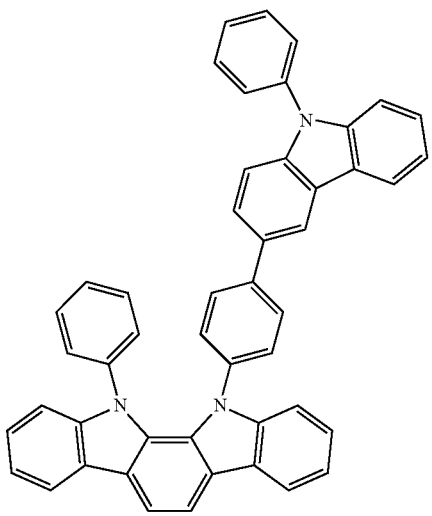
[F-35]
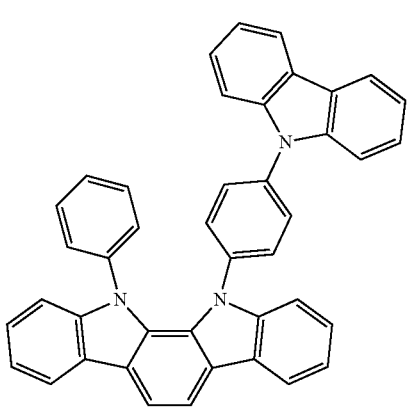
[F-36]
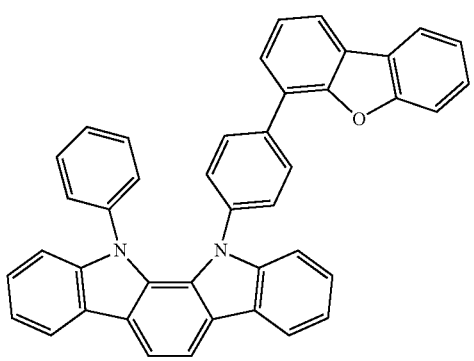
[F-37]

-continued
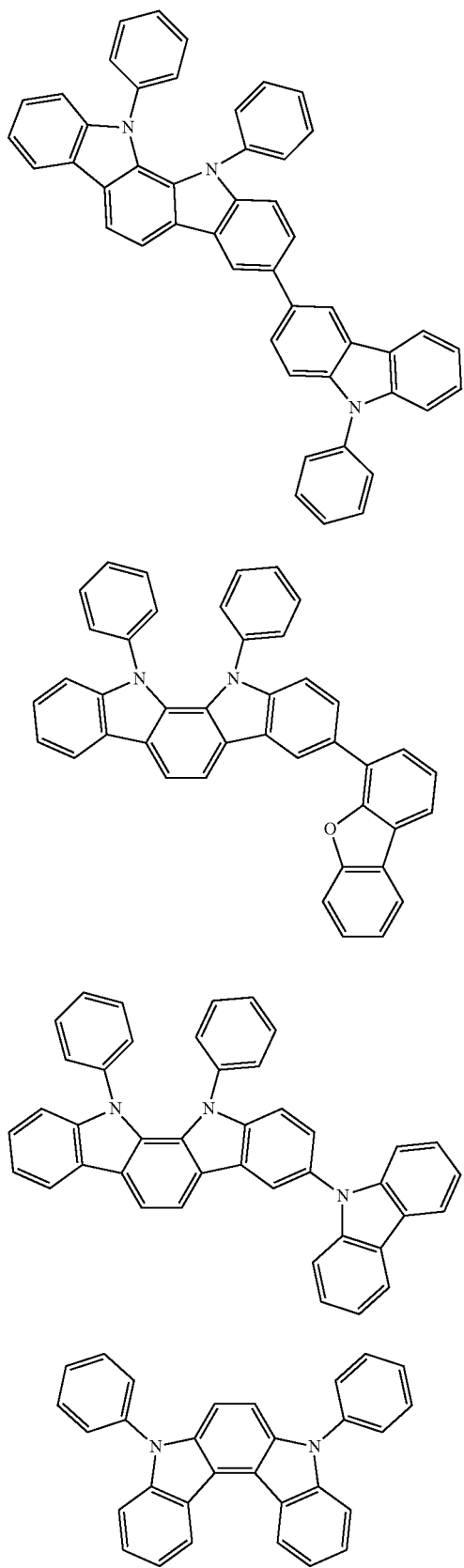
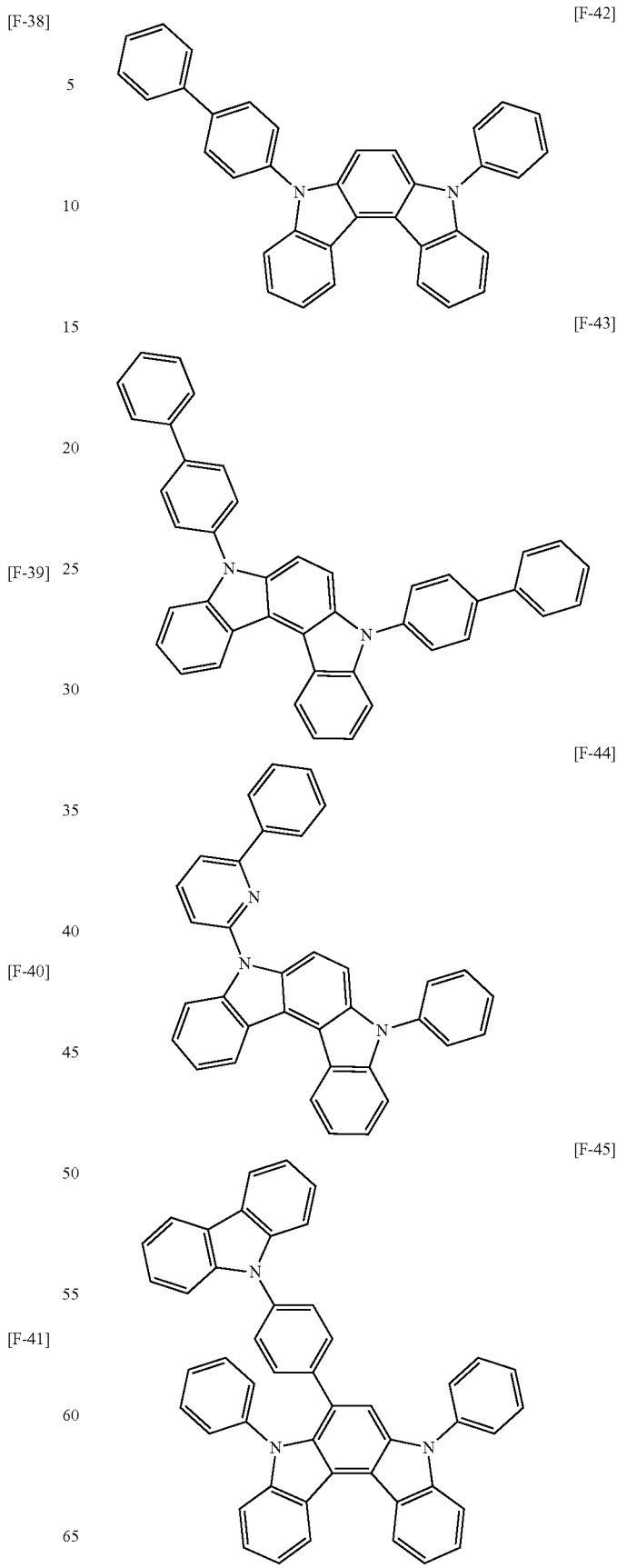

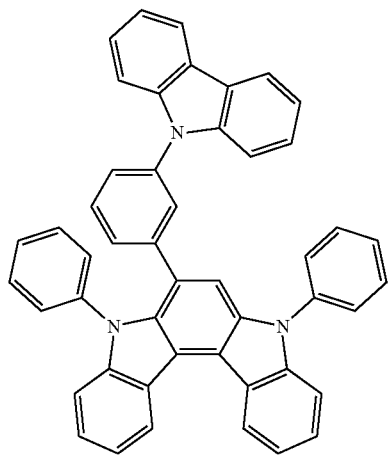
[F-46]
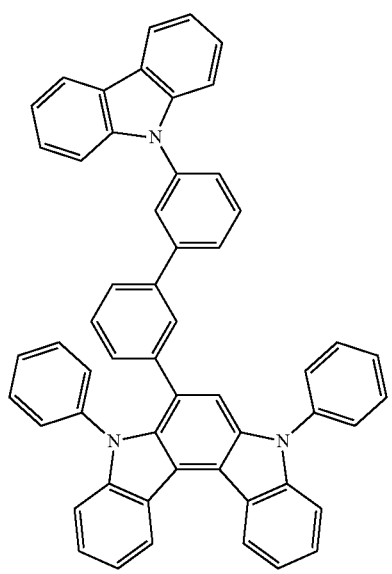
[F-47]
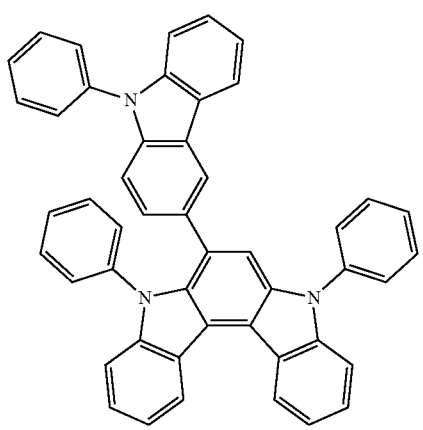
[F-48]
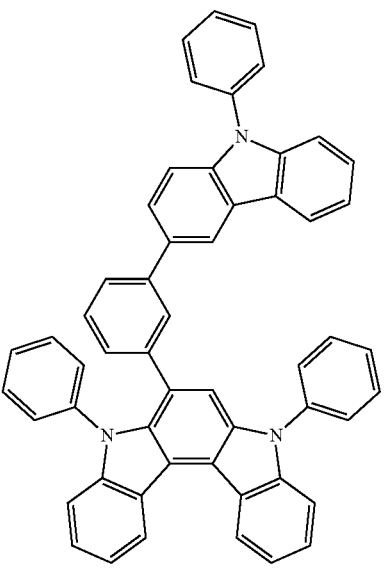
[F-49]
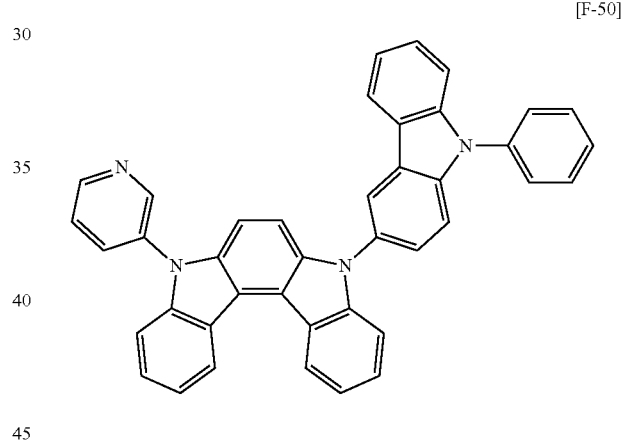
[F-50]
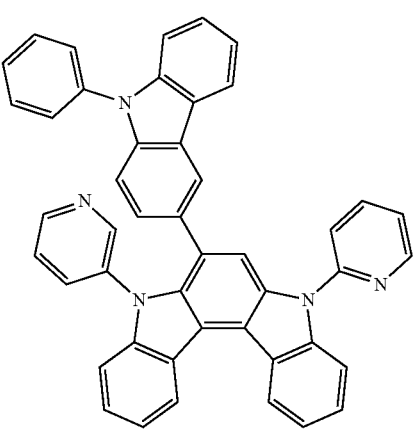
[F-51]

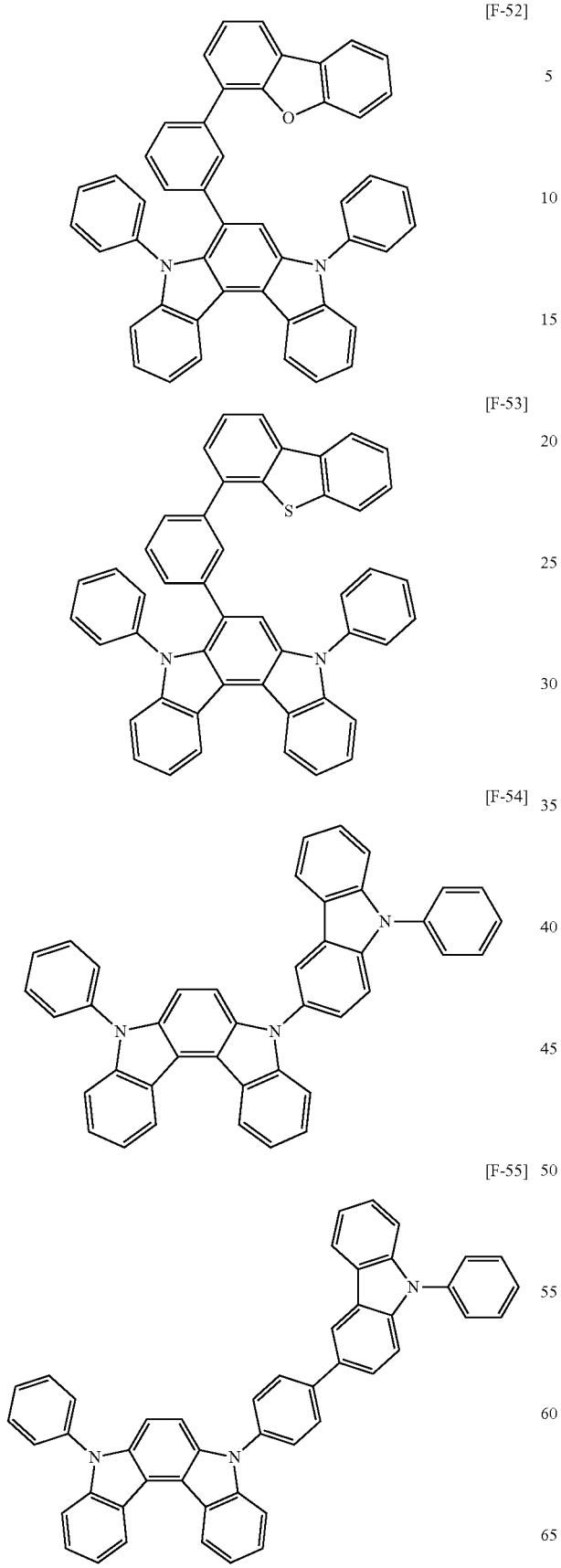
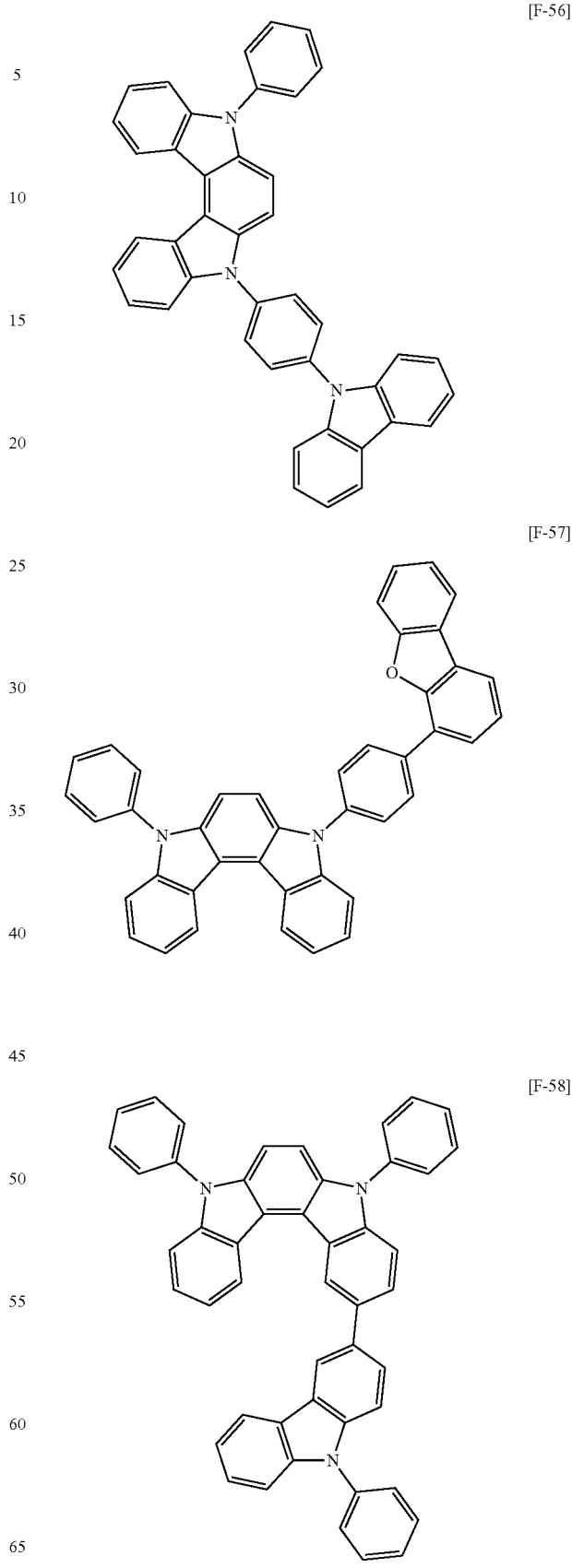

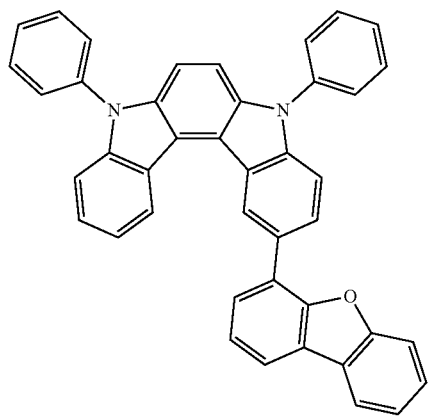 [F-59]
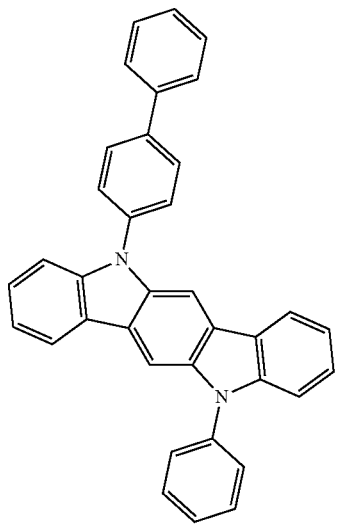 [F-62]
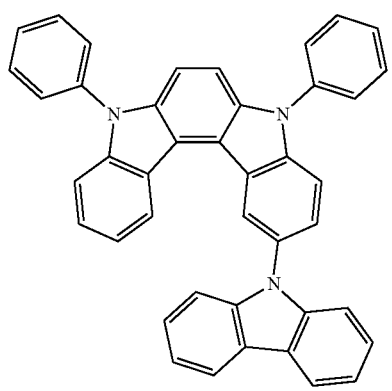 [F-60]
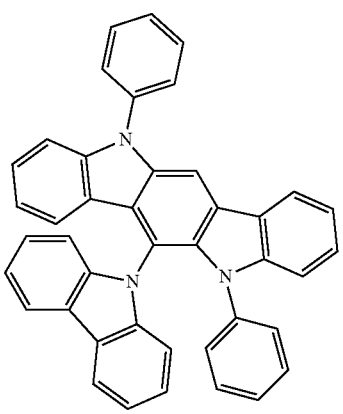 [F-63]
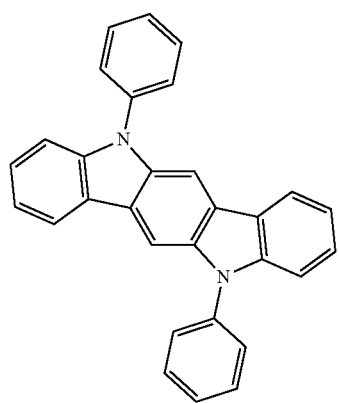 [F-61]
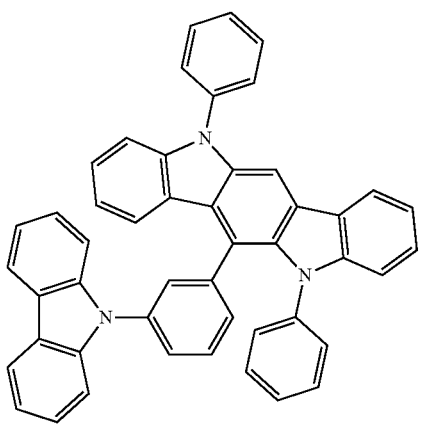 [F-64]

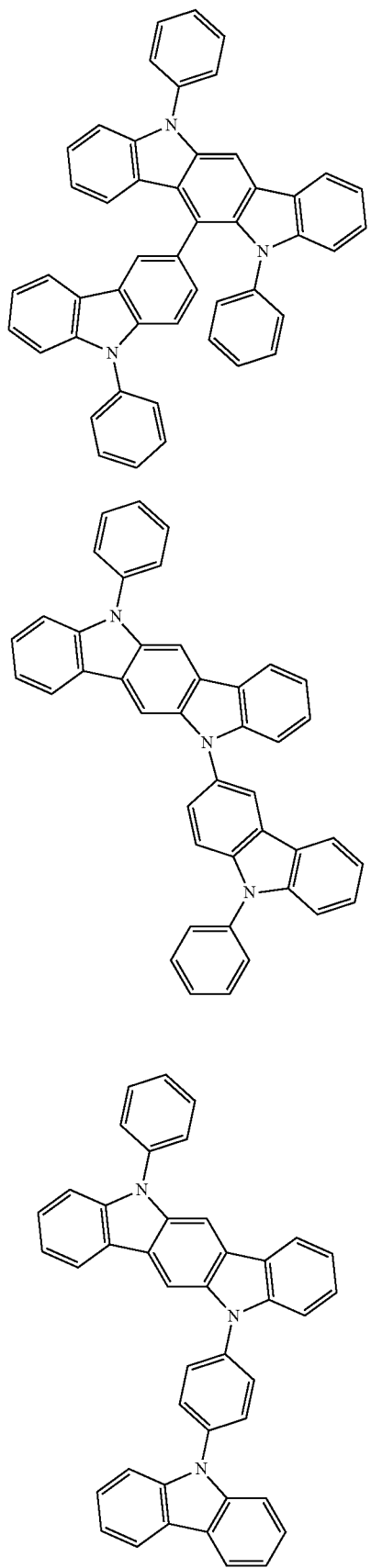
[F-65]
[F-66]
[F-67]
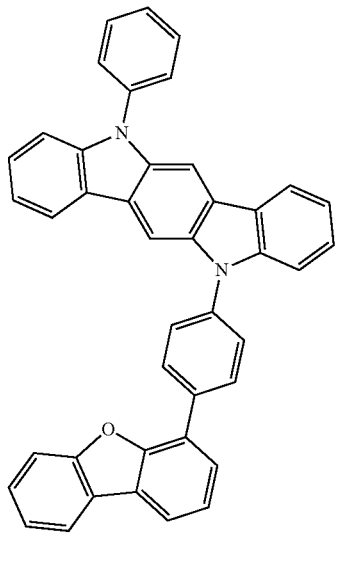
[F-68]
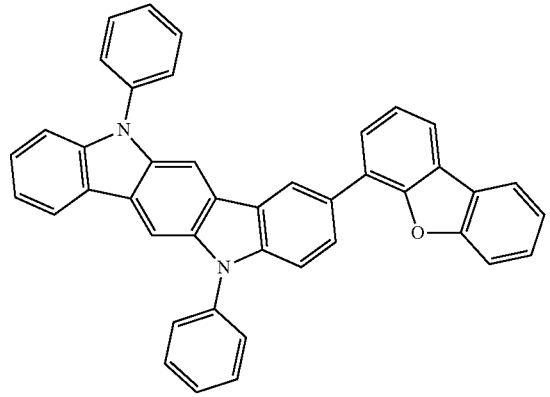
[F-69]
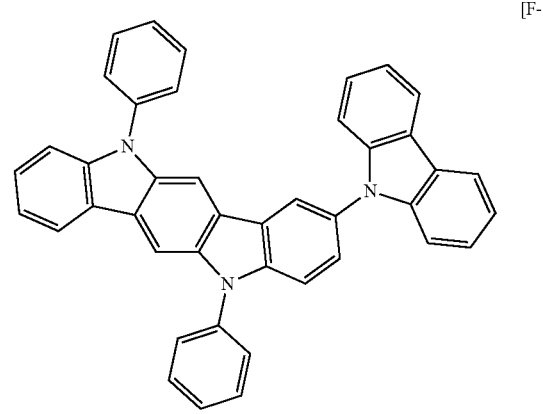
[F-70]
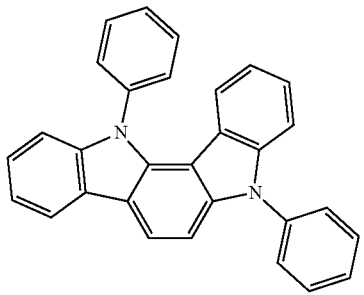
[F-71]

[F-72]
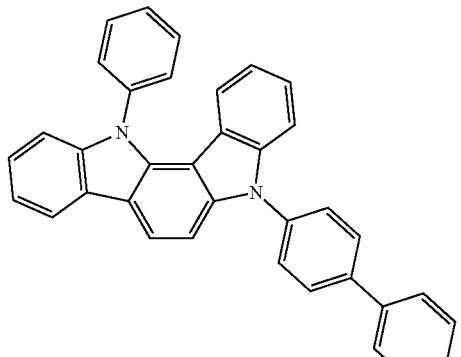
[F-73]
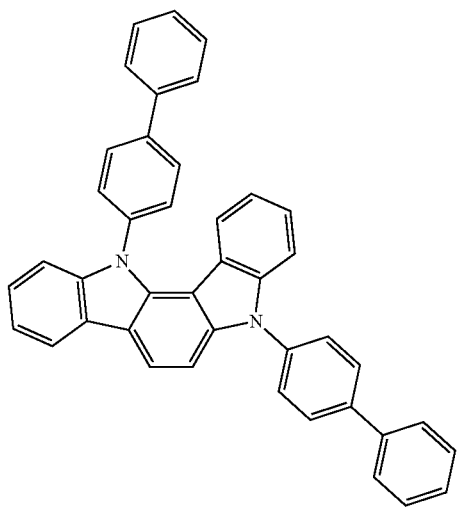
[F-74]
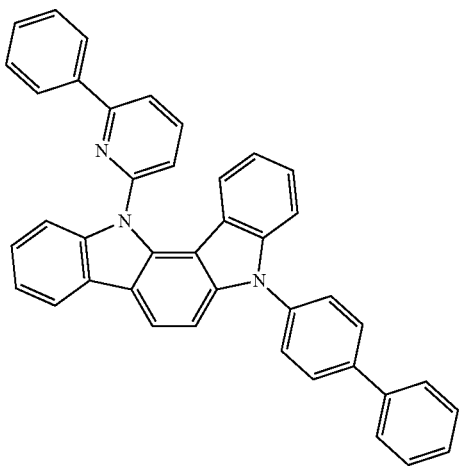
[F-75]
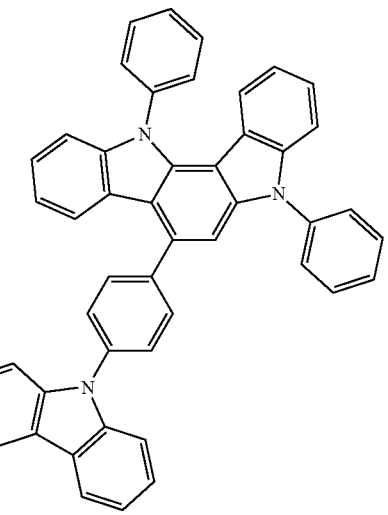
[F-76]
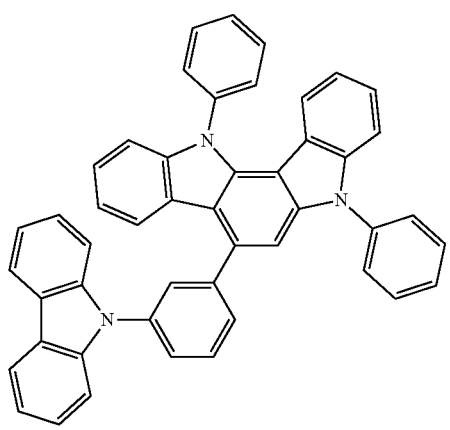
[F-77]
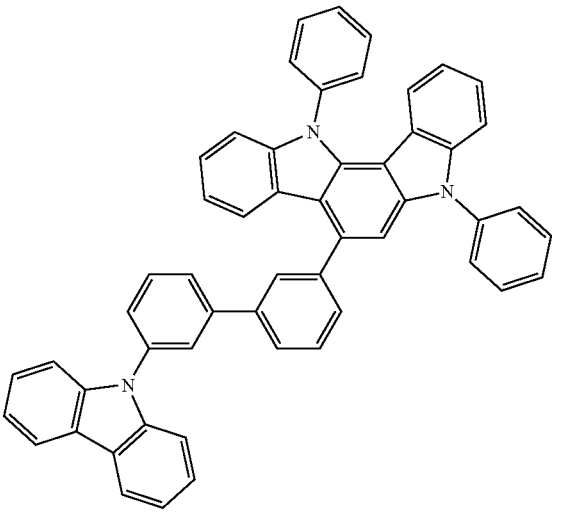

[F-78]
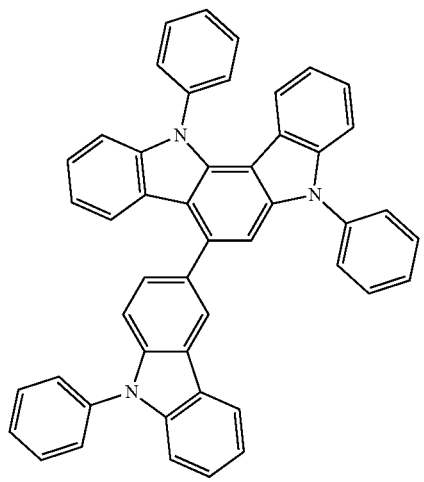
[F-79]
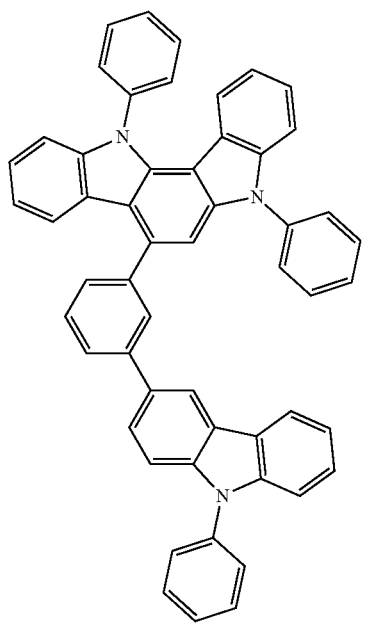
[F-80]
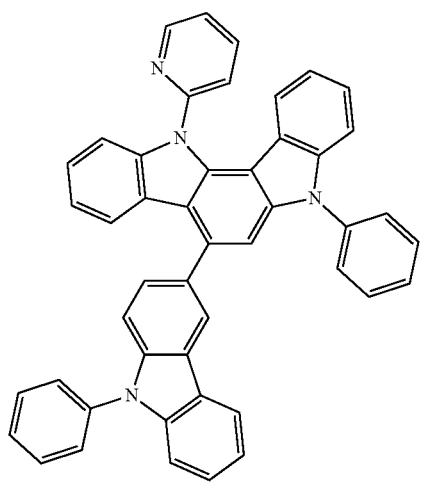
[F-81]
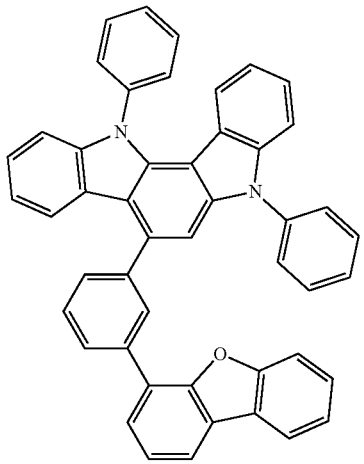
[F-82]
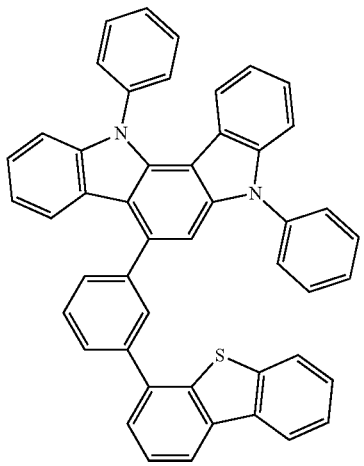
[F-83]
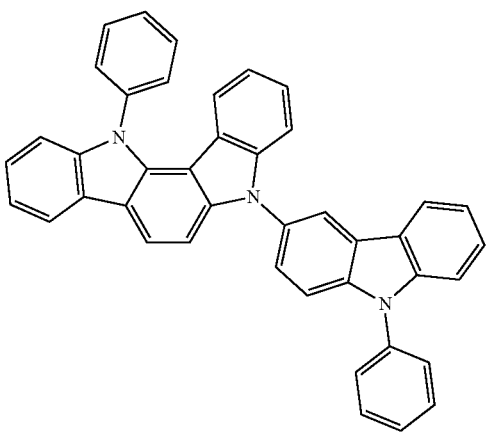

[F-84]
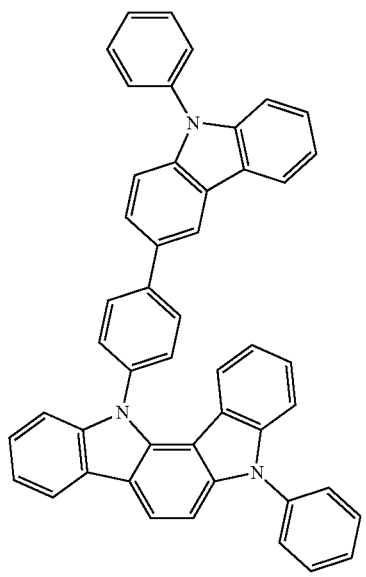
[F-85]
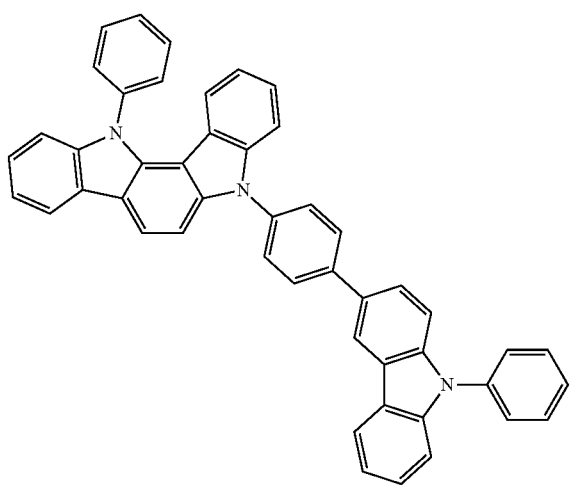
[F-86]
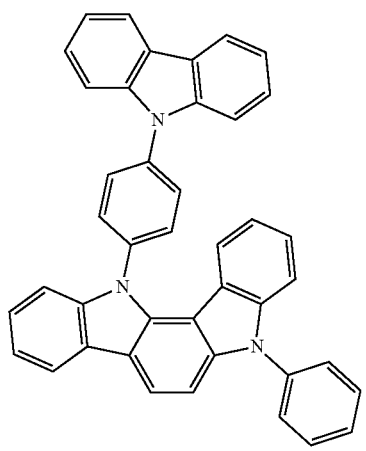
[F-87]
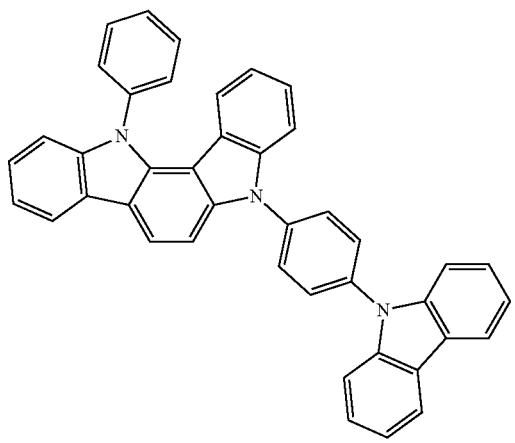
[F-88]
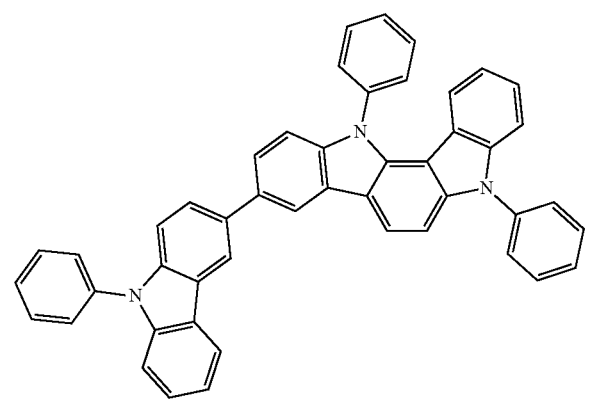
[F-89]
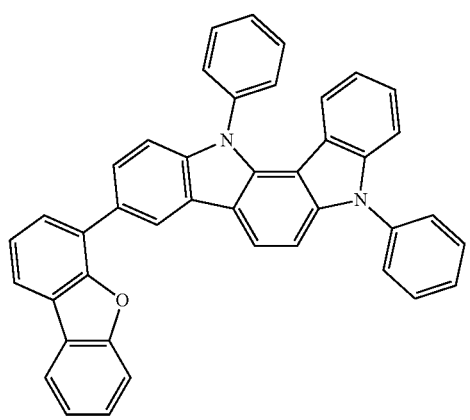

-continued
[F-90]
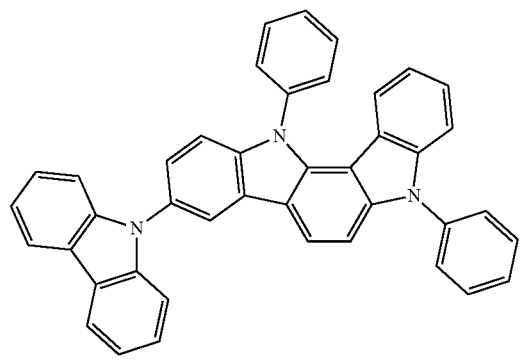
[F-91]
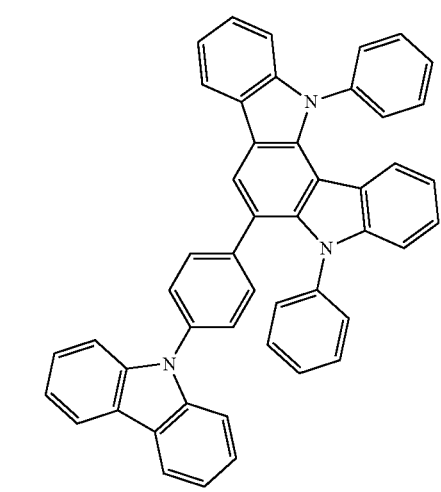
[F-92]
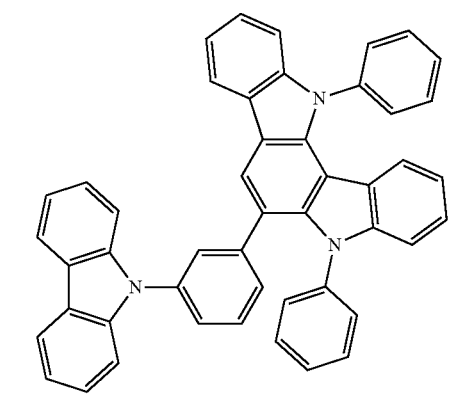
-continued
[F-93]
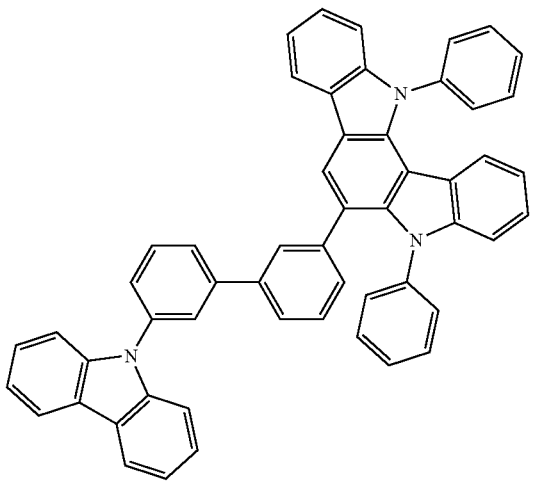
[F-94]
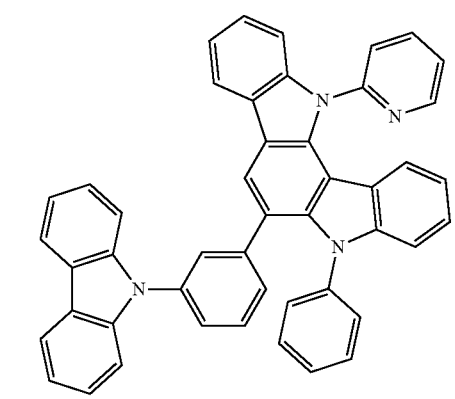
[F-95]
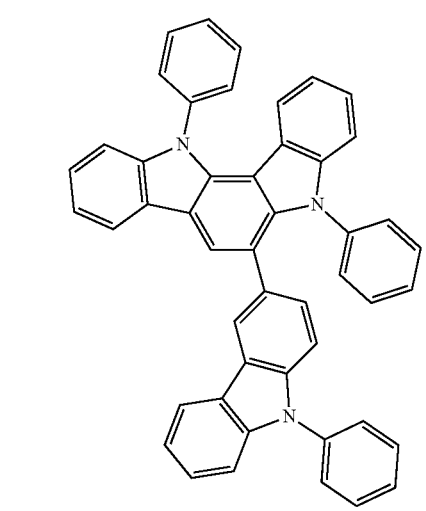

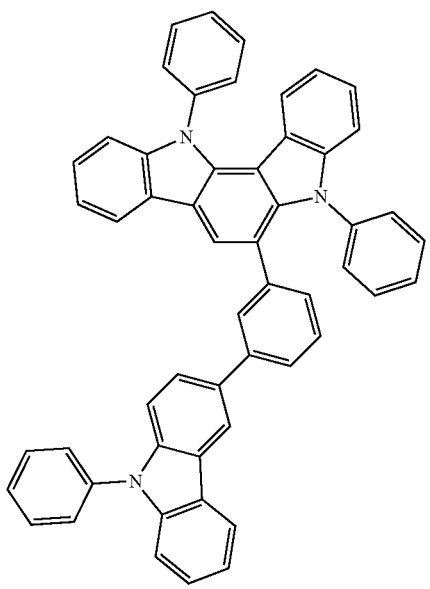

[F-96]

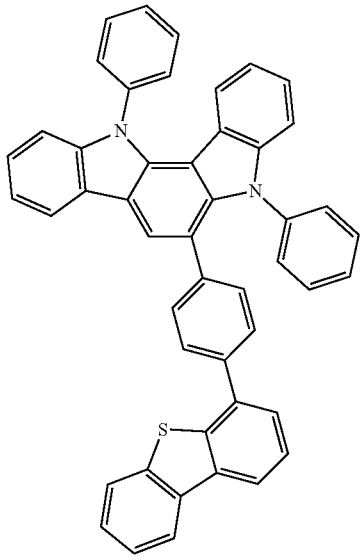

[F-98]

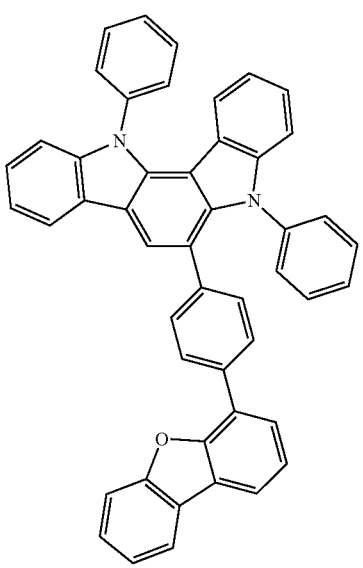

[F-97]

The first organic compound and the second organic compound may be included various combinations to form various compositions. The composition may include the first organic compound and the second compound in a weight ratio of about 1:99 to 99:1, for example about 10:90 to 90:10, about 20:80 to 80:20, about 30:70 to 70:30, about 40:60 to 60:40, or about 50:50.

The composition may further include at least one organic compound in addition to the first organic compound and the second organic compound.

The composition may further include a dopant. The dopant may be a red, green or blue dopant. The dopant is a material mixed with the aforementioned organic compound for the organic optoelectronic diode in a small amount to cause light emission and generally a material such as a metal complex that emits light by multiple excitation into a triplet or more. The dopant may be, for example an inorganic, organic, or organic/inorganic compound, and one or more types thereof may be used. The dopant may be included in about 0.1 to 20 wt % based on a total amount of the composition.

Examples of the dopant may be a phosphorescent dopant and examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L_2MX \qquad \text{[Chemical Formula Z]}$$

In Chemical Formula Z, M is a metal, L and X are the same or different and are ligands to form a complex compound with M.

The M may be for example Ir, Pt, Os, Ti, Zr, Hf, Eu, Tb, Tm, Fe, Co, Ni, Ru, Rh, Pd, or a combination thereof and L and X may be for example a bidendate ligand.

Hereinafter, an organic optoelectronic device including the aforementioned organic compound or composition is described.

The organic optoelectronic device may be, for example, an organic light emitting diode, an organic photoelectric device, or an organic solar cell. The organic optoelectronic device may be, for example, an organic light emitting diode.

The organic optoelectronic device may include an anode and a cathode facing each other, and an organic layer disposed between the anode and the cathode, wherein the organic layer may include the aforementioned organic compound or the aforementioned composition.

The organic layer may include an active layer such as a light emitting layer or a light absorbing layer and the aforementioned organic compound or the aforementioned composition may be included in the active layer.

The organic layer may include an auxiliary layer between the anode and the active layer and/or between the cathode and the active layer and the aforementioned organic compound or the aforementioned composition may be included in the auxiliary layer.

FIG. 1 is a cross-sectional view showing an organic light emitting diode which is one example of the organic optoelectronic device.

Referring to FIG. 1, an organic light emitting diode 100 according to an embodiment includes an anode 110 and a cathode 120 facing each other and an organic layer 105 disposed between the anode 110 and cathode 120.

The anode 110 may be made of a conductor having a high work function to help hole injection, and may be for example a metal, a metal oxide and/or a conductive polymer. The anode 110 may be, for example a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy) thiophene) (PEDOT), polypyrrole, and polyaniline, but is not limited thereto.

The cathode 120 may be made of a conductor having a low work function to help electron injection, and may be for example a metal, a metal oxide and/or a conductive polymer. The cathode 120 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, LiF/Al and $BaF_2$/Ca, but is not limited thereto.

The organic layer 105 may include the aforementioned organic compound or the aforementioned composition.

The organic layer 105 may include a light emitting layer 130.

The light emitting layer 130 may include the organic compound or the composition as a host. The light emitting layer 130 may further include other organic compounds as a host. The light emitting layer 130 may further include a dopant and the dopant may be for example a phosphorescent dopant.

The organic layer 105 may further include an auxiliary layer (not shown) between the anode 110 and the light emitting layer 130 and/or the cathode 120 and the light emitting layer 130. The auxiliary layer may be a hole injection layer, a hole transport layer, an electron blocking layer, an electron injection layer, an electron transport layer, a hole blocking layer, or a combination thereof. The auxiliary layer may include the aforementioned organic compound or the aforementioned composition.

FIG. 2 is a cross-sectional view of an organic light emitting diode according to another embodiment.

Referring to FIG. 2, an organic light emitting diode 200 according to an embodiment includes an anode 110 and a cathode 120 facing each other and an organic layer 105 disposed between the anode 110 and the cathode 120.

The organic layer 105 includes an electron auxiliary layer 140 disposed between the light emitting layer 230 and the cathode 120. The electron auxiliary layer 140 may be for example an electron injection layer, an electron transport layer, and/or a hole blocking layer and may help injection and transport of electrons between the cathode 120 and the light emitting layer 230.

For example, the aforementioned organic compound or the aforementioned composition may be included in the light emitting layer 230. The light emitting layer 230 may further include other organic compounds as a host. The light emitting layer 230 may further include a dopant and the dopant may be for example a phosphorescent dopant.

For example, the organic compound may be included in the electron auxiliary layer 140. The electron auxiliary layer 140 may include the organic compound alone, at least two types of the organic compounds, or a mixture of the organic compound and other organic compound.

In FIG. 2, at least one layer of a hole auxiliary layer (not shown) may be further included as an organic layer 105 between the anode 110 and the light emitting layer 230.

The organic light emitting diode may be applied to an organic light emitting display device.

MODE FOR INVENTION

Hereinafter, the embodiments are illustrated in more detail with reference to examples. However, these examples are exemplary, and the present scope is not limited thereto.

Synthesis Example 1: Synthesis of Intermediate I-1

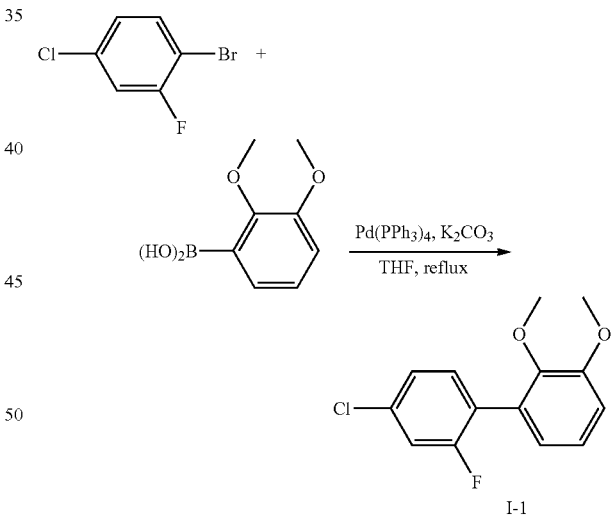

1-bromo-4-chloro-2-fluorobenzene (60 g, 289 mmol) purchased from Tokyo Chemical Industry Co., Ltd. (http://www.tcichemicals.com/) was dissolved in 0.5 L of tetrahydrofuran (THF) under a nitrogen environment, and 2,3-dimethoxyphenyl boronic acid (57.8 g, 317 mmol) purchased from Tokyo Chemical Industry Co., Ltd. (http://www.tcichemicals.com/) and tetrakis(triphenylphosphine) palladium (3.34 g, 2.89 mmol) were added thereto and then, stirred. Subsequently, potassium carbonate saturated in water (99.7 g, 722 mmol) was added thereto and then, heated and refluxed for 21 hours. When a reaction was complete, water was added to the reaction solution, and the mixture was extracted with dichloromethane (DCM), treated with anhydrous magnesium sulfate to remove moisture, filtered, and concentrated under a reduced pressure. This obtained residue was separated and purified through flash column chromatography to obtain Intermediate I-1 (67.5 g, 88%).

HRMS (70 eV, EI+): m/z calcd for C14H12ClFO2: 266.0510, found: 266.

Elemental Analysis: C, 63%; H, 5%

Synthesis Example 2: Synthesis of Intermediate I-2

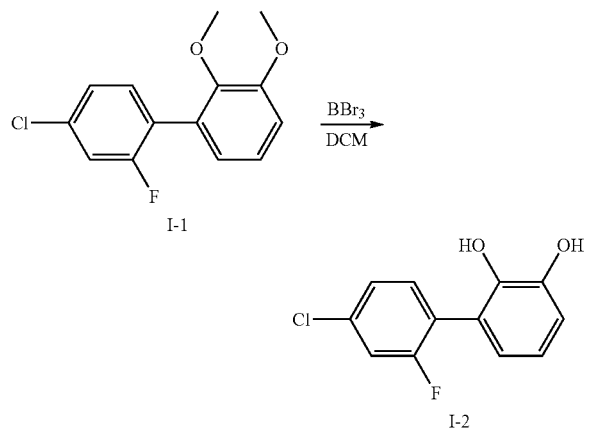

Intermediate I-1 (67.5 g, 253 mmol) was dissolved in 0.8 L of a 1.0 M boron tribromide solution under a nitrogen environment and then, stirred for 5 hours. When a reaction was complete, the reaction solution was cooled down to 0° C., 0.8 L of a saturated sodium thiosulfate aqueous solution was slowly added thereto in a dropwise fashion for 30 minutes. Subsequently, water was added thereto, and the mixture was extracted with dichloromethane (DCM), treated with anhydrous magnesium sulfate to remove moisture, filtered, and concentrated under a reduced pressure. This obtained residue was separated and purified through flash column chromatography to obtain Intermediate I-2 (60.0 g, 99%).

HRMS (70 eV, EI+): m/z calcd for C12H18ClFO2: 238.0197, found: 238.

Elemental Analysis: C, 60%; H, 3%

Synthesis Example 3: Synthesis of Intermediate I-3

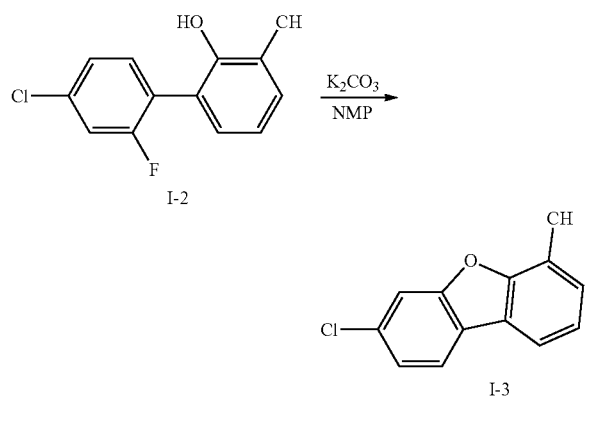

Intermediate I-2 (60.0 g, 253 mmol) was dissolved in 0.3 L of N-methyl-2-pyrrolidone (NMP) under a nitrogen environment, and potassium carbonate (70.0 g, 506 mmol) was added thereto and then, heated and refluxed for 14 hours. When a reaction was complete, the solvent was distilled and removed, water was added to the reaction solution, and the mixture was extracted with dichloromethane (DCM), treated with anhydrous magnesium sulfate to remove moisture, filtered, and concentrated under a reduced pressure.

This obtained residue was separated and purified through flash column chromatography to obtain Intermediate I-3 (40.4 g, 73%).

HRMS (70 eV, EI+): m/z calcd for C12H7ClO2: 218.0135, found: 218.

Elemental Analysis: C, 66%; H, 3%

Synthesis Example 4: Synthesis of Intermediate I-4

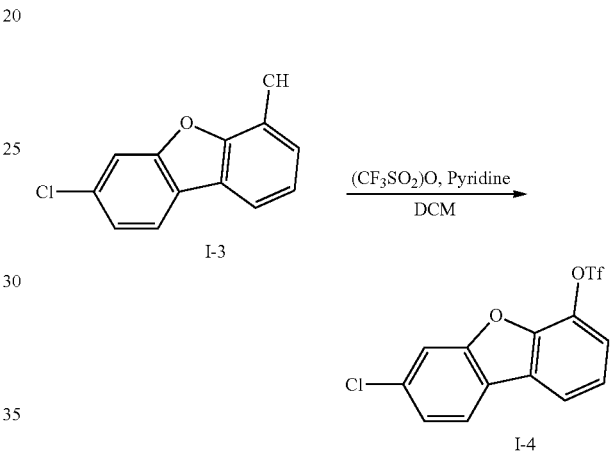

Intermediate I-3 (35 g, 160 mmol) was dissolved in 0.3 L of dichloromethane (DCM) under a nitrogen environment and then, cooled down to 0° C. Subsequently, tifluoromethanesulfonic anhydride (54.2 g, 192 mmol) was added thereto and then, stirred. After 14 hours, the reaction solution was cooled down to 0° C., water was slowly added thereto for 30 minutes, and the mixture was extracted with dichloromethane (DCM), treated with anhydrous magnesium sulfate to remove moisture, filtered, and concentrated under a reduced pressure. This obtained residue was separated and purified through flash column chromatography to obtain Intermediate I-4 (55.0 g, 98%).

HRMS (70 eV, EI+): m/z calcd for Cl3H6ClF3O4S: 349.9627, found: 350.

Elemental Analysis: C, 45%; H, 2%

Synthesis Example 5: Synthesis of Intermediate I-5

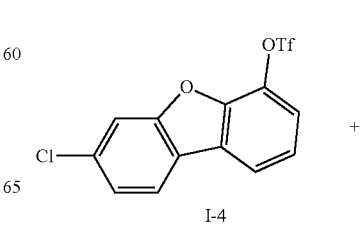

-continued

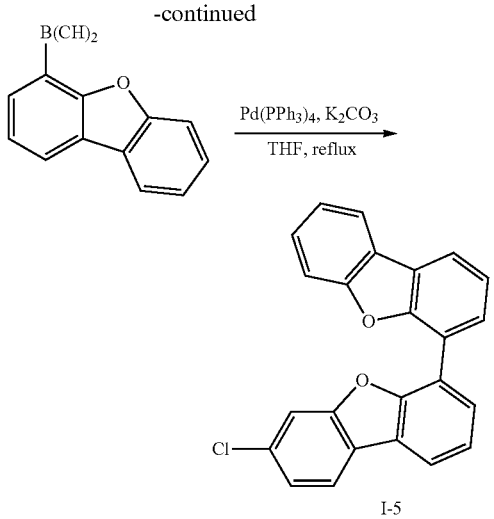

I-5

Intermediate I-5 (46.9 g, 89%) was obtained according to the same method as Synthesis Example 1 except that Intermediate I-4 (50 g, 143 mmol) and dibenzofuran-4-yl boronic acid (57.8 g, 157 mmol) purchased from Tokyo Chemical Industry Co., Ltd. were used.

HRMS (70 eV, EI+): m/z calcd for C24H13ClO2: 368.0604, found: 368.

Elemental Analysis: C, 78%; H, 4%

Synthesis Example 6: Synthesis of Intermediate I-6

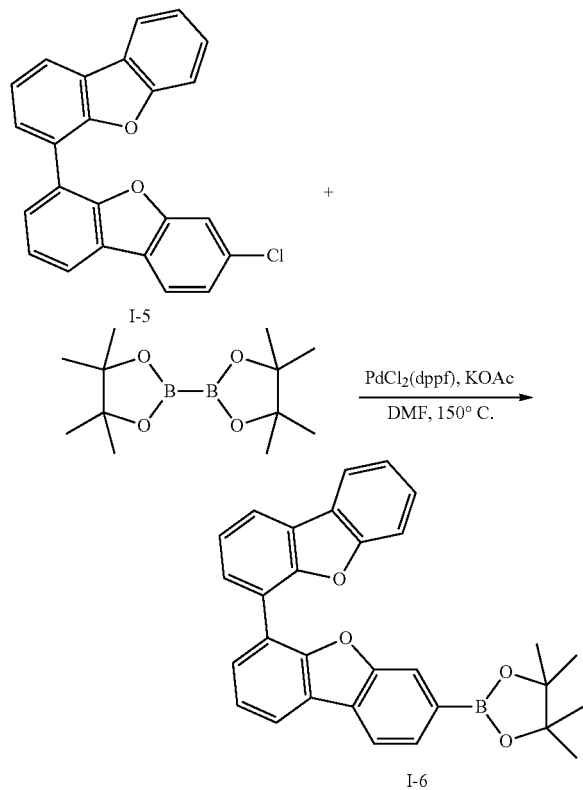

I-6

Intermediate I-5 (55 g, 149 mmol) was dissolved in 0.5 L of dimethylformamide (DMF) under a nitrogen environment, and bis(pinacolato)diboron (45.4 g, 179 mmol), (1,1'-bis(diphenylphosphine)ferrocene)dichloropalladium (II) (1.22 g, 1.49 mmol), and potassium acetate (43.9 g, 447 mmol) were added thereto and then, heated and refluxed at 150° C. for 15 hours. When a reaction was complete, water was added to the reaction solution, and the mixture was filtered and then, dried in a vacuum oven. This obtained residue was separated and purified through flash column chromatography to obtain Intermediate I-6 (48.0 g, 70%).

HRMS (70 eV, EI+): m/z calcd for C30H25BO4: 460.1846, found: 460.

Elemental Analysis: C, 78%; H, 5%

Synthesis Example 7: Synthesis of Compound 1

Compound 1 (11.7 g, 95%) was obtained according to the same method as Synthesis Example 1 except that Intermediate I-6 (10 g, 21.7 mmol) and 2-chloro-4,6-diphenyl-1,3,5-triazine (5.81 g, 21.7 mmol) purchased from Tokyo Chemical Industry Co., Ltd. were used.

HRMS (70 eV, EI+): m/z calcd for C39H23N3O2: 565.1790, found: 565.

Elemental Analysis: C, 83%; H, 4%

Synthesis Example 8: Synthesis of Compound 2

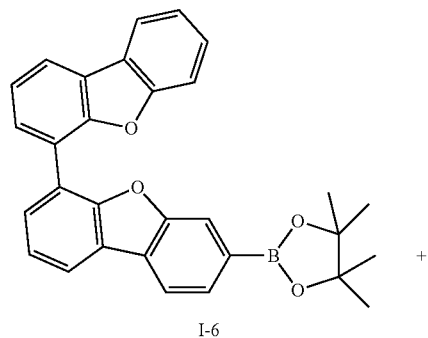

I-6

Synthesis Example 9: Synthesis of Compound 3

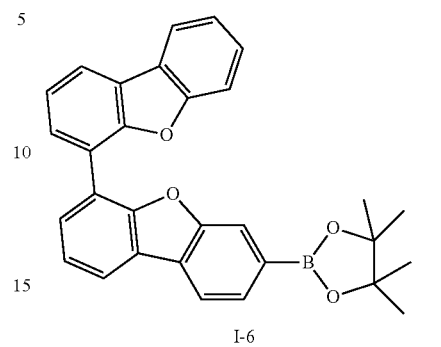

I-6

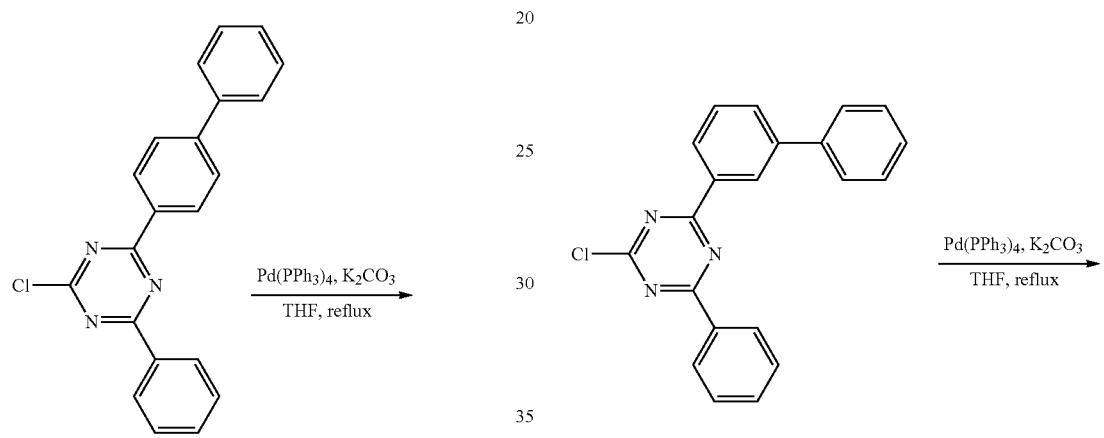

2

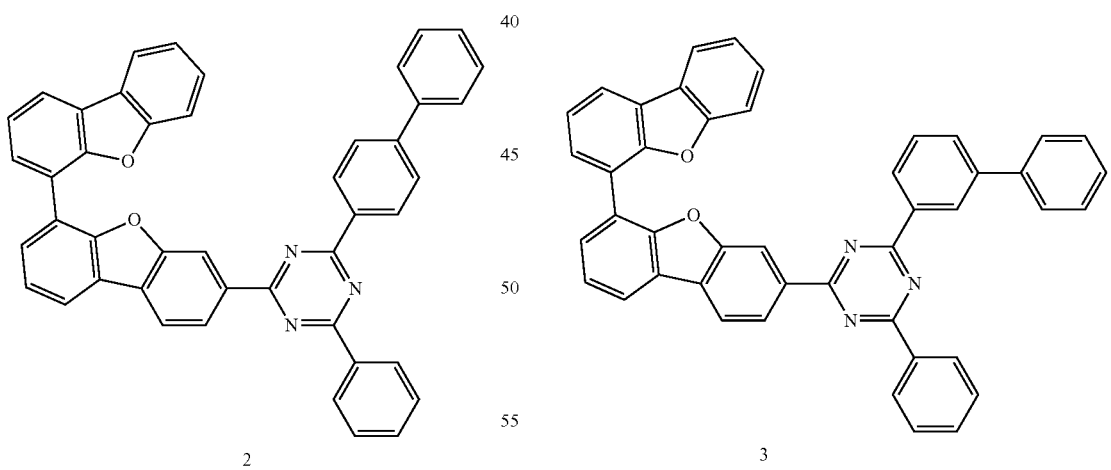

3

Compound 2 (13.0 g, 93%) was obtained according to the same method as Synthesis Example 1 except that Intermediate I-6 (10 g, 21.7 mmol) and 2-(biphenyl-4-yl)-4-chloro-6-phenyl-1,3,5-triazine (7.46 g, 21.7 mmol) purchased from Richest Group (http://www.richest-group.com/) were used.

HRMS (70 eV, EI+): m/z calcd for $C_{45}H_{27}N_3O_2$: 641.2103, found: 641.

Elemental Analysis: C, 84%; H, 4%

Compound 3 (12.8 g, 92%) was obtained according to the same method as Synthesis Example 1 except that Intermediate I-6 (10 g, 21.7 mmol) and 2-(biphenyl-3-yl)-4-chloro-6-phenyl-1,3,5-triazine (7.46 g, 21.7 mmol) purchased from Richest Group (http://www.richest-group.com/) were used.

HRMS (70 eV, EI+): m/z calcd for $C_{45}H_{27}N_3O_2$: 641.2103, found: 641.

Elemental Analysis: C, 84%; H, 4%

Synthesis Example 10: Synthesis of Compound 9

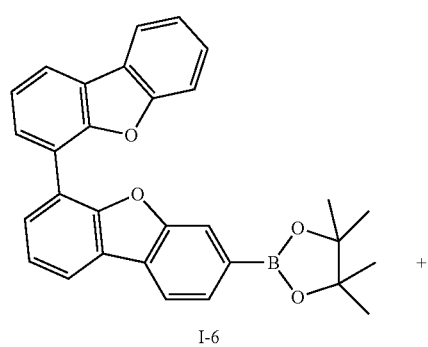

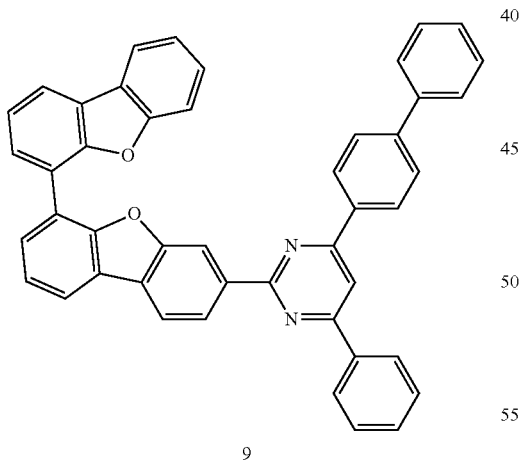

Compound 9 (13.6 g, 98%) was obtained according to the same method as Synthesis Example 1 except that Intermediate I-6 (10 g, 21.7 mmol) and 4-(biphenyl-4-yl)-2-chloro-6-phenylpyrimidine (7.44 g, 21.7 mmol) purchased from Richest Group were used.

HRMS (70 eV, EI+): m/z calcd for $C_{46}H_{28}N_2O_2$: 640.2151, found: 640.

Elemental Analysis: C, 86%; H, 4%

Synthesis Example 11: Synthesis of Intermediate I-7

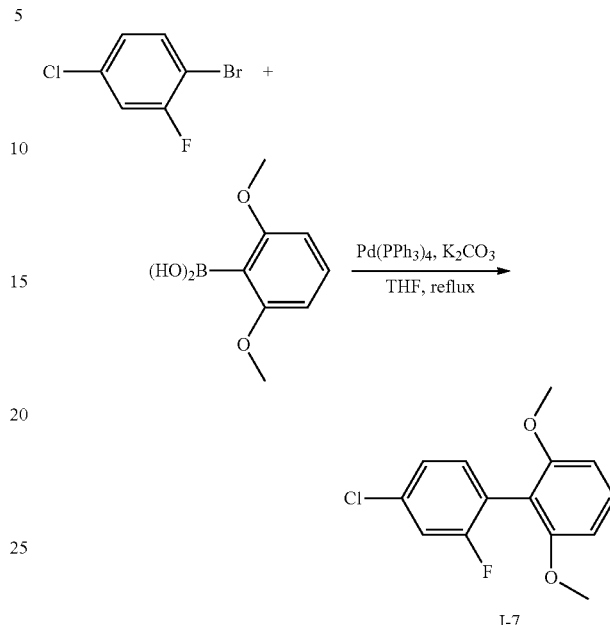

Intermediate I-7 (108 g, 85%) was obtained according to the same method as Synthesis Example 1 except that 1-bromo-4-chloro-2-fluorobenzene (100 g, 478 mmol) purchased from Tokyo Chemical Industry Co., Ltd. and 2,6-dimethoxyphenyl boronic acid (95.6 g, 525 mmol) were used.

HRMS (70 eV, EI+): m/z calcd for $C_{14}H_{12}ClFO_2$: 266.0510, found: 266.

Elemental Analysis: C, 63%; H, 5%

Synthesis Example 12: Synthesis of Intermediate I-8

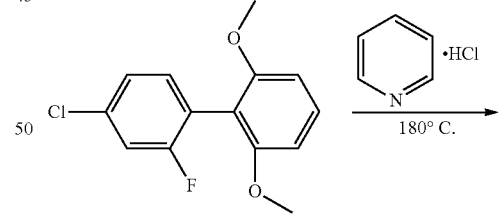

Intermediate I-7 (108 g, 406 mmol) and pyridine hydrochloride (469 g, 4061 mmol) were put under a nitrogen environment and then, heated and refluxed at 180° C. for 12 hours. When a reaction was complete, water was added to the reaction solution, and the mixture was extracted with ethylacetate (EA), treated with anhydrous magnesium sulfate to remove moisture, filtered, and concentrated under a reduced pressure. This obtained residue was separated and purified through flash column chromatography to obtain Intermediate I-8 (70.6 g, 73%).

HRMS (70 eV, EI+): m/z calcd for C12H8ClFO$_2$: 238.0197, found: 238.

Elemental Analysis: C, 60%; H, 3%

Synthesis Example 13: Synthesis of Intermediate I-9

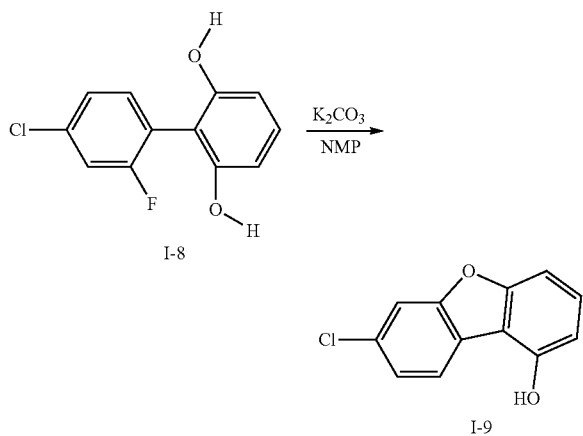

Intermediate I-9 (56.0 g, 87%) was obtained according to the same method as Synthesis Example 3 except that Intermediate I-8 (70.6 g, 296 mmol) was used.

HRMS (70 eV, EI+): m/z calcd for C12H7ClO2: 218.0135, found: 218.

Elemental Analysis: C, 66%; H, 3%

Synthesis Example 14: Synthesis of Intermediate I-10

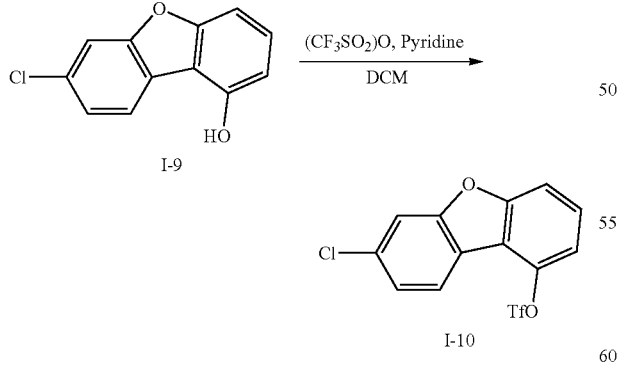

Intermediate I-10 (89.1 g, 99%) was obtained according to the same method as Synthesis Example 4 except that Intermediate I-9 (56 g, 256 mmol) was used.

HRMS (70 eV, EI+): m/z calcd for Cl3H6ClF3O4S: 349.9627, found: 350.

Elemental Analysis: C, 45%; H, 2%

Synthesis Example 15: Synthesis of Intermediate I-11

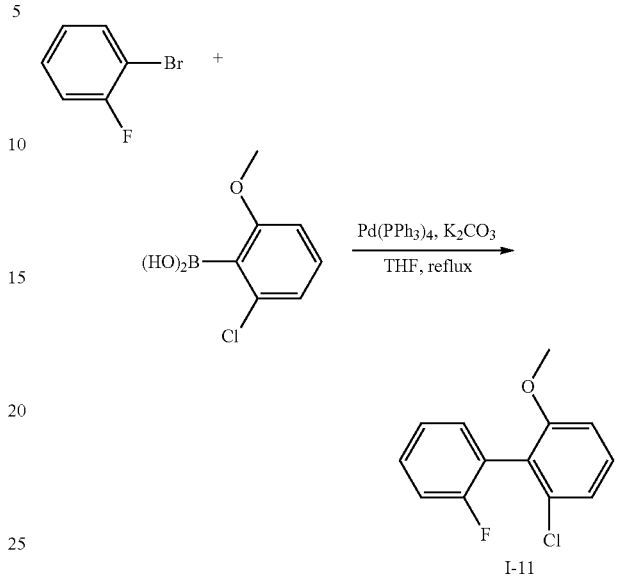

Intermediate I-11 (120 g, 89%) was obtained according to the same method as Synthesis Example 1 except that 1-bromo-2-fluorobenzene (100 g, 571 mmol) purchased from Tokyo Chemical Industry Co., Ltd. and 2-chloro-6-methoxyphenyl boronic acid (116 g, 629 mmol) purchased from Sigma Aldrich Co., Ltd. (http://www.sigmaaldrich.com/) were used.

HRMS (70 eV, EI+): m/z calcd for Cl3H10ClFO: 236.0404, found: 236.

Elemental Analysis: C, 66%; H, 4%

Synthesis Example 16: Synthesis of Intermediate I-12

Intermediate I-12 (87.6 g, 81%) was obtained according to the same method as Synthesis Example 12 except that Intermediate I-11 (115 g, 486 mmol) were used.

HRMS (70 eV, EI+): m/z calcd for C12H8ClFO: 222.0248, found: 222.

Elemental Analysis: C, 65%; H, 4%

Synthesis Example 17: Synthesis of Intermediate I-13

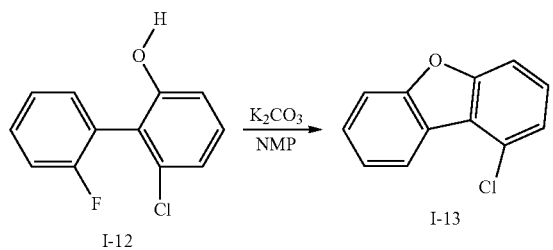

Intermediate I-13 (85.1 g, 85%) was obtained according to the same method as Synthesis Example 3 except that Intermediate I-12 (110 g, 494 mmol) were used.

HRMS (70 eV, EI+): m/z calcd for C12H7ClO: 202.0185, found: 202.

Elemental Analysis: C, 71%; H, 3%

Synthesis Example 18: Synthesis of Intermediate I-14

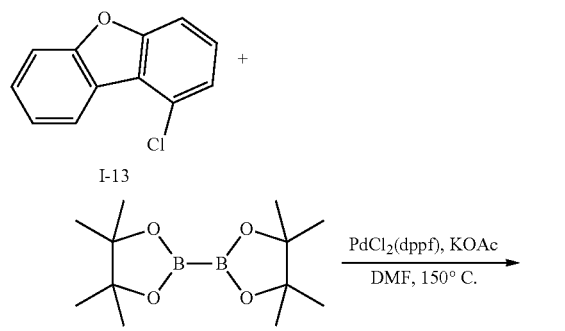

Intermediate I-14 (84.7 g, 72%) was obtained according to the same method as Synthesis Example 6 except that Intermediate I-13 (81 g, 400 mmol) were used.

HRMS (70 eV, EI+): m/z calcd for C18H9BO3: 294.1427, found: 294.

Elemental Analysis: C, 74%; H, 7%

Synthesis Example 19: Synthesis of Intermediate I-15

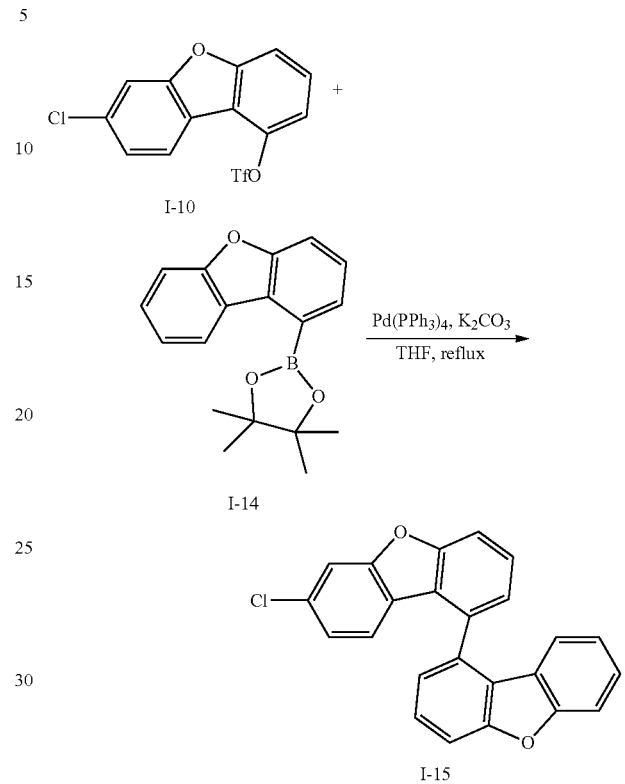

Intermediate I-15 (42.7 g, 81%) was obtained according to the same method as Synthesis Example 1 except that Intermediate I-10 (50 g, 143 mmol) and Intermediate I-14 (46.1 g, 157 mmol) were used.

HRMS (70 eV, EI+): m/z calcd for C24H13ClO2: 368.0604, found: 368.

Elemental Analysis: C, 78%; H, 4%

Synthesis Example 20: Synthesis of Intermediate I-16

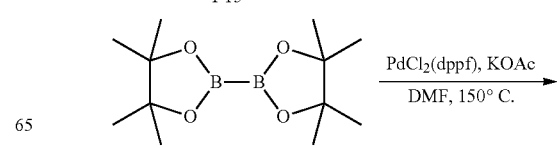

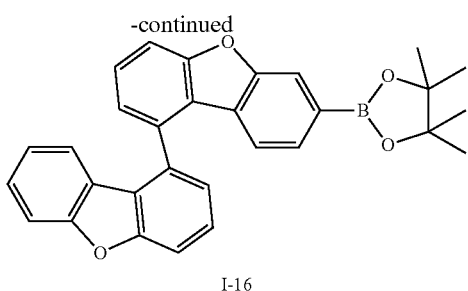

I-16

Intermediate I-16 (37.3 g, 75%) was obtained according to the same method as Synthesis Example 6 except that Intermediate I-15 (40 g, 108 mmol) were used.

HRMS (70 eV, EI+): m/z calcd for $C_{30}H_{25}BO_4$: 460.1846, found: 460.

Elemental Analysis: C, 78%; H, 5%

Synthesis Example 21: Synthesis of Compound 30

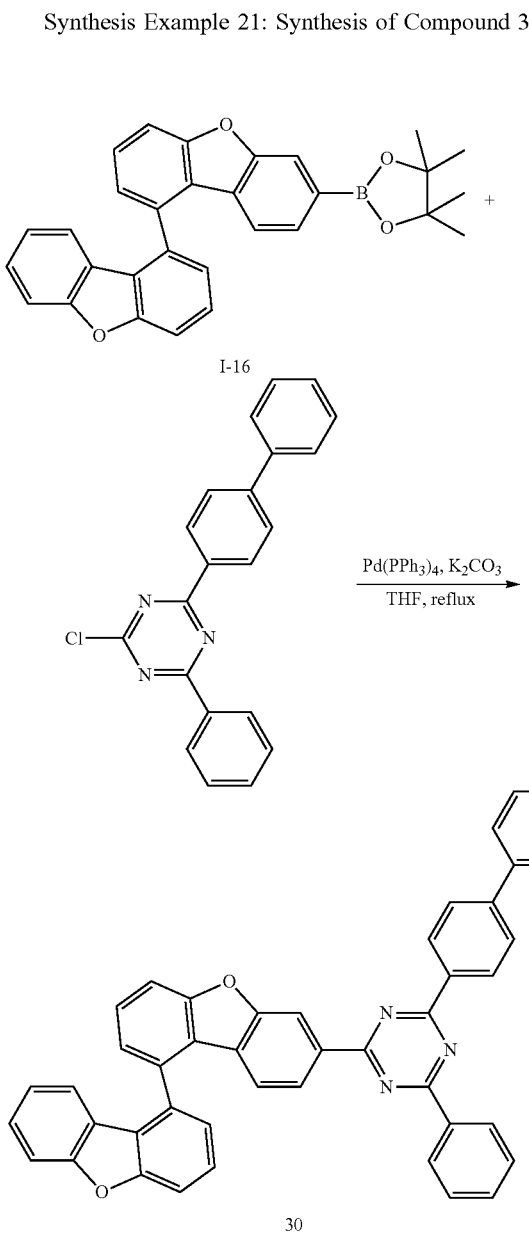

30

Compound 30 (13.2 g, 95%) was obtained according to the same method as Synthesis Example 1 except that Intermediate I-16 (10 g, 21.7 mmol) and 2-(biphenyl-4-yl)-4-chloro-6-phenyl-1,3,5-triazine (7.46 g, 21.7 mmol) purchased from Richest Group were used.

HRMS (70 eV, EI+): m/z calcd for $C_{45}H_{27}N_3O_2$: 641.2103, found: 641.

Elemental Analysis: C, 84%; H, 4%

Synthesis Example 22: Synthesis of Intermediate I-17

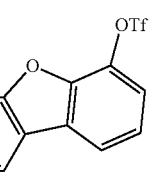

I-4

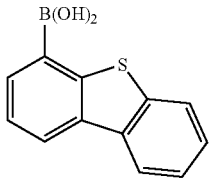

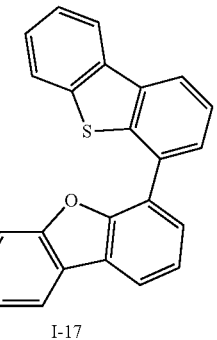

I-17

Intermediate I-17 (48.4 g, 88%) was obtained according to the same method as Synthesis Example 1 except that Intermediate I-4 (50 g, 143 mmol) and dibenzothiophen-4-yl boronic acid (35.9 g, 157 mmol) purchased from Tokyo Chemical Industry Co., Ltd. were used.

HRMS (70 eV, EI+): m/z calcd for $C_{24}H_{13}ClOS$: 384.0376, found: 384.

Elemental Analysis: C, 75%; H, 3%

Synthesis Example 23: Synthesis of Intermediate I-18

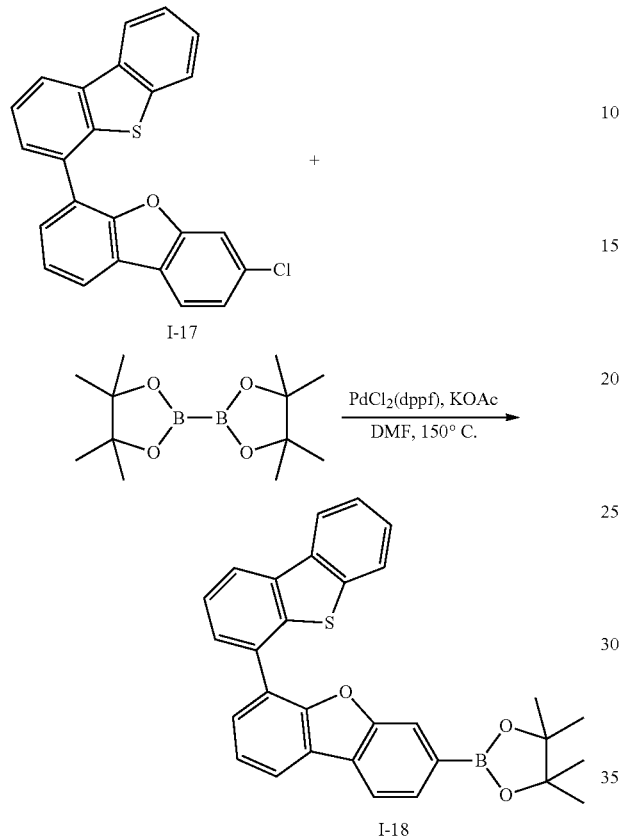

Intermediate I-18 (40.1 g, 69%) was obtained according to the same method as Synthesis Example 6 except that Intermediate I-17 (47 g, 122 mmol) was used.

HRMS (70 eV, EI+): m/z calcd for $C_{30}H_{25}BO_3S$: 476.1617, found: 476.

Elemental Analysis: C, 76%; H, 5%

Synthesis Example 24: Synthesis of Compound 46

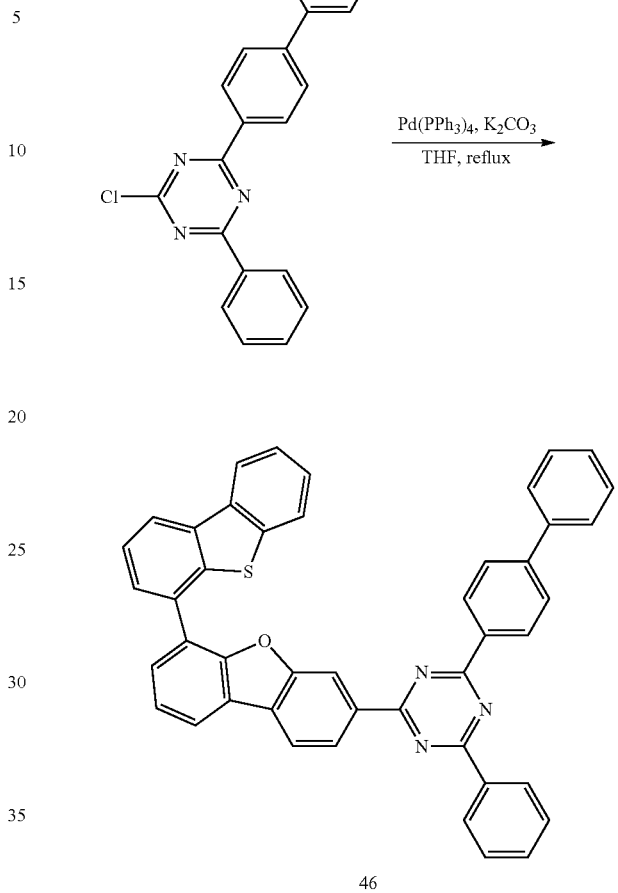

Compound 46 (12.8 g, 93%) was obtained according to the same method as Synthesis Example 1 except that Intermediate I-18 (10 g, 21.0 mmol) and 2-(biphenyl-4-yl)-4-chloro-6-phenyl-1,3,5-triazine (7.22 g, 21.0 mmol) purchased from Richest Group were used.

HRMS (70 eV, EI+): m/z calcd for $C_{45}H_{27}N_3OS$: 657.1875, found: 657.

Elemental Analysis: C, 82%; H, 4%

Synthesis Example 25: Synthesis of Intermediate I-19

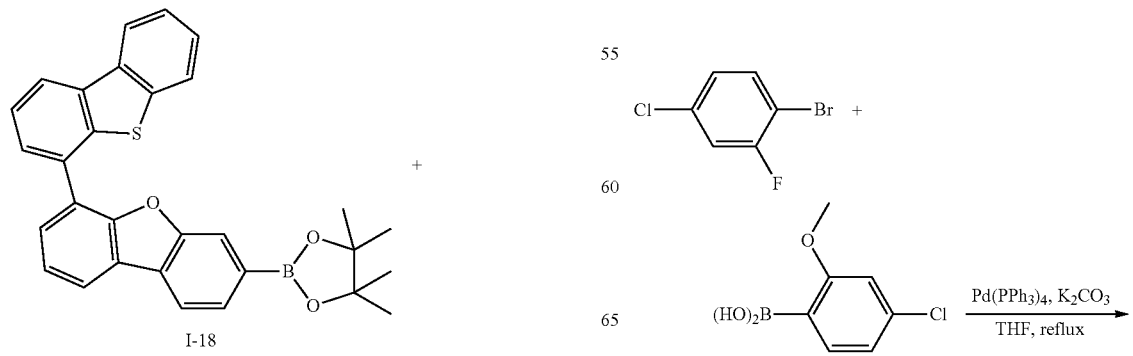

-continued

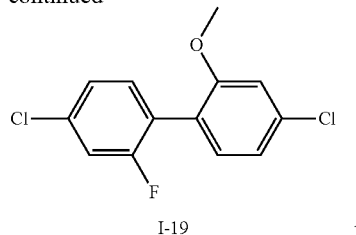
I-19

Intermediate I-19 (122 g, 93%) was obtained according to the same method as Synthesis Example 1 except that 1-bromo-4-chloro-2-fluorobenzene (100 g, 482 mmol) and 4-chloro-2-methoxyphenyl boronic acid (98.8 g, 530 mmol) purchased from Tokyo Chemical Industry Co., Ltd. were used.

HRMS (70 eV, EI+): m/z calcd for Cl3H9Cl2FO: 270.0014, found: 270.

Elemental Analysis: C, 58%; H, 3%

Synthesis Example 26: Synthesis of Intermediate I-20

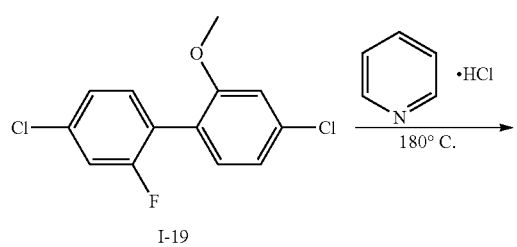

Intermediate I-20 (88.8 g, 78%) was obtained according to the same method as Synthesis Example 12 except that Intermediate I-19 (120 g, 443 mmol) was used.

HRMS (70 eV, EI+): m/z calcd for C12H8ClFO: 255.9858, found: 256.

Elemental Analysis: C, 56%; H, 3%

Synthesis Example 27: Synthesis of Intermediate I-21

-continued

I-21

Intermediate I-21 (73.0 g, 91%) was obtained according to the same method as Synthesis Example 3 except that Intermediate I-20 (87 g, 338 mmol) was used.

HRMS (70 eV, EI+): m/z calcd for C12H6Cl2O: 235.9796, found: 236.

Elemental Analysis: C, 61%; H, 3%

Synthesis Example 28: Synthesis of Intermediate I-22

I-22

Intermediate I-22 (64.2 g, 51%) was obtained according to the same method as Synthesis Example 6 except that Intermediate I-21 (71 g, 299 mmol) was used.

HRMS (70 eV, EI+): m/z calcd for C24H30B2O5: 420.2279, found: 420.

Elemental Analysis: C, 69%; H, 7%

Synthesis Example 29: Synthesis of Intermediate I-23

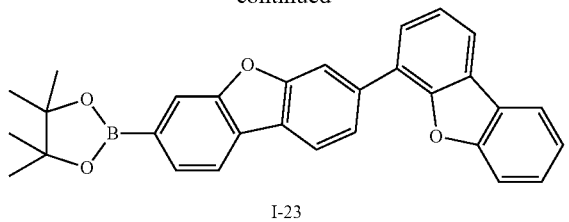

I-23

Intermediate I-23 (27.6 g, 45%) was obtained according to the same method as Synthesis Example 1 except that Intermediate I-22 (62 g, 148 mmol) and 4-bromodibenzofuran (32.8 g, 133 mmol) purchased from Tokyo Chemical Industry Co., Ltd. were used.

HRMS (70 eV, EI+): m/z calcd for C30H25BO4: 460.1846, found: 460.

Elemental Analysis: C, 78%; H, 5%

Synthesis Example 30: Synthesis of Compound 81

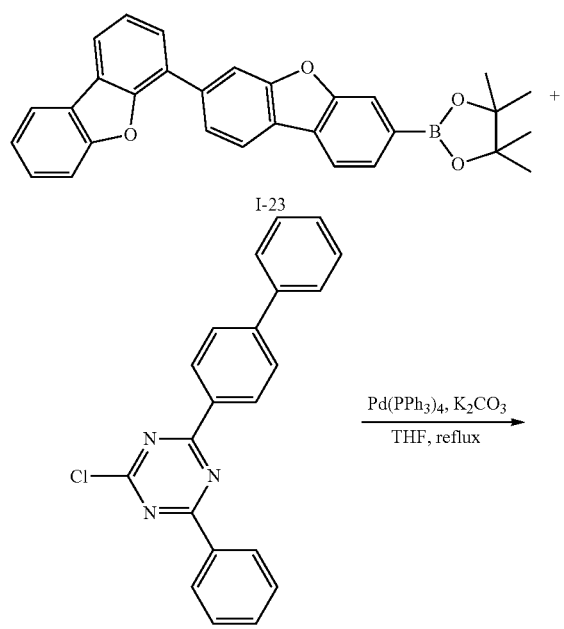

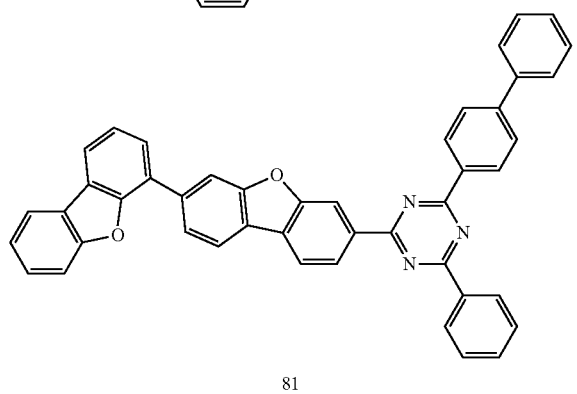

81

Compound 81 (13.9 g, 96%) was obtained according to the same method as Synthesis Example 1 except that Intermediate I-23 (10 g, 21.7 mmol) and 2-(biphenyl-4-yl)-4-chloro-6-phenyl-1,3,5-triazine (7.46 g, 21.7 mmol) purchased from Richest Group were used.

HRMS (70 eV, EI+): m/z calcd for C45H27N3O2: 641.2103, found: 641.

Elemental Analysis: C, 84%; H, 4%

Synthesis Example 31: Synthesis of Intermediate I-24

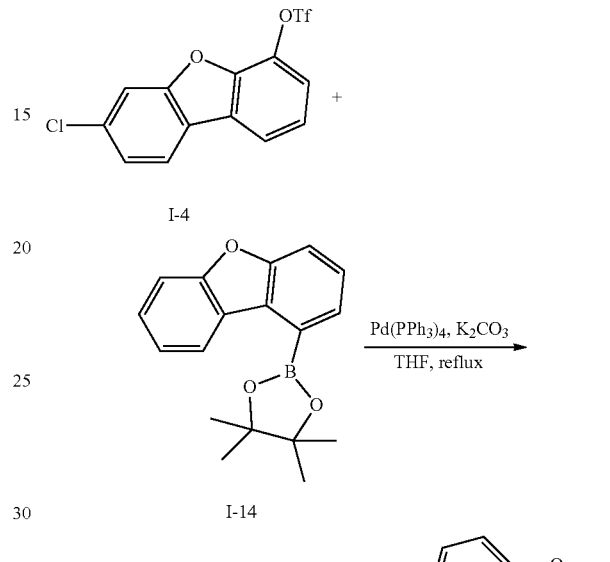

Intermediate I-24 (42.2 g, 80%) was obtained according to the same method as Synthesis Example 1 except that Intermediate I-4 (50 g, 143 mmol) and Intermediate I-14 (46.3 g, 157 mmol) were used.

HRMS (70 eV, EI+): m/z calcd for C24H13ClO2: 368.0604, found: 368.

Elemental Analysis: C, 78%; H, 4%

Synthesis Example 32: Synthesis of Compound 121

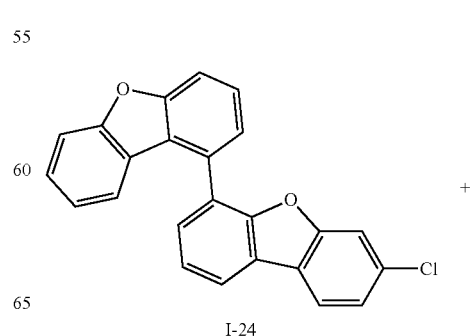

I-24

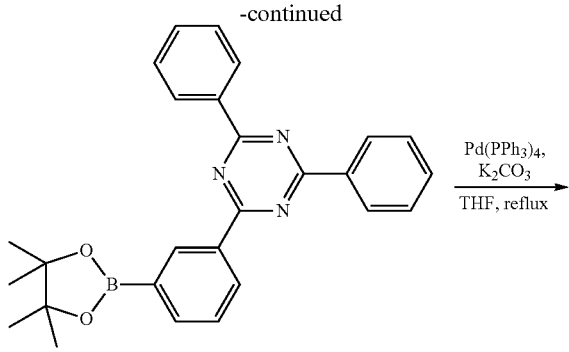

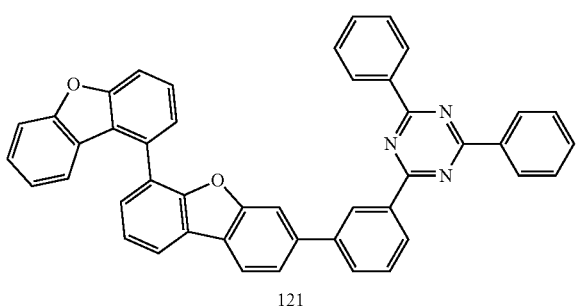

121

Compound 121 (13.2 g, 95%) was obtained according to the same method as Synthesis Example 1 except that Intermediate I-24 (10 g, 21.7 mmol) and 2,4-diphenyl-6-(3-(4,4,5,5-tetramethyl-1,3,2-dioxaborolan-2-yl)phenyl)-1,3,5-triazine (11.8 g, 21.7 mmol) purchased from P&H Tech Co., Ltd. (http://www.phtech.co.kr/) were used.

HRMS (70 eV, EI+): m/z calcd for $C_{45}H_{27}N_3O_2$: 641.2103, found: 641.

Elemental Analysis: C, 84%; H, 4%

Synthesis Example 33: Synthesis of Host 1

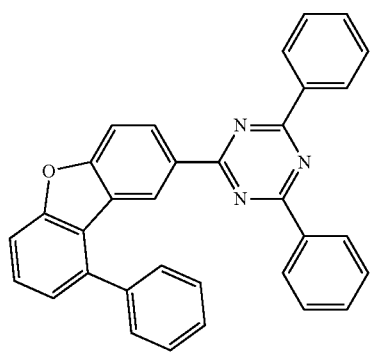

Host 1

Compound Host 1 was synthesized referring to the synthesis method of Japanese Patent Publication No. 2017-107992.

HRMS (70 eV, EI+): m/z calcd for $C_{33}H_{21}N_3O$: 475.1685, found: 475.

Elemental Analysis: C, 83%; H, 4%

Synthesis Example 34: Synthesis of Host 2

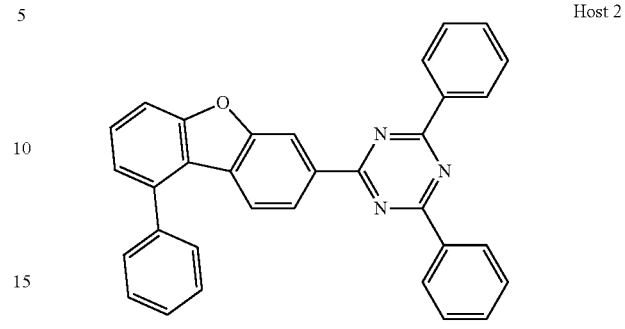

Host 2

Compound Host 2 was synthesized referring to the synthesis method of Japanese Patent Publication No. 2017-107992.

HRMS (70 eV, EI+): m/z calcd for C33H21N3O: 475.1685, found: 475.

Elemental Analysis: C, 83%; H, 4%

Synthesis Example 35: Synthesis of Host 3

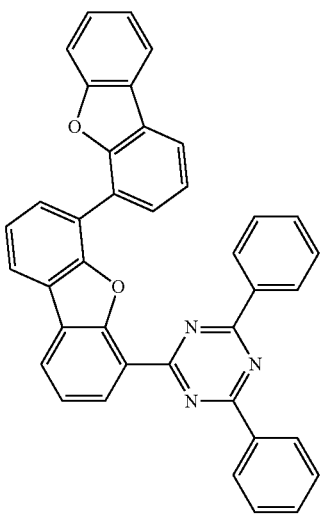

Host 3

Compound Host 3 was synthesized referring to the synthesis method of Korean Patent No. 10-1788094.

HRMS (70 eV, EI+): m/z calcd for C39H23N3O2: 565.1790, found: 565.

Elemental Analysis: C, 83%; H, 4%

Synthesis Example 36: Synthesis of Host 4

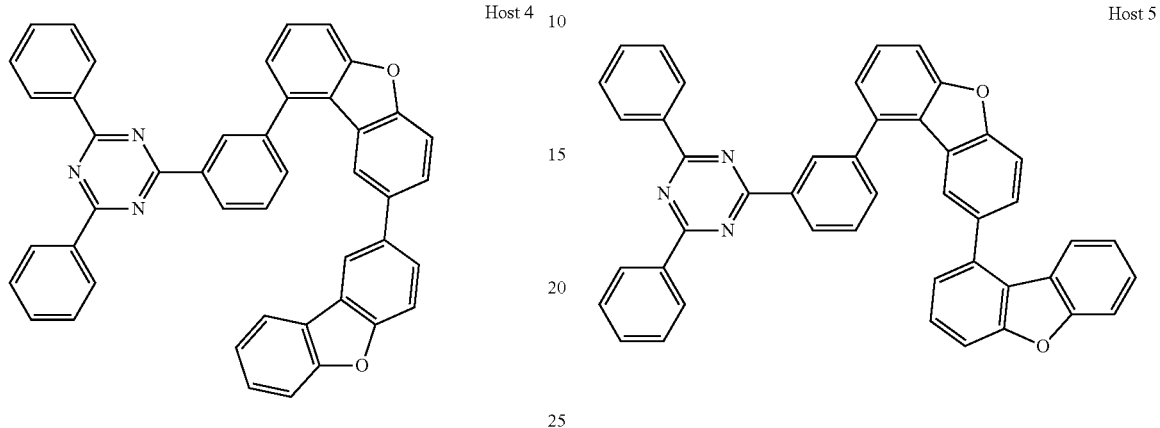

Host 4

Compound Host 4 was synthesized referring to the synthesis method of Korean Patent No. 10-1730779.

HRMS (70 eV, EI+): m/z calcd for $C_{45}H_{27}N_3O_2$: 641.2103, found: 641.

Elemental Analysis: C, 84%; H, 4%

Synthesis Example 37: Synthesis of Host 5

Host 5

Compound Host 5 was synthesized referring to the synthesis method of Korean Patent No. 10-1730779.

HRMS (70 eV, EI+): m/z calcd for $C_{45}H_{27}N_3O_2$: 641.2103, found: 641.

Elemental Analysis: C, 84%; H, 4%

Synthesis Example 38: Synthesis of Host 6

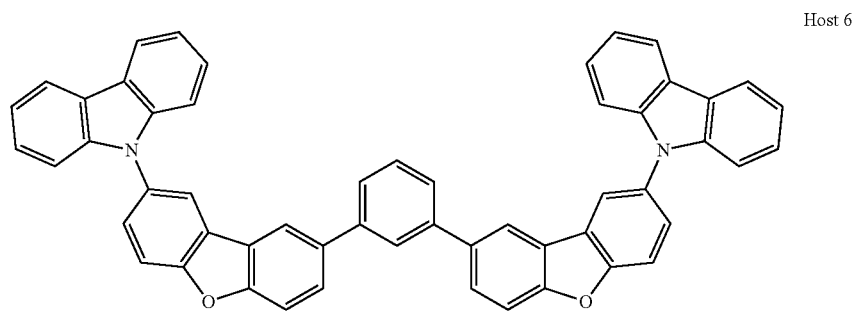 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1]

Host 6

Compound Host 6 was synthesized referring to the synthesis method of U.S. Pat. No. 8,541,112.

HRMS (70 eV, EI+): m/z calcd for $C_{54}H_{32}N_2O_2$: 740.2464, found: 740.

Elemental Analysis: C, 88%; H, 4%

Synthesis Example 39: Synthesis of Compound E-1

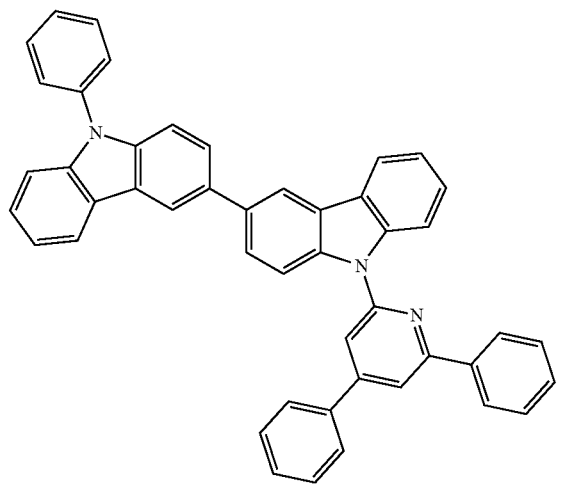

E-1

Compound E-1 was synthesized referring to the synthesis method of Korean Patent Publication No. 10-2014-0042630.

HRMS (70 eV, EI+): m/z calcd for $C_{47}H_{31}N_3$: 637.2518, found: 637.

Elemental Analysis: C, 89%; H, 5%

Synthesis Example 40: Synthesis of Compound E-23

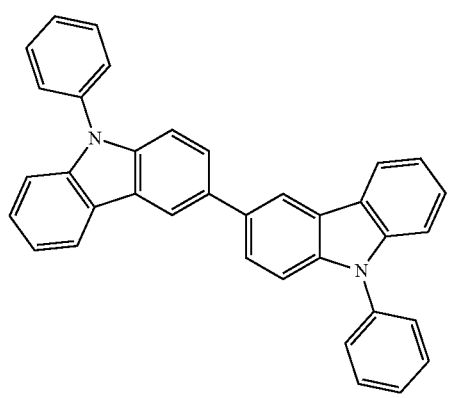

E-23

Compound E-23 was synthesized referring to the synthesis method of Korean Patent Publication No. 10-2014-0042630.

HRMS (70 eV, EI+): m/z calcd for $C_{36}H_{24}N_2$: 484.1939, found: 484.

Elemental Analysis: C, 89%; H, 5%

Synthesis Example 41: Synthesis of Compound E-25

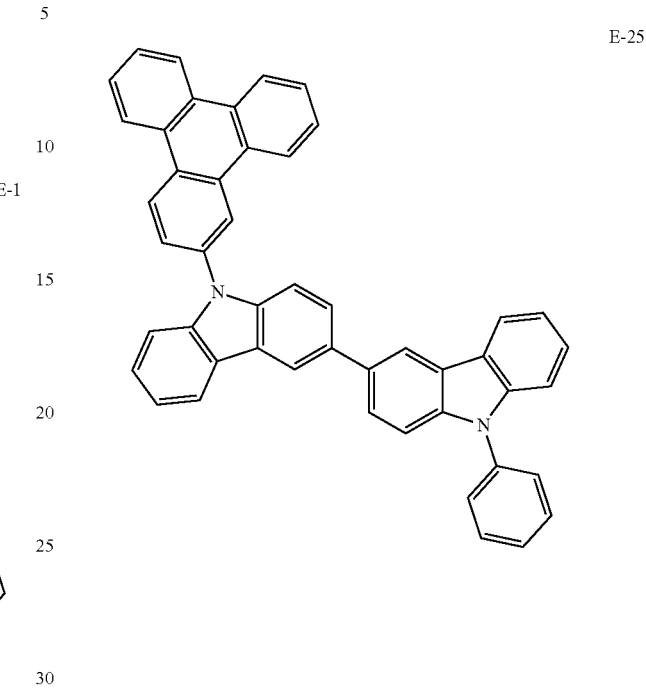

E-25

Compound E-25 was synthesized referring to the synthesis method of Korean Patent Publication No. 10-2014-0042630.

HRMS (70 eV, EI+): m/z calcd for $C_{48}H_{30}N_2$: 634.2409, found: 634.

Elemental Analysis: C, 91%; H, 5%

Synthesis Example 42: Synthesis of Compound E-31

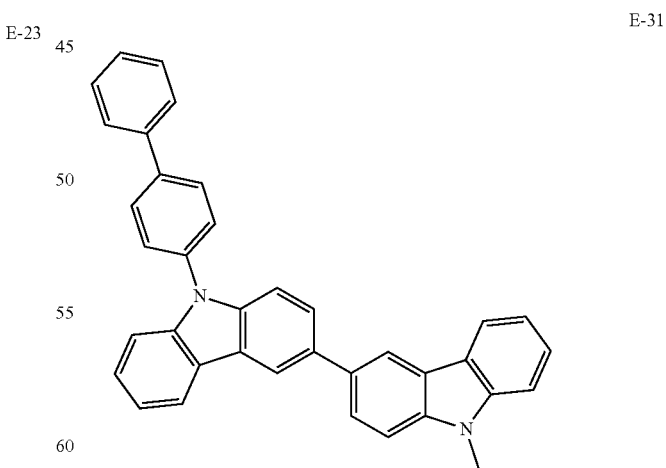

E-31

Compound E-31 was synthesized referring to the synthesis method of Korean Patent Publication No. 10-2014-0042630.

HRMS (70 eV, EI+): m/z calcd for C48H32N2: 636.2565, found: 636.

Elemental Analysis: C, 91%; H, 5%

Synthesis Example 43: Synthesis of Compound F-1

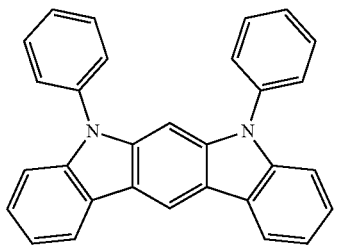

F-1

Compound F-1 was synthesized referring to the synthesis method of Korean Patent Publication No. 10-2014-0042630.

HRMS (70 eV, EI+): m/z calcd for C30H20N2: 408.1626, found: 408.

Elemental Analysis: C, 88%; H, 5%

Synthesis Example 44: Synthesis of Compound F-43

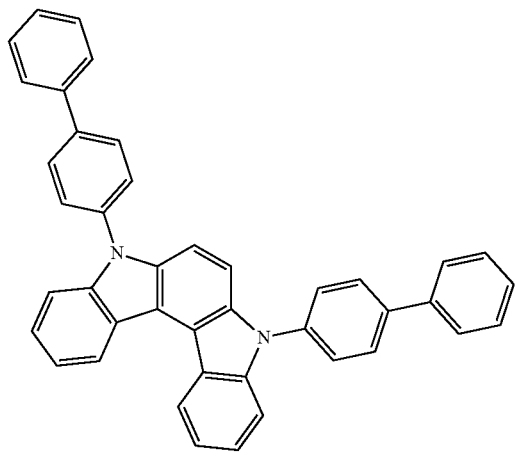

F-43

Compound F-43 was synthesized referring to the synthesis method of Korean Patent Publication No. 2017-0026359.

HRMS (70 eV, EI+): m/z calcd for C42H28N2: 560.2252, found: 560.

Elemental Analysis: C, 90%; H, 5%

Synthesis Example 45: Synthesis of Compound F-58

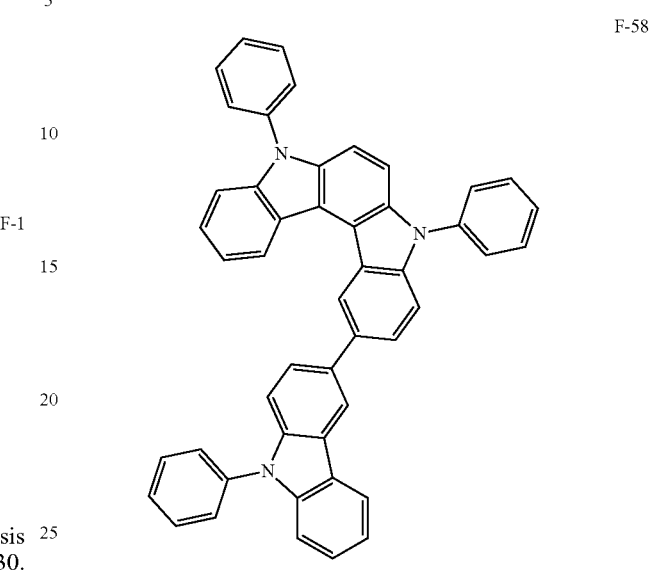

F-58

Compound F-58 was synthesized referring to the synthesis method of Korean Patent Publication No. 2016-0048868.

HRMS (70 eV, EI+): m/z calcd for C48H31N3: 649.2518, found: 649.

Elemental Analysis: C, 89%; H, 5%

Synthesis Example 46: Synthesis of Compound F-88

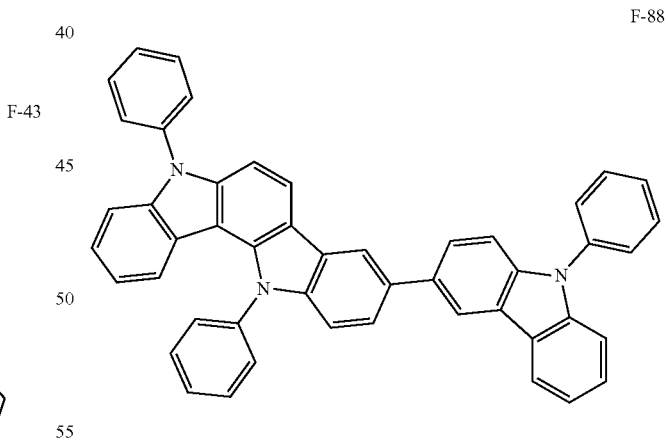

F-88

Compound F-88 was synthesized referring to the synthesis method of Korean Patent Publication No. 2016-0048868.

HRMS (70 eV, EI+): m/z calcd for C48H31N3: 649.2518, found: 649.

Elemental Analysis: C, 89%; H, 5%

Manufacture of Organic Light Emitting Diode I

Example 1

ITO (indium tin oxide) was deposited to be 1500 Å thick on a glass substrate, and the deposited glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å-thick on the hole injection layer, and Compound C was deposited to be 1020 Å-thick to form a hole transport layer. On the hole transport layer, Compound 1 obtained in Synthesis Example 7 was used as a host and was doped with 10 wt % of tris(2-phenylpyridine)iridium(III) [Ir(ppy)3] as a dopant to form a 400 Å-thick light emitting layer by vacuum deposition. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and $A^1$ to be 1200 Å thick on the electron transport layer, manufacturing an organic light emitting diode.

The organic light emitting diode had a five-layered organic thin layer structure as follows:

A structure of ITO/Compound A (700 Å)/Compound B (50 Å)/Compound C (1020 Å)/EML[Compound 1:Ir(ppy)$_{3=90}$%:10%] (400 Å)/Compound D:Liq (300 Å)/Liq (15 Å)/$A^1$ (1200 Å).

- Compound A: N4,N41-diphenyl-N4,N41-bis(9-phenyl-9H-carbazol-3-yl)biphenyl-4,4'-diamine
- Compound B: 1,4,5,8,9,11-hexaazatriphenylene-hexacarbonitrile (HAT-CN),
- Compound C: N-(biphenyl-4-yl)-9,9-dimethyl-N-(4-(9-phenyl-9H-carbazol-3-yl)phenyl)-9H-fluoren-2-amine
- Compound D: 8-(4-(4,6-di(naphthalen-2-yl)-1,3,5-triazin-2-yl)phenyl)quinolone

Example 2

An organic light emitting diode was manufactured according to the same method as Example 1 except that Compound 2 of Synthesis Example 8 was used instead of Compound 1 as a host of a light emitting layer.

Example 3

An organic light emitting diode was manufactured according to the same method as Example 1 except that Compound 3 of Synthesis Example 9 was used instead of Compound 1 as a host of a light emitting layer.

Example 4

An organic light emitting diode was manufactured according to the same method as Example 1 except that Compound 9 of Synthesis Example 10 was used instead of Compound 1 as a host of a light emitting layer.

Example 5

An organic light emitting diode was manufactured according to the same method as Example 1 except that Compound 30 of Synthesis Example 21 was used instead of Compound 1 as a host of a light emitting layer.

Example 6

An organic light emitting diode was manufactured according to the same method as Example 1 except that Compound 46 of Synthesis Example 24 was used instead of Compound 1 as a host of a light emitting layer.

Example 7

An organic light emitting diode was manufactured according to the same method as Example 1 except that Compound 81 of Synthesis Example 30 was used instead of Compound 1 as a host of a light emitting layer.

Example 8

An organic light emitting diode was manufactured according to the same method as Example 1 except that Compound 121 of Synthesis Example 32 was used instead of Compound 1 as a host of a light emitting layer.

Comparative Example 1

An organic light emitting diode was manufactured according to the same method as Example 1 except that 4,4'-di(9-carbazol-9-yl)biphenyl (CBP) was used instead of Compound 1 as a host of a light emitting layer.

Comparative Example 2

An organic light emitting diode was manufactured according to the same method as Example 1 except that Host 1 of Synthesis Example 33 was used instead of Compound 1 as a host of a light emitting layer.

Comparative Example 3

An organic light emitting diode was manufactured according to the same method as Example 1 except that Host 2 of Synthesis Example 34 was used instead of Compound 1 as a host of a light emitting layer.

Comparative Example 4

An organic light emitting diode was manufactured according to the same method as Example 1 except that Host 3 of Synthesis Example 35 was used instead of Compound 1 as a host of a light emitting layer.

Comparative Example 5

An organic light emitting diode was manufactured according to the same method as Example 1 except that Host 4 of Synthesis Example 36 was used instead of Compound 1 as a host of a light emitting layer.

Comparative Example 6

An organic light emitting diode was manufactured according to the same method as Example 1 except that Host 5 of Synthesis Example 37 was used instead of Compound 1 as a host of a light emitting layer.

Comparative Example 7

An organic light emitting diode was manufactured according to the same method as Example 1 except that Host 6 of Synthesis Example 38 was used instead of Compound 1 as a host of a light emitting layer.

Evaluation I

Driving voltages, luminous efficiency, and life-span characteristics of the organic light emitting diodes according to Examples 1 to 8 and Comparative Examples 1 to 7 were evaluated.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change Luminance was measured by using a luminance meter (Minolta Cs-1000A), while the voltage of the organic light emitting diodes was increased from 0 V to 10 V.

(3) Measurement of Luminous Efficiency Current efficiency (cd/A) at the same current density (10 mA/cm$^2$) were calculated by using the luminance, current density, and voltages (V) from the items (1) and (2).

(4) Measurement of Life-span Life-span was obtained by measuring time taken until current efficiency (cd/A) decreased down to 97% while luminance (cd/m$^2$) was maintained at 6000 cd/m$^2$.

TABLE 1

| Nos. | Compound of light emitting layer | Driving voltage (V) | Color (EL color) | Efficiency (cd/A) | Life-span T97 (h) |
| --- | --- | --- | --- | --- | --- |
| Example 1 | Compound 1 | 4.5 | Green | 48.7 | 500 |
| Example 2 | Compound 2 | 4.8 | Green | 45.0 | 650 |
| Example 3 | Compound 3 | 4.9 | Green | 44.8 | 730 |
| Example 4 | Compound 9 | 4.6 | Green | 55.2 | 450 |
| Example 5 | Compound 30 | 4.5 | Green | 46.5 | 700 |
| Example 6 | Compound 46 | 4.9 | Green | 49.9 | 610 |
| Example 7 | Compound 81 | 4.7 | Green | 40.5 | 600 |
| Example 8 | Compound 121 | 4.9 | Green | 48.5 | 720 |
| Comparative Example 1 | CBP | 5.5 | Green | 19.3 | 0.5 |
| Comparative Example 2 | Host 1 | 4.8 | Green | 30.2 | 150 |
| Comparative Example 3 | Host 2 | 5.2 | Green | 31.0 | 200 |
| Comparative Example 4 | Host 3 | 4.7 | Green | 42.5 | 250 |
| Comparative Example 5 | Host 4 | 5.0 | Green | 38.5 | 350 |
| Comparative Example 6 | Host 5 | 5.1 | Green | 35.7 | 310 |
| Comparative Example 7 | Host 6 | 5.0 | Green | 20.5 | 10 |

Referring to Table 1, the organic light emitting diodes according to Examples 1 to 8 exhibited significantly improved driving voltage, luminous efficiency, and life-span characteristics compared with the organic light emitting diodes according to Comparative Examples 1 to 7.

Manufacture of Organic Light Emitting Diode II

Example 9

ITO (indium tin oxide) was deposited to be 1500 Å thick on a glass substrate, and the ITO-deposited glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å-thick on the injection layer, and Compound C was deposited to be 1020 Å-thick to form a hole transport layer. On the hole transport layer, Compound 1 obtained in Synthesis Example 7 and Compound E-31 obtained in Synthesis Example 42 were simultaneously used as a co-host and were doped with 10 wt % of tris(2-phenylpyridine)iridium(III) [Ir(ppy)3] as a dopant to form a 400 Å-thick light emitting layer by vacuum deposition. Herein, Compound 1 and Compound E-31 were used in a weight ratio of 3:7. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer structure as follows:

A structure of ITO/Compound A (700 Å)/Compound B (50 Å)/Compound C (1020 Å)/EML[Compound 1:Compound E-31Ir(ppy)$_3$=X:X:10%] (400 Å)/Compound D:Liq (300 Å)/Liq (15 Å)/A$^1$ (1200 Å). (X=weight ratio)

Example 10

An organic light emitting diode was manufactured according to the same method as Example 9 except that Compound 2 of Synthesis Example 8 was used instead of Compound 1.

Example 11

An organic light emitting diode was manufactured according to the same method as Example 9 except that Compound 3 of Synthesis Example 9 was used instead of Compound 1.

Example 12

An organic light emitting diode was manufactured according to the same method as Example 9 except that Compound 9 of Synthesis Example 10 was used instead of Compound 1.

Example 13

An organic light emitting diode was manufactured according to the same method as Example 9 except that Compound 30 of Synthesis Example 21 was used instead of Compound 1.

Example 14

An organic light emitting diode was manufactured according to the same method as Example 9 except that Compound 46 of Synthesis Example 24 was used instead of Compound 1.

Example 15

An organic light emitting diode was manufactured according to the same method as Example 9 except that Compound 81 of Synthesis Example 30 was used instead of Compound 1.

Example 16

An organic light emitting diode was manufactured according to the same method as Example 9 except that Compound 121 of Synthesis Example 32 was used instead of Compound 1.

Example 17

An organic light emitting diode was manufactured according to the same method as Example 10 except that Compound E-1 of Synthesis Example 39 was used instead of Compound E-31.

Example 18

An organic light emitting diode was manufactured according to the same method as Example 10 except that Compound E-23 of Synthesis Example 40 was used instead of Compound E-31.

Example 19

An organic light emitting diode was manufactured according to the same method as Example 10 except that Compound E-25 of Synthesis Example 41 was used instead of Compound E-31.

Example 20

An organic light emitting diode was manufactured according to the same method as Example 10 except that Compound F-1 of Synthesis Example 43 was used instead of Compound E-31.

Example 21

An organic light emitting diode was manufactured according to the same method as Example 10 except that Compound F-43 of Synthesis Example 44 was used instead of Compound E-31.

Example 22

An organic light emitting diode was manufactured according to the same method as Example 10 except that Compound F-58 of Synthesis Example 45 was used instead of Compound E-31.

Example 23

An organic light emitting diode was manufactured according to the same method as Example 10 except that Compound F-88 of Synthesis Example 46 was used instead of Compound E-31.

Comparative Example 8

An organic light emitting diode was manufactured according to the same method as Example 9 except that Compound E-31 alone was used as a host of a light emitting layer.

Comparative Example 9

An organic light emitting diode was manufactured according to the same method as Example 9 except that Host 1 of Synthesis Example 33 was used instead of Compound 1.

Comparative Example 10

An organic light emitting diode was manufactured according to the same method as Example 9 except that Host 2 of Synthesis Example 34 was used instead of Compound 1.

Comparative Example 11

An organic light emitting diode was manufactured according to the same method as Example 9 except that Host 3 of Synthesis Example 35 was used instead of Compound 1.

Comparative Example 12

An organic light emitting diode was manufactured according to the same method as Example 9 except that Host 4 of Synthesis Example 36 was used instead of Compound 1.

Comparative Example 13

An organic light emitting diode was manufactured according to the same method as Example 9 except that Host 5 of Synthesis Example 37 was used instead of Compound 1.

Comparative Example 14

An organic light emitting diode was manufactured according to the same method as Example 9 except that Host 6 of Synthesis Example 38 was used instead of Compound 1.

Evaluation II

The driving voltage, luminous efficiency, and life-span characteristics of the organic light emitting diodes according to Examples 9 to 23 and Comparative Examples 8 to 14 were evaluated.

The results are shown in Table 2.

TABLE 2

| Nos. | Compound of light emitting layer | | Driving voltage (V) | Color (EL color) | Efficiency (cd/A) | Life-span T97 (h) |
| --- | --- | --- | --- | --- | --- | --- |
| Example 9 | Compound 1 | E-31 | 4.0 | Green | 68.0 | 850 |
| Example 10 | Compound 2 | E-31 | 4.3 | Green | 66.6 | 1,000 |
| Example 11 | Compound 3 | E-31 | 4.5 | Green | 65.8 | 1,200 |
| Example 12 | Compound 9 | E-31 | 4.1 | Green | 69.1 | 750 |

TABLE 2-continued

| Nos. | Compound of light emitting layer | | Driving voltage (V) | Color (EL color) | Efficiency (cd/A) | Lifespan T97 (h) |
|---|---|---|---|---|---|---|
| Example 13 | Compound 30 | E-31 | 4.1 | Green | 63.0 | 1,150 |
| Example 14 | Compound 46 | E-31 | 4.4 | Green | 67.5 | 950 |
| Example 15 | Compound 81 | E-31 | 4.2 | Green | 60.5 | 900 |
| Example 16 | Compound 121 | E-31 | 4.5 | Green | 63.6 | 980 |
| Example 17 | Compound 2 | E-1 | 4.1 | Green | 62.5 | 800 |
| Example 18 | Compound 2 | E-23 | 4.1 | Green | 65.4 | 850 |
| Example 19 | Compound 2 | E-25 | 4.6 | Green | 64.5 | 1,100 |
| Example 20 | Compound 2 | F-1 | 4.0 | Green | 67.0 | 880 |
| Example 21 | Compound 2 | F-43 | 3.9 | Green | 65.1 | 900 |
| Example 22 | Compound 2 | F-58 | 4.1 | Green | 68.0 | 850 |
| Example 23 | Compound 2 | F-88 | 4.0 | Green | 67.3 | 800 |
| Comparative Example 8 | — | E-31 | 5.3 | Green | 2.8 | 10 |
| Comparative Example 9 | Host 1 | E-31 | 4.9 | Green | 39.5 | 350 |
| Comparative Example 10 | Host 2 | E-31 | 5.0 | Green | 38.5 | 450 |
| Comparative Example 11 | Host 3 | E-31 | 4.8 | Green | 35.2 | 480 |
| Comparative Example 12 | Host 4 | E-31 | 4.9 | Green | 48.0 | 520 |
| Comparative Example 13 | Host 5 | E-31 | 5.0 | Green | 45.5 | 450 |
| Comparative Example14 | Host 6 | E-31 | 5.8 | Green | 25.5 | 80 |

Referring to Table 2, the organic light emitting diodes according to Examples 9 to 23 exhibited significantly improved driving voltages, luminous efficiency, and lifespan characteristics compared with the organic light emitting diodes according to Comparative Examples 8 to 14.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

DESCRIPTION OF SYMBOLS

100, 200: organic light emitting diode
105: organic layer
110: anode
120: cathode
130, 230: light emitting layer
140: electron auxiliary layer.

The invention claimed is:

1. An organic compound represented by Chemical Formula 1A or Chemical Formula 1B:

[Chemical Formula 1A]

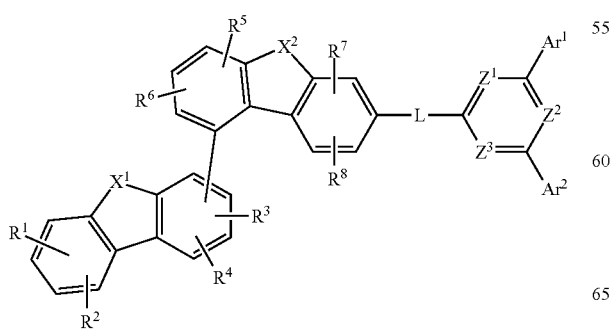

-continued

[Chemical Formula 1B]

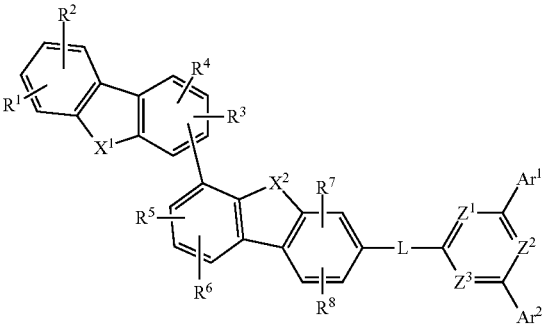

wherein, in Chemical Formulae 1A and 1B, $Z^1$ to $Z^3$ are independently N or CH, at least two of $Z^1$ to $Z^3$ are N, $Ar^1$ and $Ar^2$ are independently a substituted or unsubstituted phenyl group, a substituted or unsubstituted biphenyl group, a substituted or unsubstituted terphenyl group, or a substituted or unsubstituted pyridinyl group, L is a single bond or a substituted or unsubstituted phenylene group, $X^1$ and $X^2$ are independently O or S, $R^1$ to $R^8$ are independently hydrogen, deuterium, a substituted or unsubstituted C1 to C10 alkyl group, a substituted or unsubstituted phenyl group, or a cyano group, and 'substituted' refers to replacement of at least one hydrogen of a substituent by deuterium, a C1 to C5 alkyl group, a C6 to C18 aryl group, a pyridinyl group, or a cyano group.

2. The organic compound of claim 1, wherein:

the organic compound is represented by Chemical Formula 1A, the organic compound represented by Chemical Formula 1A is represented by one of Chemical Formulae 1Aa to 1Ad:

[Chemical Formula 1Aa]

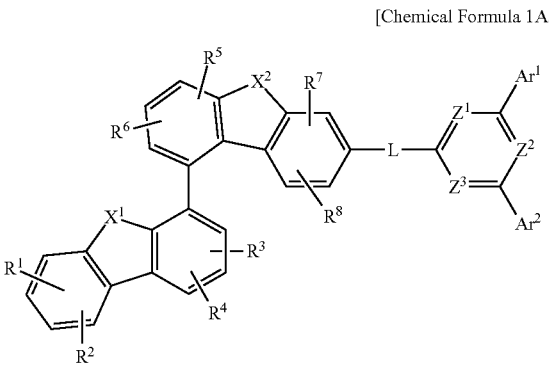

-continued

[Chemical Formula 1Ab]

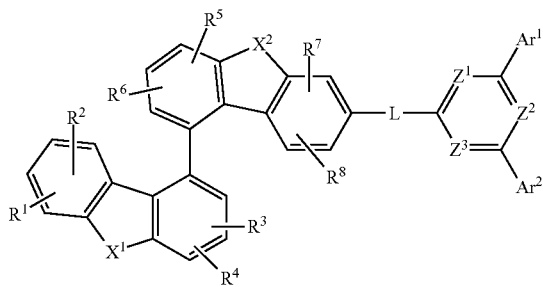

[Chemical Formula 1Ac]

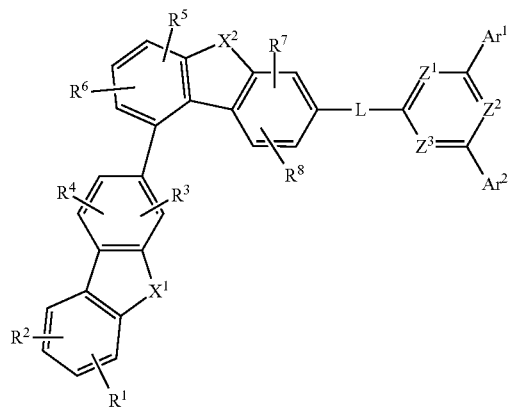

[Chemical Formula 1Ad]

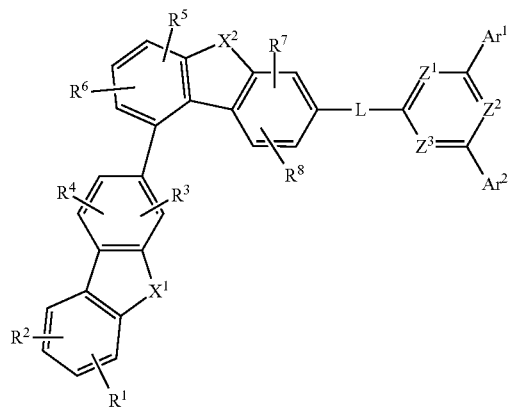

wherein, in Chemical Formulae 1Aa to 1Ad,
$Z^1$ to $Z^3$ are independently N or CH,
at least two of $Z^1$ to $Z^3$ are N,
$Ar^1$ and $Ar^2$ are independently a substituted or unsubstituted phenyl group, a substituted or unsubstituted biphenyl group, a substituted or unsubstituted terphenyl group, or a substituted or unsubstituted pyridinyl group,
L is a single bond or a substituted or unsubstituted phenylene group, $X^1$ and $X^2$ are independently O or S, $R^1$ to $R^8$ are independently hydrogen, deuterium, a substituted or unsubstituted C1 to C10 alkyl group, a substituted or unsubstituted phenyl group, or a cyano group, and 'substituted' refers to replacement of at least one hydrogen of a substituent by deuterium, a C1 to C5 alkyl group, a C6 to C18 aryl group, a pyridinyl group, or a cyano group.

3. The organic compound of claim 1, wherein:

the organic compound is represented by Chemical Formula 1B, the organic compound represented by Chemical Formula 1B is represented by one of Chemical Formulae 1Ba to 1Bd:

[Chemical Formula 1Ba]

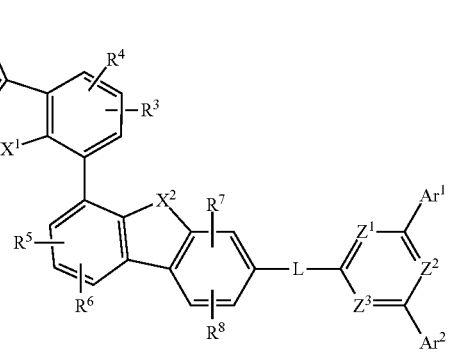

[Chemical Formula 1Bb]

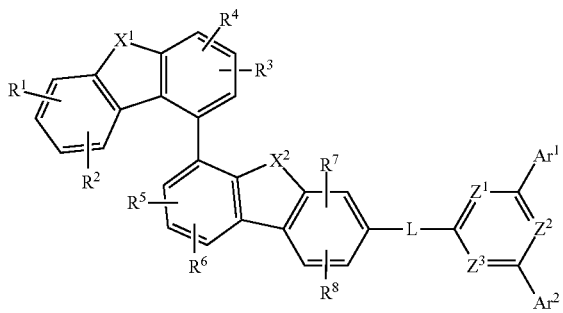

[Chemical Formula 1Bc]

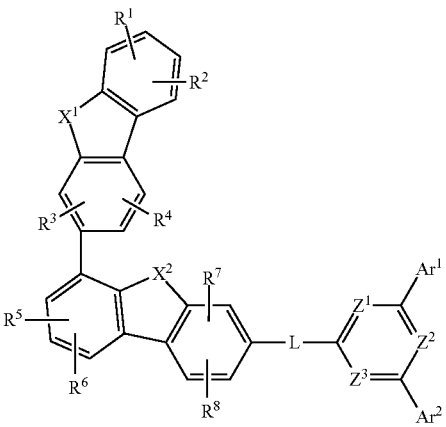

[Chemical Formula 1Bd]

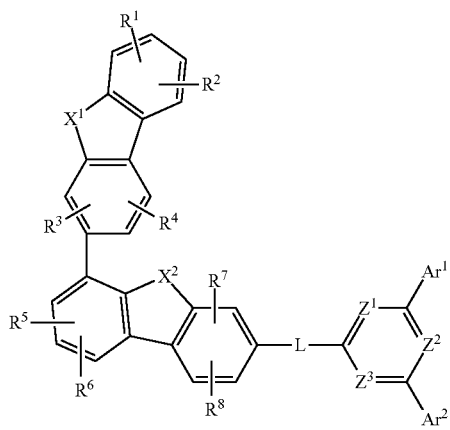

wherein, in Chemical Formulae 1Ba to 1Bd, $Z^1$ to $Z^3$ are independently N or CH, at least two of $Z^1$ to $Z^3$ are N, $Ar^1$ and $Ar^2$ are independently a substituted or unsubstituted phenyl group, a substituted or unsubstituted biphenyl group, a substituted or unsubstituted terphenyl group, or a substituted or unsubstituted pyridinyl group, L is a single bond or a substituted or unsubstituted phenylene group, $X^1$ and $X^2$ are independently O or S, $R^1$ to $R^8$ are independently hydrogen, deuterium, a substituted or unsubstituted C1 to C10 alkyl group, a substituted or unsubstituted phenyl group, or a cyano group, and 'substituted' refers to replacement of at least one hydrogen of a substituent by deuterium, a C1 to C5 alkyl group, a C6 to C18 aryl group, a pyridinyl group, or a cyano group.

4. The organic compound of claim 1, wherein L is a single bond, a phenylene group, or a cyano-substituted phenylene group.

5. The organic compound of claim 1, wherein $X^1$ and $X^2$ are each O.

6. The organic compound of claim 1, wherein the organic compound is one of compounds listed in Group 1:

1

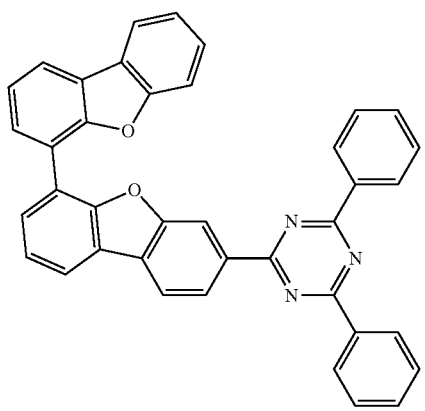

2

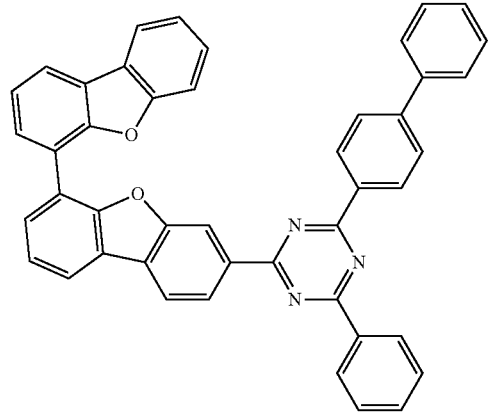

3

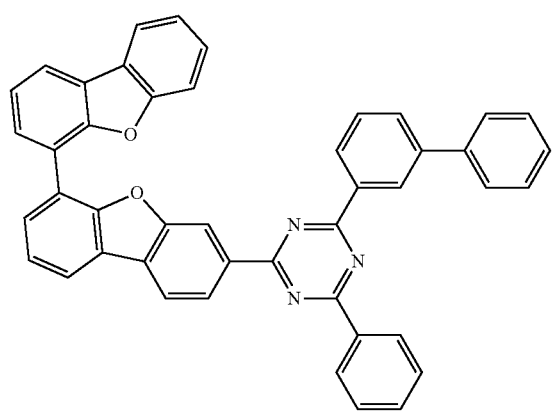

4

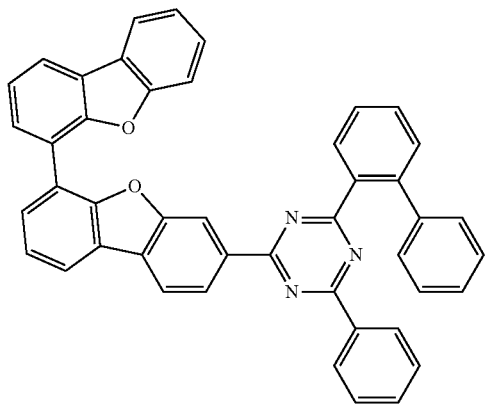

203
-continued
5
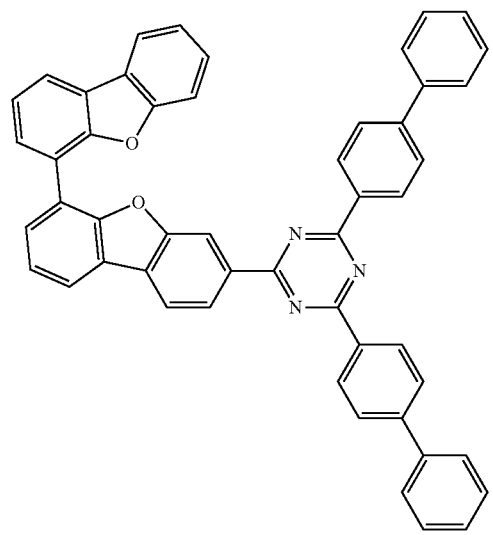
6
7
204
-continued
8
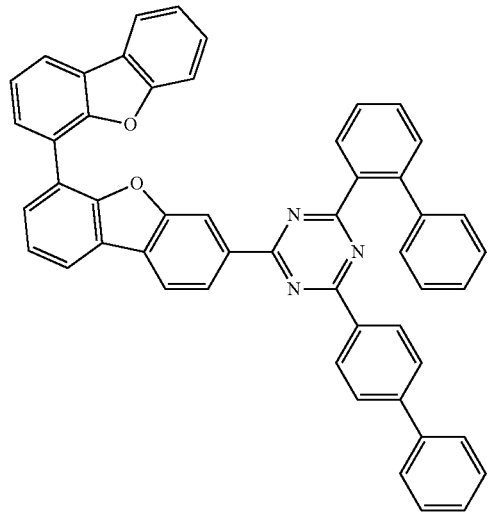
9
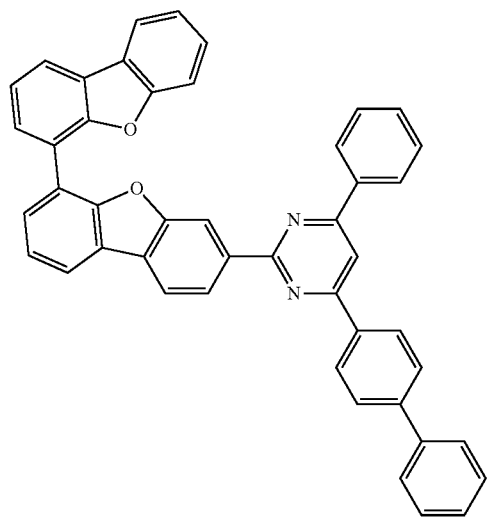
10
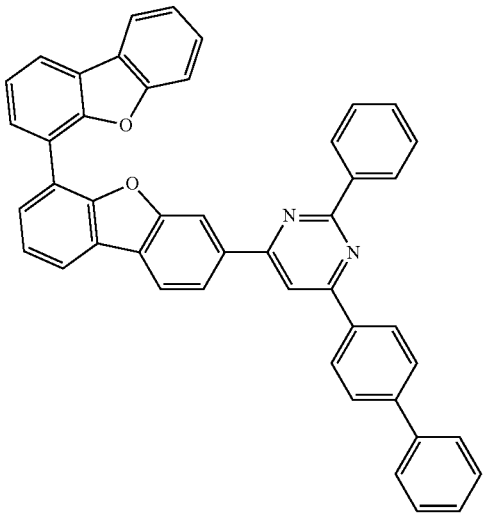

205
-continued
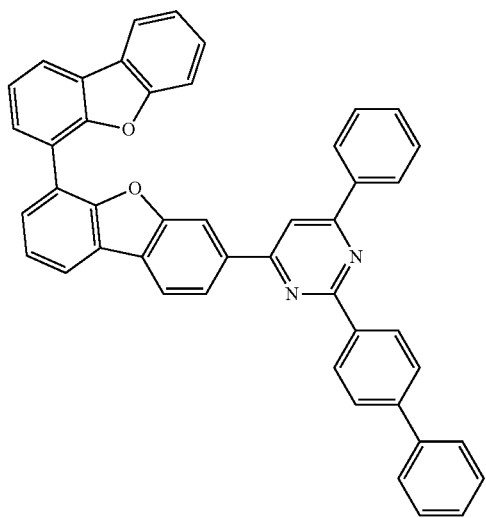
11
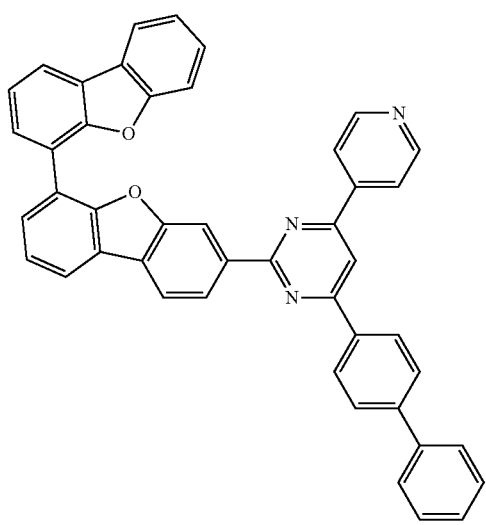
12
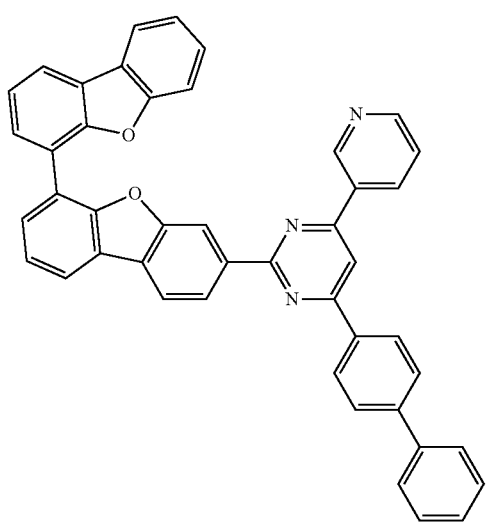
13
206
-continued
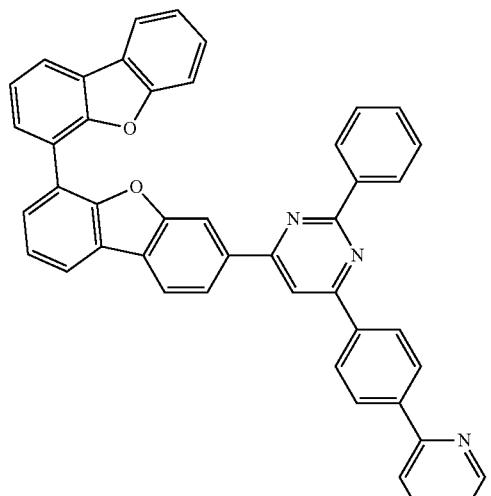
14
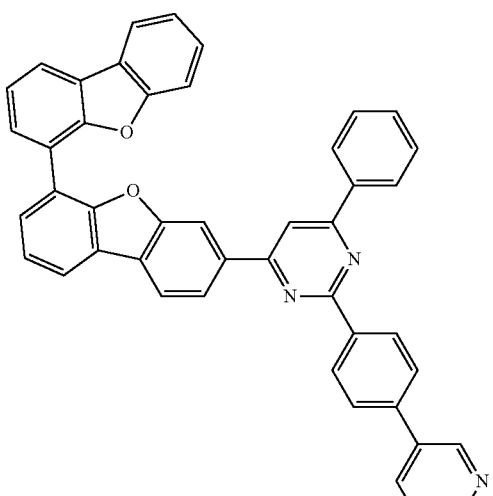
15
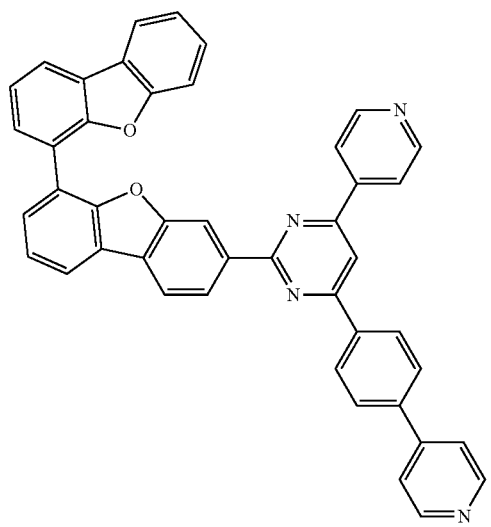
16

207
-continued
17
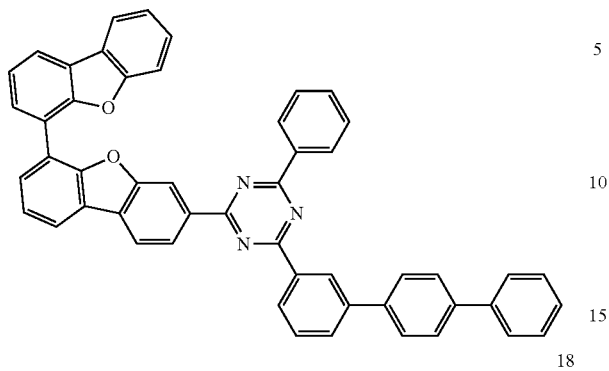
18
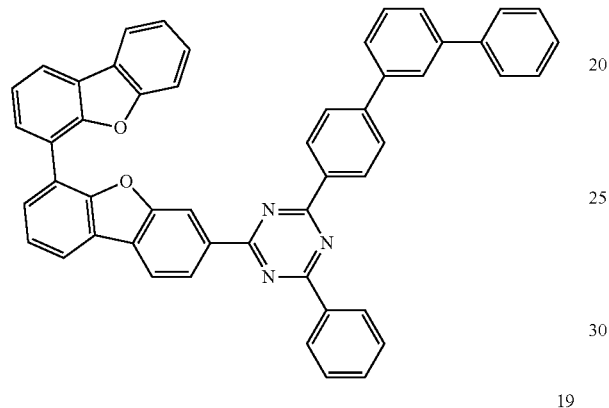
19
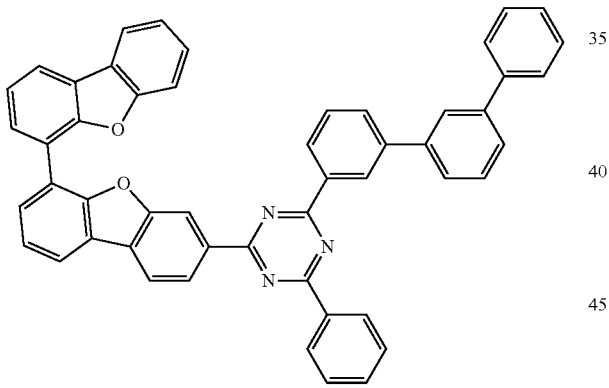
20
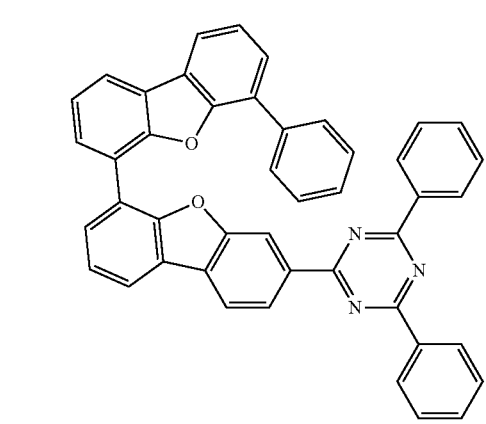
208
-continued
21
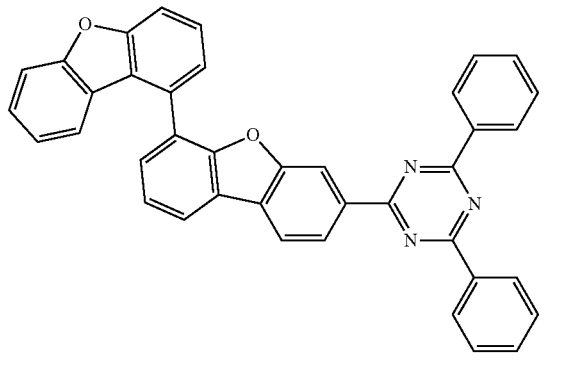
22
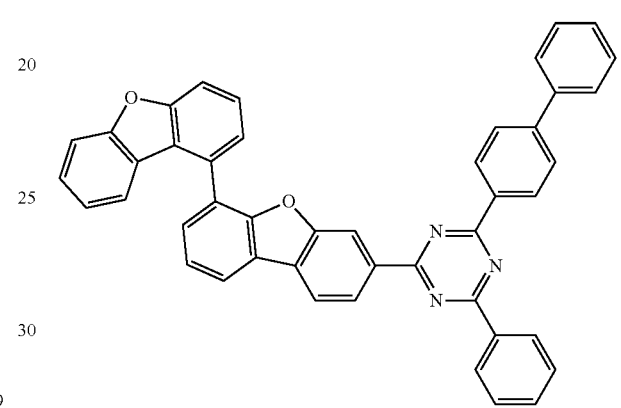
23
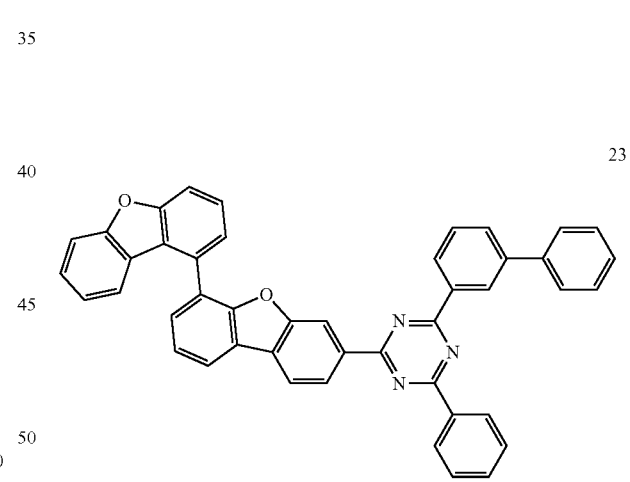
24
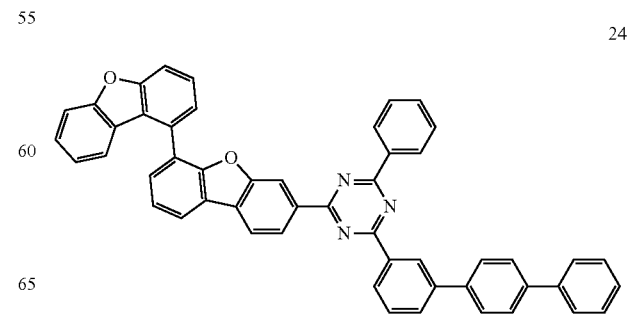

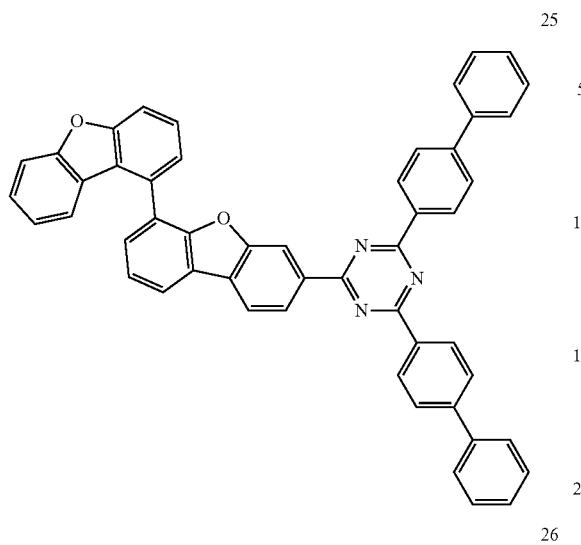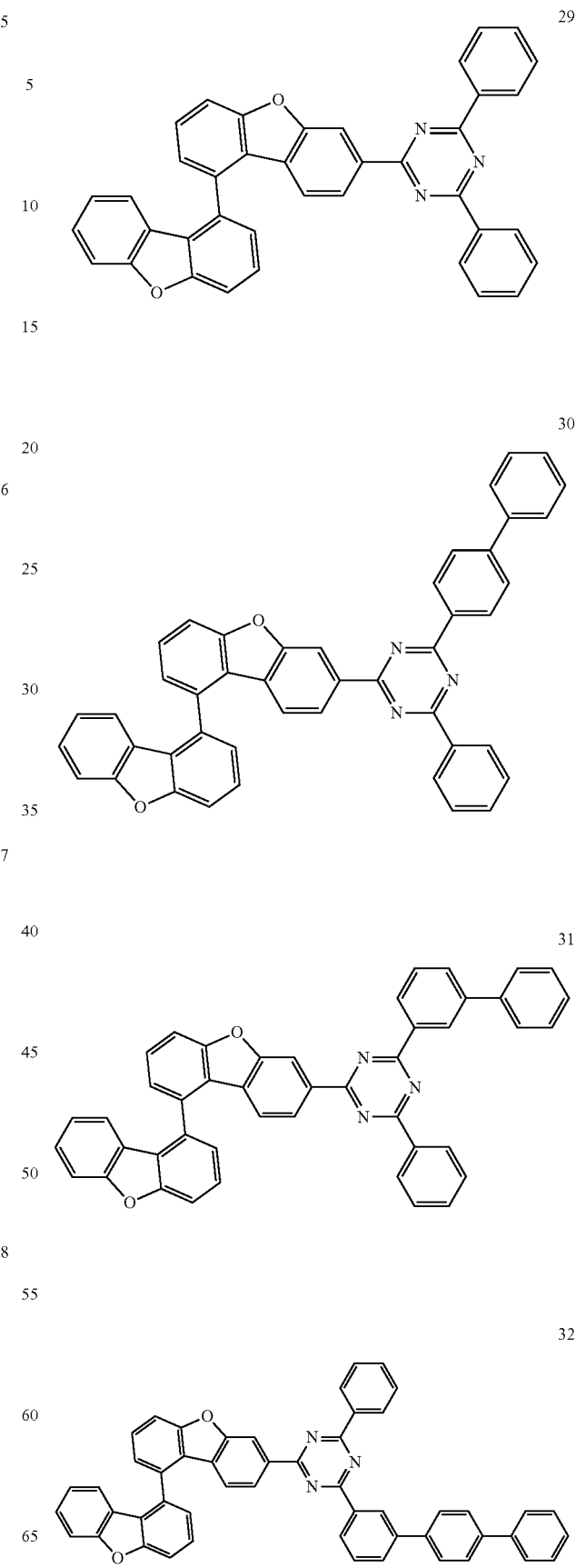

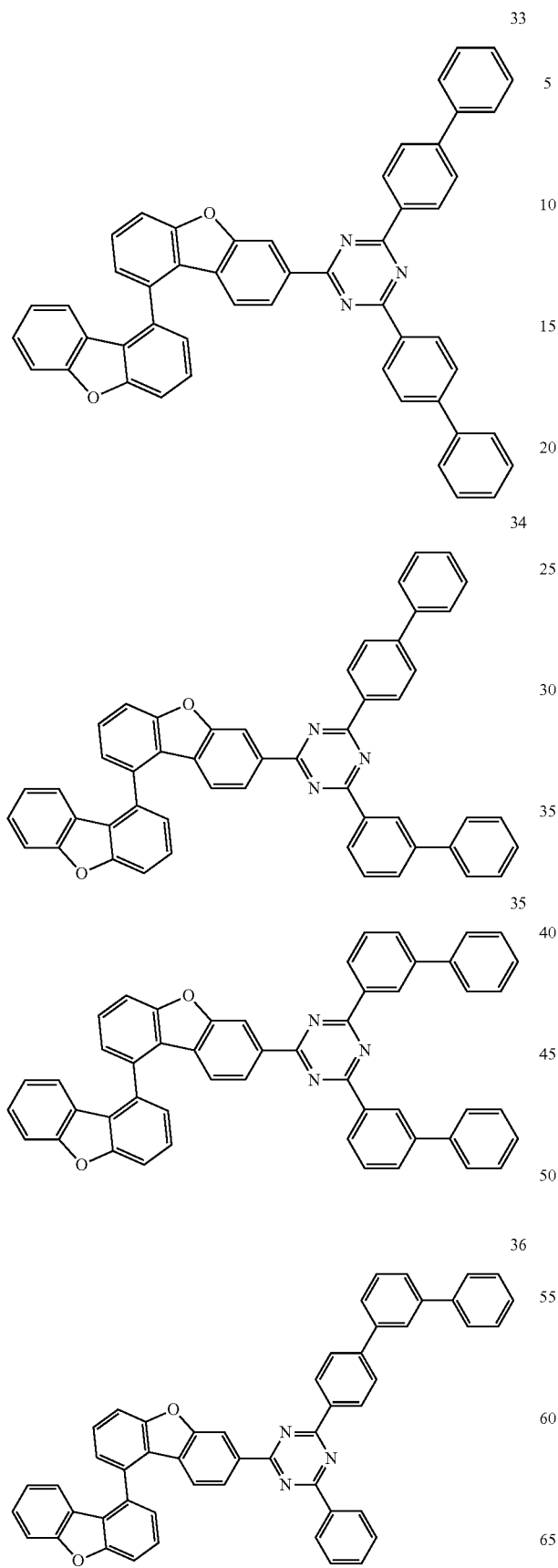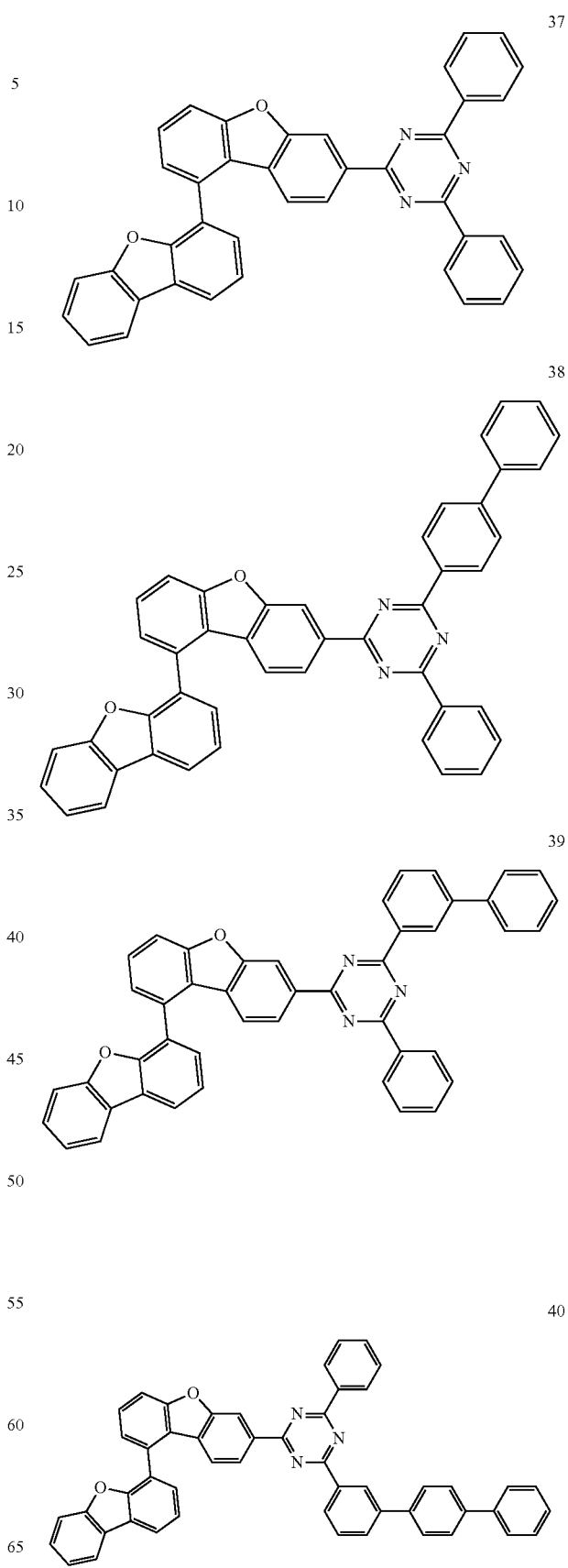

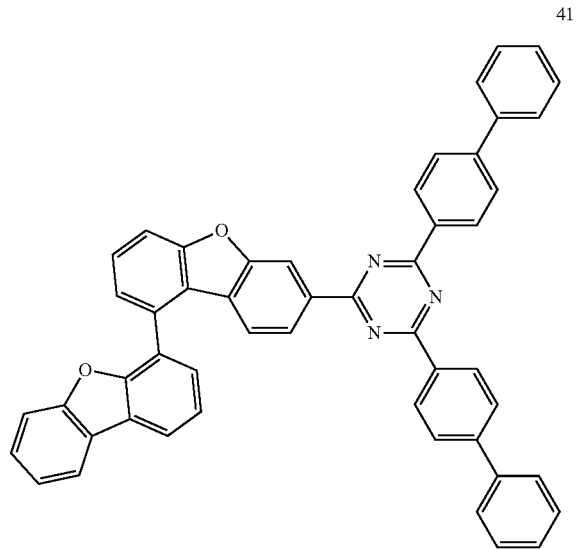
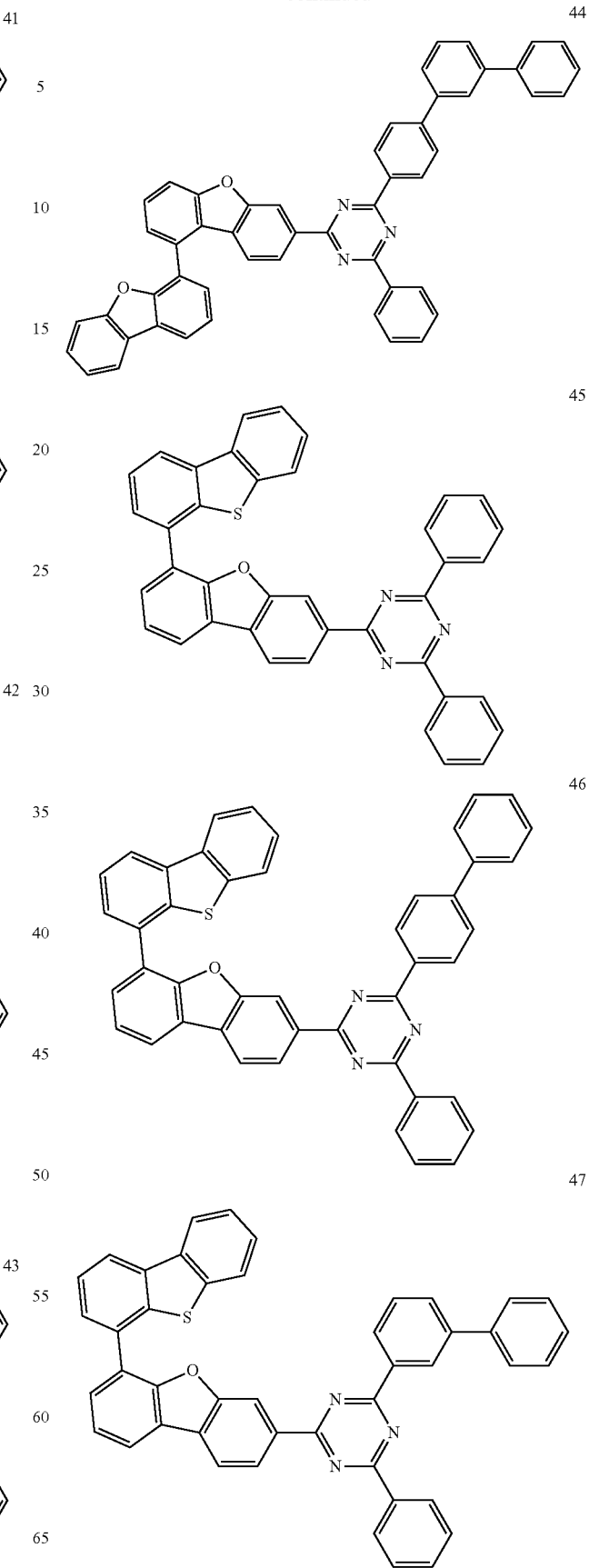

48
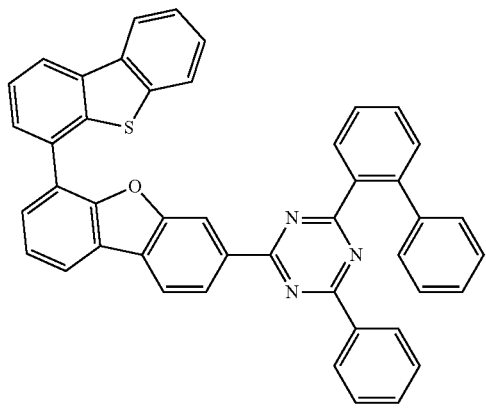
49
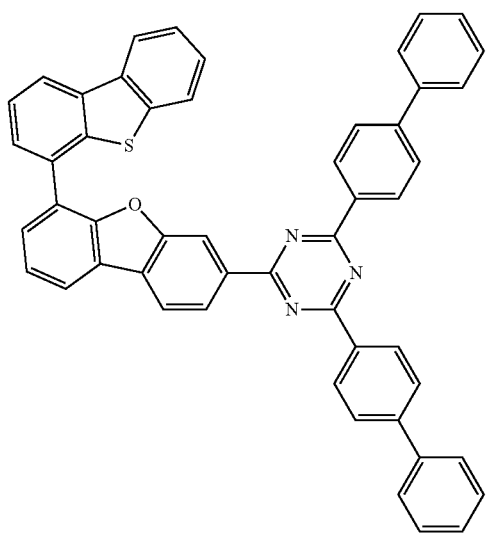
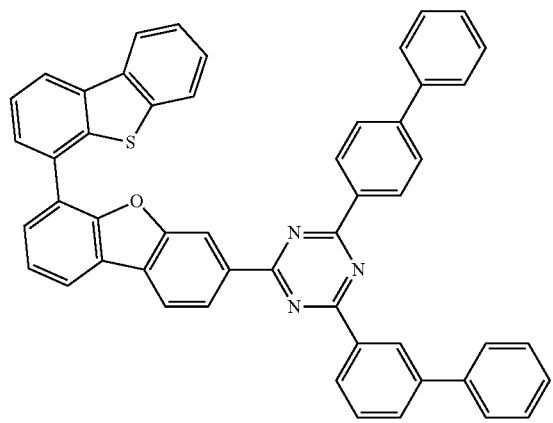
51
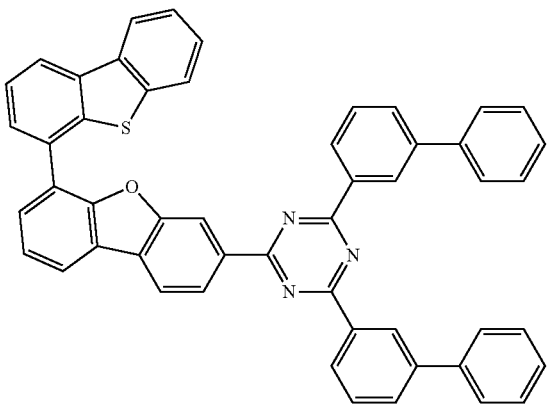
52
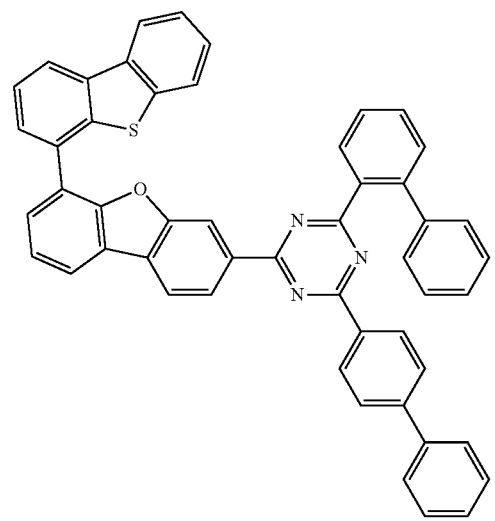
53
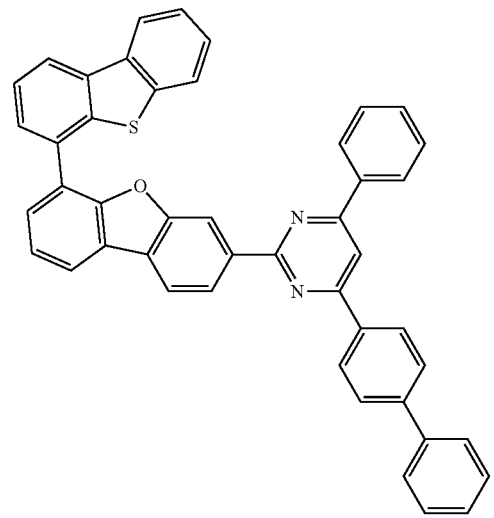

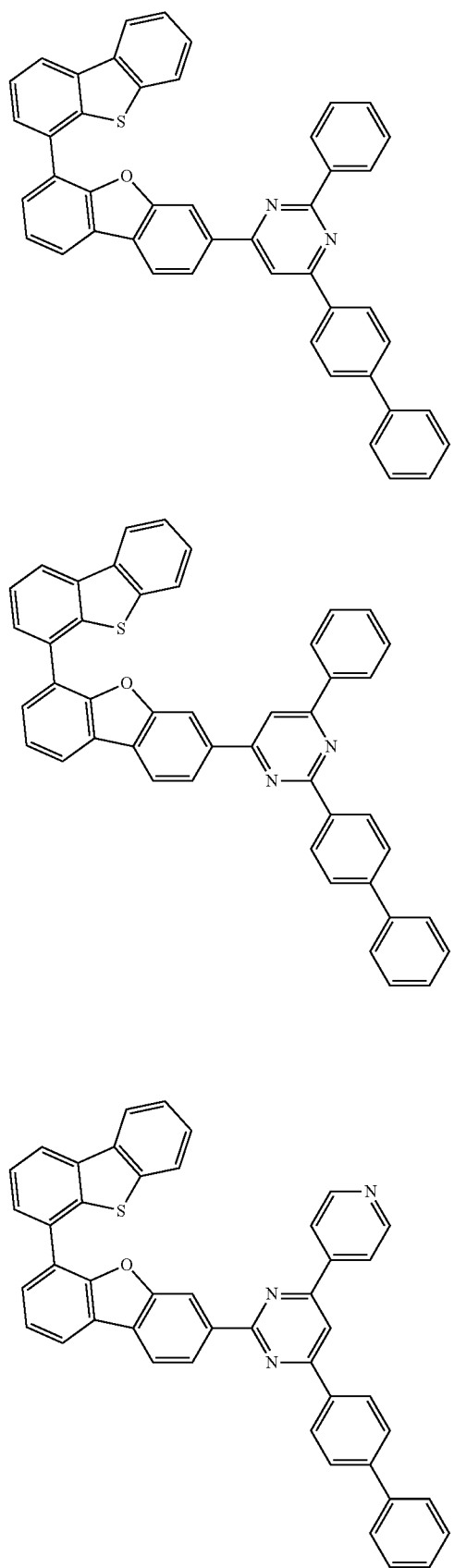
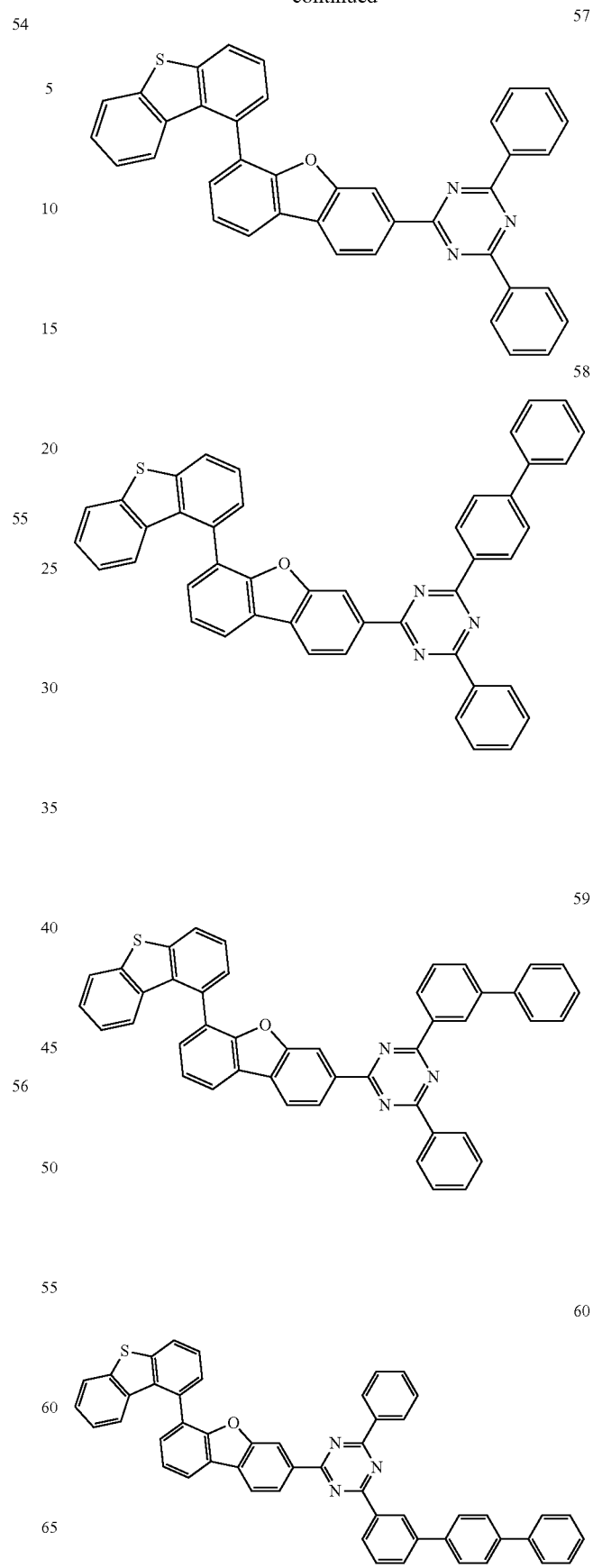

61
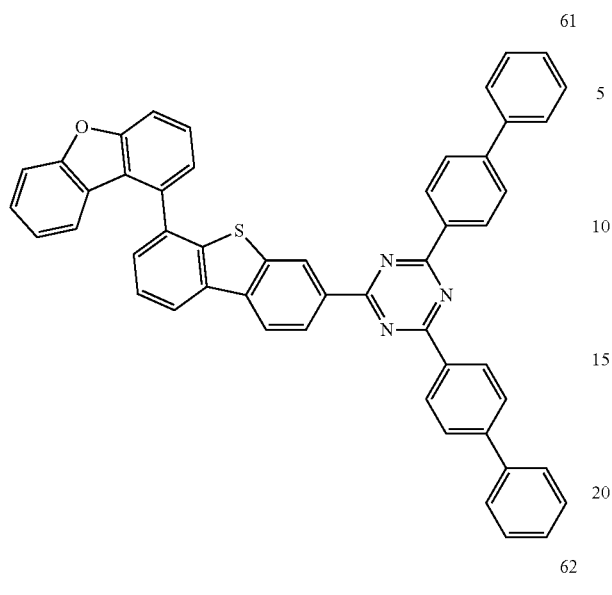
62
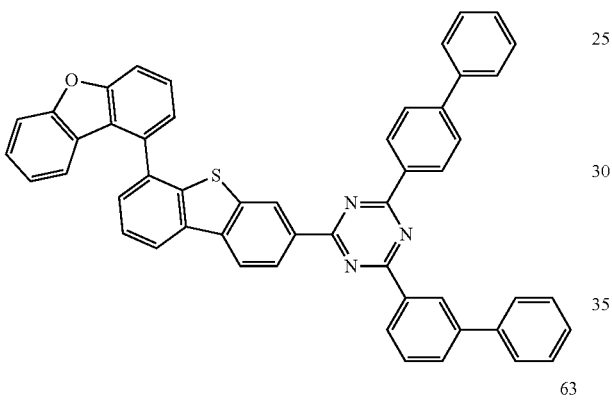
63
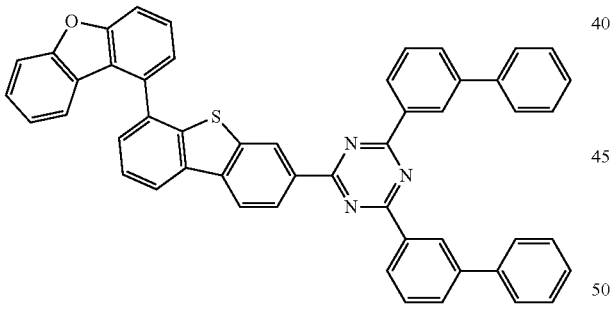
64
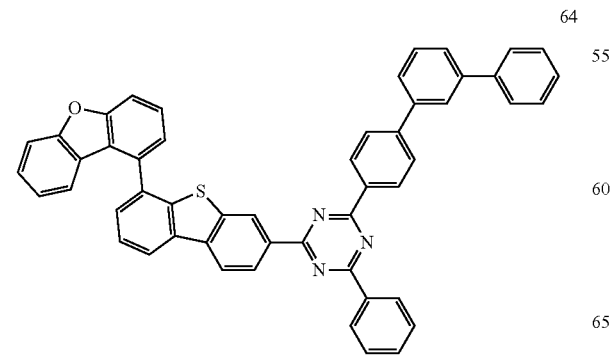
65
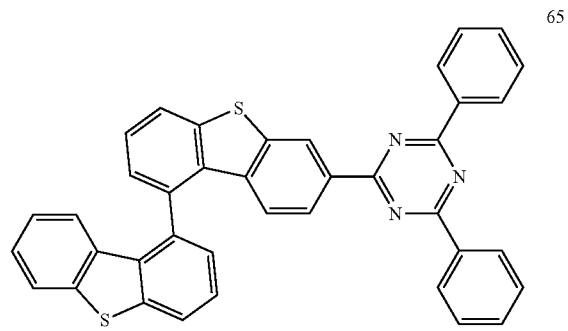
66
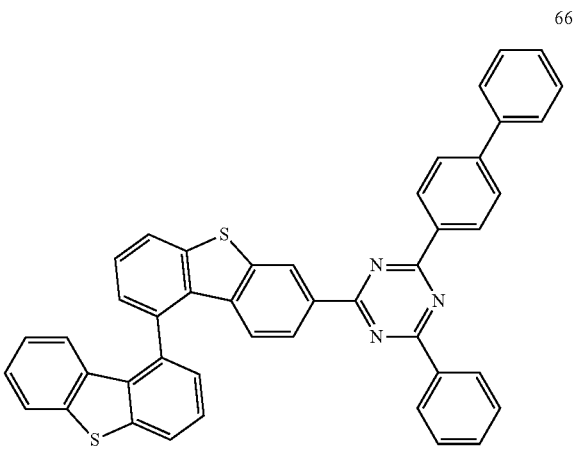
67
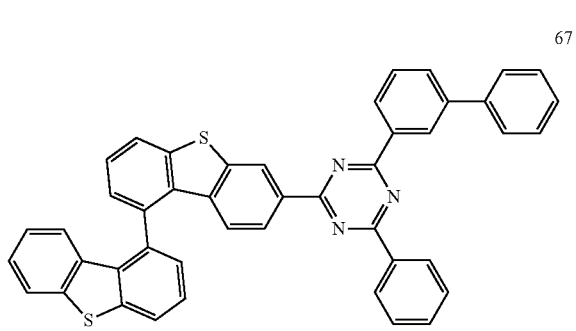
68
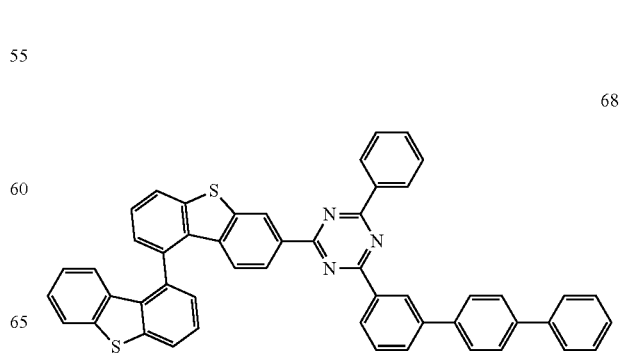

221
-continued
222
-continued
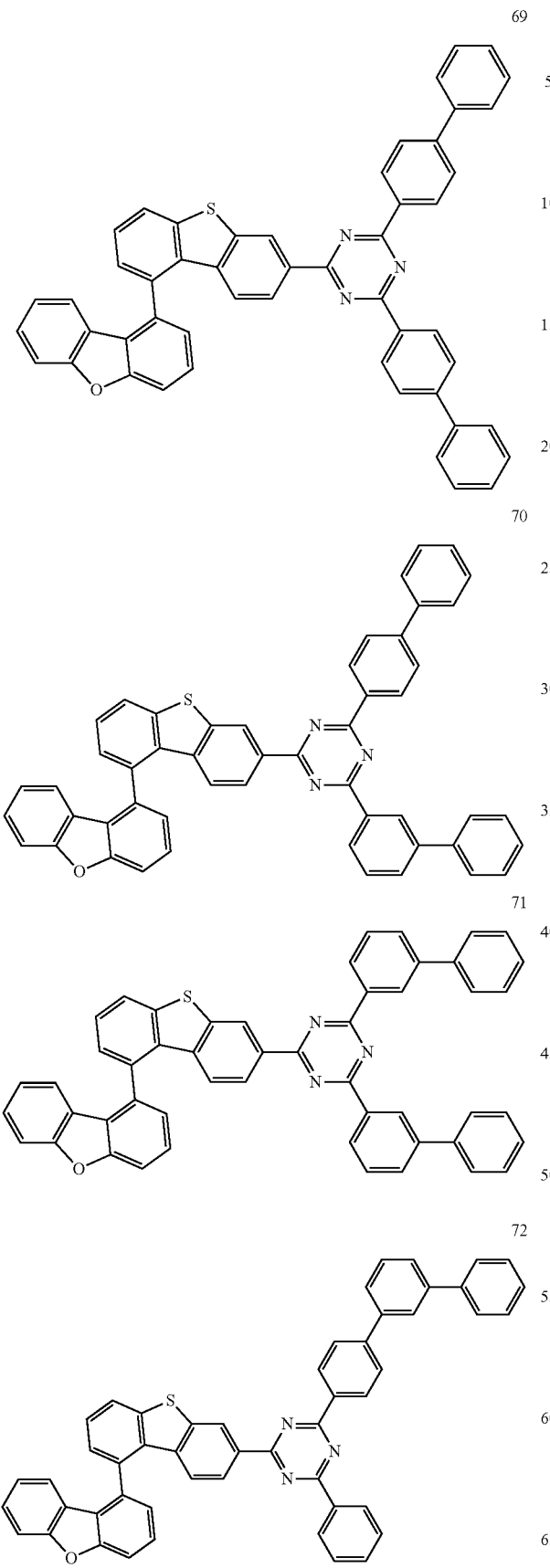
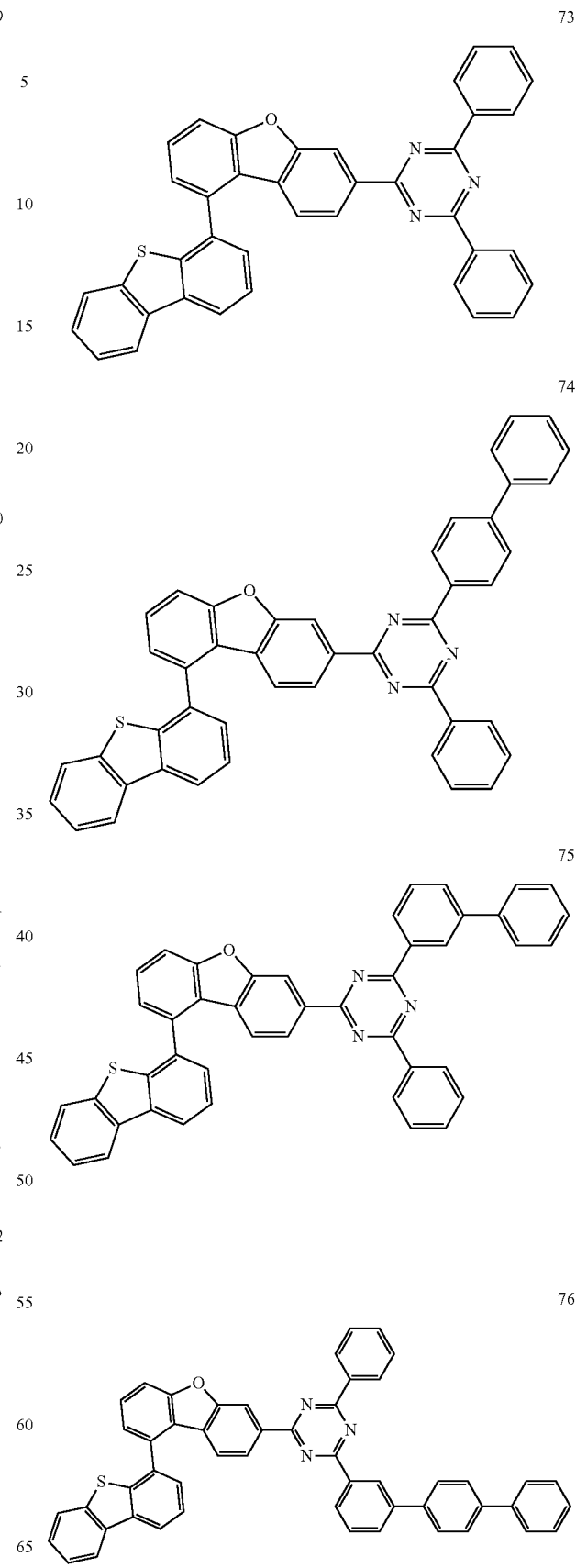

77
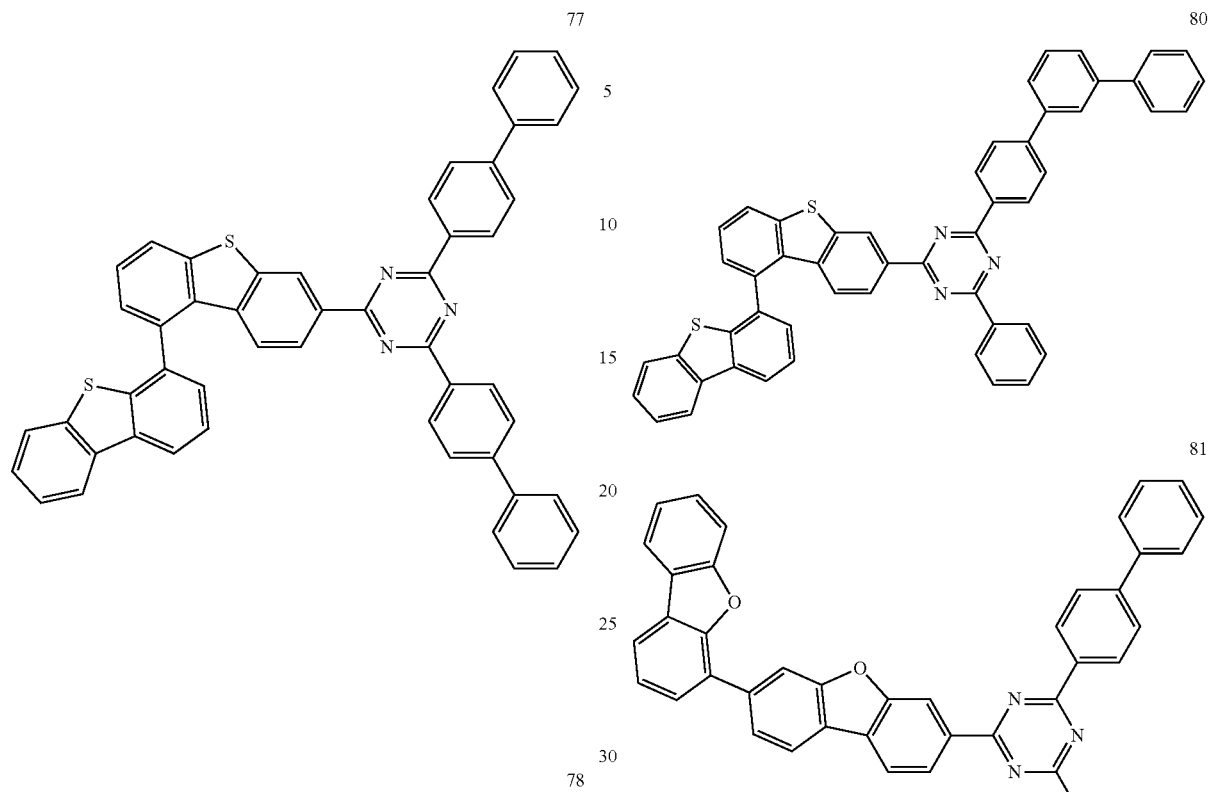
78
79
80
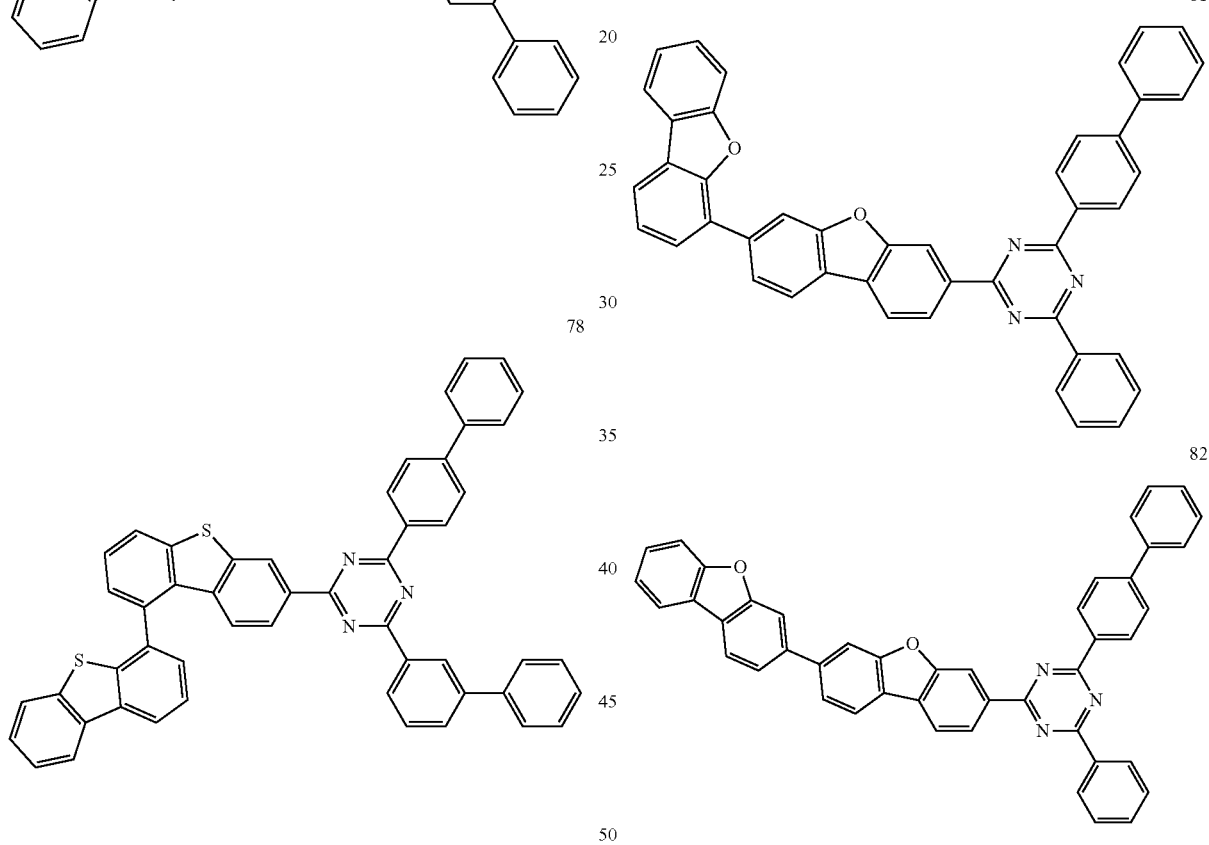
81
82
83
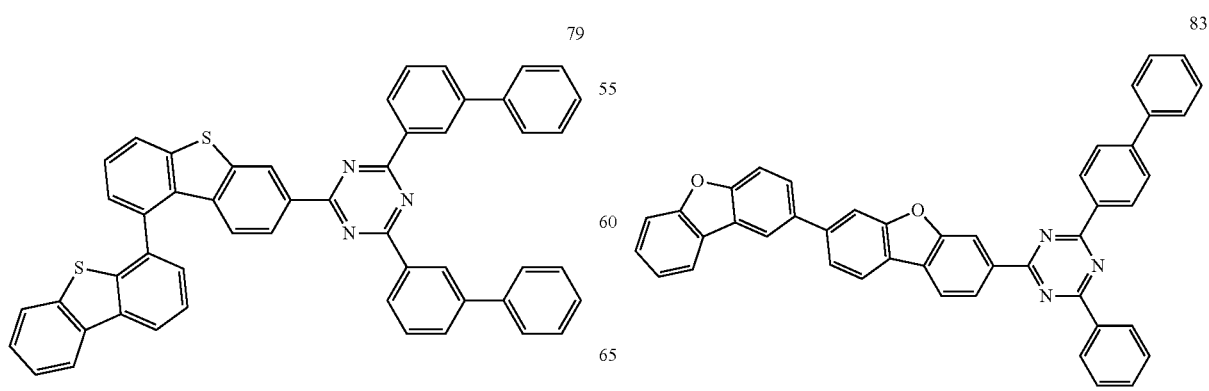

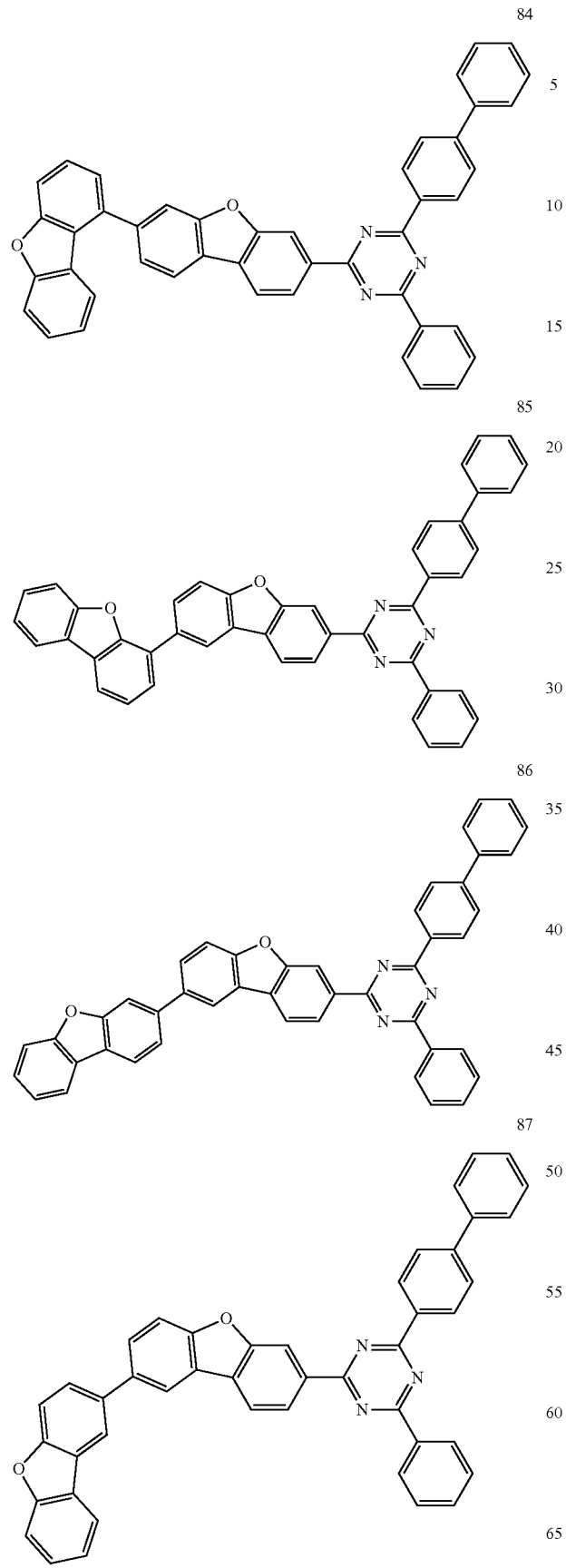
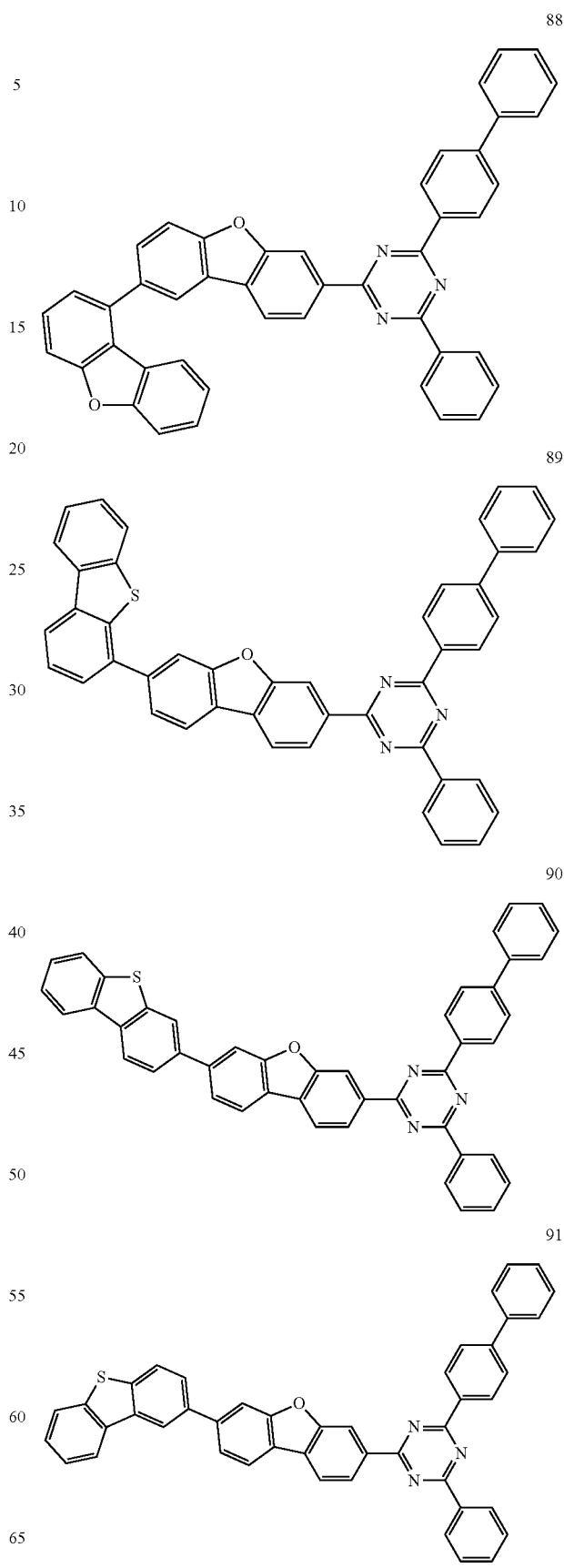

227
-continued
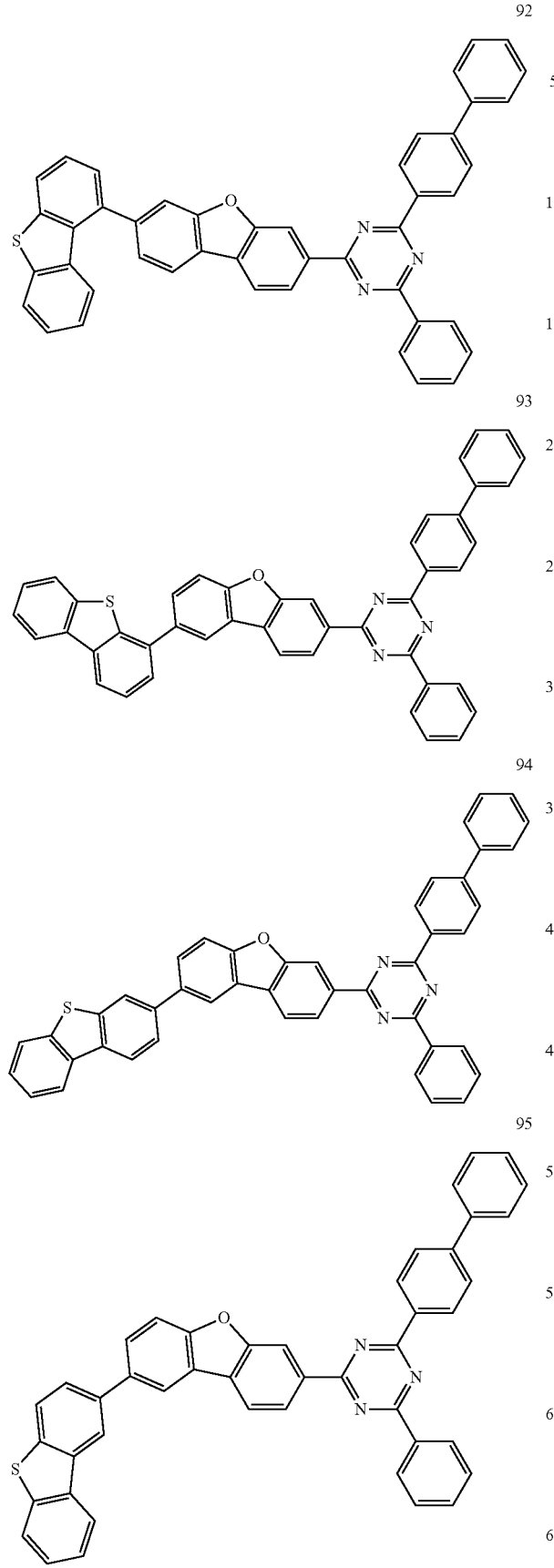
228
-continued
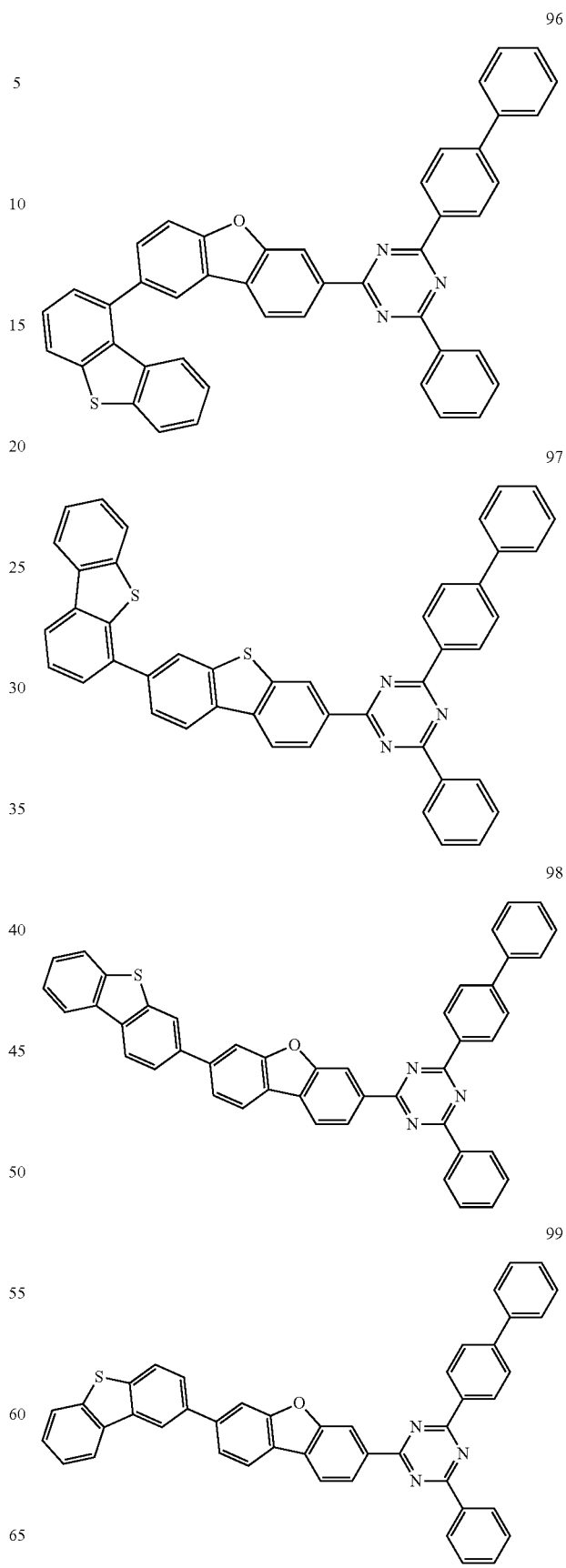

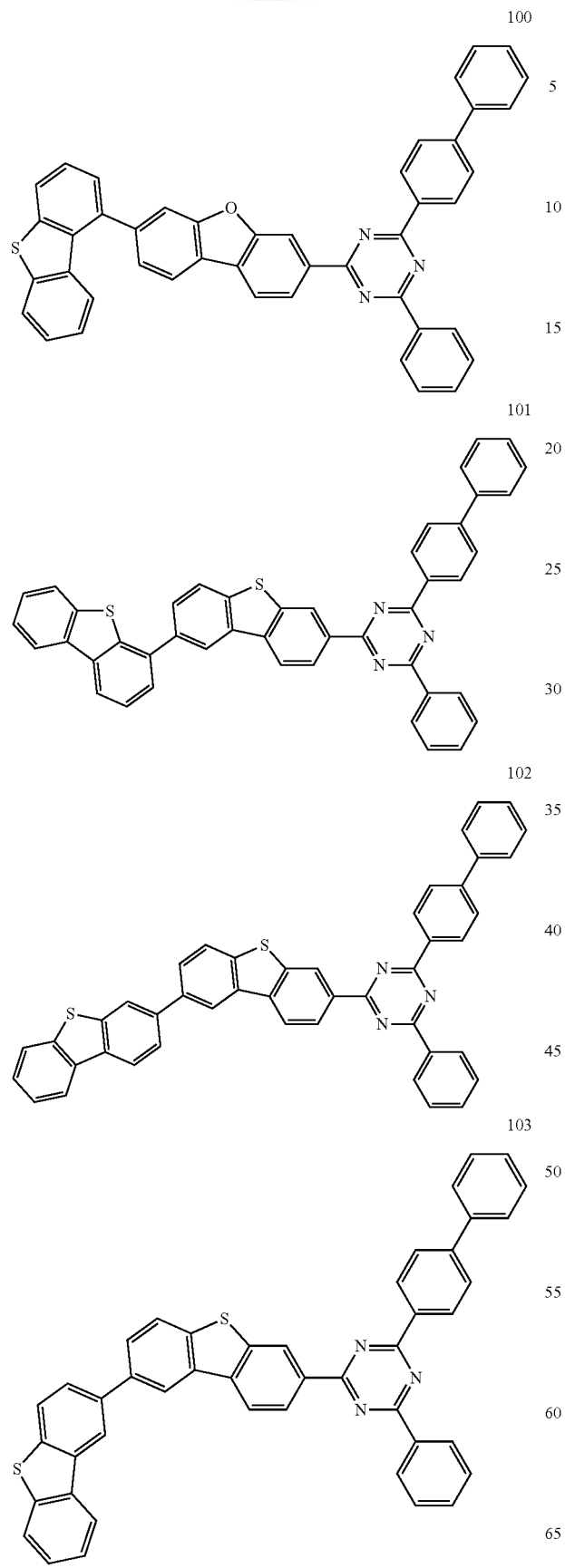
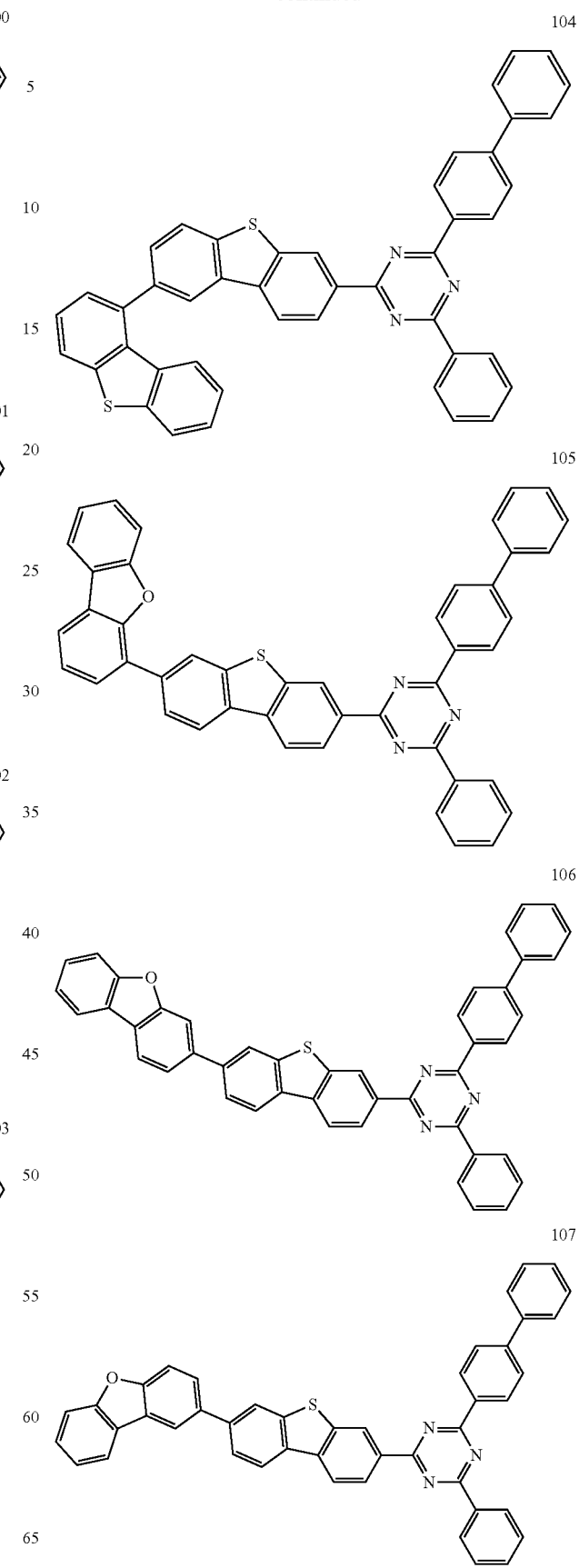

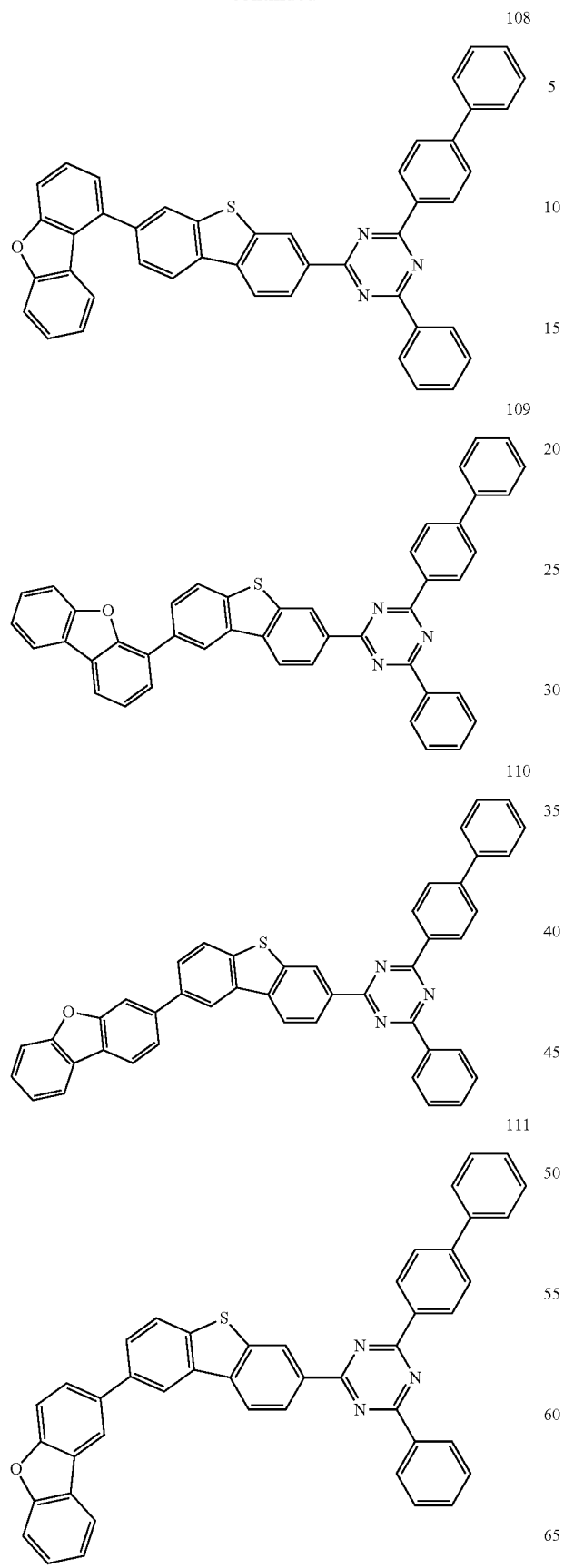
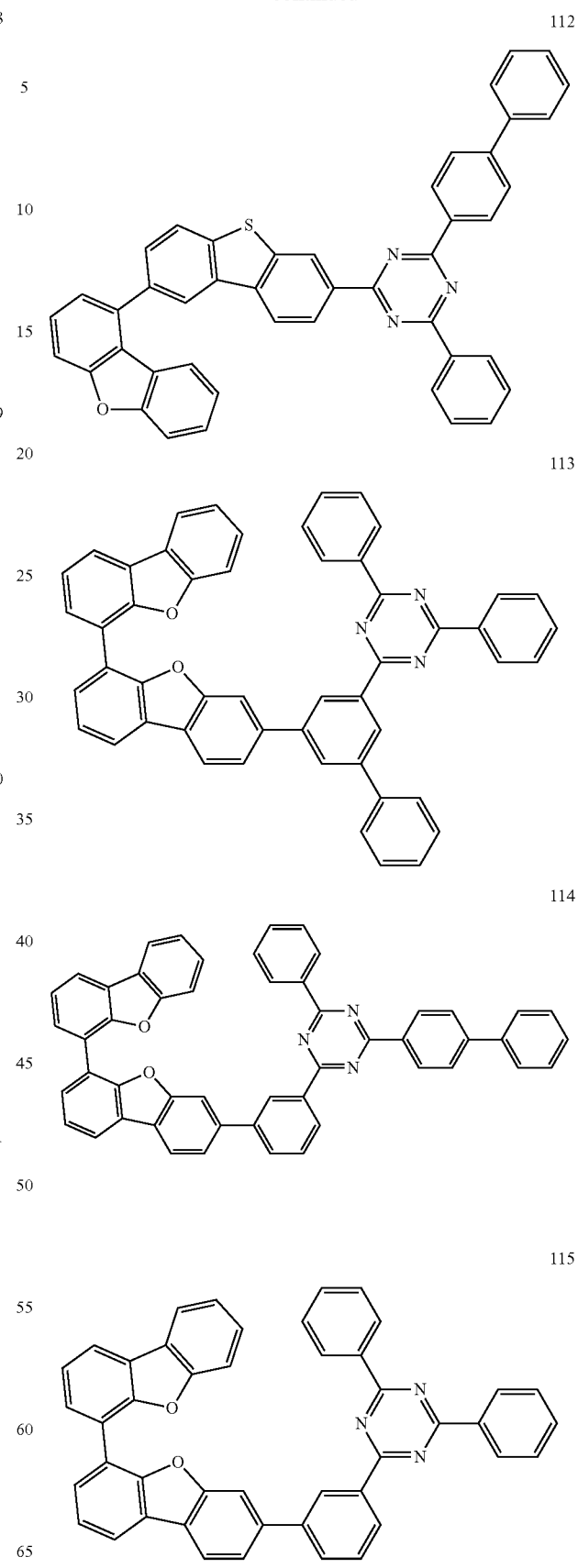

233
-continued
116
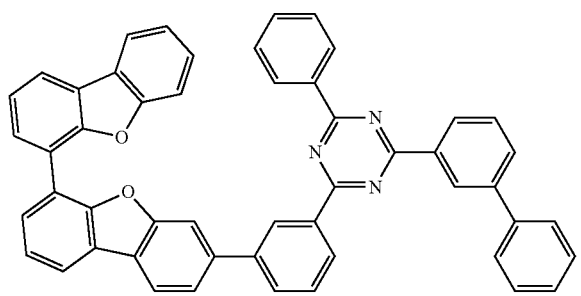
117
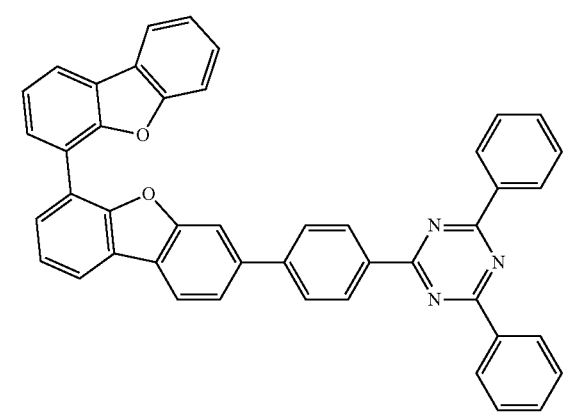
118
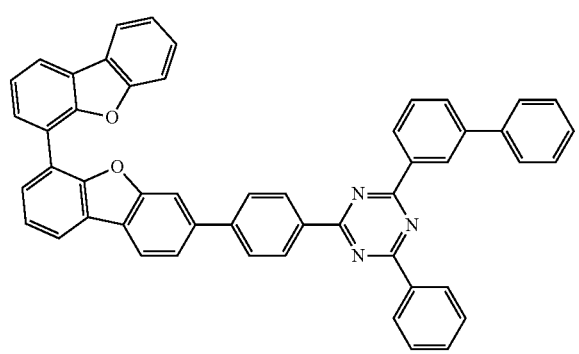
119
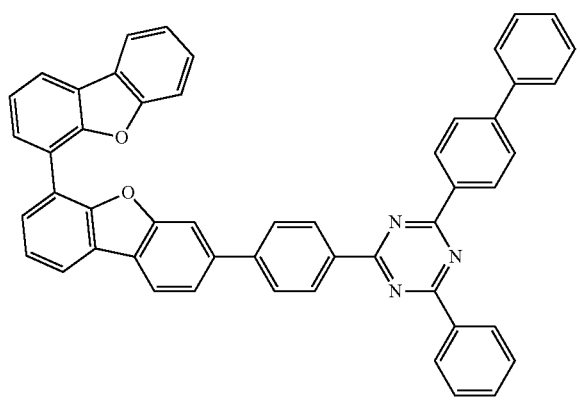
234
-continued
120
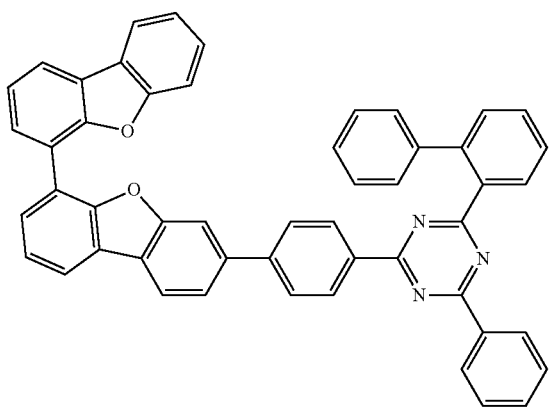
121
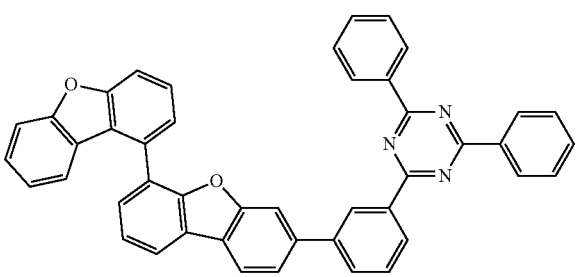
122
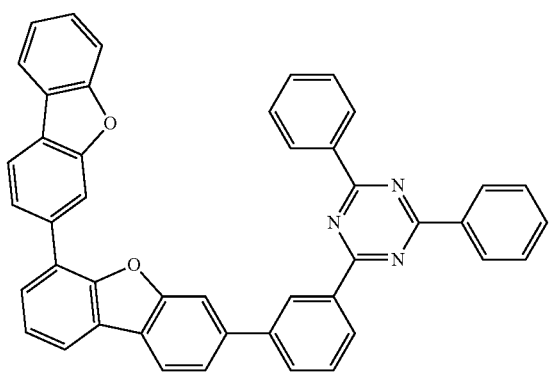
123
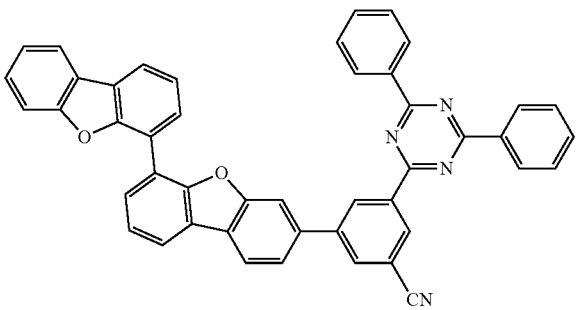

124
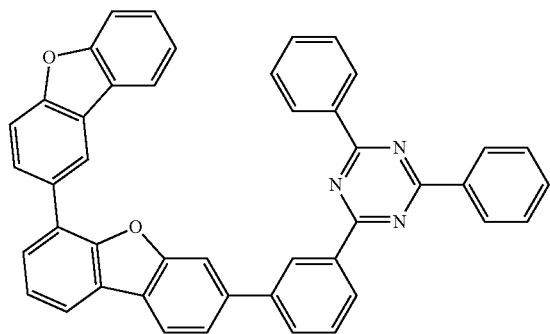
125
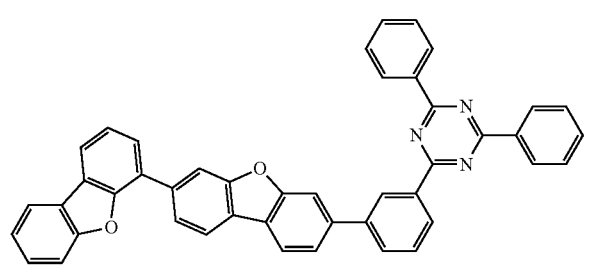
126
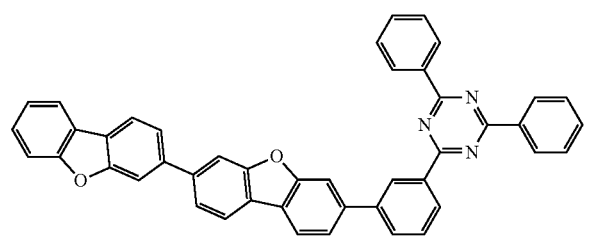
127
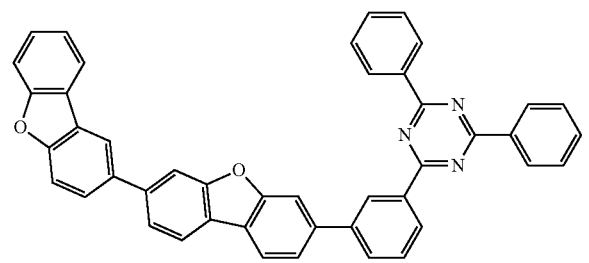
128
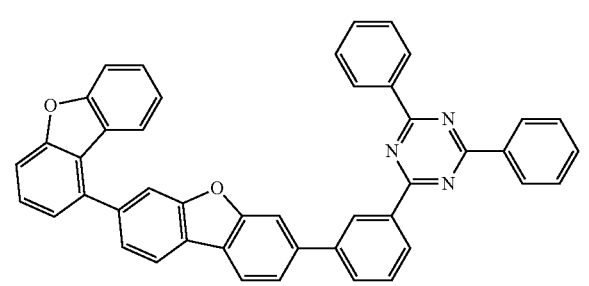
129
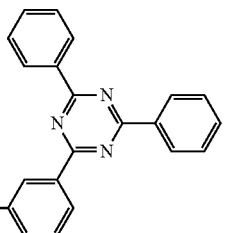
130
131
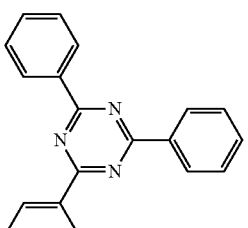
132
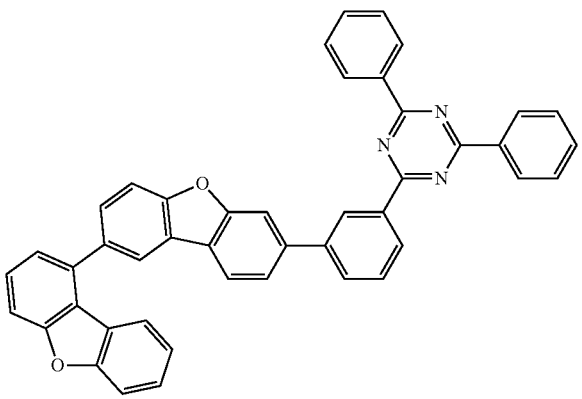

133
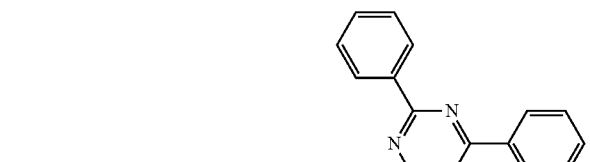
136
134
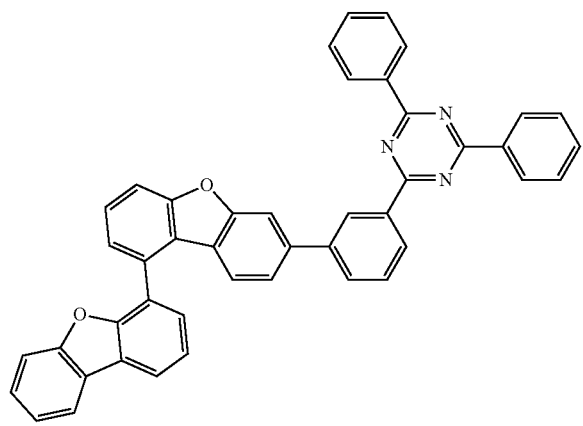
137
138
135
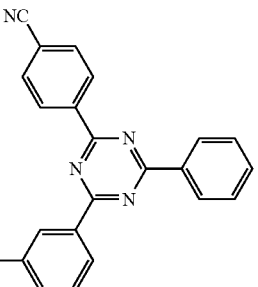
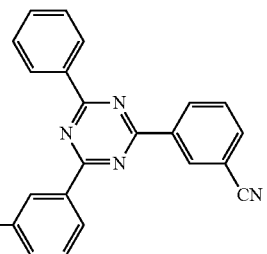
139
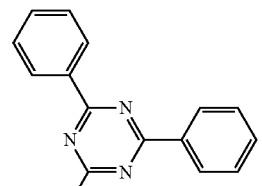

-continued
140
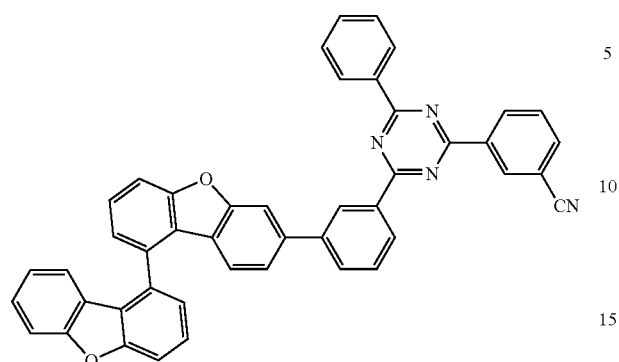
141
142
143
-continued
144
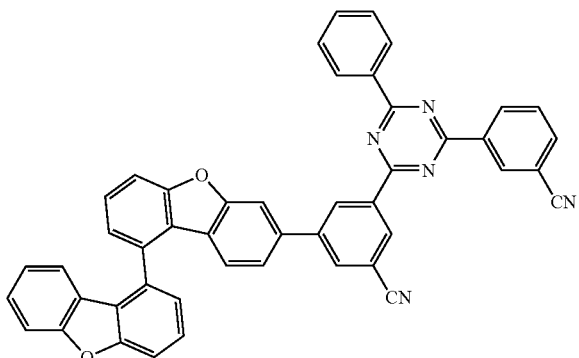
145
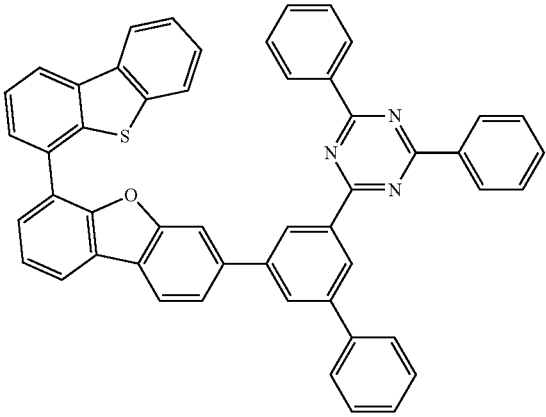
146
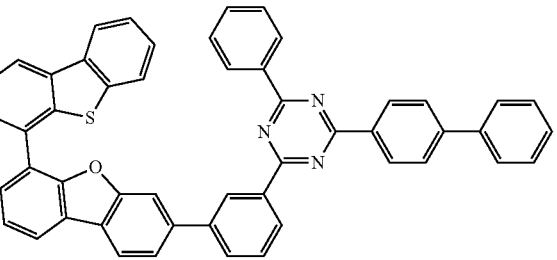
147
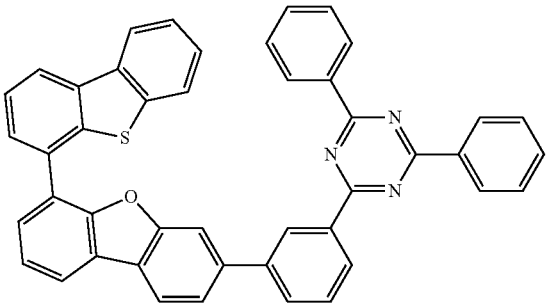

148
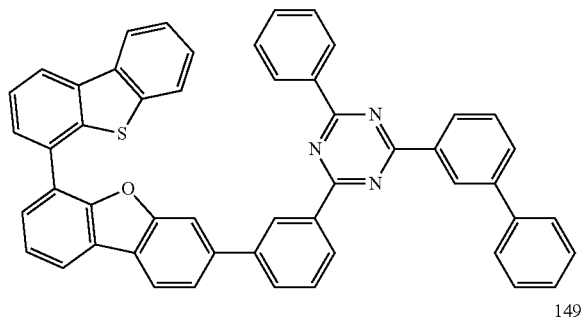
149
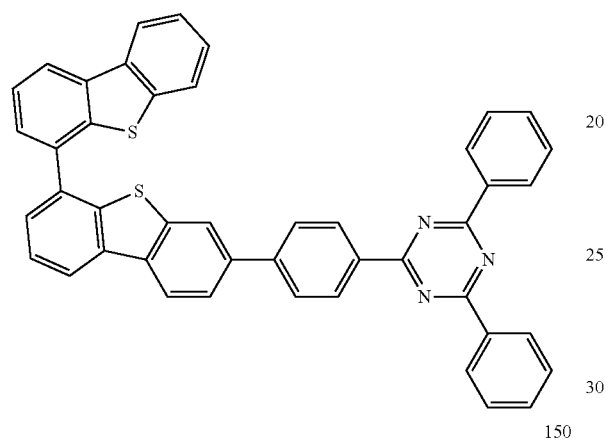
150
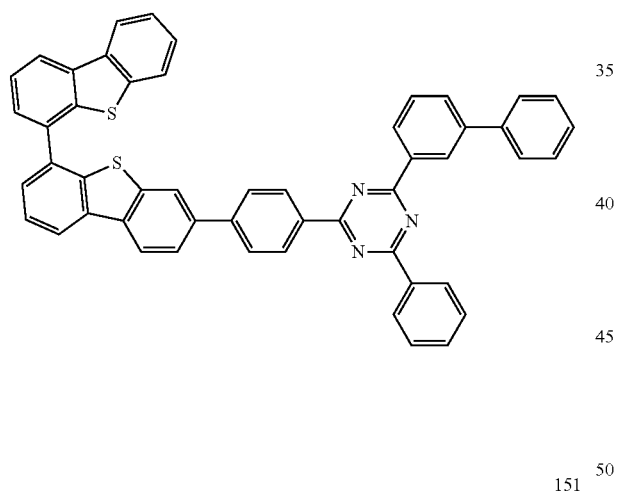
151
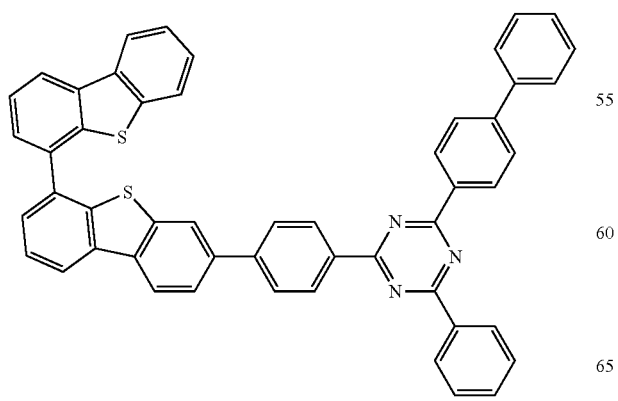
152
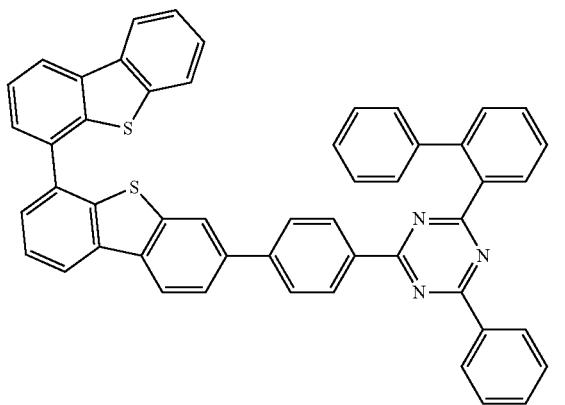
153
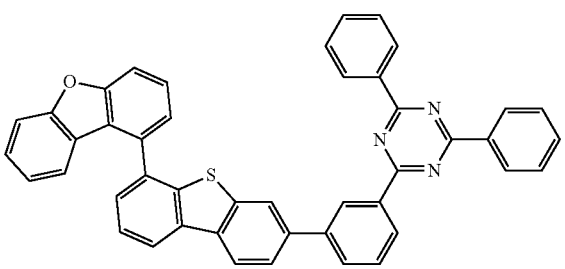
154
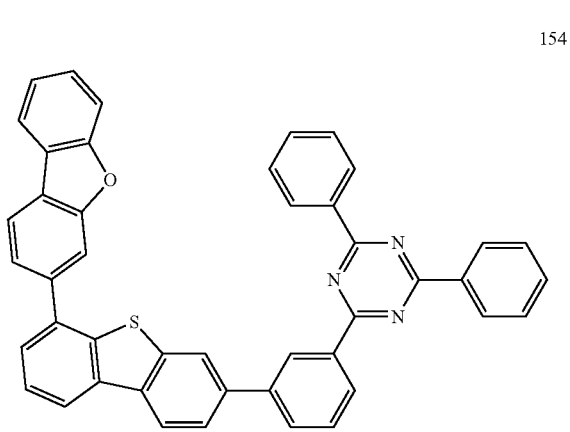
155
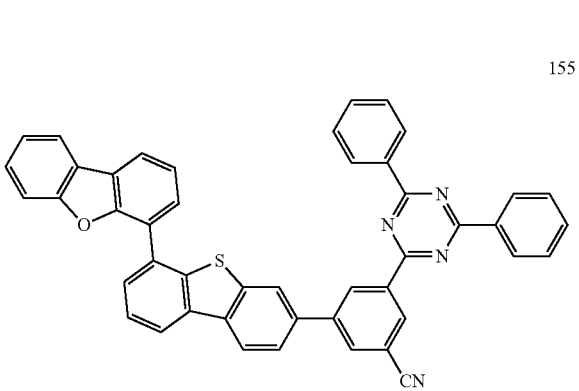

156
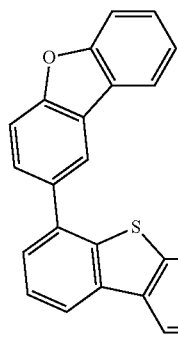
157
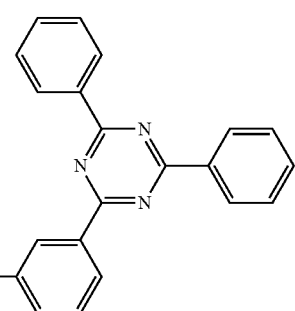
158
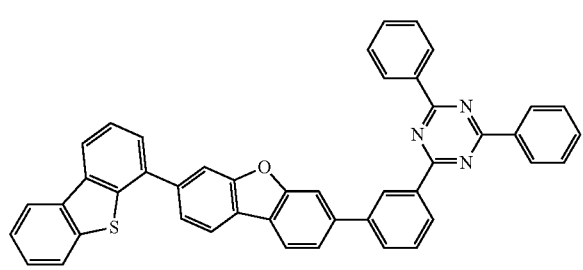
159
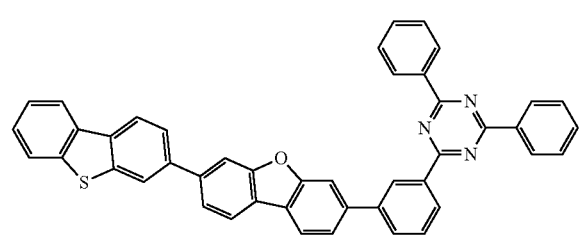
160
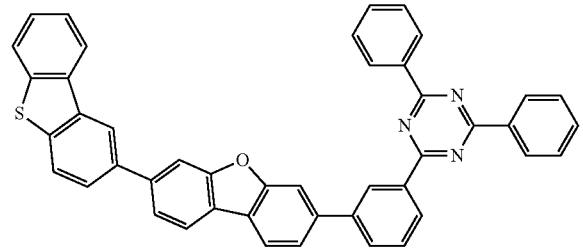
161
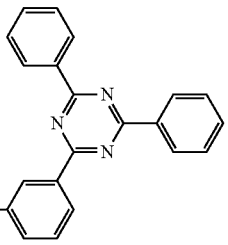
162
163
164
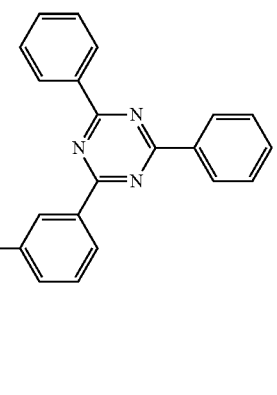

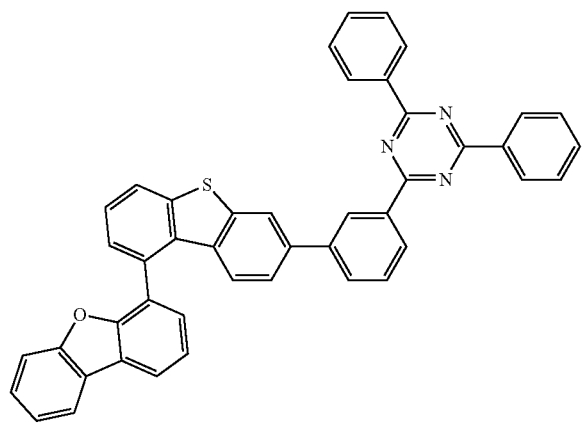
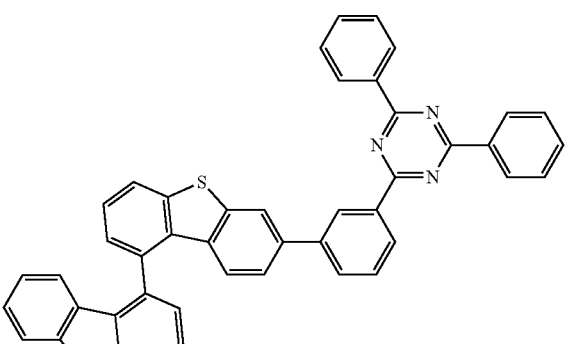

172
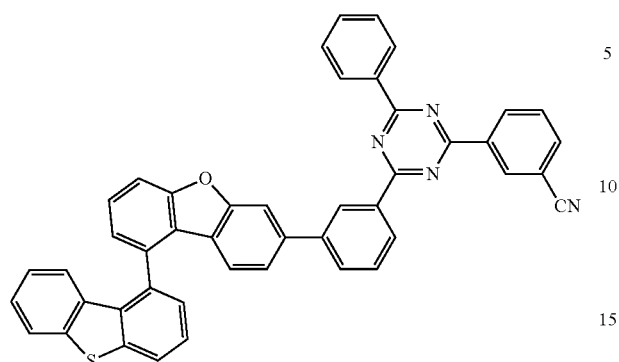
173
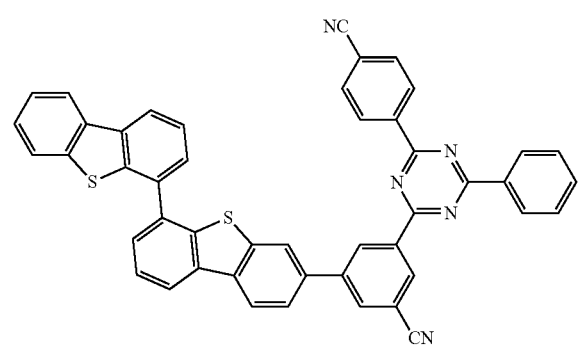
174
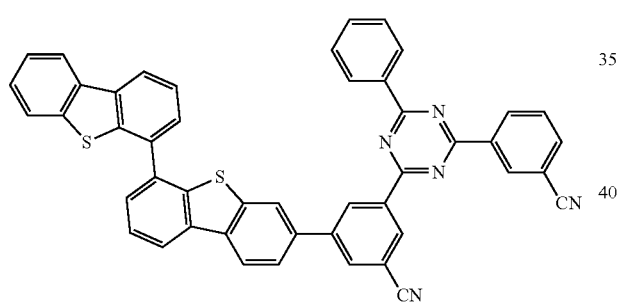
175
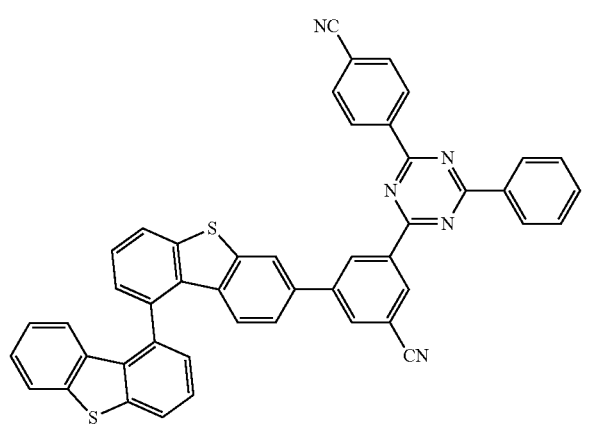
176
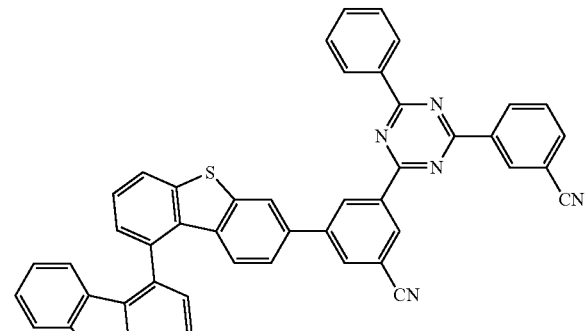
177
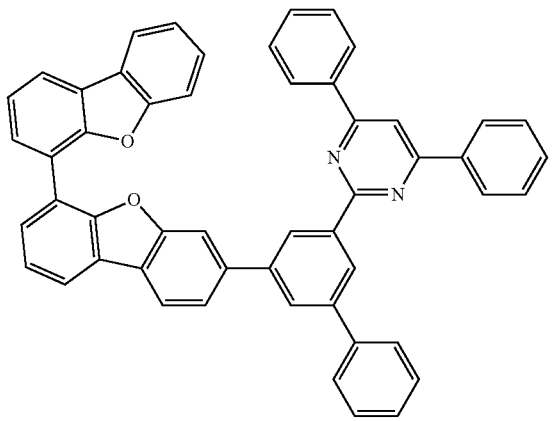
178
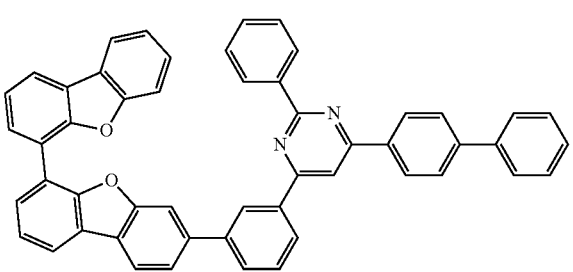
179
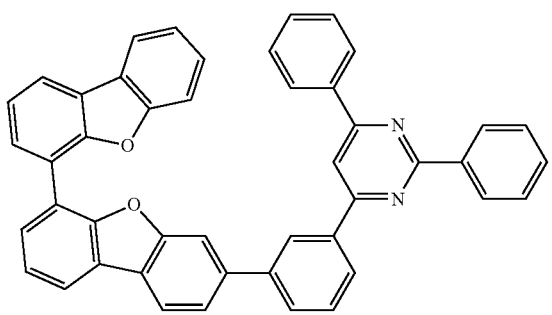

180
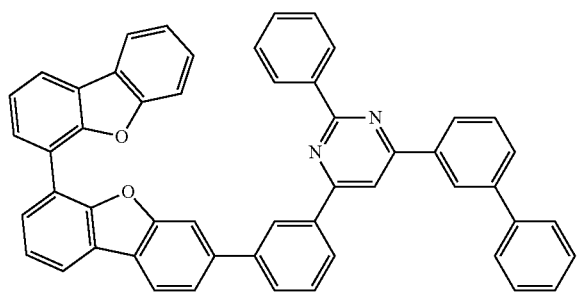
181
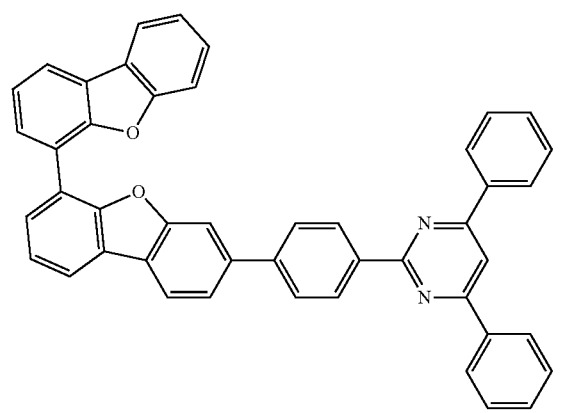
182
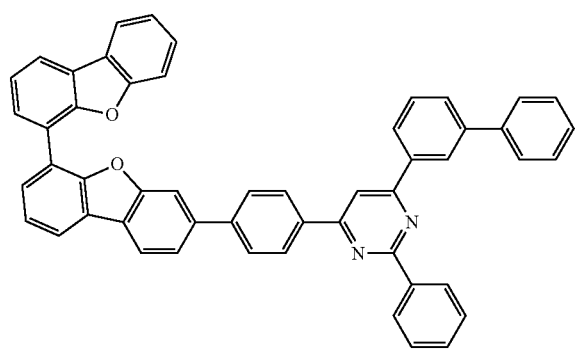
183
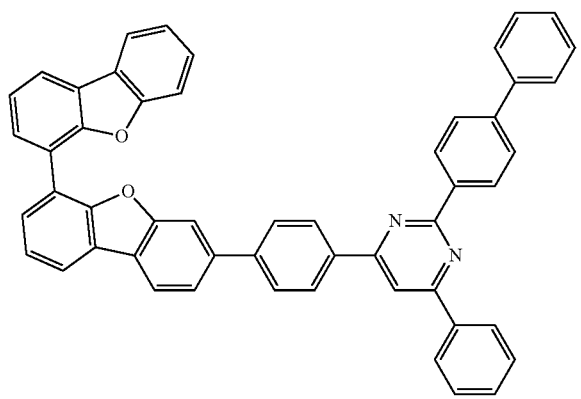
184
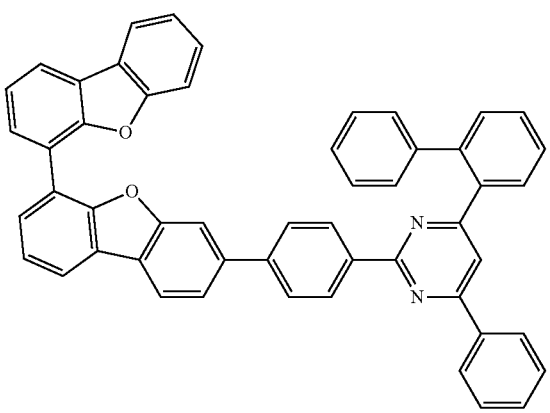
186
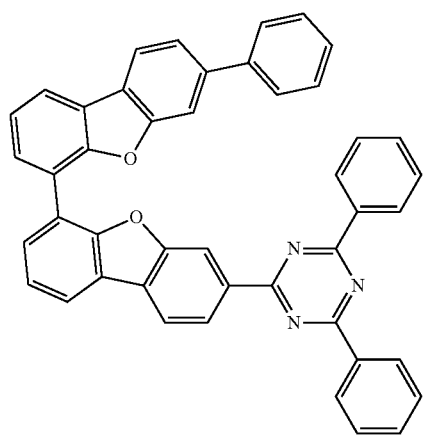
187
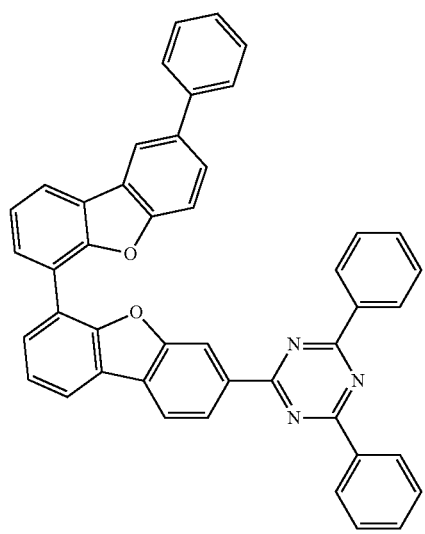

251
-continued
188
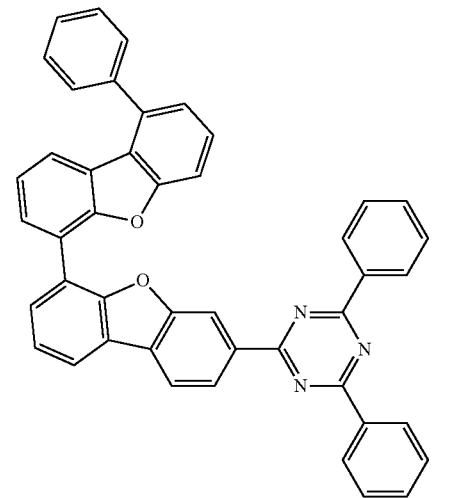
189
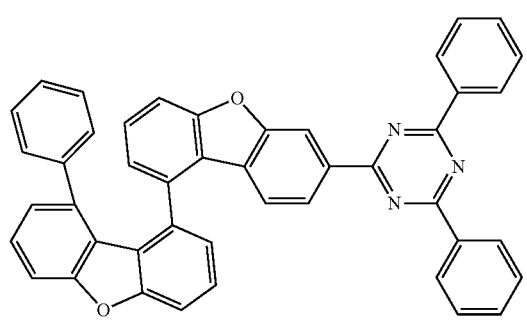
190
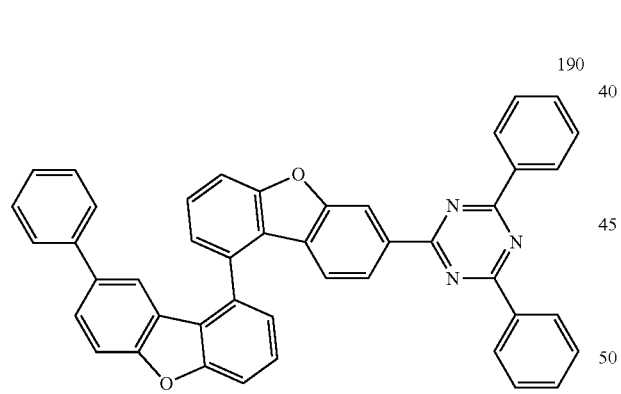
191
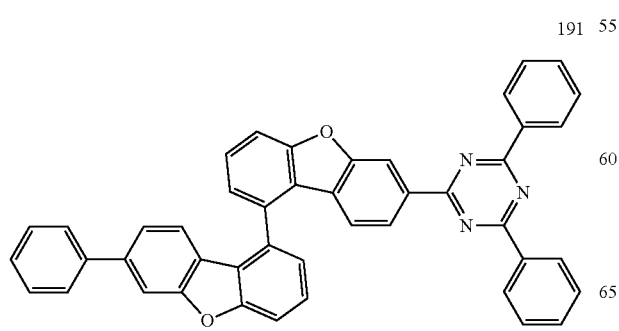
252
-continued
192
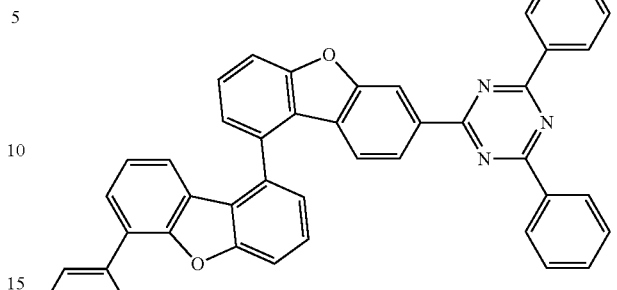
193
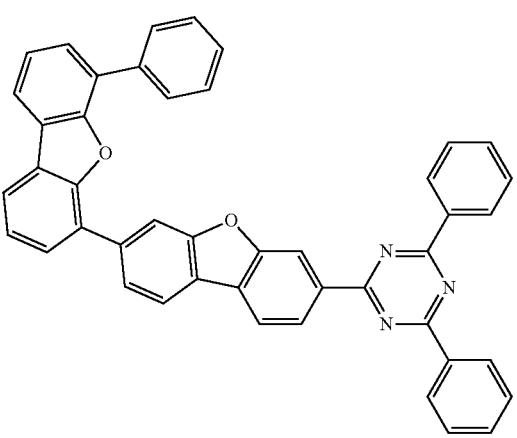
194
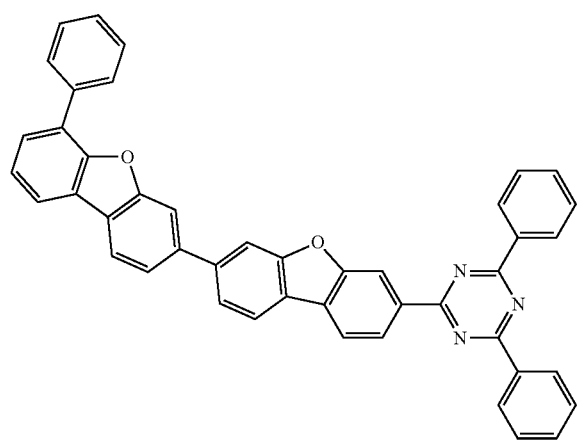
195
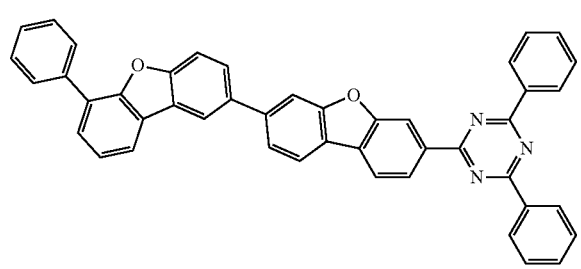

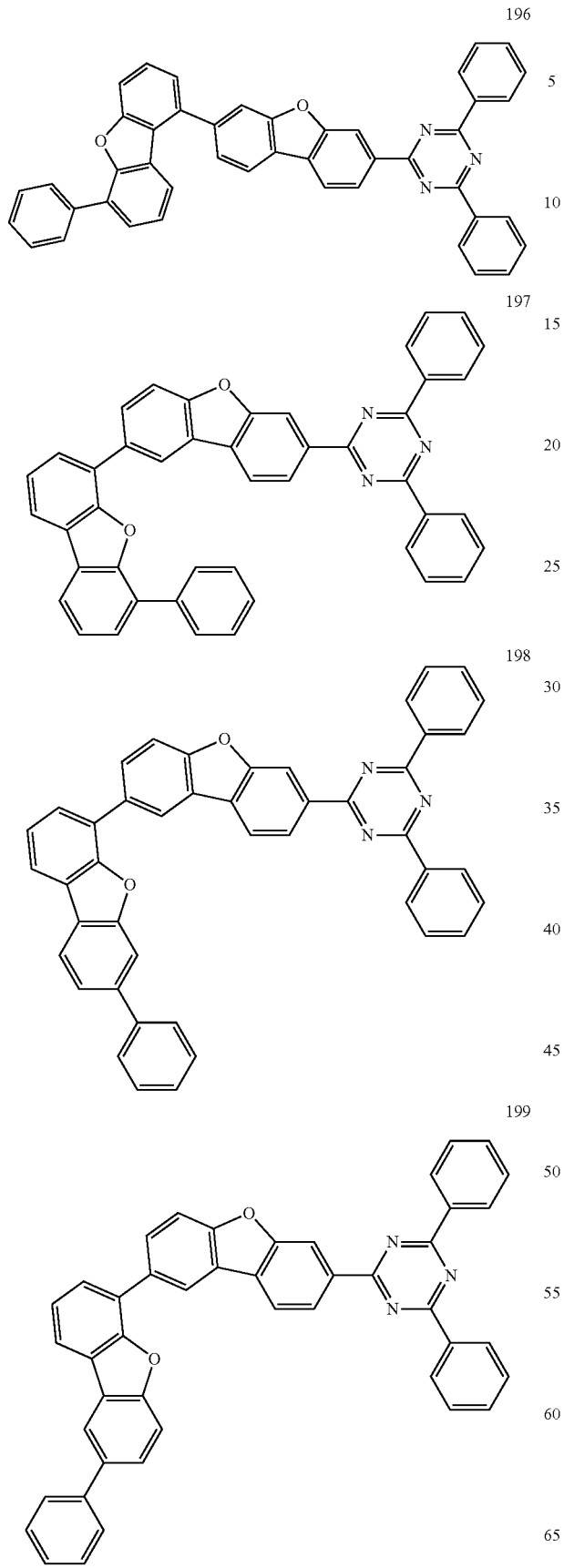

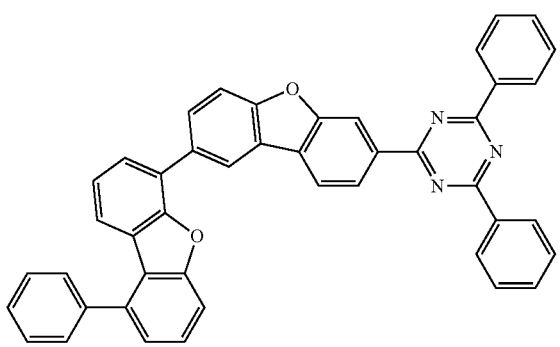

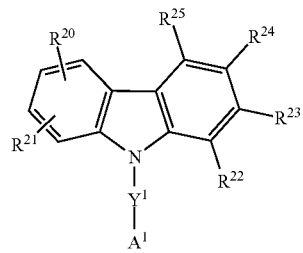

7. An organic optoelectronic device, comprising:
an anode and a cathode facing each other, and
an organic layer disposed between the anode and the cathode,
wherein the organic layer comprises the organic compound of claim 1.

8. The organic optoelectronic device of claim 7, wherein:
the organic layer comprises a light emitting layer, and
the organic compound is a host of the light emitting layer.

9. A display device comprising the organic optoelectronic device of claim 7.

10. A composition comprising
a first organic compound, the first organic compound being the organic compound of claim 1, and
a second organic compound comprising a carbazole moiety represented by Chemical Formula 2:

[Chemical Formula 2]

wherein, in Chemical Formula 2,
$Y^1$ is a single bond, a substituted or unsubstituted C6 to C30 arylene group, or a divalent substituted or unsubstituted C2 to C30 heterocyclic group,
$A^1$ is a substituted or unsubstituted C6 to C30 aryl group, or a substituted or unsubstituted C2 to C30 heterocyclic group,
$R^{20}$ to $R^{25}$ are independently hydrogen, deuterium, a substituted or unsubstituted C1 to C20 alkyl group, a substituted or unsubstituted C6 to C30 aryl group, or a substituted or unsubstituted C2 to C30 heterocyclic group, and
$R^{22}$ to $R^{25}$ are independently present or adjacent groups of $R^{22}$ to $R^{25}$ are linked to each other to form a ring.

11. The composition of claim 10, wherein the second organic compound is represented by Chemical Formula 2A or a combination of Chemical Formulae 2B-1 and 2B-2:

[Chemical Formula 2A]

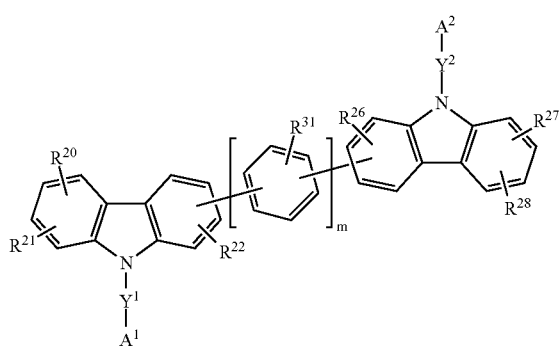

[Chemical Formula 2B-1]

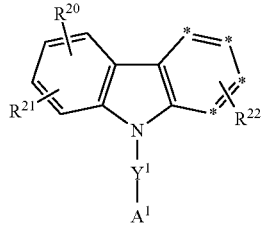

[Chemical Formula 2B-2]

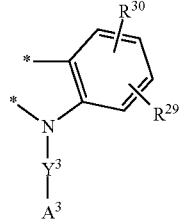

wherein, in Chemical Formula 2A, Chemical Formula 2B-1, or Chemical Formula 2B-2, $Y^1$ to $Y^3$ are independently a single bond, a substituted or unsubstituted C6 to C30 arylene group, a divalent substituted or unsubstituted C2 to C30 heterocyclic group, or a combination thereof, $A^1$ to $A^3$ are independently a substituted or unsubstituted C6 to C30 aryl group, a substituted or unsubstituted C2 to C30 heterocyclic group, or a combination thereof, $R^{20}$ to $R^{22}$ and $R^{26}$ to $R^{31}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, m is an integer of 0 to 2, two adjacent *'s in Chemical Formula 2B-1 are combined with two *'s in Chemical Formula 2B-2, and the other two *'s of Chemical Formula 2B-1 are each $CR^c$ and $CR^d$, wherein $R^c$ and $R^d$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof.

12. The composition of claim 11, wherein $A^1$ to $A^3$ of Chemical Formula 2A, Chemical Formula 2B-1, and Chemical Formula 2B-2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, or a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

13. The composition of claim 11, wherein the second organic compound is represented by one of Chemical Formulae 2A-1 and 2B-a to 2B-e:

[Chemical Formula 2A-1]

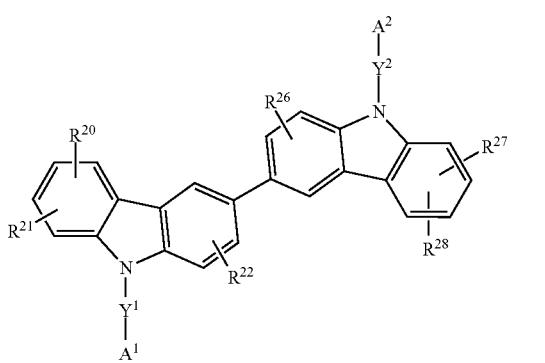

[Chemical Formula 2B-a]

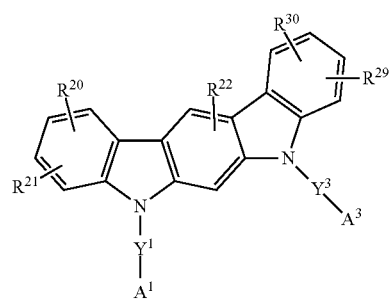

[Chemical Formula 2B-b]

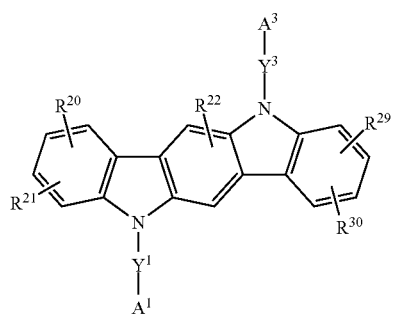

[Chemical Formula 2B-c]

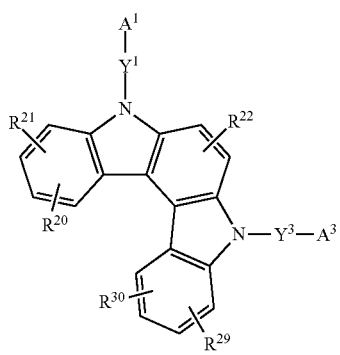

[Chemical Formula 2B-d]

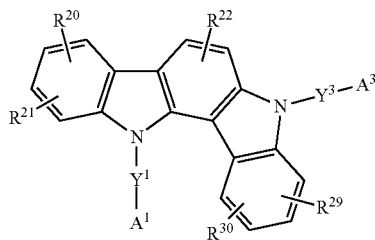

[Chemical Formula 2B-e]

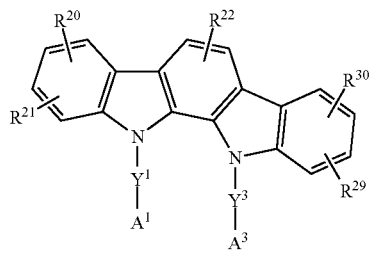

wherein, in Chemical Formulae 2A-1 and 2B-a to 2B-e, $Y^1$ to $Y^3$ are independently a single bond, a substituted or unsubstituted C6 to C30 arylene group, a divalent substituted or unsubstituted C2 to C30 heterocyclic group, or a combination thereof, $A^1$ to $A^3$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, or a substituted or unsubstituted triphenylene group, a substituted or unsubstituted pyridinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof, and $R^{20}$ to $R^{22}$ and $R^{26}$ to $R^{30}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof.

14. An organic optoelectronic device, comprising:
an anode and a cathode facing each other, and
an organic layer disposed between the anode and the cathode,
wherein the organic layer comprises the composition of claim 10.

15. The organic optoelectronic device of claim 14, wherein:
the organic layer comprises a light emitting layer, and
the composition is a host of the light emitting layer.

16. A display device comprising the organic optoelectronic device of claim 14.

* * * * *